United States Patent
Meehan et al.

(10) Patent No.: US 12,042,527 B2
(45) Date of Patent: Jul. 23, 2024

(54) USE OF mRNAs ENCODING OX40L, IL-23 AND IL-36GAMMA IN COMBINATION WITH IMMUNE CHECKPOINT BLOCKADE FOR TREATING PARTICULAR CANCERS

(71) Applicant: ModernaTX, Inc., Cambridge, MA (US)

(72) Inventors: Robert Meehan, Cambridge, MA (US); Tal Zaks, Newton, MA (US)

(73) Assignee: ModernaTX, Inc., Cambridge, MA (US)

( * ) Notice: Subject to any disclaimer, the term of this patent is extended or adjusted under 35 U.S.C. 154(b) by 305 days.

(21) Appl. No.: 16/736,941

(22) Filed: Jan. 8, 2020

(65) Prior Publication Data

US 2020/0360481 A1 Nov. 19, 2020

Related U.S. Application Data

(60) Provisional application No. 62/789,972, filed on Jan. 8, 2019.

(51) Int. Cl.
| | |
|---|---|
| *A61K 38/20* | (2006.01) |
| *A61K 9/00* | (2006.01) |
| *A61K 9/51* | (2006.01) |
| *A61K 38/19* | (2006.01) |
| *A61K 39/395* | (2006.01) |
| *A61P 35/00* | (2006.01) |

(52) U.S. Cl.
CPC ............ *A61K 38/20* (2013.01); *A61K 9/0019* (2013.01); *A61K 9/5123* (2013.01); *A61K 38/191* (2013.01); *A61K 39/3955* (2013.01); *A61K 39/39558* (2013.01); *A61P 35/00* (2018.01)

(58) Field of Classification Search
CPC .......... A61K 2039/54; A61K 2039/585; B82Y 5/00; C12N 15/88
See application file for complete search history.

(56) References Cited

U.S. PATENT DOCUMENTS

| | | |
|---|---|---|
| 10,143,723 B2 | 12/2018 | Frederick et al. |
| 10,172,808 B2 | 1/2019 | Frederick et al. |
| 10,285,950 B2 | 5/2019 | Frederick et al. |
| 10,293,058 B2 | 5/2019 | Fotin-Mleczek et al. |
| 10,322,090 B2 | 6/2019 | Frederick et al. |
| 10,322,091 B2 | 6/2019 | Frederick et al. |
| 10,335,486 B2 | 7/2019 | Frederick et al. |
| 10,379,767 B2 | 8/2019 | Frederick et al. |
| 10,383,951 B2 | 8/2019 | Frederick et al. |
| 10,406,113 B2 | 9/2019 | Frederick et al. |
| 10,918,740 B2 | 2/2021 | Fotin-Mleczek et al. |
| 11,003,366 B2 | 5/2021 | Frederick et al. |
| 11,071,716 B2 | 7/2021 | Frederick et al. |
| 11,185,510 B2 | 11/2021 | Frederick et al. |
| 11,403,008 B2 | 8/2022 | Frederick et al. |
| 11,596,609 B2 | 3/2023 | Frederick et al. |
| 2008/0025944 A1 | 1/2008 | Hoerr et al. |
| 2011/0244026 A1 | 10/2011 | Guild et al. |
| 2012/0065252 A1 | 3/2012 | Schrum et al. |
| 2014/0200261 A1 | 7/2014 | Hoge et al. |
| 2015/0164799 A1 | 6/2015 | Yaworski et al. |
| 2016/0331844 A1 | 11/2016 | Fotin-Mleczek et al. |
| 2018/0207295 A1 | 7/2018 | Fotin-Mleczek et al. |
| 2018/0318229 A1 | 11/2018 | Frederick et al. |
| 2018/0318385 A1 | 11/2018 | Frederick et al. |
| 2018/0369374 A1 | 12/2018 | Frederick et al. |
| 2019/0016781 A1 | 1/2019 | Bolen et al. |
| 2019/0060246 A1 | 2/2019 | Frederick et al. |
| 2019/0105280 A1 | 4/2019 | Frederick et al. |
| 2019/0105281 A1 | 4/2019 | Frederick et al. |
| 2019/0111003 A1 | 4/2019 | Frederick et al. |
| 2019/0114089 A1 | 4/2019 | Frederick et al. |
| 2019/0114090 A1 | 4/2019 | Frederick et al. |
| 2019/0185529 A1 | 6/2019 | Hoge et al. |
| 2020/0000935 A1 | 1/2020 | Frederick et al. |
| 2020/0054747 A1 | 2/2020 | Frederick et al. |
| 2020/0113844 A1 | 4/2020 | Frederick et al. |
| 2021/0038529 A1 | 2/2021 | Frederick et al. |
| 2021/0318817 A1 | 10/2021 | Frederick et al. |
| 2022/0001026 A1 | 1/2022 | Meehan et al. |
| 2022/0378868 A1 | 12/2022 | Frederick et al. |
| 2023/0041964 A1 | 2/2023 | Frederick et al. |

FOREIGN PATENT DOCUMENTS

| | | |
|---|---|---|
| EP | 2700708 A2 | 2/2014 |
| WO | WO 2012/135805 A2 | 10/2012 |
| WO | 2013/053775 A1 | 4/2013 |
| WO | WO-2013123242 A1 | 8/2013 |
| WO | WO 2014/113089 A2 | 7/2014 |
| WO | 2015/007871 A2 | 1/2015 |

(Continued)

OTHER PUBLICATIONS

NCBI—Cobalt alignment of Seq ID No. 1 and 3.Jan. 29, 2023. (Year: 2023).*
U.S. Appl. No. 16/207,641, filed Dec. 3, 2018, Frederick et al.
U.S. Appl. No. 17/352,904, filed Jun. 21, 2021, Frederick et al.
International Search Report and Written Opinion of the International Searching Authority for International Application No. PCT/US2021/034858, dated Oct. 4, 2021, 12 pages.
Jimeno et al., "Abstract #9264: A Phase 1/2, Open-Label, Multicenter, Dose Escalation and Efficacy Study of mRNA-2416, A Lipid Nanoparticle Encapsulated mRNA Encoding Human OX40L, for Intratumoral Injection Alone or in Combination with Durvalumab for Patients with Advanced Malignancies," AACR 2020 Abstract #9264, Apr. 27, 2020, 16 pages.

(Continued)

*Primary Examiner* — Elly-Gerald Stoica
(74) *Attorney, Agent, or Firm* — K&L Gates LLP

(57) ABSTRACT

The disclosure features methods for treating solid tumor malignancies and lymphomas by administering LNP encapsulated mRNAs encoding human OX40L, IL-23 and IL-36γ polypeptides alone or in combination with checkpoint blockade. The disclosure also features compositions for use in the methods.

25 Claims, 6 Drawing Sheets

Specification includes a Sequence Listing.

(56) References Cited

FOREIGN PATENT DOCUMENTS

| WO | 2015048744 A2 | | 4/2015 | |
|---|---|---|---|---|
| WO | WO 2015/095423 A2 | | 6/2015 | |
| WO | WO 2015/164674 A1 | | 10/2015 | |
| WO | WO-2015168379 A2 | | 11/2015 | |
| WO | 2016/170176 A1 | | 10/2016 | |
| WO | WO2017036889 | * | 2/2017 | ............ A61K 48/00 |
| WO | 2017112943 A1 | | 6/2017 | |
| WO | 2017191274 A2 | | 11/2017 | |
| WO | 2017201325 A1 | | 11/2017 | |
| WO | 2017201352 A1 | | 11/2017 | |
| WO | WO2017201352 | * | 11/2017 | ........... A61K 39/395 |
| WO | WO 2021/243207 A1 | | 12/2021 | |

OTHER PUBLICATIONS

Lo et al., "Antitumor and Antimetastatic Activity of IL-23," The Journal of Immunology, 2003, 171: 600-607.
Patel et al., "A phase I study of mRNA-2752, a lipid nanoparticle encapsulating mRNAs encoding human OX40L, IL-23, and IL-36γ, for intratumoral (iTu) injection alone and in combination with durvalumab," Journal of Clinical Oncology 38, No. 15_suppl (May 20, 2020) 3092.
Tagawa, M., "Cancer Gene Therapy Based on Enhanced Antigen Presentation and Expressed Cytokine Genes," Biotherapy, Nov. 2003, 17(6): 505-513 (English translation only, 15 pages).
U.S. Appl. No. 16/542,381, filed Aug. 16, 2019, Joshua P. Frederick.
U.S. Appl. No. 16/225,989, filed Dec. 19, 2018, Joshua P. Frederick.
U.S. Appl. No. 16/207,641, filed Dec. 3, 2018, Joshua P. Frederick.
U.S. Appl. No. 16/207,575, filed Dec. 3, 2018, Joshua P. Frederick.
U.S. Appl. No. 15/996,140, filed Jun. 1, 2018, Joshua P. Frederick.
U.S. Appl. No. 16/543,102, filed Aug. 16, 2019, Joshua P. Frederick.
U.S. Appl. No. 16/227,810, filed Dec. 20, 2018, Joshua P. Frederick.
U.S. Appl. No. 16/222,155, filed Dec. 17, 2018, Joshua P. Frederick.
U.S. Appl. No. 16/219,418, filed Dec. 13, 2018, Joshua P. Frederick.
U.S. Appl. No. 16/184,282, filed Nov. 8, 2018, Joshua P. Frederick.
U.S. Appl. No. 15/995,889, filed Jun. 1, 2018, Joshua P. Frederick.
U.S. Appl. No. 16/036,170, filed Jul. 16, 2018, Stephen G. Hoge.
U.S. Appl. No. 14/041,011, filed Sep. 30, 2013, Stephen G. Hoge.
U.S. Appl. No. 16/542,381, Aug. 18, 2020.
U.S. Appl. No. 16/225,989, Jul. 11, 2019.
U.S. Appl. No. 16/225,989, Mar. 29, 2019.
U.S. Appl. No. 16/207,575, Jul. 3, 2019.
U.S. Appl. No. 16/207,575, Jun. 13, 2019.
U.S. Appl. No. 16/207,575, Jan. 8, 2019.
U.S. Appl. No. 15/996,140, Oct. 3, 2018.
U.S. Appl. No. 15/996,140, Sep. 20, 2018.
U.S. Appl. No. 16/543,102, Sep. 21, 2020.
U.S. Appl. No. 16/227,810, Apr. 3, 2019.
U.S. Appl. No. 16/227,810, Feb. 25, 2019.
U.S. Appl. No. 16/222,155, Apr. 19, 2019.
U.S. Appl. No. 16/222,155, Mar. 8, 2019.
U.S. Appl. No. 16/219,418, Apr. 18, 2019.
U.S. Appl. No. 16/219,418, Feb. 25, 2019.
U.S. Appl. No. 15/995,889, Sep. 21, 2018.
U.S. Appl. No. 16/184,282, Apr. 3, 2019.
U.S. Appl. No. 16/184,282, Feb. 7, 2019.
U.S. Appl. No. 16/036,170, Jun. 29, 2020.
U.S. Appl. No. 14/041,011, Jan. 22, 2018.
U.S. Appl. No. 14/041,011, Sep. 16, 2016.
U.S. Appl. No. 14/041,011, Feb. 2, 2016.
U.S. Appl. No. 14/041,011, Apr. 22, 2015.
Andarini, S. et al., "Adenovirus Vector-Mediated in Vivo Gene Transfer of OX40 Ligand to Tumor Cells Enhances Antitumor Immunity of Tumor-Bearing Hosts", Cancer Research, vol. 64(9): 3281-3287(2004).
Andries, O. et al., "N1-methyl pseudouridine-incorporated mRNA outperforms pseudouridine-incorporated mRNA by providing enhanced protein expression and reduced immunogenicity in mammalian cell lines and mice," Journal of Controlled Release, vol. 217: 337-344 (2015).
Cawood R. et al., "Use of tissue-specific microRNA to control pathology of wild-type adenovirus without attenuation of its ability to kill cancer cells," PLOS Pathogens, vol. 5 (5): e1000440, (2005).
Charoensit, P. et al., "Enhanced growth inhibition of metastatic lung tumors by intravenous injection of ATRA-cationic liposome/IL-12 pDNA complexes in mice," Cancer Gene Therapy, vol. 17(7) 512-522 (2010).
Colombo, M. et al., "Interleukin-12 in anti-tumor immunity and immunotherapy," Cytokine and Growth Factor Reviews, vol. 13 (2):155-168 (2002).
Dannull, J. et al., "Enhancing the immunostimulatory function of dendritic cells by transfection with mRNA encoding OX40 ligand," Blood, vol. 105 (8):3206-3213 (2005).
Database Geneseq [Online] Mar. 12, 2015 (Mar. 12, 2015), "Human TNFSF4 gene, Seq ID 11.", XP002767824, retrieved from EBI accession No. GSN:BBT93694 Database accession No. BBT93694 Sequence NCBI (2014, Reference Sequence: NM_003326.4).
Hara I et al., "Effectiveness of cancer vaccine therapy using cells transduced with the interleukin-12 gene combined with systemic interleukin-18 administration," Cancer Gene Therapy, vol. 7(1):83-90 (2000).
Hu, D. et al., "Immunoglobulin Expression and Its Biological Significance in Cancer Cells," Cellular and Molecular Immunology, vol. 5(5): 319-324 (2008).
International Preliminary Report on Patentability, PCT/US2016/068552, dated Jun. 26, 2018, 9 pages.
International Preliminary Report on Patentability, PCT/US2017/033395, dated Nov. 20, 2018, 9 pages.
International Preliminary Report on Patentability, PCT/US2017/033425, dated Nov. 29, 2018, 12 pages.
International Search Report and Written Opinion, PCT/US2016/068552, dated Mar. 21, 2017, 14 pages.
International Search Report and Written Opinion, PCT/US2017/033395, dated Sep. 1, 2017, 15 pages.
International Search Report and Written Opinion, PCT/US2017/033425, dated Jul. 25, 2017, 16 pages.
Karkada M. et al., "A liposome-based platform, VacciMax (R), and its modified water-free platform DepoVax(TM) enhance efficacy of in vivo nucleic acid delivery", Vaccine, vol. 28(38):6176-6182 (2010).
Kormann, M.S. et al., "Expression of therapeutic proteins after delivery of chemically modified mRNA in mice," Nature Biotechnology, vol. 29(2):154-159 (2011).
Kron, M. et al., "miRNA-mediated silencing in hepatocytes can increase adaptive immune responses to adenovirus vector-delivered transgenic antigens," Molecular Therapy, vol. 19(8):1547-1557 (2011).
Lennox, KA, et al., "Chemical modification and design of anti-miRNA oligonucleotides," Gene Therapy, vol. 18(12):1111-1120 (2011).
Linch S. et al., "0X40 agonists and combination immunotherapy: Putting the pedal to the metal," Frontiers in Oncology, Frontiers Research Foundation, vol. 5:1-14 (2015).
Mcnamara, M. et al., "RNA-Based Vaccines in Cancer Immunotherapy," Journal of Immunology Research, vol. 2015, pp. 1-9 (2015).
Melero, I. et al., "Evolving synergistic combinations of targeted immunotherapies to combat cancer," Nature Reviews, Cancer, vol. 15(8):457-472 (2015).
Mendiratta, S. et al., "Combination of Interleukin 12 and Interferon [alpha] Gene Therapy Induces a Synergistic Antitumor Response against Colon and Renal Cell Carcinoma", Human Gene Therapy, vol. 11(13):1851-1862 (2000).
Meraz, I. et al., "Adjuvant Cationic Liposomes Presenting MPL and IL-12 Induce Cell Death, Suppress Tumor Growth, and Alter the Cellular Phenotype of Tumors in a Murine Model of Breast Cancer," Molecular Pharmaceutics, vol. 11(10):3484-3491(2014).
Ngiow, S. et al."A balance of interleukin-12 and -23 in cancer," Trends in Immunology, vol. 34 (11):548-555 (2013).
Overwijk, W. W. et al., "Immunological and Antitumor Effects of IL-23 as a Cancer Vaccine Adjuvant," The Journal of Immunology, vol. 176 (9):5213-5222 (2006).

(56) References Cited

OTHER PUBLICATIONS

Pichard, V. et al., "Specific Micro RNA-Regulated TetR-KRAB Transcriptional Control of Transgene Expression in Viral Vector-Transduced Cells", PLOS One, vol. 7(12):e51952 (2012).
Rotondaro, L. et al., "Efficiency of different viral promoters in directing gene expression in mammalian cells: effect of 3'-untranslated sequences," Gene, vol. 168(2):195-198 (1996).
Sahin, U. et al., "mRNA-based therapeutics—developing a new class of drugs," Nature Reviews Drug Discovery, vol. 13(10):759-780 (2014).
Shim, G. et al., "Application of cationic liposomes for delivery of nucleic acids," Asian Journal of Pharmaceutical Sciences, vol. 8 (2):72-80 (2013).
Singh, R. et al., "Nanoengineering artificial lipid envelopes around adenovirus by self-assembly," ACS Nano, vol. 2(5):1040-1050 (2008).
Smirnov, D.A. et al., "ATM Gene mutations result in both recessive and dominant expression phenotypes of genes and microRNAs", The American Journal of Human Genetics, vol. 83: 243-253 (2008).
Suzuki, T. et al., "miR-122a-Regulated Expression of a Suicide Gene Prevents Hepatotoxicity Without Altering Antitumor Effects in Suicide Gene Therapy," Molecular Therapy, vol. 16(10): 1719-1726 (2008).
Tugues, S. et al., "New insights into IL-12-mediated tumor suppression," Call Death and Differentiation, Cell Death and Differentiation, vol. 22(2):237-246 (2014).
Van Der Jeught, K. et al., "Targeting the tumor microenvironment to enhance antitumor immune responses," Oncotarget, vol. 6(3): 1359-1381(2014).
Vinuesa, C. et al., "Logic and Extent of miRNA-Mediated Control of Autoimmune Gene Expression", Int Rev Immunol., vol. 28(3-4):112-138 (2009).
Wang J. et al., "Synergistic anti-tumor effect by combinatorial gene-gun therapy using IL-23 and IL-18 cDNA", Journal of Dermatological, vol. 36 (1):66-68 (2004).
Wang X. et al., "IL-36[gamma] Transforms the Tumor Microenvironment and Promotes Type 1 Lymphocyte-Mediated Antitumor Immune Respo," Cancer Cell, vol. 28(3):296-306 (2015).
Wang. Y. et al "Systemic delivery of modified mRNA encoding herpes simplex virus 1 thymidine kinase for targeted cancer gene therapy," Molecular Therapy, Nature Publishing Group, GB, vol. 21(2):358-367 (2012).
Weiss, J. et al., "Immunotherapy of cancer by IL-12-based cytokine combinations," Expert Opinion on Biological Therapy, vol. 7(11):1705-1721 (2007).
Wiltrout, J. et al., "IL-12/IL-2 combination cytokine therapy for solid tumours: translation from bench to bedside," The Expert Opinion on Biological, Informa Healthcare, vol. 2 (5):513-524 (2012).
U.S. Appl. No. 17/927,940, filed Nov. 22, 2022, Meehan et al.
Desmyter, A. et al., "Neutralization of Human Interleukin 23 by Multivalent Nanobodies Explained by the Structure of Cytokine-Nanobody Complex", Frontiers in Immunology, 2017, vol. 8, Article 884, 10 pages.
Hewitt et al., "Durable anticancer immunity from intratumoral administration of IL-23, IL-36γ, and OX40L mRNAs," Sci. Transl. Med. (2019) 11(477): eaat9143, 15 pages.
Neurath, M., "IL-36 in chronic inflammation and cancer," Cytokine and Growth Factor Reviews (2020) 55: 70-79.
Belladonna et al., "IL-23 and IL-12 Have Overlapping, but Distinct, Effects on Murine Dendritic Cells," The Journal of Immunology, 2002, 168: 5448-5454.
Findlay et al., "OX40L blockade is therapeutic in arthritis, despite promoting osteodastogenesis," PNAS, Feb. 11, 2014, vol. 111, No. 6, pp. 2289-2294.
Frederick et al., "Abstract 1607: Durable efficacy and anti-cancer immunity following intratumoral administration of messenger RNAs encoding IL-36γ, IL-23 and OX40L," Cancer Res, Jul. 1, 2017 (77) (13 Supplement) 1607; 2 pages, DOI: 10.1158/1538-7445.AM2017-1607.
International Preliminary Report on Patentability, PCT/US2019/060381, dated May 11, 2021, 6 pages.
International Search Report and Written Opinion of the International Searching Authority for International Application No. PCT/US2019/060381, dated May 12, 2020, 10 pages.
Langowski et al., "IL-23 promotes tumour incidence and growth," Nature, Jul. 27, 2006, vol. 442, pp. 461-465.
Tang et al., "Interleukin-23: as a drug target for autoimmune inflammatory diseases," Immunology, 2011, 135, 112-124.
Teng et al., "IL-12 and IL-23 cytokines: from discovery to targeted therapies for immune-mediated inflammatory diseases," Nature Medicine, Jul. 2015, vol. 21, No. 7, pp. 719-729.

\* cited by examiner

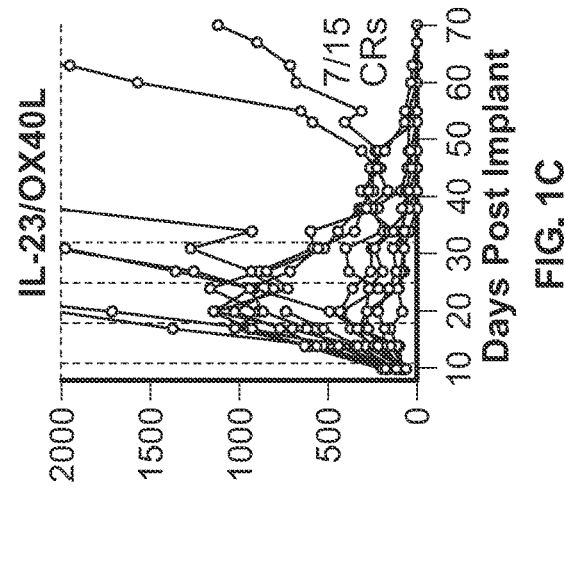
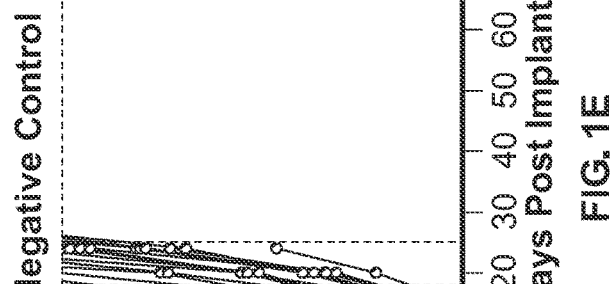
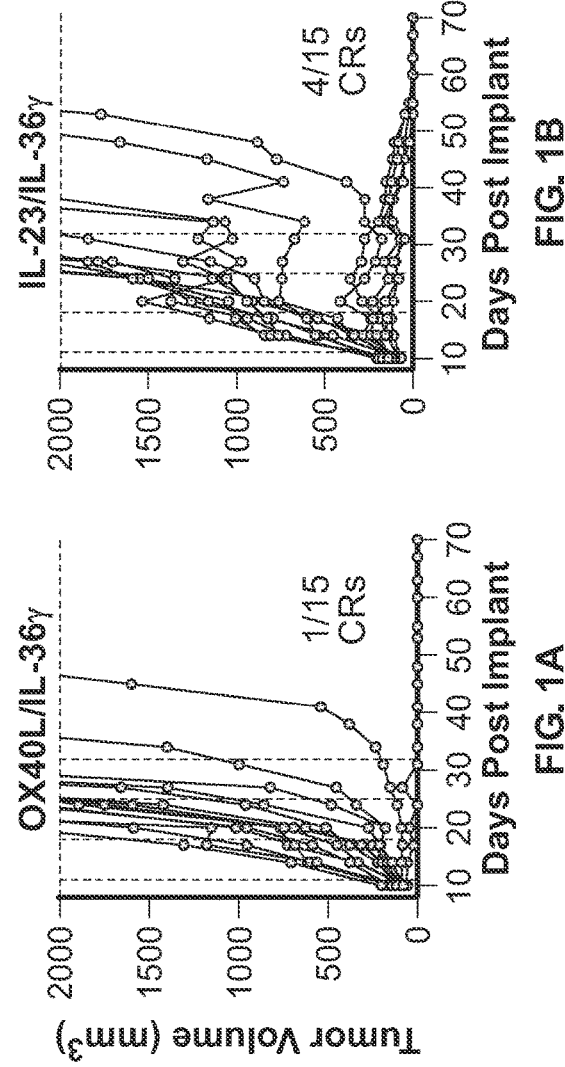
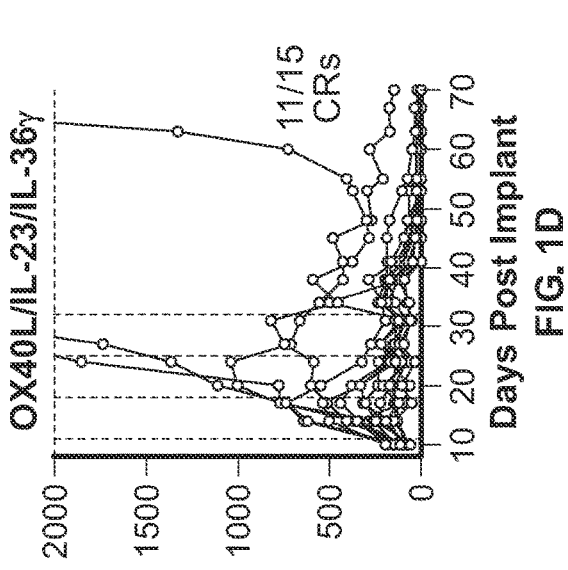

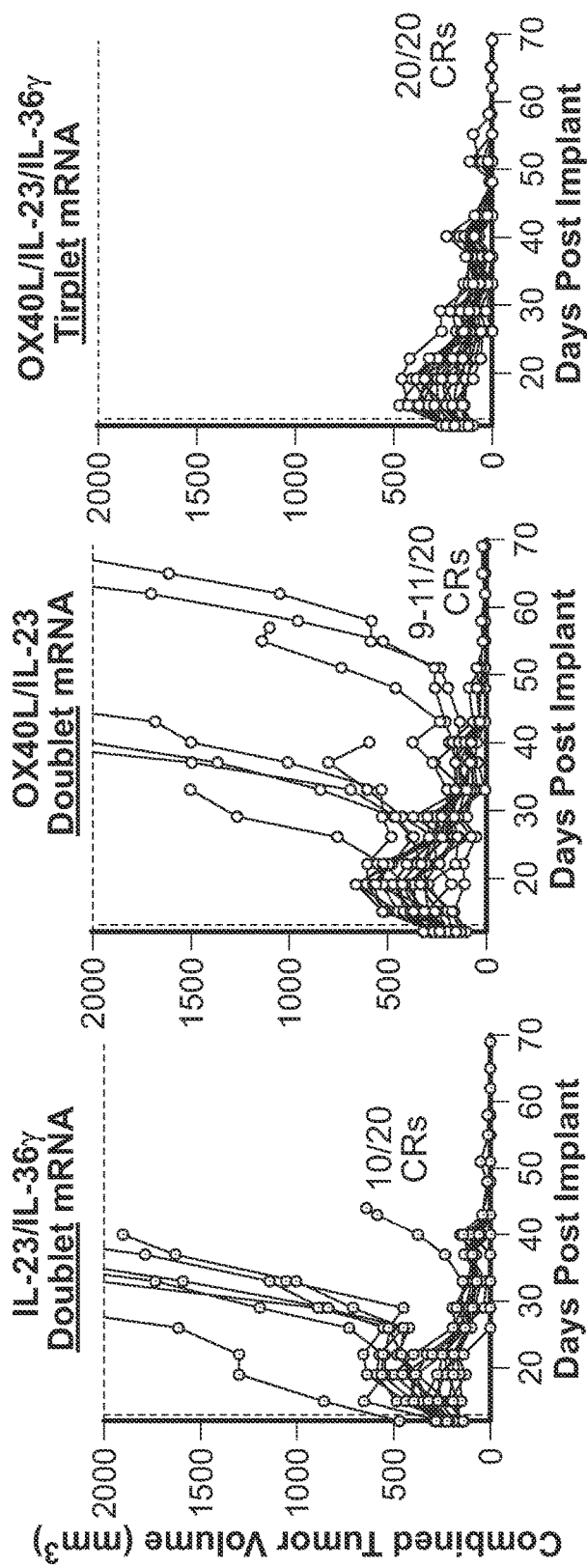
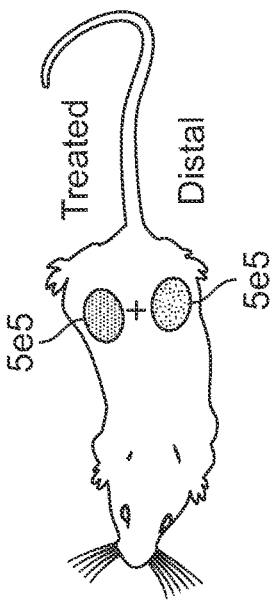
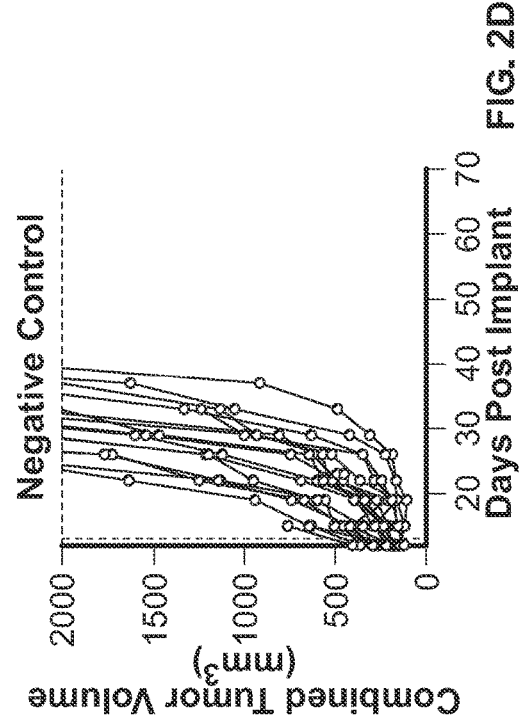
FIG. 2A  FIG. 2B  FIG. 2C  FIG. 2D  FIG. 2E

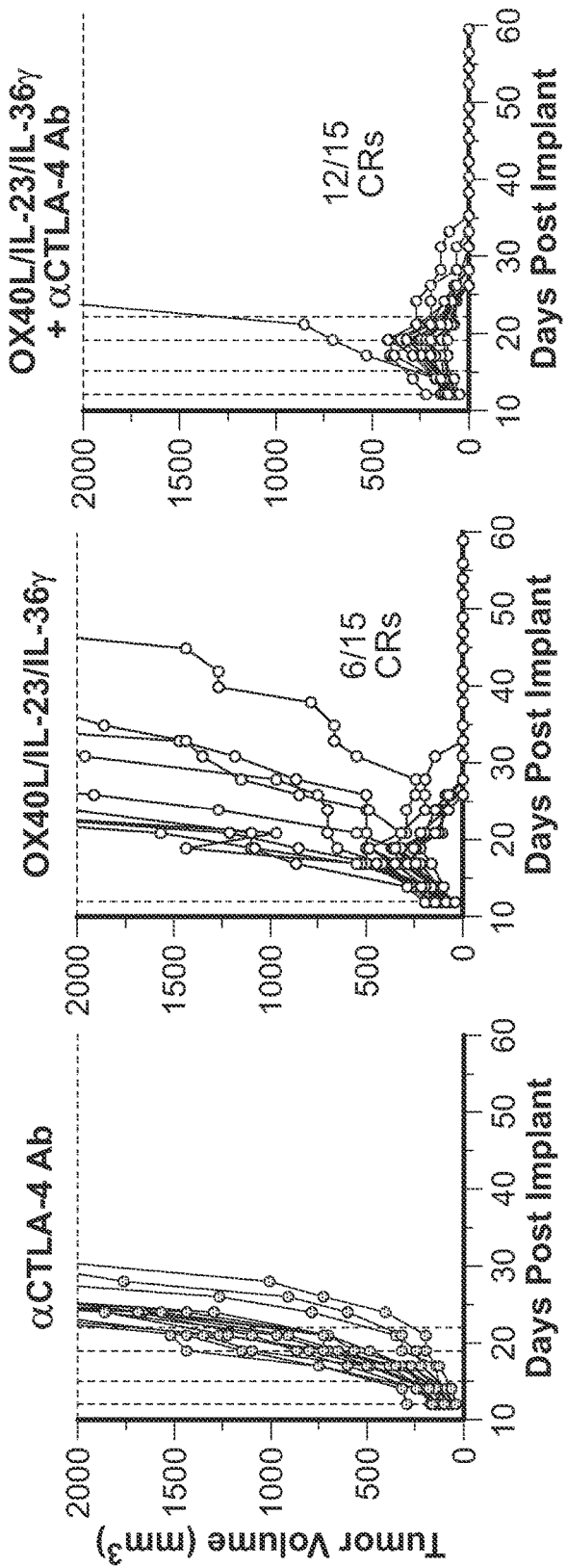

SEQUENCE LISTING

<160> NUMBER OF SEQ ID NOS: 37

<210> SEQ ID NO 1
<211> LENGTH: 183
<212> TYPE: PRT
<213> ORGANISM: Homo sapiens
<220> FEATURE:
<221> NAME/KEY: misc_feature
<222> LOCATION: (1)..(183)
<223> OTHER INFORMATION: OX40L (TNSFR4) - Tumor necrosis factor ligand superfamily member 4 isoform 1

<400> SEQUENCE: 1

```
Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Leu Ile Leu Ile His Gln Asn
                165                 170                 175

Pro Gly Glu Phe Cys Val Leu
            180
```

<210> SEQ ID NO 2
<211> LENGTH: 133
<212> TYPE: PRT
<213> ORGANISM: Homo sapiens
<220> FEATURE:
<221> NAME/KEY: misc_feature -continued

```
<222> LOCATION: (1)..(133)
<223> OTHER INFORMATION: OX40L (TNSFR4) - TNFSF4 isoform 2

<400> SEQUENCE: 2

Met Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 3
<211> LENGTH: 198
<212> TYPE: PRT
<213> ORGANISM: Mus musculus
<220> FEATURE:
<221> NAME/KEY: misc_feature
<222> LOCATION: (1)..(198)
<223> OTHER INFORMATION: OX40L (TNSFR4) - TNFSF4

<400> SEQUENCE: 3

Met Glu Gly Glu Gly Val Gln Pro Leu Asp Glu Asn Leu Glu Asn Gly
1               5                   10                  15

Ser Arg Pro Arg Phe Lys Trp Lys Lys Thr Leu Arg Leu Val Val Ser
            20                  25                  30

Gly Ile Lys Gly Ala Gly Met Leu Leu Cys Phe Ile Tyr Val Cys Leu
        35                  40                  45

Gln Leu Ser Ser Ser Pro Ala Lys Asp Pro Pro Ile Gln Arg Leu Arg
    50                  55                  60

Gly Ala Val Thr Arg Cys Glu Asp Gly Gln Leu Phe Ile Ser Ser Tyr
65                  70                  75                  80

Lys Asn Glu Tyr Gln Thr Met Glu Val Gln Asn Asn Ser Val Val Ile
            85                  90                  95

Lys Cys Asp Gly Leu Tyr Ile Ile Tyr Leu Lys Gly Ser Phe Phe Gln
            100                 105                 110

Glu Val Lys Ile Asp Leu His Phe Arg Glu Asp His Asn Pro Ile Ser
            115                 120                 125

Ile Pro Met Leu Asn Asp Gly Arg Arg Ile Val Phe Thr Val Val Ala
        130                 135                 140

Ser Leu Ala Phe Lys Asp Lys Val Tyr Leu Thr Val Asn Ala Pro Asp
145                 150                 155                 160

Thr Leu Cys Glu His Leu Gln Ile Asn Asp Gly Glu Leu Ile Val Val
            165                 170                 175

Gln Leu Thr Pro Gly Tyr Cys Ala Pro Glu Gly Ser Tyr His Ser Thr
            180                 185                 190
```

Val Asn Gln Val Pro Leu
        195

<210> SEQ ID NO 4
<211> LENGTH: 549
<212> TYPE: RNA
<213> ORGANISM: Homo sapiens
<220> FEATURE:
<221> NAME/KEY: misc_feature
<222> LOCATION: (1)..(549)
<223> OTHER INFORMATION: Human OX40L mRNA (ORF)

<400> SEQUENCE: 4

```
auggaaaggg uccaaccccu ggaagagaau gugggaaaug cagccaggcc aagauucgag    60
aggaacaagc uauugcuggu ggccucugua auucagggac uggggcugcu ccugugcuuc   120
accuacaucu gccugcacuu ucucgcucuu cagguaucac aucgguaucc ucgaauucaa   180
aguaucaaag uacaauuuac cgaauauaag aaggagaaag guuucauccu cacuucccaa   240
aaggaggaug aaaucaugaa ggugcagaac aaccucaguc ucaucaacug ugaugggcuu   300
uaucucaucu cccugaaggg cuacuucucc caggaaguca acauuagccu cauuaccag   360 aaggaugagg agccccucuu ccaacugaag aaggucaggu cugucaacuc cuugauggug   420
gccucucuga cuuacaaaga caaagucuac uugaauguga ccacugacaa uaccucccug   480
gaugacuucc augugaaugg cggagaacug auucuuaucc aucaaaaucc uggugaauuc   540
uguguccuu                                                          549
```

<210> SEQ ID NO 5
<211> LENGTH: 841
<212> TYPE: RNA
<213> ORGANISM: Homo sapiens
<220> FEATURE:
<221> NAME/KEY: misc_feature
<223> OTHER INFORMATION: 5'7MeGpppG2'Ome, OH3'
<220> FEATURE:
<221> NAME/KEY: misc_feature
<222> LOCATION: (1)..(841)
<223> OTHER INFORMATION: A,C G & U = AMP, CMP, GMP & N1-Psi-UMP,
      respectively; Me = methyl; p = inorganic phosphate
<220> FEATURE:
<221> NAME/KEY: misc_feature
<222> LOCATION: (1)..(841)
<223> OTHER INFORMATION: Full-length mRNA Nucleotide sequence (5' UTR,
      ORF, 3' UTR, polyA tail) of human OX40L

<400> SEQUENCE: 5

```
ggaaauaaga gagaaaagaa gaguaagaag aaauauaaga gccaccaugg aaagggucca    60
accccuggaa gagaaugugg gaaaugcagc caggccaaga uucgagagga caagcuauu   120 gcugguggcc ucuguaauuc agggacuggg gcugcccug ugcuuccu acaucugccu   180 gcacuucucu gcucuucagg uaucacaucg guauccucga auucaaagua ucaaaguaca   240
auuuaccgaa uauaagaagg agaaagguuu cauccucacu ucccaaaagg aggaugaaau   300
caugaaggug cagaacaacu cagucaucau caacugugau gggcuuuauc ucaucccu   360 gaagggcuac uucucccagg aagucaacau uagccuucau uaccagaagg augaggagcc   420
ccucuuccaa cugaagaagg ucaggucugu caacuccuug augguggccu cucugacuua   480
caaagacaaa gucuacuuga augugaccac ugacaauacc ucccuggaug acuuccaugu   540
gaauggcgga gaacugauuc uuauccauca aaauccuggu gaauucugug uccuuugaua   600
auaggcugga gccucggugg ccaugcuucu ugcccuuugg gccucccccc agccccuccu   660
```

| cccuuccug cacccguacc ccccaaacac cauugucaca cuccaguggu cuuugaauaa | 720 |
| agucugagug ggcggcaaaa aaaaaaaaaa aaaaaaaaaa aaaaaaaaaa aaaaaaaaaa | 780 |
| aaaaaaaaaa aaaaaaaaaa aaaaaaaaaa aaaaaaaaaa aaaaaaaaaa aaaaaaucua | 840 |
| g | 841 |

<210> SEQ ID NO 6
<211> LENGTH: 3484
<212> TYPE: RNA
<213> ORGANISM: Homo sapiens
<220> FEATURE:
<221> NAME/KEY: misc_feature
<222> LOCATION: (1)..(3484)
<223> OTHER INFORMATION: OX40L - TNFSF4, transcript variant 1

<400> SEQUENCE: 6

| ggcccuggga ccuuugccua uuuucugauu gauaggcuuu guuugucuu uaccuccuuc | 60 |
| uuucugggga aaacuucagu uuuaucgcac guuccccuuu uccauaucuu caucuuccccu | 120 |
| cuacccagau ugugaagaug gaaagggucc aacccuguga agagaaugug ggaaaugcag | 180 |
| ccaggccaag auucgagagg aacaagcuau ugcguggugc ucucuguaauu cagggacugg | 240 |
| ggcugcuccu guugcuucacc uacaucgccc ugcacuuucuc ugcucuuucag guaucacauc | 300 |
| gguauccucg aauucaaagu aucaaaguac aauuuaccga auauaagaag gagaaagguu | 360 |
| ucauccucac uucccaaaag gaggaugaaa ucaugaaggu gcagacaac ucagucauca | 420 |
| ucaacuguga ugggguuuau cucaucuccc ugaagggcua cuucccccag gaagucaaca | 480 |
| uuagccuuca uuaccagaag gaugaggagc cccucuucca acugaagaag gucaggucug | 540 |
| ucaacuccuu gaugguggcc ucucugacuu acaaagacaa agucuacuug aaugugacca | 600 |
| cugacaauac cucccuggau gacuuccaug ugaauggcgg agaacugauu cuuauccauc | 660 |
| aaaauccugg ugaauucugu guccuuugag gggcugaugg caauaucuaa aaccaggcac | 720 |
| cagcaugaac accaagcugg ggguggacag ggcauggauu cuucauugca agugaaggag | 780 |
| ccuccccagcu cagccacgug ggaugugaca agaagcagau ccuggcccuc ccgcccccac | 840 |
| cccucaggga uauuuaaaac uuauuuuaua uaccaguuaa ucuuauuuau ccuuauauuu | 900 |
| ucuaaauugc cuagccguca caccccaaga uugccuugag ccuacuaggc accuuuguga | 960 |
| gaaagaaaaa auagaugccu cuucuucaag augcauuguu ucuauggguc aggcaauugu | 1020 |
| cauaauaaac uuaugucauu gaaaacggua ccugacuacc auuugcugga aauuugacau | 1080 |
| gugugugggca uuaucaaaau gaagaggagc aaggagugaa ggagugggu uaugaaucug | 1140 |
| ccaaaggugg uaugaaccaa ccccuggaag ccaaagcggc cucuccaagg uuaaauugau | 1200 |
| ugcaguuugc auauugccua aauuuaaacu uucucauuug gugggggguuc aaaagaagaa | 1260 |
| ucagcuugug aaaaaucagg acuugaagag agccgucuaa gaaauaccac gugcuuuuuu | 1320 |
| ucuuuaccau uuugcuuucc cagccuccaa acauaguuaa uagaaauuuc ccuucaaaga | 1380 |
| acugucuggg gaugugaugc uuugaaaaau cuaaucagug acuuaagaga gauuuucuug | 1440 |
| uauacaggga gagugagaua acuuauuguguga aagggguuagc uuuacuguac aggauagcag | 1500 |
| ggaacuggac aucucagggu aaaagucagu acggauuuua auagccuggg gaggaaaaca | 1560 |
| cauucuuugc cacagacagg caaagcaaca caugcucauc cuccugccua ugcugagaua | 1620 |
| cgcacucagc uccaugucuu guacacacag aaacauugcu gguuucaaga augaggguga | 1680 |
| uccuauuauc aaauucaauc ugaugucaaa uagcacuaag aaguuauugu gccuauagaaa | 1740 |
| aauuaaugau cucugucuag aaauaccaua gaccauauau agucucacau ugauaauuga | 1800 |

-continued

```
aacuagaagg gucuauaauc agccuaugcc agggcuucaa uggaauagua uccccuuaug    1860
uuuaguugaa auguccccuu aacuugauau aaugaguuau gcuuauggcg cuguggacaa    1920
ucugauuuuu caugucaacu uuccagauga uuuguaacuu cucugugcca aaccuuuuau    1980
aaacauaaau uuuugagaua uguauuuuaa aauugaugca cauguuuccc ugacauuuuc    2040
aauagaggau acaacaucac agaaucuuuc uggaugauuc uguguuauca aggaauugua    2100
cugugcuaca auuaucucua gaaucuccag aaagguggag ggcuguucgc ccuuacacua    2160
aauggucuca guuggauuuu uuuuuccugu uuucuauuuc cucuuaagua caccuucaac    2220
uauauuccca ucccucuauu uuaaucuguu augaaggaag guaaauaaaa augcuaaaua    2280
gaagaaauug uagguaaggu aagaggaauc aaguucugag uggcugccaa ggcacucaca    2340
gaaucauaau cauggcuaaa uauuuaugga gggccuacug uggaccaggc acugggcuaa    2400
auacuuacau uuacaagaau cauucugaga cagauauuca augauaucug gcuucacuac    2460
ucagaagauu gugugugugu uugugugugu gugugugugu uauuucacu uuuguuauu    2520 gaccauguuc ugcaaaauug caguuacuca gugagugaua uccgaaaaag uaaacguuua    2580
ugacuauagg uaauauuuaa gaaaaugcau gguucauuuu uaaguuugga auuuuuaucu    2640
auauuucuca cagaugugca gugcacaugc aggccuaagu auauguugug uguuuguuu    2700 gucuuugaug ucauggaccc cucucuuagg ugcucacucg cuuugggugc accuggccug    2760
cucuucccau guuggccucu gcaaccacac agggauauuu cugcuaugca ccagccucac    2820
uccaccuucc uuccaucaaa aauaugugug ugucucag ucccuguaag ucauguccuu    2880
cacagggaga auuaacccuu cgauauacau ggcagaguuu ugugggaaaa gaauugaaug    2940
aaaagucagg agaucagaau uuuaaauuug acuuagccac uaacuagcca uguaaccuug    3000
ggaaagucau uucccauuuc uggcucugc uuuucuuucu guuaaaugag aggaauguua    3060
aauaucuaac aguuuagaau cuuaugcuua caguguauc ugaugca cauauuuaaau    3120 gucuauguuc uguugcuau gagucaagga guguaaccuu cuccuuuacu auguugaaug    3180 uauuuuuuc uggacaagcu uacaucuucc ucagccaucu uugugagucc uucaagagca    3240
guuaucaauu guuaguuaga uauuuucuau uuagagaaug cuuaagggau ccaaucccg     3300 auccaaauca uaauuuguuc uuaaguauac ugggcagguc cccuauuuua agcauaauu    3360 uuguauuuag ugcuuuccug gcucucagag aguauuaaua uugauauuaa uaauauaguu    3420
aauaguaaua uugcuauuua cauggaaaca aauaaaagau cucagaauuc acuaaaaaaa    3480
aaaa                                                                3484
```

<210> SEQ ID NO 7
<211> LENGTH: 737
<212> TYPE: RNA
<213> ORGANISM: Homo sapiens
<220> FEATURE:
<221> NAME/KEY: misc_feature
<222> LOCATION: (1)..(737)
<223> OTHER INFORMATION: mRNA sequence: Human OX40L with 5'-UTR, 3'-UTR, and miR-122 binding site

<400> SEQUENCE: 7

```
gggaaauaag agagaaaaga agaguaagaa gaaauauaag agccaccaug gaaagggucc      60
aaccccugga agagaaugug ggaaaugcag ccaggccaag auucgagagg aacaagcuau     120
ugcugguggc cucuguaauu cagggacugg ggcugcuccu ugcuucacc uacaucugcc     180 ugcacuucuc ugcucuucag guaucacauc gguauccucg aauucaaagu aucaaaguac     240
```

```
aauuuaccga auauaagaag gagaaagguu ucauccucac uucccaaaag gaggaugaaa    300
ucaugaaggu gcagaacaac ucagucauca ucaacuguga uggguuuuau cucaucuccc    360
ugaagggcua cuucucccag gaagucaaca uuagccuuca uuaccagaag gaugaggagc    420
cccucuucca acugaagaag gucaggucug ucaacuccuu gaugguggcc ucucugacuu    480
acaaagacaa agucuacuug aaugugacca cugacaauac cucccuggau gacuuccaug    540
ugaauggcgg agaacugauu cuuauccauc aaaauccugg ugaauucugu guccuuugau    600
aauaggcugg agccucggug gccaugcuuc uugccccuug ggccucccccc cagccccucc    660 uccccuuccu gcacccguac cccccaaaca ccauugucac acuccagugg ucuuugaaua    720
aagucugagu gggcggc                                                   737

<210> SEQ ID NO 8
<211> LENGTH: 549
<212> TYPE: RNA
<213> ORGANISM: Homo sapiens
<220> FEATURE:
<221> NAME/KEY: misc_feature
<222> LOCATION: (1)..(549)
<223> OTHER INFORMATION: mRNA open reading frame sequence 1 for Human
      OX40L

<400> SEQUENCE: 8
auggagcggg ugcagccccu ggaggagaac gugggcaacg ccgcucggcc acgguucgag     60
cggaacaagc ugcugcuggu ggcuagcgug auccagggcc ugggccugcu gcugugcuuc    120
accuacaucu gccugcacuu cagcgcccug caggugagcc accgguaucc ccggauccag    180
agcaucaagg ugcaguucac cgaguacaag aaggagaagg cuucauccu gaccagccag    240 aaggaggacg agaucaugaa ggugcagaac aacagcguga ucaacug cgacggcuuc      300 uaccugauca gccugaaggg cuacuucagc caggaggug acaucagccu gcacuaccag    360
aaggacgagg agccccuguu ccagcugaag aaggugcgga gcgugaacag ccugaugguu    420
gccagccuga ccuacaagga caaggugac cugaacguga ccaccgacaa caccagccug    480
gacgacuucc acgugaacgg cggcgagcug auccugaucc accagaaccc cggcgaguuc    540
ugcgugcug                                                           549

<210> SEQ ID NO 9
<211> LENGTH: 549
<212> TYPE: RNA
<213> ORGANISM: Homo sapiens
<220> FEATURE:
<221> NAME/KEY: misc_feature
<222> LOCATION: (1)..(549)
<223> OTHER INFORMATION: mRNA open reading frame sequence 2 for Human
      OX40L

<400> SEQUENCE: 9
auggaaaggg uccaaccccu cgaagagaac gugggaaacg cagccaggcc aagauucgag     60
aggaacaagc uauugcucgu ggccucagua auucagggac ucggguuacu ccuugcuuc    120 accuacaucu gcuugcacuu cagugcucug cagguaucac aucgguaucc ucgaauucaa    180
aguaucaaag uacaauuuac cgaauauaag aaggagaaag guucauccu cacuucccag    240 aaggaggaug aaaucaugaa ggugcagaac aacucaguca ucaacug ugaugggvvuu      300 uaucucaucu cccugaaggg cuacuucucc caggaaguca acauuagccu ucauuaccag    360
aaggaugagg agcccucuuu ccaacugaag aaggucaggu cugucaacuc cuugaugqua    420
```

```
gccucucuga cuuacaaaga caaagucuac uugaauguga ccacugacaa uaccucccug    480
gaugacuucc augugaaugg cggagaacug auucuuaucc aucagaaucc uggugaauuc    540
uguguccuu                                                           549

<210> SEQ ID NO 10
<211> LENGTH: 549
<212> TYPE: RNA
<213> ORGANISM: Homo sapiens
<220> FEATURE:
<221> NAME/KEY: misc_feature
<222> LOCATION: (1)..(549)
<223> OTHER INFORMATION: mRNA open reading frame sequence 3 for Human
      OX40L

<400> SEQUENCE: 10
auggagcggg ugcagccccu ggaggagaac gugggcaacg ccgcucggcc acgguucgag    60
cggaacaagc ugcugcuggu ggcuagcgug auccagggcc ugggccugcu gcugugcuuc    120
accuacaucu gccugcacuu cagcgcccug caggugagcc accgguaucc ccggauccag    180
agcaucaagg ugcaguucac cgaguacaag aaggagaagg cuucauccu gaccagccag    240 aaggaggacg agaucaugaa ggugcagaac aacagcguga ucaucaacug cgacggcuuc    300
uaccugauca gccugaaggg cuacuucagc caggagguga acaucagccu gcacuaccag    360
aaggacgagg agccccuguu ccagcugaag aaggugcgga gcgugaacag ccugauggug    420
gccagccuga ccuacaagga caaggugcuac cugaacguga ccaccgacaa caccagccug    480
gacgacuucc acgugaacgg cggcgagcug auccugaucc accagaaccc cggcgaguuc    540
ugcgugcug                                                           549

<210> SEQ ID NO 11
<211> LENGTH: 57
<212> TYPE: RNA
<213> ORGANISM: Artificial Sequence
<220> FEATURE:
<223> OTHER INFORMATION: Synthetic: 5' UTR

<400> SEQUENCE: 11
aggaaauaag agagaaaaga agaguaagaa gaaauauaag accccggcgc cgccacc       57

<210> SEQ ID NO 12
<211> LENGTH: 85
<212> TYPE: RNA
<213> ORGANISM: Artificial Sequence
<220> FEATURE:
<223> OTHER INFORMATION: Synthetic: miR-122

<400> SEQUENCE: 12
ccuuagcaga gcuguggagu gugacaaugg uguuuguguc uaaacuauca aacgccauua    60
ucacacuaaa uagcuacugc uaggc                                         85

<210> SEQ ID NO 13
<211> LENGTH: 22
<212> TYPE: RNA
<213> ORGANISM: Artificial Sequence
<220> FEATURE:
<223> OTHER INFORMATION: Synthetic: miR-122-3p

<400> SEQUENCE: 13
aacgccauua ucacacuaaa ua                                            22

<210> SEQ ID NO 14
```

-continued

```
<211> LENGTH: 22
<212> TYPE: RNA
<213> ORGANISM: Artificial Sequence
<220> FEATURE:
<223> OTHER INFORMATION: Synthetic: miR-122-3p binding site

<400> SEQUENCE: 14
uauuuagugu gauaauggcg uu                                              22

<210> SEQ ID NO 15
<211> LENGTH: 92
<212> TYPE: RNA
<213> ORGANISM: Artificial Sequence
<220> FEATURE:
<223> OTHER INFORMATION: Synthetic: 5' UTR

<400> SEQUENCE: 15
ucaagcuuuu ggacccucgu acagaagcua auacgacuca cuauagggaa auaagagaga     60
aaagaagagu aagaagaaau auaagagcca cc                                   92

<210> SEQ ID NO 16
<211> LENGTH: 47
<212> TYPE: RNA
<213> ORGANISM: Artificial Sequence
<220> FEATURE:
<223> OTHER INFORMATION: Synthetic: 5' UTR

<400> SEQUENCE: 16
gggaaauaag agagaaaaga agaguaagaa gaaauauaag agccacc                   47

<210> SEQ ID NO 17
<211> LENGTH: 141
<212> TYPE: RNA
<213> ORGANISM: Artificial Sequence
<220> FEATURE:
<223> OTHER INFORMATION: Synthetic: 3' UTR

<400> SEQUENCE: 17
ugauaauagg cuggagccuc gguggccaug cuucuugccc cuugggccuc ccccagccc      60 cuccucccu uccugcaccc guacccccca aacaccauug ucacaccca gugucuuug       120 aauaaagucu gagugggcgg c                                              141

<210> SEQ ID NO 18
<211> LENGTH: 164
<212> TYPE: RNA
<213> ORGANISM: Artificial Sequence
<220> FEATURE:
<223> OTHER INFORMATION: Synthetic: 3' UTR with mi-122 and mi-142.3p
      sites

<400> SEQUENCE: 18
ugauaauagg cuggagccuc gguggccaug cuucuugccc cuugggccca aacaccauug     60 ucacaccca uccccccagc cccuccuccc cuuccuccau aaaguaggaa acacuacaug    120
cacccguacc cccgugugucu uugaauaaag ucugagugggc ggc                    164

<210> SEQ ID NO 19
<211> LENGTH: 22
<212> TYPE: RNA
<213> ORGANISM: Artificial Sequence
<220> FEATURE:
<223> OTHER INFORMATION: Synthetic: miR-122-5p

<400> SEQUENCE: 19
```
uggaguguga caauggguguu ug                                                  22

<210> SEQ ID NO 20
<211> LENGTH: 22
<212> TYPE: RNA
<213> ORGANISM: Artificial Sequence
<220> FEATURE:
<223> OTHER INFORMATION: Synthetic: miR-122-5p binding site

<400> SEQUENCE: 20
caaacaccau ugucacacuc ca                                                   22

<210> SEQ ID NO 21
<211> LENGTH: 6
<212> TYPE: DNA
<213> ORGANISM: Artificial Sequence
<220> FEATURE:
<223> OTHER INFORMATION: Synthetic: Kozak Consensus
<220> FEATURE:
<221> NAME/KEY: misc_feature
<222> LOCATION: (4)..(4)
<223> OTHER INFORMATION: n = A or G

<400> SEQUENCE: 21 gccncc                                                                      6

<210> SEQ ID NO 22
<211> LENGTH: 141
<212> TYPE: RNA
<213> ORGANISM: Artificial Sequence
<220> FEATURE:
<223> OTHER INFORMATION: Synthetic: 3UTR with miR-122

<400> SEQUENCE: 22
ugauaauagg cuggagccuc gguggccuag cuucuugccc cuugggccuc ccccagccc           60 cuccuccccu uccugcaccc guacccccca aacaccauug ucacacucca guggucuuug          120
aauaaagucu gagugggcgg c                                                   141

<210> SEQ ID NO 23
<211> LENGTH: 12
<212> TYPE: RNA
<213> ORGANISM: Artificial Sequence
<220> FEATURE:
<223> OTHER INFORMATION: Synthetic: [CCG]4

<400> SEQUENCE: 23
ccgccgccgc cg                                                              12

<210> SEQ ID NO 24
<211> LENGTH: 15
<212> TYPE: RNA
<213> ORGANISM: Artificial Sequence
<220> FEATURE:
<223> OTHER INFORMATION: Synthetic: [CCG]5

<400> SEQUENCE: 24
ccgccgccgc cgccg                                                           15

<210> SEQ ID NO 25
<211> LENGTH: 10
<212> TYPE: RNA
<213> ORGANISM: Artificial Sequence
<220> FEATURE:
<223> OTHER INFORMATION: Synthetic: V1 GC-rich RNA element

<400> SEQUENCE: 25
ccccggcgcc                                                                10

<210> SEQ ID NO 26
<211> LENGTH: 7
<212> TYPE: RNA
<213> ORGANISM: Artificial Sequence
<220> FEATURE:
<223> OTHER INFORMATION: Synthetic: V2 GC-rich RNA element

<400> SEQUENCE: 26 ccccggc                                                                   7

<210> SEQ ID NO 27
<211> LENGTH: 6
<212> TYPE: RNA
<213> ORGANISM: Artificial Sequence
<220> FEATURE:
<223> OTHER INFORMATION: Synthetic: EK GC-rich RNA element

<400> SEQUENCE: 27 gccgcc                                                                    6

<210> SEQ ID NO 28
<211> LENGTH: 41
<212> TYPE: DNA
<213> ORGANISM: Artificial Sequence
<220> FEATURE:
<223> OTHER INFORMATION: Synthetic: 5' UTR

<400> SEQUENCE: 28
gggaaataag agagaaaaga agagtaagaa gaaatataag a                             41

<210> SEQ ID NO 29
<211> LENGTH: 57
<212> TYPE: DNA
<213> ORGANISM: Artificial Sequence
<220> FEATURE:
<223> OTHER INFORMATION: Synthetic: V1-5' UTR

<400> SEQUENCE: 29
gggaaataag agagaaaaga agagtaagaa gaaatataag accccggcgc cgccacc            57

<210> SEQ ID NO 30
<211> LENGTH: 54
<212> TYPE: DNA
<213> ORGANISM: Artificial Sequence
<220> FEATURE:
<223> OTHER INFORMATION: Synthetic: V2-5' UTR

<400> SEQUENCE: 30
gggaaataag agagaaaaga agagtaagaa gaaatataag accccggcgc cacc               54

<210> SEQ ID NO 31
<211> LENGTH: 47
<212> TYPE: DNA
<213> ORGANISM: Artificial Sequence
<220> FEATURE:
<223> OTHER INFORMATION: Synthetic: Standard UTR

<400> SEQUENCE: 31
gggaaataag agagaaaaga agagtaagaa gaaatataag agccacc                       47

<210> SEQ ID NO 32
<211> LENGTH: 505
<212> TYPE: PRT

```
<213> ORGANISM: Homo sapiens
<220> FEATURE:
<221> NAME/KEY: misc_feature
<222> LOCATION: (1)..(505)
<223> OTHER INFORMATION: Amino Acid sequence of human IL-23 (IL-12p40
      subunit and IL-23p19 subunit linked by GS Linker)

<400> SEQUENCE: 32
```

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Gly Ser Arg
                325                 330                 335

Ala Val Pro Gly Gly Ser Ser Pro Ala Trp Thr Gln Cys Gln Gln Leu
            340                 345                 350

Ser Gln Lys Leu Cys Thr Leu Ala Trp Ser Ala His Pro Leu Val Gly
        355                 360                 365

His Met Asp Leu Arg Glu Glu Gly Asp Glu Glu Thr Thr Asn Asp Val

```
        370                 375                 380
Pro His Ile Gln Cys Gly Asp Gly Cys Asp Pro Gln Gly Leu Arg Asp
385                 390                 395                 400

Asn Ser Gln Phe Cys Leu Gln Arg Ile His Gln Gly Leu Ile Phe Tyr
                405                 410                 415

Glu Lys Leu Leu Gly Ser Asp Ile Phe Thr Gly Glu Pro Ser Leu Leu
            420                 425                 430

Pro Asp Ser Pro Val Gly Gln Leu His Ala Ser Leu Leu Gly Leu Ser
        435                 440                 445

Gln Leu Leu Gln Pro Glu Gly His His Trp Glu Thr Gln Gln Ile Pro
    450                 455                 460

Ser Leu Ser Pro Ser Gln Pro Trp Gln Arg Leu Leu Leu Arg Phe Lys
465                 470                 475                 480

Ile Leu Arg Ser Leu Gln Ala Phe Val Ala Val Ala Ala Arg Val Phe
                485                 490                 495

Ala His Gly Ala Ala Thr Leu Ser Pro
            500                 505

<210> SEQ ID NO 33
<211> LENGTH: 1515
<212> TYPE: RNA
<213> ORGANISM: Homo sapiens
<220> FEATURE:
<221> NAME/KEY: misc_feature
<222> LOCATION: (1)..(1515)
<223> OTHER INFORMATION: Nucleotide sequence (ORF) of human IL-23
      (IL-12p40 subunit and IL-23p19 subunit linked by GS Linker)

<400> SEQUENCE: 33
augugucacc agcaguuggu caucucuugg uuuucccugg uauuucggc aucuccccuc      60 guggccauau gggaacugaa gaaagauguu uaugucguag aauuggauug guauccggau    120
gccccuggag aaaugguggu ccucaccugu gacaccccug aagaagaugg uaucaccugg    180
accuuggacc agagcaguga ggucuuaggc ucuggcaaga cccugaccau ccaagucaaa    240
gaguuuggag augcuggcca guacaccugu cacaaaggag gcgagguucu aagccauucg    300
cuccugcugc uucacaagaa ggaagaugga auuuggucca cugauauuuu aaaggaccag    360
aaagaacccc agaauaagac cuuucuaaga ugcgaggcca agaauuauuc uggacguuuc    420
accugcuggu ggcugacgac aaucaguacu gauuugacau ucagucaa gagcagcaga    480 ggcucuucug accccaagg ggugacgugc ggagcugcua cacucucugc agagagaguc    540
agaggggaca caaggaguga ugaguacuca guggagugcc aggaggacag ugccugccca    600
gcugcugagg agagucugcc cauugagguc augguggaug ccguucacaa gcucaaguau    660
gagaacuaca ccagcagcuu cuucaucagg gacaucauca accugaccc acccaagaac    720 uugcagcuga agccauuaaa gaauucucgg caggugggagg ucagcugggga uacccugac    780 accuggagua cuccacauuc cuacuucucc cugacauucu cguucaggu ccagggcaag    840 agcaagagag agaagaaaga uagagucuuc acggacaaga ccucagccac ggucaucugc    900
cgcaagaaug ccagcauuag cgugcgggcc caggaccgcu acuauagcuc aucuuggagc    960
gaaugggcau cugugcccug cagugg cgga ggggcggag ggagcagagc ugugccuggg    1020
ggcagcagcc cugccuggac ucagugccag cagcuuucac agaagcucug cacacuggcc    1080
uggagugcac auccacuagu gggacacaug gaucuaagag aagagggaga ugaagagacu    1140
acaaaugaug uuccccauau ccaguguggga gauggcugug accccaagg acucagggac    1200
```

| | |
|---|---|
| aacagucagu ucugcuugca aaggauccac cagggucuga ucuuuuauga gaagcugcua | 1260 |
| ggaucggaua uuuucacagg ggagccuucu cugcucccug auagcccugu gggccagcuu | 1320 |
| caugccuccc uacugggccu cagccaacuc cugcagccug agggucacca cugggagacu | 1380 |
| cagcagauuc caagccucag ucccagccag ccauggcagc gucuccuucu ccgcuucaag | 1440 |
| auccuucgca gccuccaggc cuuuguggcu guagccgccc ggucuuugc ccauggagca | 1500 |
| gcaacccuga guccc | 1515 |

<210> SEQ ID NO 34
<211> LENGTH: 1807
<212> TYPE: RNA
<213> ORGANISM: Homo sapiens
<220> FEATURE:
<221> NAME/KEY: misc_feature
<223> OTHER INFORMATION: 5'7MeGpppG2'Ome, OH3'
<220> FEATURE:
<221> NAME/KEY: misc_feature
<222> LOCATION: (1)..(1807)
<223> OTHER INFORMATION: A,C G & U = AMP, CMP, GMP & N1-Psi-UMP,
      respectively; Me = methyl; p = inorganic phosphate
<220> FEATURE:
<221> NAME/KEY: misc_feature
<222> LOCATION: (1)..(1807)
<223> OTHER INFORMATION: Full-length mRNA Nucleotide sequence (5' UTR,
      ORF, 3' UTR, mir-122-5p polyA tail) of human IL-23 (IL-12p40
      subunit and IL-23p19 subunit linked by GS Linker)

<400> SEQUENCE: 34

| | |
|---|---|
| ggaaauaaga gagaaaagaa gaguaagaag aaauauaaga gccaccaugu gucaccagca | 60 |
| guuggucauc ucuugguuuu cccugguauu ucuggcaucu cccucgugg ccauauggga | 120 |
| acugaagaaa gauguuuaug ucguagaauu ggauggguau ccggaugccc cuggagaaau | 180 |
| gguggucccuc accgugaca ccccugaaga agauggauauc accggaccu uggaccagag | 240 |
| cagugaggug uuaggcucug gcaagacccu gaccauccaa gucaaagagu uggagaugc | 300 |
| uggccaguac accgugcaca aaggaggcga gguucuaagc cauucgcucc ugcugcuuca | 360 |
| caagaaggaa gauggaauuu ggccacuga uauuuuaaag gaccagaaag aacccaagaa | 420 |
| uaagaccuuu cuaagaugcg aggccaagaa uuauucgga cguuucaccu gcugguggcu | 480 |
| gacgacaauc aguacugauu ugacauucag ugucaagagc agcagaggcu cuucugaccc | 540 |
| ccaagggugu acgugcggag cugcuacacu cucugcagag agagucagag gggacaacaa | 600 |
| ggaguaugag uacucagugg agugccagga ggacagugcc ugcccagcug cugaggagag | 660 |
| ucugcccauu gaggucaugg uggaugccgu ucacaagcuc aaguaugaga acuacaccag | 720 |
| cagcuucuuc aucagggaca ucaucaaacc ugacccaccc aagaacuugc agcugaagcc | 780 |
| auuaaagaau ucucggcagg uggaggucag cuggagauac ccugacaccu ggaguacucc | 840 |
| acauuccuac uucucccuga cauucugcgu ucagguccag gcaagagca agagagagaa | 900 |
| gaaagauaga gucuuacgg acaagaccuc agccacgguc aucuccgcca gaaugccag | 960 |
| cauuagcgug cgggcccagg accgcuacua uagcucaucu uggagcgaau gggcaucugu | 1020 |
| gcccugcagu ggcggagggg gcggagggag cagagcugug ccuggggca gcagcccugc | 1080 |
| cuggacucag ugccagcagc uuucacagaa gcucugcaca cuggccugga gugcacaucc | 1140 |
| acuaguggga cacauggauc uaagagaaga gggagaugaa gagacuacaa augauguucc | 1200 |
| ccauauccag ugguggagaug gcugugaccc caaggacuc aggacaaca gucaguucug | 1260 |
| cuugcaaagg auccaccagg gucugaucuu uuaugagaau cugcuaggau cggauauuuu | 1320 |
| cacaggggag ccuucucugc ucccugauag cccugugggc cagcuucaug ccucccuacu | 1380 |

```
gggccucagc caacuccugc agccugaggg ucaccacugg gagacucagc agauuccaag    1440
ccucaguccc agccagccau ggcagcgucu ccuucccgc uucaagaucc uucgcagccu    1500
ccaggccuuu guggcuguag ccgcccgggu cuuugcccau ggagcagcaa cccugaqucc    1560 cugauaauag gcuggagccu cgguggccau gcucuugcc ccuugggccu cccccagcc    1620 ccuccucccc uuccugcacc cguaccccc aaacaccauu gucacaccc aguggucuuu    1680 gaauaaaguc ugagugggcg gcaaaaaaaa aaaaaaaaa aaaaaaaaa aaaaaaaaa     1740 aaaaaaaaaa aaaaaaaaaa aaaaaaaaaa aaaaaaaaaa aaaaaaaaaa aaaaaaaaaa   1800
aaucuag                                                               1807
```

<210> SEQ ID NO 35
<211> LENGTH: 172
<212> TYPE: PRT
<213> ORGANISM: Artificial Sequence
<220> FEATURE:
<223> OTHER INFORMATION: Synthetic: hIGKV4-hIL-36gamma construct
      (protein)

<400> SEQUENCE: 35

```
Met Val Leu Gln Thr Gln Val Phe Ile Ser Leu Leu Trp Ile Ser
1               5                   10                  15

Gly Ala Tyr Gly Ser Met Cys Lys Pro Ile Thr Gly Thr Ile Asn Asp
            20                  25                  30

Leu Asn Gln Gln Val Trp Thr Leu Gln Gly Gln Asn Leu Val Ala Val
        35                  40                  45

Pro Arg Ser Asp Ser Val Thr Pro Val Thr Val Ala Val Ile Thr Cys
    50                  55                  60

Lys Tyr Pro Glu Ala Leu Glu Gln Gly Arg Gly Asp Pro Ile Tyr Leu
65                  70                  75                  80

Gly Ile Gln Asn Pro Glu Met Cys Leu Tyr Cys Glu Lys Val Gly Glu
                85                  90                  95

Gln Pro Thr Leu Gln Leu Lys Glu Gln Lys Ile Met Asp Leu Tyr Gly
            100                 105                 110

Gln Pro Glu Pro Val Lys Pro Phe Leu Phe Tyr Arg Ala Lys Thr Gly
        115                 120                 125

Arg Thr Ser Thr Leu Glu Ser Val Ala Phe Pro Asp Trp Phe Ile Ala
    130                 135                 140

Ser Ser Lys Arg Asp Gln Pro Ile Ile Leu Thr Ser Glu Leu Gly Lys
145                 150                 155                 160

Ser Tyr Asn Thr Ala Phe Glu Leu Asn Ile Asn Asp
                165                 170
```

<210> SEQ ID NO 36
<211> LENGTH: 516
<212> TYPE: RNA
<213> ORGANISM: Homo sapiens
<220> FEATURE:
<221> NAME/KEY: misc_feature
<222> LOCATION: (1)..(516)
<223> OTHER INFORMATION: Human IL-36 gamma mRNA (ORF)

<400> SEQUENCE: 36

```
augguguugc agacccaggu cuucauuucu cuguugcucu ggaucucugg ugccuacggg     60
ucaaugugua aaccuauuac ugggacuauu augauuuga aucagcaagu guggacccuu    120
cagggucaga accuuguggc aguuccacga agugacagu ugaccccagu cacuguugcu    180
```

```
guuaucacau gcaaguaucc agaggcucuu gagcaaggca gaggggaucc cauuuauuug      240
ggaauccaga auccagaaau guguuuguau ugugagaagg uuggagaaca gcccacauug      300
cagcuaaaag agcagaagau cauggaucug uauggccaac ccgagcccgu gaaacccuuc      360
cuuuucuacc gugccaagac ugguaggacc uccacccuug agucuguggc cuucccggac      420
ugguucauug ccuccuccaa gagagaccag cccaucauuc ugacuucaga acuugggaag      480
ucauacaaca cugccuuuga auuaaauaua aaugac                               516

<210> SEQ ID NO 37
<211> LENGTH: 808
<212> TYPE: RNA
<213> ORGANISM: Homo sapiens
<220> FEATURE:
<221> NAME/KEY: misc_feature
<223> OTHER INFORMATION: 5'7MeGpppG2'Ome, OH3'
<220> FEATURE:
<221> NAME/KEY: misc_feature
<222> LOCATION: (1)..(808)
<223> OTHER INFORMATION: A,C G & U = AMP, CMP, GMP & N1-Psi-UMP,
      respectively; Me = methyl; p = inorganic phosphate
<220> FEATURE:
<221> NAME/KEY: misc_feature
<222> LOCATION: (1)..(808)
<223> OTHER INFORMATION: Full-length mRNA Nucleotide sequence (5' UTR,
      ORF, 3' UTR, mir-122-5p polyA tail) of human IL-36-gamma

<400> SEQUENCE: 37
ggaaauaaga gagaaaagaa gaguaagaag aaauauaaga gccaccaugg uguugcagac       60
ccaggucuuc auuucucugu ugcucuggau cucuggugcc uacgggucaa uguguaaacc      120
uauuacuggg acuauuaaug auuugaauca gcaagugugg acccuucagg gucagaaccu      180
uguggcaguu ccacgaagug acagugugac cccagucacu guugcuguua ucacaugcaa      240
guauccagag gcucuugagc aaggcagagg ggaucccauu uauuugggaa uccagaaucc      300
agaaaugugu uuguauugug agaagguugg agaacagccc acauugcagc uaaaagagca      360
gaagaucaug gaucuguaug gccaacccga gcccgugaaa cccuuccuuu ucuaccgugc      420
caagacuggu aggaccucca cccuugaguc uguggccuuc ccggacuggu cauugccuc      480 cuccaagaga gaccagccca ucauucgac uucagaacuu gggaagucau acaacacugc      540
cuuugaauua aauauaaaug acugauaaua ggcuggagcc ucgguggcca ugcuucuugc      600 cccugggcc uccccccagc cccuccuccc cuuccugcac ccguacccc caaacaccau      660 ugucacacuc cagggucuuu ugaauaaagu cugaguggc ggcaaaaaaa aaaaaaaaa      720 aaaaaaaaa aaaaaaaaa aaaaaaaaa aaaaaaaaa aaaaaaaaa aaaaaaaaa      780 aaaaaaaaa aaaaaaaaa aaaucuag                                         808
```

USE OF mRNAs ENCODING OX40L, IL-23 AND IL-36GAMMA IN COMBINATION WITH IMMUNE CHECKPOINT BLOCKADE FOR TREATING PARTICULAR CANCERS

CROSS-REFERENCE TO RELATED APPLICATIONS

This application claims the benefit of U.S. Provisional Application Ser. No. 62/789,972, filed on Jan. 8, 2019. The entire contents of the above-referenced provisional patent application is incorporated herein by reference.

SEQUENCE LISTING

The application contains a Sequence Listing which has been submitted electronically in ASCII format and is hereby incorporated by reference in its entirety. Said ASCII copy, created on Jun. 22, 2020, is named 2020.06.22 MDN-824_ST25 MDN-824 and is 35,293 bytes in size.

BACKGROUND

Cancer is a disease characterized by uncontrolled cell division and growth within the body. In the United States, roughly a third of all women and half of all men will experience cancer in their lifetime. Cancer cells utilize a number of mechanisms to evade the immune system, which results in persistence of tumor cells. Much research has focused on methods of stimulating the immune system to allow it to recognize and attack tumor cells. One area of intense research is the use of immune checkpoint blockade (CTLA-4, PD-1, and PD-L1) to turn on immune responses to tumor cells.

The tumor necrosis factor receptor superfamily also contains molecules which may be useful as immunomodulators. For example, several anti-OX40 antibodies have been tested in the clinic for their ability to treat cancer. However, it is often difficult to reconcile in vitro and in vivo data in this area of research. Further data from human patients is required to determine what immunomodulatory therapies or combinations thereof work best for what types of cancers; and what therapeutic modalities—protein therapy, gene therapy, mRNA therapy, or combinations thereof, are most effective.

SUMMARY OF DISCLOSURE

The present disclosure is based, at least in part, on the discovery that messenger RNAs (mRNAs) encoding human OX40 ligand (OX40L), human IL-23 and human IL-36γ administered by intratumoral injection (ITu) to solid tumor malignancies or lymphoma resulted in a significant reduction in tumor size or complete resolution of a tumor at a treated or uninjected tumor. Significantly, a local regional abscopal effect was observed for proximal, uninjected tumors within the vicinity of the injection site. Without being bound by theory, it is believed that the induction of OX40L, IL-23 and IL-36γ expression by tumor cells and/or cells presenting tumor antigens following administration of mRNAs encoding human OX40L, IL-23 and IL-36γ induces a specific cell-mediated immune response with systemic anti-tumor effects, resulting in a reduction in tumor size of both treated and untreated tumors.

Systemic administration of checkpoint-inhibitor (CPI) antibodies such as T-cell co-inhibitor pathways of PD-1/PD-L1 and CTLA-4 has resulted in survival improvements in metastatic diseases with unmet medical need. Although these approaches have yielded responses in a variety of indications, there are a significant number of cancer patients whose tumors are resistant to CPIs. Combination therapies with systematically administered CPIs, although demonstrated improvements in patient responses, also displayed increased on-target anti-normal tissue toxicities. Thus, there still exists an unmet need for safe and effective cancer therapies.

Without being bound by theory, local administration of ITu immune-mediated therapies for cancer, such as mRNAs encoding human OX40L, IL-23 and IL-36γ, results in systemic immune recognition of tumoral antigens, which as monotherapy cause regression of multiple metastatic lesions. As such, the mRNA therapeutic agents can improve outcomes from systemically delivered antibodies, such as CPIs, and have an improved tolerability profile compared to systemic therapy alone.

Accordingly, in some aspects the disclosure provides a method for treating solid tumor malignancies or lymphomas in a human patient by inducing or enhancing an anti-tumor immune response, comprising administering to the patient by intratumoral injection an effective amount of a pharmaceutical composition comprising: a lipid nanoparticle (LNP) comprising mRNAs encoding human OX40L, IL-23 and IL-36γ polypeptides; and a pharmaceutically acceptable carrier, thereby treating solid tumors or lymphomas in the patient by inducing or enhancing an anti-tumor immune response. Without being bound by theory, ITu delivery of LNP encapsulated mRNAs encoding human OX40L, IL-23 and IL-36γ polypeptides, which have distinct functions yet work synergistically to mediate anti-cancer responses either as a monotherapy or in combination with CPI antibodies (anti-PD-L1 and anti-CTLA-4).

The present disclosure provides methods for treating advanced or metastatic solid tumor malignancy or lymphoma in a human patient by inducing or enhancing an anti-tumor immune response, comprising administering to the patient by intratumoral injection an effective amount of a lipid nanoparticle (LNP) encapsulated messenger RNA (mRNA) therapeutic agent comprising three mRNA drug substances:
  (i) a first mRNA comprising an open reading frame (ORF) encoding a human OX40L polypeptide;
  (ii) a second mRNA comprising an ORF encoding a human IL-23 polypeptide; and
  (iii) a third mRNA comprising an ORF encoding a human IL-36γ polypeptide,
  wherein the patient is administered a dose of 0.10-10.0 mg of the mRNA therapeutic agent in a dosing regimen from 7 to 28 days, thereby treating the advanced or metastatic solid tumor malignancy or lymphoma in the patient by inducing or enhancing an anti-tumor immune response.

In some aspects of the methods of the present disclosure, the patient is administered a dose of the mRNA therapeutic agent selected from: 0.25-8.0 mg; 0.25-4.0 mg; 0.25-2.0 mg; 0.25-1.0 mg; 0.25-5 mg; 0.5-8.0 mg; 0.5-4.0 mg; 0.5-2.0 mg; 0.5-1.0 mg; 1.0-8.0 mg; 1.0-4.0 mg; 1.0-2.0 mg; 2.0-8.0 mg; 2.0-4.0 mg; and 4.0-8.0 mg. In some aspects, the patient is administered a dose of 0.10 mg of the mRNA therapeutic agent. In some aspects, the patient is administered a dose of 0.25 mg of the mRNA therapeutic agent. In some aspects, the patient is administered a dose of 0.50 mg of the mRNA therapeutic agent. In some aspects, the patient is administered a dose of 1.0 mg of the mRNA therapeutic agent. In some aspects, the patient is administered a dose of 2.0 mg of the mRNA therapeutic agent. In some aspects, the patient is administered a dose of 4.0 mg of the mRNA therapeutic agent. In some aspects, the patient is administered a dose of 8.0 mg of the mRNA therapeutic agent. In some aspects, the patient is administered a dose of 10.0 mg of the mRNA therapeutic agent.

In any of the foregoing or related aspects of the methods of the present disclosure, the mRNA therapeutic agent is administered to the patient in a dosing regimen selected from 7 to 21 days, 7 to 14 days, 28 days, 21 days, 14 days, and 7 days. In some aspects, the patient is administered a dose of the mRNA therapeutic agent every 2 weeks. In some aspects, the patient is administered a dose of the mRNA therapeutic agent every 3 weeks. In some aspects, the patient is administered a dose of the mRNA therapeutic agent every 4 weeks.

In some aspects, the disclosure provides a method for treating advanced or metastatic solid tumor malignancy or lymphoma in a human patient by inducing or enhancing an anti-tumor immune response, comprising administering to the patient by intratumoral injection an effective amount of an LNP encapsulated mRNA therapeutic agent comprising three mRNA drug substances:
(i) a first mRNA comprising an ORF encoding a human OX40L polypeptide;
(ii) a second mRNA comprising an ORF encoding a human IL-23 polypeptide; and
(iii) a third mRNA comprising an ORF encoding a human IL-36γ polypeptide,
wherein the patient is administered a dose of the mRNA therapeutic agent selected from 0.25 mg, 0.5 mg, 1 mg, 2 mg, 4 mg, and 8 mg, thereby treating the advanced or metastatic solid tumor malignancy or lymphoma in the patient by inducing or enhancing an anti-tumor immune response. In some aspects, the patient is administered a dose of 0.25 mg of the mRNA therapeutic agent. In some aspects, the patient is administered a dose of 0.50 mg of the mRNA therapeutic agent. In some aspects, the patient is administered a dose of 1.0 mg of the mRNA therapeutic agent. In some aspects, the patient is administered a dose of 2.0 mg of the mRNA therapeutic agent. In some aspects, the patient is administered a dose of 4.0 mg of the mRNA therapeutic agent. In some aspects, the patient is administered a dose of 8.0 mg of the mRNA therapeutic agent.

In any of the foregoing or related aspects of the methods of the present disclosure, the patient is administered a dose of the mRNA therapeutic agent every 2 weeks. In some aspects, the patient is administered a dose of the mRNA therapeutic agent every 3 weeks. In some aspects, the patient is administered a dose of the mRNA therapeutic agent every 4 weeks.

In any of the foregoing or related aspects of the methods of the present disclosure, the patient is administered a second composition comprising an effective amount of a PD-1 antagonist, a PD-L1 antagonist or a CTLA-4 antagonist. In some aspects, the PD-1 antagonist is an antibody or antigen binding portion thereof that specifically binds to PD-1. In some aspects, the PD-1 antagonist is selected from the group consisting of nivolumab, pembrolizumab, and pidilizumab. In some aspects, the PD-L1 antagonist is an antibody or antigen binding portion thereof that specifically binds to PD-L1. In some aspects, the PD-L1 antagonist is selected from the group consisting of durvalumab, avelumab, and atezolizumab. In some aspects, the PD-L1 antagonist is durvalumab. In some aspects, the CTLA-4 antagonist is an antibody or antigen binding portion thereof that specifically binds to CTLA-4. In some aspects, the CTLA-4 antagonist is selected from the group consisting of ipilimumab and tremelimumab. In some aspects, the CTLA-4 antagonist is tremelimumab.

In any of the foregoing or related aspects of the methods of the present disclosure, the patient is administered a dose of an effective amount of a PD-1 antagonist, a PD-L1 antagonist or a CTLA-4 antagonist every 4 weeks. In some aspects, the patient is administered a dose of the mRNA therapeutic agent prior to administration of the PD-1 antagonist, PD-L1 antagonist or CTLA4 antagonist. In some aspects, the patient is administered a dose of the PD-1 antagonist, PD-L1 antagonist or CTLA4 antagonist prior to administration of the mRNA therapeutic agent. In some aspects, the patient is administered a dose of the mRNA therapeutic agent simultaneously with administration of a dose of the PD-1 antagonist, PD-L1 antagonist or CTLA4 antagonist.

In any of the foregoing or related aspects of the methods of the present disclosure, the advanced or metastatic solid tumor malignancy in the patient is selected from triple negative breast cancer, head and neck squamous cell carcinoma, and melanoma and the lymphoma is Non-Hodgkin lymphoma.

In some aspects, the disclosure provides a method for treating triple negative breast cancer (TNBC) in a human patient, comprising administering to the patient:
(a) an effective amount of an LNP encapsulated mRNA therapeutic agent comprising three mRNA drug substances:
(i) a first mRNA comprising an ORF encoding a human OX40L polypeptide;
(ii) a second mRNA comprising an ORF encoding a human IL-23 polypeptide; and
(iii) a third mRNA comprising an ORF encoding a human IL-36γ polypeptide;
and
(b) an effective amount of PD-L1 antagonist selected from the group consisting of durvalumab, avelumab, and atezolizumab,
thereby treating the TNBC in the patient.

In some aspects, the disclosure provides a method for treating head and neck squamous cell carcinoma (HNSCC) in a human patient, comprising administering to the patient:
(a) an effective amount of an LNP encapsulated mRNA therapeutic agent comprising three mRNA drug substances:
(i) a first mRNA comprising an ORF encoding a human OX40L polypeptide;
(ii) a second mRNA comprising an ORF encoding a human IL-23 polypeptide; and
(iii) a third mRNA comprising an ORF encoding a human IL-36γ polypeptide;
and
(b) an effective amount of PD-L1 antagonist selected from the group consisting of durvalumab, avelumab, and atezolizumab,
thereby treating the HNSCC in the patient.

In some aspects, the disclosure provides a method for treating Non-Hodgkin lymphoma (NHL) in a human patient, comprising administering to the patient:
(a) an effective amount of an LNP encapsulated mRNA therapeutic agent comprising three mRNA drug substances:
(i) a first mRNA comprising an ORF encoding a human OX40L polypeptide;

(ii) a second mRNA comprising an ORF encoding a human IL-23 polypeptide; and
(iii) a third mRNA comprising an ORF encoding a human IL-36γ polypeptide;
and
(b) an effective amount of PD-L1 antagonist selected from the group consisting of durvalumab, avelumab, and atezolizumab,
thereby treating the NHL in the patient.

In some aspects, the disclosure provides a method for treating melanoma in a human patient, comprising administering to the patient:
(a) an effective amount of an LNP encapsulated mRNA therapeutic agent comprising three mRNA drug substances:
(i) a first mRNA comprising an ORF encoding a human OX40L polypeptide;
(ii) a second mRNA comprising an ORF encoding a human IL-23 polypeptide; and
(iii) a third mRNA comprising an ORF encoding a human IL-36γ polypeptide;
and
(b) an effective amount of CTLA-4 antagonist selected from the group consisting of selected from the group consisting of ipilimumab and tremelimumab,
thereby treating the melanoma in the patient.

In any of the foregoing or related aspects of the methods of the present disclosure, the mRNA therapeutic agent is administered to the patient by intratumoral injection.

In any of the foregoing or related aspects of the methods of the present disclosure, the PD-L1 antagonist or CTLA-4 antagonist is administered to the patient by intravenous injection.

In any of the foregoing or related aspects of the methods of the present disclosure, the PD-L1 antagonist is durvalumab. In some aspects, the patient is administered a dose of durvalumab of 1500 mg.

In any of the foregoing or related aspects of the methods of the present disclosure, the CTLA-4 antagonist is tremelimumab. In some aspects, the patient is administered a dose of tremelimumab of 225 mg.

In any of the foregoing or related aspects of the methods of the present disclosure, the patient is administered a dose of the mRNA therapeutic agent selected from 0.25 mg, 0.5 mg, 1 mg, 2 mg, 4 mg, and 8 mg.

In any of the foregoing or related aspects of the methods of the present disclosure, the patient is administered a dose of the mRNA therapeutic agent every 4 weeks.

In any of the foregoing or related aspects of the methods of the present disclosure, the patient is administered a dose of the PD-L1 antagonist or CTLA-4 antagonist every 4 weeks.

In any of the foregoing or related aspects of the methods of the present disclosure, the mRNA therapeutic agent and the PD-L1 antagonist or the CTLA-4 antagonist are administered to the patient in a dosing regimen selected from 7 to 28 days, 7 to 21 days, 7 to 14 days, 28 days, 21 days, 14 days, and 7 days.

In any of the foregoing or related aspects of the methods of the present disclosure, the mRNA therapeutic agent and the PD-L1 antagonist or the CTLA-4 antagonist are administered to the patient in a dosing regimen of 28 days.

In any of the foregoing or related aspects of the methods of the present disclosure, the patient is administered a dose of the mRNA therapeutic agent prior to administration of the PD-L1 antagonist or the CTLA-4 antagonist.

In any of the foregoing or related aspects of the methods of the present disclosure, the human OX40L polypeptide comprises the amino acid sequence as set forth in SEQ ID NO: 1; the human IL-23 polypeptide comprises the amino acid sequence as set forth in SEQ ID NO: 32; and the human IL-36γ polypeptide comprises the amino acid sequence as set forth in SEQ ID NO: 35.

In any of the foregoing or related aspects of the methods of the present disclosure, the LNP encapsulated mRNA therapeutic agent comprises three mRNA drug substances, wherein
(i) the first mRNA encoding a human OX40L polypeptide comprises an ORF comprising a nucleotide sequence at least 80% identical to the nucleotide sequence set forth in SEQ ID NO: 4 or comprises the nucleotide sequence set forth in SEQ ID NO: 4;
(ii) the second mRNA encoding a human IL-23 polypeptide comprises an ORF comprising a nucleotide sequence at least 80% identical to the nucleotide sequence set forth in SEQ ID NO: 33 or comprises the nucleotide sequence set forth in SEQ ID NO: 33; and
(iii) the third mRNA encoding a human IL-36γ polypeptide comprises an ORF comprising a nucleotide sequence at least 80% identical to the nucleotide sequence set forth in SEQ ID NO: 36 or comprises the nucleotide sequence set forth in SEQ ID NO: 36.

In any of the foregoing or related aspects of the methods of the present disclosure, each of the first mRNA, second mRNA, and third mRNA comprise a 3' untranslated region (UTR) comprising at least one microRNA-122 (miR-122) binding site. In some aspects, the miR-122 binding site is a miR-122-3p binding site or a miR-122-5p binding site. In some aspects, the miR-122-5p binding site comprises the nucleotide sequence set forth in SEQ ID NO: 20. In some aspects, the 3'UTR comprises a nucleotide sequence at least 90% identical to the sequence set forth in SEQ ID NO: 17 or comprises the nucleotide sequence as set forth in SEQ ID NO: 17. In some aspects, each of the first, second, and third mRNAs comprise a 5'cap, a 5' untranslated region (UTR), and a poly-A tail of about 100 nucleotides in length. In some aspects, the 5'UTR comprises a nucleotide sequence at least 90% identical to the sequence set forth in SEQ ID NO: 15 or comprises the nucleotide sequence as set forth in SEQ ID NO: 15. In some aspects, the 5'UTR comprises a nucleotide sequence at least 90% identical to the sequence set forth in SEQ ID NO: 16 or comprises the nucleotide sequence as set forth in SEQ ID NO: 16.

In any of the foregoing or related aspects of the methods of the present disclosure, the LNP encapsulated mRNA therapeutic agent comprises three mRNA drug substances, wherein
(i) the first mRNA encoding the human OX40L polypeptide comprises a nucleotide sequence at least 90% identical to the nucleotide sequence set forth in SEQ ID NO: 5 or comprises the nucleotide sequence set forth in SEQ ID NO: 5;
(ii) the second mRNA encoding a human IL-23 polypeptide comprises a nucleotide sequence at least 90% identical to the nucleotide sequence set forth in SEQ ID NO: 34 or comprises the nucleotide sequence set forth in SEQ ID NO: 34; and
(iii) the third mRNA encoding a human IL-36γ polypeptide comprises a nucleotide sequence at least 90% identical to the nucleotide sequence set forth in SEQ ID NO: 37 or comprises the nucleotide sequence set forth in SEQ ID NO: 37.

In some aspects, the disclosure provides a method for treating advanced or metastatic solid tumor malignancy or lymphoma in a human patient by inducing or enhancing an anti-tumor immune response, comprising administering to the patient by intratumoral injection an effective amount of an LNP encapsulated mRNA therapeutic agent comprising three mRNA drug substances:

(i) a first mRNA encoding a human OX40L polypeptide comprising an ORF comprising a nucleotide sequence at least 80% identical to the nucleotide sequence set forth in SEQ ID NO: 4 or comprises the nucleotide sequence set forth in SEQ ID NO: 4;

(ii) a second mRNA encoding a human IL-23 polypeptide comprising an ORF comprising a nucleotide sequence at least 80% identical to the nucleotide sequence set forth in SEQ ID NO: 33 or comprises the nucleotide sequence set forth in SEQ ID NO: 33; and (iii) a third mRNA encoding a human IL-36γ polypeptide comprising an ORF comprising a nucleotide sequence at least 80% identical to the nucleotide sequence set forth in SEQ ID NO: 36 or comprises the nucleotide sequence set forth in SEQ ID NO: 36, wherein the patient is administered a dose of the mRNA therapeutic agent selected from 0.25 mg, 0.5 mg, 1 mg, 2 mg, 4 mg, and 8 mg, thereby treating the advanced or metastatic solid tumor malignancy or lymphoma in the patient by inducing or enhancing an anti-tumor immune response. In some aspects, the patient is administered a dose of 0.25 mg of the mRNA therapeutic agent. In some aspects, the patient is administered a dose of 0.50 mg of the mRNA therapeutic agent. In some aspects, the patient is administered a dose of 1.0 mg of the mRNA therapeutic agent. In some aspects, the patient is administered a dose of 2.0 mg of the mRNA therapeutic agent. In some aspects, the patient is administered a dose of 4.0 mg of the mRNA therapeutic agent. In some aspects, the patient is administered a dose of 8.0 mg of the mRNA therapeutic agent. In some aspects, the patient is administered a dose of the mRNA therapeutic agent every 2 weeks. In some aspects, the patient is administered a dose of the mRNA therapeutic agent every 3 weeks. In some aspects, the patient is administered a dose of the mRNA therapeutic agent every 4 weeks.

In some aspects, the disclosure provides a method for treating advanced or metastatic solid tumor malignancy or lymphoma in a human patient by inducing or enhancing an anti-tumor immune response, comprising administering to the patient by intratumoral injection an effective amount of an LNP encapsulated mRNA therapeutic agent comprising three mRNA drug substances:

(i) a first mRNA encoding the human OX40L polypeptide comprising a nucleotide sequence at least 90% identical to the nucleotide sequence set forth in SEQ ID NO: 5 or comprising the nucleotide sequence set forth in SEQ ID NO: 5;

(ii) a second mRNA encoding a human IL-23 polypeptide comprising a nucleotide sequence at least 90% identical to the nucleotide sequence set forth in SEQ ID NO: 34 or comprising the nucleotide sequence set forth in SEQ ID NO: 34; and (iii) a third mRNA encoding a human IL-36γ polypeptide comprising a nucleotide sequence at least 90% identical to the nucleotide sequence set forth in SEQ ID NO: 37 or comprising the nucleotide sequence set forth in SEQ ID NO: 37, wherein the patient is administered a dose of the mRNA therapeutic agent selected from 0.25 mg, 0.5 mg, 1 mg, 2 mg, 4 mg, and 8 mg, thereby treating the advanced or metastatic solid tumor malignancy or lymphoma in the patient by inducing or enhancing an anti-tumor immune response. In some aspects, the patient is administered a dose of 0.25 mg of the mRNA therapeutic agent. In some aspects, the patient is administered a dose of 0.50 mg of the mRNA therapeutic agent. In some aspects, the patient is administered a dose of 1.0 mg of the mRNA therapeutic agent. In some aspects, the patient is administered a dose of 2.0 mg of the mRNA therapeutic agent. In some aspects, the patient is administered a dose of 4.0 mg of the mRNA therapeutic agent. In some aspects, the patient is administered a dose of 8.0 mg of the mRNA therapeutic agent. In some aspects, the patient is administered a dose of the mRNA therapeutic agent every 2 weeks. In some aspects, the patient is administered a dose of the mRNA therapeutic agent every 3 weeks. In some aspects, the patient is administered a dose of the mRNA therapeutic agent every 4 weeks.

In any of the foregoing or related aspects of the methods of the present disclosure, the LNP encapsulated mRNA therapeutic agent comprises three mRNA drug substances, wherein the first, second, and third mRNAs are formulated in the lipid nanoparticle at a mass ratio of OX40L:IL-23:IL-36γ of 1:1:2.

In any of the foregoing or related aspects of the methods of the present disclosure, the LNP encapsulated mRNA therapeutic agent comprises three mRNA drug substances, wherein each of the first, second and third mRNAs is chemically modified.

In any of the foregoing or related aspects of the methods of the present disclosure, the LNP encapsulated mRNA therapeutic agent comprises three mRNA drug substances, wherein each of the first, second, and third mRNAs is fully modified with chemically-modified uridines. In some aspects, the chemically-modified uridines are N1-methylpseudouridines (m1ψ). In some aspects, each of the first, second and third mRNAs is fully modified with 5-methylcytosine or is fully modified with N1-methylpseudouridines (m1ψ) and 5-methylcytosine.

In any of the foregoing or related aspects of the methods of the present disclosure, the LNP encapsulated mRNA therapeutic agent comprises three mRNA drug substances, wherein the LNP comprises a compound having the formula:

(Compound II)

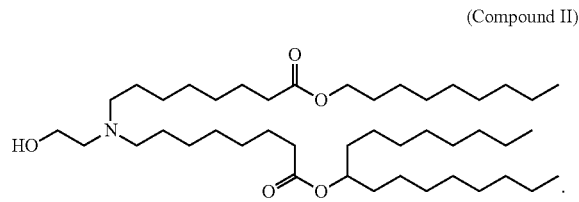 [SMILES: CCCCCCCCCOC(=O)CCCCCCCN(CCO)CCCCCCCC(=O)OC(CCCCCCCC)CCCCCCCC]

In some aspects, the LNP further comprising a phospholipid, a structural lipid, and a PEG lipid. In some aspects, the LNP comprises a molar ratio of about 20-60% ionizable amino lipid, about 5-25% phospholipid, about 25-55% structural lipid, and about 0.5-1.5% PEG lipid. In some aspects, the LNP comprises a molar ratio of about 50% ionizable amino lipid, about 10% phospholipid, about 38.5% structural lipid, and about 1.5% PEG lipid. In some aspects, the LNP comprises a molar ratio of about 50% ionizable amino lipid, about 10% phospholipid, about 38.5% cholesterol, and about 1.5% PEG-DMG.

In any of the foregoing or related aspects of the methods of the present disclosure, the LNP encapsulated mRNA therapeutic agent comprises three mRNA drug substances, wherein the mRNA therapeutic agent is administered by a single injection. In some aspects, the mRNA therapeutic agent is administered by multiple injections into one or more different sites within the same tumor lesion or divided across several tumor lesions.

In any of the foregoing or related aspects of the methods of the present disclosure, the LNP encapsulated mRNA therapeutic agent comprises three mRNA drug substances, wherein the LNP is formulated in a pharmaceutically acceptable carrier. In some aspects, the pharmaceutically acceptable carrier is a solution suitable for intratumoral injection. In some aspects, the solution comprises a buffer.

In any of the foregoing or related aspects of the methods of the present disclosure, treatment results in an anti-tumor immune response in the patient comprising T cell activation, T cell proliferation, and/or T cell expansion. In some aspects, the T cells are CD4+ T cells, CD8+ T cells, or both CD4+ T cells and CD8+ T cells. In some aspects, treatment results in a reduction in size or inhibition of growth of the injected tumor. In some aspects, treatment results in a reduction in size or inhibition of growth of an uninjected tumor.

In other aspects, the disclosure provides an LNP encapsulated mRNA therapeutic agent for use in the manufacture of a medicament for treating advanced or metastatic solid tumor malignancy or lymphoma in a human patient by inducing or enhancing an anti-tumor immune response, wherein the medicament comprises the LNP encapsulated mRNA therapeutic agent, and an optional pharmaceutically acceptable carrier, and wherein the treatment comprises administration of the medicament by intratumoral injection at a dose of 0.10-10.0 mg of the mRNA therapeutic agent in a dosing regimen from 7 to 28 days, and wherein the LNP encapsulated mRNA therapeutic agent comprises three mRNA drug substances:
  (i) a first mRNA comprising an ORF encoding a human OX40L polypeptide;
  (ii) a second mRNA comprising an ORF encoding a human IL-23 polypeptide; and
  (iii) a third mRNA comprising an ORF encoding a human IL-36γ polypeptide.

In yet other aspects, the disclosure provides a kit comprising a container comprising a pharmaceutical composition comprising: an LNP encapsulated mRNA therapeutic agent; and a pharmaceutically acceptable carrier, and instructions for use in treating advanced or metastatic solid tumor malignancy or lymphoma in a human patient by inducing or enhancing an anti-tumor immune response, wherein the treatment comprises administration of the pharmaceutical composition by intratumoral injection at a dose of 0.10-10.0 mg of the mRNA therapeutic agent in a dosing regimen from 7 to 28 days, and wherein the LNP encapsulated mRNA therapeutic agent comprises three mRNA drug substances:
  (i) a first mRNA comprising an ORF encoding a human OX40L polypeptide;
  (ii) a second mRNA comprising an ORF encoding a human IL-23 polypeptide; and
  (iii) a third mRNA comprising an ORF encoding a human IL-36γ polypeptide.

In any of the foregoing or related aspects of the use or kits of the present disclosure, treatment comprises administration of the medicament at a dose of the mRNA therapeutic agent selected from: 0.25-8.0 mg; 0.25-4.0 mg; 0.25-2.0 mg; 0.25-1.0 mg; 0.25-5 mg; 0.5-8.0 mg; 0.5-4.0 mg; 0.5-2.0 mg; 0.5-1.0 mg; 1.0-8.0 mg; 1.0-4.0 mg; 1.0-2.0 mg; 2.0-8.0 mg; 2.0-4.0 mg; and 4.0-8.0 mg.

In any of the foregoing or related aspects of the use or kits of the present disclosure, treatment comprises administration of the medicament at a dose of the mRNA therapeutic agent selected from 0.10 mg, 0.25 mg, 0.50 mg, 1.0 mg, 2.0 mg, 4.0 mg, 8.0 mg and 10.0 mg.

In any of the foregoing or related aspects of the use or kits of the present disclosure, treatment comprises administration of the medicament to the patient in a dosing regimen selected from 7 to 21 days, 7 to 14 days, 28 days, 21 days, 14 days, and 7 days.

In any of the foregoing or related aspects of the use or kits of the present disclosure, treatment comprises administration of the medicament every 2 weeks. In any of the foregoing or related aspects of the use or kits of the present disclosure, treatment comprises administration of the medicament every 3 weeks. In any of the foregoing or related aspects of the use or kits of the present disclosure, treatment comprises administration of the medicament every 4 weeks.

In any of the foregoing or related aspects of the use or kits of the present disclosure, treatment comprises administration of the medicament or pharmaceutical composition in combination with a composition comprising a PD-1 antagonist, a PD-L1 antagonist, or a CTLA-4 antagonist, and an optional pharmaceutically acceptable carrier.

In any of the foregoing or related aspects of the use or kits of the present disclosure, the PD-1 antagonist is an antibody or antigen binding portion thereof that specifically binds to PD-1. In some aspects, the PD-1 antagonist is selected from the group consisting of nivolumab, pembrolizumab, and pidilizumab.

In any of the foregoing or related aspects of the use or kits of the present disclosure, the PD-L1 antagonist is an antibody or antigen binding portion thereof that specifically binds to PD-L1. In some aspects, the PD-L1 antagonist is selected from the group consisting of durvalumab, avelumab, and atezolizumab. In some aspects, the PD-L1 antagonist is durvalumab.

In any of the foregoing or related aspects of the use or kits of the present disclosure, the CTLA-4 antagonist is an antibody or antigen binding portion thereof that specifically binds to CTLA-4. In some aspects, the CTLA-4 antagonist is selected from the group consisting of ipilimumab and tremelimumab. In some aspects, the CTLA-4 antagonist is tremelimumab.

In any of the foregoing or related aspects of the use or kits of the present disclosure, treatment comprises administration of a dose of the composition comprising the PD-1 antagonist, the PD-L1 antagonist or the CTLA-4 antagonist every 4 weeks.

In any of the foregoing or related aspects of the use or kits of the present disclosure, treatment comprises administration of the medicament comprising an LNP encapsulated mRNA therapeutic agent prior to administration of the PD-1 antagonist, PD-L1 antagonist or CTLA-4 antagonist.

In any of the foregoing or related aspects of the use or kits of the present disclosure, the advanced or metastatic solid tumor malignancy in the patient is selected from triple negative breast cancer, head and neck squamous cell carcinoma, and melanoma and the lymphoma is Non-Hodgkin lymphoma.

In any of the foregoing or related aspects of the use or kits of the present disclosure, the human OX40L polypeptide comprises the amino acid sequence as set forth in SEQ ID NO: 1; the human IL-23 polypeptide comprises the amino acid sequence as set forth in SEQ ID NO: 32; and the human IL-36γ polypeptide comprises the amino acid sequence as set forth in SEQ ID NO: 35.

In other aspects, the disclosure provides an LNP encapsulated mRNA therapeutic agent for use in the manufacture of a medicament for treating advanced or metastatic solid tumor malignancy or lymphoma in a human patient by inducing or enhancing an anti-tumor immune response, wherein the medicament comprises the LNP encapsulated mRNA therapeutic agent, and an optional pharmaceutically acceptable carrier, and wherein the treatment comprises administration of the medicament by intratumoral injection at a dose of 0.10-10.0 mg of the mRNA therapeutic agent in a dosing regimen from 7 to 28 days, and wherein the LNP encapsulated mRNA therapeutic agent comprises three mRNA drug substances:
(i) a first mRNA encoding a human OX40L polypeptide comprising an ORF comprising a nucleotide sequence at least 80% identical to the nucleotide sequence set forth in SEQ ID NO: 4 or comprises the nucleotide sequence set forth in SEQ ID NO: 4;
(ii) a second mRNA encoding a human IL-23 polypeptide comprising an ORF comprising a nucleotide sequence at least 80% identical to the nucleotide sequence set forth in SEQ ID NO: 33 or comprises the nucleotide sequence set forth in SEQ ID NO: 33; and
(iii) a third mRNA encoding a human IL-36γ polypeptide comprising an ORF comprising a nucleotide sequence at least 80% identical to the nucleotide sequence set forth in SEQ ID NO: 36 or comprises the nucleotide sequence set forth in SEQ ID NO: 36.

In yet other aspects, the disclosure provides a kit comprising a container comprising a pharmaceutical composition comprising: an LNP encapsulated mRNA therapeutic agent; and a pharmaceutically acceptable carrier, and instructions for use in treating advanced or metastatic solid tumor malignancy or lymphoma in a human patient by inducing or enhancing an anti-tumor immune response, wherein the treatment comprises administration of the pharmaceutical composition by intratumoral injection at a dose of 0.10-10.0 mg of the mRNA therapeutic agent in a dosing regimen from 7 to 28 days, and wherein the LNP encapsulated mRNA therapeutic agent comprises three mRNA drug substances:
(i) a first mRNA encoding a human OX40L polypeptide comprising an ORF comprising a nucleotide sequence at least 80% identical to the nucleotide sequence set forth in SEQ ID NO: 4 or comprises the nucleotide sequence set forth in SEQ ID NO: 4;
(ii) a second mRNA encoding a human IL-23 polypeptide comprising an ORF comprising a nucleotide sequence at least 80% identical to the nucleotide sequence set forth in SEQ ID NO: 33 or comprises the nucleotide sequence set forth in SEQ ID NO: 33; and
(iii) a third mRNA encoding a human IL-36γ polypeptide comprising an ORF comprising a nucleotide sequence at least 80% identical to the nucleotide sequence set forth in SEQ ID NO: 36 or comprises the nucleotide sequence set forth in SEQ ID NO: 36.

In any of the foregoing or related aspects of the use or kits of the present disclosure, each of the first mRNA, second mRNA, and third mRNA comprise a 3' untranslated region (UTR) comprising at least one microRNA-122 (miR-122) binding site. In some aspects, the miR-122 binding site is a miR-122-3p binding site or a miR-122-5p binding site. In some aspects, the miR-122-5p binding site comprises the nucleotide sequence set forth in SEQ ID NO: 20. In some aspects, the 3'UTR comprises a nucleotide sequence at least 90% identical to the sequence set forth in SEQ ID NO: 17 or comprises the nucleotide sequence as set forth in SEQ ID NO: 17. In some aspects, each of the first, second, and third mRNAs comprise a 5'cap, a 5' untranslated region (UTR), and a poly-A tail of about 100 nucleotides in length. In some aspects, the 5'UTR comprises a nucleotide sequence at least 90% identical to the sequence set forth in SEQ ID NO: 15 or comprises the nucleotide sequence as set forth in SEQ ID NO: 15. In some aspects, the 5'UTR comprises a nucleotide sequence at least 90% identical to the sequence set forth in SEQ ID NO: 16 or comprises the nucleotide sequence as set forth in SEQ ID NO: 16.

In any of the foregoing or related aspects of the use or kits of the present disclosure, the LNP encapsulated mRNA therapeutic agent comprises three mRNA drug substances, wherein:
(i) the first mRNA encoding the human OX40L polypeptide comprises a nucleotide sequence at least 90% identical to the nucleotide sequence set forth in SEQ ID NO: 5 or comprises the nucleotide sequence set forth in SEQ ID NO: 5;
(ii) the second mRNA encoding a human IL-23 polypeptide comprises a nucleotide sequence at least 90% identical to the nucleotide sequence set forth in SEQ ID NO: 34 or comprises the nucleotide sequence set forth in SEQ ID NO: 34; and
(iii) the third mRNA encoding a human IL-36γ polypeptide comprises a nucleotide sequence at least 90% identical to the nucleotide sequence set forth in SEQ ID NO: 37 or comprises the nucleotide sequence set forth in SEQ ID NO: 37.

In any of the foregoing or related aspects of the use or kits of the present disclosure, the first, second, and third mRNAs are formulated in the lipid nanoparticle at a mass ratio of OX40L:IL-23:IL-36γ of 1:1:2.

In any of the foregoing or related aspects of the use or kits of the present disclosure, each of the first, second and third mRNAs is chemically modified.

In any of the foregoing or related aspects of the use or kits of the present disclosure, each of the first, second, and third mRNAs is fully modified with chemically-modified uridines. In some aspects, the chemically-modified uridines are N1-methylpseudouridines (m1ψ).

In any of the foregoing or related aspects of the use or kits of the present disclosure, each of the first, second and third mRNAs is fully modified with 5-methylcytosine or is fully modified with N1-methylpseudouridines (m1ψ) and 5-methylcytosine.

In any of the foregoing or related aspects of the use or kits of the present disclosure, the LNP comprises a compound having the formula:

(Compound II)

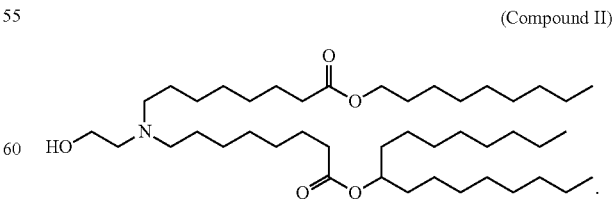

In some aspects, the LNP further comprising a phospholipid, a structural lipid, and a PEG lipid. In some aspects, the LNP comprises a molar ratio of about 20-60% ionizable amino lipid, about 5-25% phospholipid, about 25-55% structural lipid, and about 0.5-1.5% PEG lipid. In some aspects, the LNP comprises a molar ratio of about 50% ionizable amino lipid, about 10% phospholipid, about 38.5% structural lipid, and about 1.5% PEG lipid. In some aspects, the LNP comprises a molar ratio of about 50% ionizable amino lipid, about 10% phospholipid, about 38.5% cholesterol, and about 1.5% PEG-DMG.

BRIEF DESCRIPTION OF FIGURES

The patent or application file contains at least one drawing executed in color. Copies of this patent or patent application publication with color drawing(s) will be provided by the Office upon request and payment of the necessary fee.

FIGS. 1A-1E show the effect of doublet combination therapy and triple combination therapy using mRNAs encoding IL-23, IL-36γ, and OX40L, wherein each mRNA comprises an miR-122 binding site. FIG. 1A shows doublet treatment with OX40L/IL-36γ encoding mRNAs. One complete response was observed. FIG. 1B shows doublet combination treatment with IL-23/IL-36γ encoding mRNAs. Four complete responses were observed. FIG. 1C shows doublet combination treatment with IL-23/OX40L encoding mRNAs. Seven complete responses were observed. FIG. 1D shows treatment with triplet mRNA combination encoding OX40L/IL-23/IL-36γ. Eleven complete responses were observed. FIG. 1E shows treatment with negative control mRNA FIGS. 2A-2E show in vivo tumor efficacy in both primary treated and untreated distal tumors with Compound II-based LNPs comprising doublet mRNA therapy encoding IL-23/IL-36γ (FIG. 2A), OX40L/IL-23 (FIG. 2B) and triplet mRNAs encoding OX40L/IL-23/IL-36γ (FIG. 2C). FIG. 2A shows the effect of the doublet mRNA therapy (mRNA encoding IL-23 and mRNA encoding IL-36γ) on the combined tumor volume. FIG. 2B shows the effect of the doublet mRNA therapy (mRNA encoding IL-23 and mRNA encoding OX40L) on the combined tumor volume. FIG. 2C shows the effect of the triplet mRNA therapy (mRNA encoding OX40L/IL-23/IL-36γ) on the combined tumor volume. FIG. 2D shows the effect of the negative control mRNA (non-translating mRNA encoding for OX40L) on the combined tumor volume. FIG. 2E shows a schematic description of the MC38-S dual flank model used in the experiments.

FIG. 3A shows tumor growth in animals treated with intraperitoneal injections of anti-PD-L1 antibody (10F.9G2) alone. FIG. 3B shows tumor growth in animals treated with intratumoral injections of triplet mRNA therapy. FIG. 3C shows tumor growth in animals treated with intratumoral injections of triplet mRNA therapy plus anti-PD-L1 antibody (10F.9G2). Vertical dashed lines indicate day of administration of the control antibody, the anti-PD-L1 antibody, the triplet mRNA therapy, or the triplet mRNA therapy plus anti-PD-L1 antibody. FIG. 3D shows tumor growth in animals treated with intratumoral injections negative control mRNA.

FIGS. 4A-4D show in vivo anti-tumor efficacy of triplet mRNA therapy combined with an anti-CTLA-4 antibody (9D9) in immunosuppressive MC38 tumors. FIG. 4A shows tumor growth in animals treated with intraperitoneal injections of anti-CTLA-4 antibody (9D9) alone. FIG. 4B shows tumor growth in animals treated with intratumoral injections of triplet mRNA therapy. FIG. 4C shows tumor growth in animals treated with intratumoral injections of triplet mRNA therapy plus anti-CTLA-4 antibody (9D9). Vertical dashed lines indicate day of administration of the control antibody, the anti-CTLA-4 antibody, the triplet mRNA therapy, or the triplet mRNA therapy plus anti-CTLA-4 antibody. FIG. 4D shows tumor growth in animals treated with intratumoral injections of negative control mRNA.

DETAILED DESCRIPTION

Figure 2F:
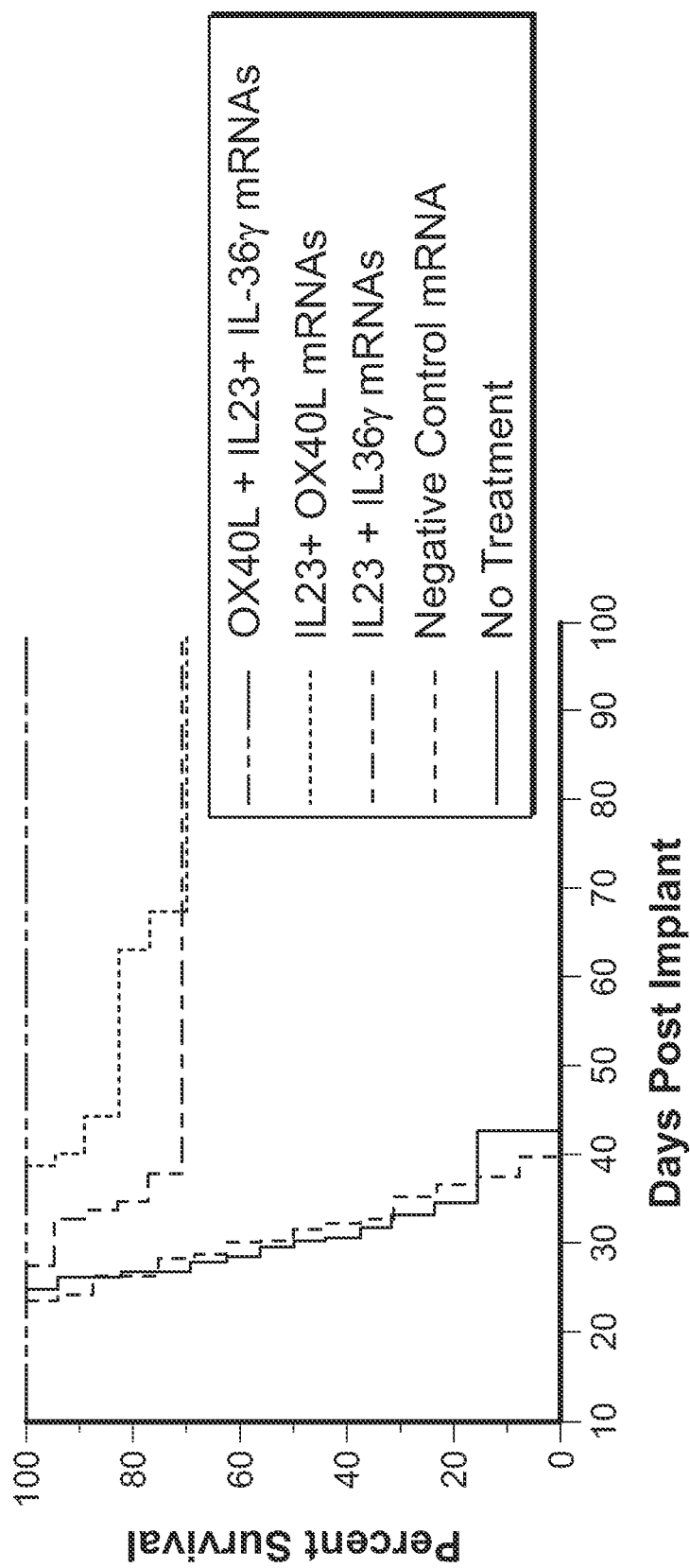
FIG. 2F shows survival curves in the MC38 dual flank mice model in which mice were treated with control, doublet combinations or triplet mRNA therapy. Mice administered OX40L/IL-23/IL-36γ triplet mRNAs show 100% (n=20) survival rate. All mice that were not treated or given negative control mRNA were dead by approximately 40 days post-implantation of the MC38 tumor. Seventy percent of mice administered either OX40L/IL-23 or IL-23/IL-36γ doublet mRNAs survived at 100 days post-implantation with MC38.

The present disclosure is directed to methods of treating solid tumor and/or lymphoma in a human patient by administering an effective amount of mRNAs encoding human OX40L, human IL-23 and human IL-36γ polypeptides. In some aspects, the mRNAs are encapsulated in a lipid nanoparticle. In some aspects, administering an effective amount of the mRNA combination encoding human OX40L, IL-23 and IL-36γ polypeptides reduces or decreases the size of a tumor (e.g., the tumor which has been injected and/or a proximal, un-injected tumor) in a triple negative breast cancer (TNBC), head and neck squamous cell carcinoma (HNSCC), non-Hodgkin lymphoma (NHL), or a melanoma cancer patient. In some aspects, administering an effective amount of mRNAs encoding human OX40L, IL-23 and IL-36γ polypeptides induces a specific cell-mediated immune response with systemic anti-tumor effects in a cancer patient having solid tumor malignancy or lymphoma. In some aspects, the expression of human OX40L, IL-23 and IL-36γ polypeptides in tumor cells and/or in immune cells in the tumor microenvironment is increased after administration of mRNAs encoding human OX40L, IL-23 and IL-36γ polypeptides.

Methods of Use and Dosing Regimens

In some embodiments, the present disclosure provides methods of intratumoral (ITu) administration of an LNP encapsulated mRNAs therapeutic agent comprising three mRNA drug substances encoding human OX40L, IL-23 and IL-36γ polypeptides for treating solid tumor malignancies or lymphoma in a subject.

In some embodiments, the methods described herein comprise administering to the subject an LNP encapsulated mRNAs therapeutic agent comprising three mRNA drug substances encoding human OX40L, IL-23 and IL-36γ of the disclosure, and pharmaceutical compositions suitable for ITu injection.

Compositions of the disclosure are administered to the subject in an effective amount. In general, an effective amount of the composition will allow for efficient production of the encoded polypeptide in cells of the subject. Metrics for efficiency may include polypeptide translation (indicated by polypeptide expression), level of mRNA degradation, and immune response indicators.

The methods of the disclosure for treating solid tumor malignancies or lymphomas are used in a variety of clinical or therapeutic applications. For example, the methods are used to stimulate anti-tumor immune responses in a subject with solid tumor malignancies or lymphomas. The mRNA and compositions of the present disclosure are useful in methods for treating or delaying progression of solid tumor malignancy or lymphoma in a subject, e.g., a human patient by intratumoral injection. The injection can be in a single injection at a single site or multiple injections at one or more sites (one or more tumors). The injection can be a bolus injection or a continuous infusion.

A suitable dose of an mRNA is a dose which treats or delays progression of solid tumor malignancy or lymphoma a human patient, and may be affected by a variety of factors including, e.g., the age, sex, and weight of a subject to be treated and the particular mRNA to be used. Other factors affecting the dose administered to the subject include, e.g., the type or severity of the malignancy or lymphoma in the patient. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject.

In some embodiments, a subject is administered at least one mRNA composition described herein. In related embodiments, the subject is provided with or administered a nanoparticle (e.g., a lipid nanoparticle) comprising the mRNA(s). In further related embodiments, the subject is provided with or administered a pharmaceutical composition of the disclosure to the subject. In particular embodiments, the pharmaceutical composition comprises an mRNA(s) as described herein, or it comprises a nanoparticle comprising the mRNA(s). In particular embodiments, the mRNA(s) is present in a nanoparticle, e.g., a lipid nanoparticle. In particular embodiments, the mRNA(s) or nanoparticle is present in a pharmaceutical composition, e.g., a composition suitable for intratumoral injection.

In some embodiments, the mRNA(s), nanoparticle, or pharmaceutical composition is administered to the patient parenterally, e.g., intratumorally. In particular embodiments, the subject is a mammal, e.g., a human. In various embodiments, the subject is provided with an effective amount of the mRNA(s).

Suitable doses for human patients can be evaluated in, e.g., a Phase I dose escalation study. Data obtained from the cell culture assays and animal studies can be used in formulating a range of dosage for use in humans. The dosage of such mRNA described herein lies generally within a range of local concentrations of the mRNA that include the ED50 with little or no toxicity. The dosage may vary within this range depending upon the dosage form employed and the route of administration utilized. For the mRNA and compositions described herein, the therapeutically effective dose can be estimated initially from cell culture assays. A dose can be formulated in animal models to achieve a therapeutically effective concentration within the local site that includes the IC50 (i.e., the concentration of the mRNA which achieves a half-maximal inhibition of symptoms) as determined in cell culture. Such information can be used to more accurately determine useful doses in humans.

In some embodiments, the frequency of dosing will take into account the pharmacokinetic parameters of the mRNA in the formulation used. In certain embodiments, a clinician will administer the composition until a dosage is reached that achieves or maintains the desired effect. In some embodiments, the desired effect is tumor size reduction or resolution of the injected or uninjected tumors. In some embodiments, the desired effect is expression of OX40L, IL-23 and IL-36γ within the tumor. In some embodiments, achievement of a desired effect occurs immediately after administration of a dose. In some embodiments, achievement occurs at any point in time following administration. In some embodiments, achievement occurs at any point in time during a dosing interval. In some embodiments, achievement of a desired effect is determined by analyzing a biological sample (e.g., tumor biopsy) immediately after administration of a dose, at any point in time following administration of a dose, at any point in time during a doing interval, or combinations thereof.

In some embodiments, maintenance of a desired effect (e.g., OX40L, IL-23 or IL-36γ protein expression) is determined by analyzing a biological sample (e.g., tumor biopsy) at least once during a dosing interval. In some embodiments, maintenance of a desired effect (e.g., OX40L, IL-23 or IL-36γ protein expression) is determined by analyzing a biological sample (e.g., tumor biopsy) at regular intervals during a dosing interval. In some embodiments, maintenance of a desired effect (e.g., OX40L, IL-23 or IL-36γ protein expression) is determined by analyzing a biological sample (e.g., tumor biopsy) before a subsequent dose is administered.

Tumor Size Reduction or Growth Inhibition

In some embodiments, the subject having a solid tumor malignancy or lymphoma as described supra. In some embodiments, the human OX40L, IL-23 and IL-36γ encoding mRNAs are administered locally to a tumor (i.e., intratumorally). In some embodiments, administration of the human OX40L, IL-23 and IL-36γ encoding mRNAs to a tumor reduces the size or volume, or inhibits the growth of the injected tumor. In some embodiments, administration of the human OX40L, IL-23 and IL-36γ encoding mRNAs to a tumor reduces the size or inhibits the growth of the injected tumor and an uninjected tumor in the subject. In some embodiments, the uninjected tumor is located near or proximal to the injected tumor. In some embodiments, the uninjected tumor is located distal to the injected tumor. In some embodiments, the reduction in size or inhibition of growth in an uninjected tumor is through an abscopal effect.

In some embodiments, reduction in tumor size is by at least 25%. In some embodiments, reduction in tumor size is by at least 50%. In some embodiments, reduction in tumor size is by at least 75%. In some embodiments, the tumor is complete resolved.

In some embodiments, a reduction in tumor size is measured by comparison to the size of patient's tumor at baseline, against an expected tumor size, against an expected tumor size based on a large patient population, or against the tumor size of a control population.

In some embodiments, tumor size is determined by visual methods, such as image scanning. Methods for determining tumor size and tumor volume are known to those of skill in the art.

OX40L, IL-23 and IL-36γ Protein Expression

In some embodiments, human OX40L, IL-23 and IL-36γ protein expression are enhanced in a tumor administered OX40L, IL-23 and IL-36γ encoding mRNAs. In some embodiments, enhancement of human OX40L, IL-23 and IL-36γ protein expression are relative to expression prior to administration of the OX40L, IL-23 and IL-36γ encoding mRNAs. In some embodiments, a biopsy is obtained from the tumor before and after administration of the OX40L, IL-23 and IL-36γ encoding mRNAs, and protein expression are assessed.

In some embodiments, human OX40L, IL-23 and IL-36γ protein expression are increased by at least 1-fold, 2-fold, 3-fold, 4-fold, 5-fold, 6-fold, 7-fold, 8-fold, 9-fold, or 10-fold, on tumor cells or immune cells within a tumor at any point in time following administration of the OX40L, IL-23 and IL-36γ encoding mRNAs or composition of the disclosure, as determined by a method described herein. In some embodiments, OX40L, IL-23 and IL-36γ protein expression are increased by at least 1-fold, 2-fold, 3-fold, 4-fold, 5-fold, 6-fold, 7-fold, 8-fold, 9-fold, or 10-fold, on tumor cells or immune cells within a tumor at any point in time during the duration of a dosing interval, as determined by a method described herein. In some embodiments, OX40L, IL-23 and IL-36γ protein expression are increased by at least 1-fold, 2-fold, 3-fold, 4-fold, 5-fold, 6-fold, 7-fold, 8-fold, 9-fold, or 10-fold, on tumor cells or immune cells within a tumor at any point in time during the duration of a dosing interval comprising a duration of 7-35 days, as determined by a method described herein. In some embodiments, OX40L, IL-23 and IL-36γ protein expression are increased by at least 1-fold, 2-fold, 3-fold, 4-fold, 5-fold, 6-fold, 7-fold, 8-fold, 9-fold, or 10-fold, on tumor cells or immune cells within a tumor at any point in time during the duration of a dosing interval comprising a duration of 14-28 days, as determined by a method described herein. In some embodiments, OX40L, IL-23 and IL-36γ protein expression are increased by at least 1-fold, 2-fold, 3-fold, 4-fold, 5-fold, 6-fold, 7-fold, 8-fold, 9-fold, or 10-fold, on tumor cells or immune cells within a tumor at any point in time during the duration of a dosing interval comprising a duration of 21-28 days, as determined by a method described herein. In some embodiments, OX40L, IL-23 and IL-36γ protein expression are increased by at least 1-fold, 2-fold, 3-fold, 4-fold, 5-fold, 6-fold, 7-fold, 8-fold, 9-fold, or 10-fold, on tumor cells or immune cells within a tumor on, during or after day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or day 35 of the dosing interval, as determined by a method described herein.

Methods for determining human OX40L, IL-23 and IL-36γ protein expression on appropriate cell types, such as immune cells or tumor cells located within a tumor are known to those of skill in the art and described herein. Such methods include, but are not limited to, quantitative immunofluorescence (QIF), flow cytometry, reverse transcription polymerase chain reaction (RT-PCR), competitive RT-PCR, real-time RT-PCR, RNase protection assay (RPA), northern blotting, nucleic acid microarray using DNA, western blotting, enzyme-linked immunosorbent assay (ELISA), radioimmunoassay (RIA), tissue immunostaining, immunoprecipitation assay, complement fixation assay, fluorescence-activated cell sorting (FACS), mass spectrometry, magnetic bead-antibody immunoprecipitation, or protein chip.

Enhancing Anti-Tumor Immune Responses

In some embodiments, the disclosure provides a method for enhancing an immune response in a subject with solid tumor malignancy or lymphoma. In some embodiments, the disclosure provides a method for enhancing an immune response to a solid tumor. In some embodiments, enhancing an immune response comprises stimulating cytokine production. In another embodiment, enhancing an immune response comprises enhancing cellular immunity (T cell responses), such as activating T cells. In some embodiments, enhancing an immune response comprises activating NK cells. Enhancement of an immune response in a subject can be evaluated by a variety of methods established in the art for assessing immune response, including but not limited to determining the level of T cell activation and NK cell activation by intracellular staining of activation markers in the area of the tumor.

In some embodiments, local administration of mRNAs encoding a human OX40L, IL-23 and IL-36γ polypeptides to a tumor induces T cell activation within the tumor. In some embodiments, the activation of T cells results in an anti-tumor immune response in the subject. In some embodiments, the activated T cells in the subject reduce or decrease the size of a tumor or inhibit the growth of a tumor in the subject. Activation of T cells can be measured using applications in the art such as measuring T cell proliferation; measuring cytokine production with enzyme-linked immunosorbant assays (ELISA) or enzyme-linked immunospot assays (ELISPOT); or detection of cell-surface markers associated with T cell activation (e.g., CD69, CD40L, CD137, CD25, CD71, CD26, CD27, CD28, CD30, CD154, and CD134) with techniques such as flow cytometry.

In some embodiments, the activated T cells are $CD4^+$ cells, $CD8^+$ cells, $CD62^+$ ($L$-selectin$^+$) cells, $CD69^+$ cells, $CD40L^+$ cells, $CD137^+$ cells, $CD25^+$ cells, $CD71^+$ cells, $CD26^+$ cells, $CD27^+$ cells, $CD28^+$ cells, $CD30^+$ cells, $CD45^+$ cells, $CD45RA^+$ cells, $CD45RO^+$ cells, $CD11b'$ cells, $CD154^+$ cells, $CD134^+$ cells, $CXCR3^+$ cells, $CCR4^+$ cells, $CCR6^+$ cells, $CCR7^+$ cells, $CXCR5^+$ cells, $Crth2^+$ cells, gamma delta T cells, or any combination thereof. In some embodiments, the activated T cells are $Th_1$ cells. In other embodiments, the T cells are $Th_2$ cells. In other embodiments, the activated T cells activated are cytotoxic T cells.

In some embodiments, local administration of mRNAs encoding human OX40L, IL-23 and IL-36γ polypeptides to a tumor induces T cell proliferation within the tumor. In some embodiments, T cell proliferation results in an anti-tumor immune response in the subject. In some embodiments, T cell proliferation in the subject reduce or decrease the size of a tumor or inhibit the growth of a tumor in the subject. T cell proliferation can be measured using applications in the art such as cell counting, viability staining, optical density assays, or detection of cell-surface markers associated with T cell activation (e.g., CD69, CD40L, CD137, CD25, CD71, CD26, CD27, CD28, CD30, CD154, and CD134) with techniques such as flow cytometry.

In some embodiments, local administration of mRNAs encoding human OX40L, IL-23 and IL-36γ polypeptides to a tumor induces infiltration of T cells to the tumor. In some embodiments, T cell infiltration results in an anti-tumor immune response in the subject. In some embodiments, T cell infiltration in the subject reduce or decrease the size of a tumor or inhibit the growth of a tumor in the subject. T cell infiltration in a tumor can be measured using applications in the art such as tissue sectioning and staining for cell markers, measuring local cytokine production at the tumor site, or detection of T cell-surface markers with techniques such as flow cytometry.

In some embodiments, the infiltrating T cells are CD4$^+$ cells, CD8$^+$ cells, CD62$^+$ (L-selectin$^+$) cells, CD69$^+$ cells, CD40L$^+$ cells, CD137$^+$ cells, CD25$^+$ cells, CD71$^+$ cells, CD26$^+$ cells, CD27$^+$ cells, CD28$^+$ cells, CD30$^+$ cells, CD45$^+$ cells, CD45RA$^+$ cells, CD45RO$^+$ cells, CD11b$^+$ cells, CD154$^+$ cells, CD134$^+$ cells, CXCR3$^+$ cells, CCR4$^+$ cells, CCR6$^+$ cells, CCR7$^+$ cells, CXCR5$^+$ cells, Crth2$^+$ cells, gamma delta T cells, or any combination thereof. In some embodiments, the infiltrating T cells are Th$_1$ cells. In other embodiments, the infiltrating T cells are Th$_2$ cells. In other embodiments, the infiltrating T cells are cytotoxic T cells.

In some embodiments, local administration of mRNAs encoding human OX40L, IL-23 and IL-36γ polypeptides to a tumor increases the number of Natural Killer (NK) cells within the tumor. In some embodiments, the increase in the number of NK cells results in an anti-tumor immune response in the subject. In some embodiments, the increase in the number of NK cells reduces or decreases the size of a tumor or inhibits the growth of a tumor in the subject. Increases in the number of NK cells in a subject can be measured using applications in the art such as detection of NK cell-surface markers (e.g., CD335/NKp46; CD336/NKp44; CD337/NPp30) or intracellular NK cell markers (e.g., perforin; granzymes; granulysin).

In some embodiments, administration of mRNAs encoding OX40L, IL-23 and IL-36γ polypeptides increases the total number of NK cells in the tumor compared to the number of NK cells in a tumor that is not administered with mRNAs encoding an OX40L, IL-23 and IL-36γ polypeptides.

In certain embodiments, the number of NK cells is increased at least about two-fold, at least about three-fold, at least about four-fold, at least about five-fold, at least about six-fold, at least about seven-fold, at least about eight-fold, at least about nine-fold, or at least about ten-fold compared to a control (e.g., saline or an mRNA without OX40L, IL-23 and IL-36γ expression).

Dosing

In some embodiments, the mRNA or composition can therefore be administered as a single dose or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In some embodiments, the dosing regimen is determined by the pharmacodynamics effects of the human OX40L, IL-23 and IL-36γ polypeptides. In some embodiments, the pharmacodynamics effects include an increase in T cells within tumors after administration. In some embodiments, the increase in T cells is maintained over a specified period of time (e.g., 14 days).

In some embodiments, the composition comprising mRNAs encoding human OX40L, IL-23 and IL-36γ are administered at a dosing interval comprising a duration of about 14-28 days or about 21-28 days. In some embodiments, the composition comprising an mRNAs encoding human OX40L, IL-23 and IL-36γ is administered at a dosing interval comprising a duration of about 7-42 days, about 7-21 days, about 14-28 days, about 21-28 days, about 21-35 days, about 28-35 days, about 21-42 days, or about 28-42 days. In some embodiments, the dosing interval is about 7 days. In some embodiments, the dosing interval is about 14 days. In some embodiments, the dosing interval is about 21 days. In some embodiments, the dosing interval is about 28 days. In some embodiments, the dosing interval is about 35 days. In some embodiments, the dosing interval is about 42 days. In some embodiments, the dosing interval is at least about 7 days. In some embodiments, the dosing interval is at least about 14 days. In some embodiments, the dosing interval is at least about 21 days. In some embodiments, the dosing interval is at least about 28 days. In some embodiments, the dosing interval is at least about 35 days. In some embodiments, the dosing interval is at least about 42 days.

In some embodiments, the composition comprising mRNAs encoding human OX40L, IL-23 and IL-36γ is administered to a subject about every 7-42 days for a specified time period. In some embodiments, the composition comprising mRNAs encoding human OX40L, IL-23 and IL-36γ is administered to a subject about every 7-21 days for a specified time period. In some embodiments, the composition comprising mRNAs encoding human OX40L, IL-23 and IL-36γ is administered to a subject about every 14-21 days for a specified time period. In some embodiments, the composition comprising mRNAs encoding human OX40L, IL-23 and IL-36γ is administered to a subject about every 14-28 days for a specified time period. In some embodiments, the composition comprising mRNAs encoding human OX40L, IL-23 and IL-36γ is administered to a subject about every 21-28 days for a specified time period. In some embodiments, the composition comprising mRNAs encoding human OX40L, IL-23 and IL-36γ is administered to a subject about every 21-35 days for a specified time period. In some embodiments, the composition comprising mRNAs encoding human OX40L, IL-23 and IL-36γ is administered to a subject about every 28-42 days for a specified time period.

In some embodiments, the composition is administered to a subject about every 7 days for a specified time period. In some embodiments, the composition is administered to a subject about every 14 days for a specified time period. In some embodiments, the composition is administered to a subject about every 21 days for a specified time period. In some embodiments, the composition is administered to a subject about every 28 days for a specified time period. In some embodiments, the composition is administered to a subject about every 35 days for a specified time period. In some embodiments, the composition is administered to a subject about every 42 days for a specified time period.

In some embodiments, the specified time period is determined by a clinician. In some embodiments, dosing occurs until a positive therapeutic outcome is achieved. For example, in some embodiments, dosing occurs until growth of cancer cells, tumor cells or tumors is inhibited. In some embodiments, dosing occurs until growth of cancer cells, tumor cells or tumors is reduced. In some embodiments, dosing occurs until there is no detection of cancer cells, tumor cells or tumors in a biological sample. In some embodiments, dosing occurs until progression of a cancer is delayed. In some embodiments, dosing occurs until progression of a cancer is inhibited. In some embodiments, the specified time period is determined once a positive therapeutic outcome is achieved.

In some embodiments, dosing of a composition comprising mRNAs encoding human OX40L, IL-23 and IL-36γ will occur indefinitely, or until a positive therapeutic outcome is achieved. In some embodiments, the dosing interval remains consistent. In some embodiments, the dosing interval changes as needed based on a clinician's assessment. In some embodiments, dosing occurs indefinitely to maintain remission of a cancer.

In some embodiments, the composition comprising mRNAs encoding human OX40L, IL-23 and IL-36γ is administered to a subject about every 7-42 days indefinitely, or until a positive therapeutic outcome is achieved. In some embodiments, the composition comprising mRNAs encoding human OX40L, IL-23 and IL-36γ is administered to a subject about every 7-21 days indefinitely, or until a positive therapeutic outcome is achieved. In some embodiments, the composition comprising mRNAs encoding human OX40L, IL-23 and IL-36γ is administered to a subject about every 14-21 days indefinitely, or until a positive therapeutic outcome is achieved. In some embodiments, the composition comprising mRNAs encoding human OX40L, IL-23 and IL-36γ is administered to a subject about every 14-28 days indefinitely, or until a positive therapeutic outcome is achieved. In some embodiments, the composition comprising mRNAs encoding human OX40L, IL-23 and IL-36γ is administered to a subject about every 21-28 days indefinitely, or until a positive therapeutic outcome is achieved. In some embodiments, the composition comprising mRNAs encoding human OX40L, IL-23 and IL-36γ is administered to a subject about every 21-35 days indefinitely, or until a positive therapeutic outcome is achieved. In some embodiments, the composition comprising mRNAs encoding human OX40L, IL-23 and IL-36γ is administered to a subject about every 28-42 days indefinitely, or until a positive therapeutic outcome is achieved.

In some embodiments, the composition is administered to a subject about every 7 days indefinitely, or until a positive therapeutic outcome is achieved. In some embodiments, the composition is administered to a subject about every 14 days indefinitely, or until a positive therapeutic outcome is achieved. In some embodiments, the composition is administered to a subject about every 21 days indefinitely, or until a positive therapeutic outcome is achieved. In some embodiments, the composition is administered to a subject about every 28 days indefinitely, or until a positive therapeutic outcome is achieved. In some embodiments, the composition is administered to a subject about every 35 days indefinitely, or until a positive therapeutic outcome is achieved. In some embodiments, the composition is administered to a subject about every 42 days indefinitely, or until a positive therapeutic outcome is achieved.

In certain embodiments, compositions of the disclosure may be administered at dosage levels sufficient to deliver from about 0.0001 mg/kg to about 10 mg/kg, from about 0.001 mg/kg to about 10 mg/kg, from about 0.005 mg/kg to about 10 mg/kg, from about 0.01 mg/kg to about 10 mg/kg, from about 0.1 mg/kg to about 10 mg/kg, from about 1 mg/kg to about 10 mg/kg, from about 2 mg/kg to about 10 mg/kg, from about 5 mg/kg to about 10 mg/kg, from about 0.0001 mg/kg to about 5 mg/kg, from about 0.001 mg/kg to about 5 mg/kg, from about 0.005 mg/kg to about 5 mg/kg, from about 0.01 mg/kg to about 5 mg/kg, from about 0.1 mg/kg to about 10 mg/kg, from about 1 mg/kg to about 5 mg/kg, from about 2 mg/kg to about 5 mg/kg, from about 0.0001 mg/kg to about 1 mg/kg, from about 0.001 mg/kg to about 1 mg/kg, from about 0.005 mg/kg to about 1 mg/kg, from about 0.01 mg/kg to about 1 mg/kg, or from about 0.1 mg/kg to about 1 mg/kg in a given dose, where a dose of 1 mg/kg provides 1 mg of mRNA or nanoparticle per 1 kg of subject body weight. In particular embodiments, a dose of about 0.005 mg/kg to about 5 mg/kg of mRNA or nanoparticle of the disclosure may be administrated.

In some embodiments, an mRNA composition is administered at a dose between about 0.010 mg/kg to about 0.5 mg/kg for a human patient. In some embodiments, the mRNA composition is administered at a dose between about 0.015 mg/kg to about 0.4 mg/kg. In some embodiments, the mRNA composition is administered at a dose between about 0.020 mg/kg to about 0.3 mg/kg. In some embodiments, the mRNA composition is administered at a dose between about 0.025 mg/kg to about 0.2 mg/kg. In some embodiments, the mRNA composition is administered at a dose between about 0.030 mg/kg to about 0.1 mg/kg.

In some embodiments, a mRNA composition is administered at a dose between about 0.5 mg to about 10.0 mg of mRNA for a human patient. In some embodiments, a composition is administered at a dose of 1.0 mg. In some embodiments, a composition is administered at a dose of 2.0 mg. In some embodiments, a composition is administered at a dose of 4.0 mg. In some embodiments, a composition is administered at a dose of 8.0 mg.

In some embodiments, a single dose may be administered, for example, prior to or after, or in lieu of a surgical procedure or in the instance of an acute disease, disorder, or condition. The specific therapeutically effective, prophylactically effective, or otherwise appropriate dose level for any particular patient will depend upon a variety of factors including the severity and identify of a disorder being treated, if any; the one or more mRNAs employed; the specific composition employed; the age, body weight, general health, sex, and diet of the patient; the time of administration, route of administration, and rate of excretion of the specific pharmaceutical composition employed; the duration of the treatment; drugs used in combination or coincidental with the specific pharmaceutical composition employed; and like factors well known in the medical arts.

Combination Therapy

In some embodiments, a pharmaceutical composition of the disclosure may be administered in combination with another agent, for example, another therapeutic agent, a prophylactic agent, and/or a diagnostic agent. By "in combination with," it is not intended to imply that the agents must be administered at the same time and/or formulated for delivery together, although these methods of delivery are within the scope of the present disclosure. For example, one or more compositions including one or more different mRNAs may be administered in combination. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of compositions of the disclosure, or imaging, diagnostic, or prophylactic compositions thereof in combination with agents that improve their bioavailability, reduce and/or modify their metabolism, inhibit their excretion, and/or modify their distribution within the body.

Exemplary therapeutic agents that may be administered in combination with the compositions of the disclosure include, but are not limited to, cytotoxic, chemotherapeutic, hypomethylating agents, pro-apoptotic agents, small molecules/kinase inhibitors, immunostimulatory agents and other therapeutic agents including therapeutics approved for solid tumor malignancy or lymphoma, now or at a later date. Cytotoxic agents may include, for example, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, rachelmycin, and analogs thereof. Radioactive ions may also be used as therapeutic agents and may include, for example, radioactive iodine, strontium, phosphorous, palladium, cesium, iridium, cobalt, yttrium, samarium, and praseodymium. Other therapeutic agents may include, for example, antimetabolites (e.g., methotrexate, 6-mercaptopurine, 6-thioguanine, cytarabine, and 5-fluorouracil, and decarbazine), alkylating agents (e.g., mechlorethamine, thiotepa, chlorambucil, rachelmycin, melphalan, carmustine, lomustine, cyclophosphamide, busulfan, dibromomannitol, streptozotocin, mitomycin C, and cis-dichlorodiamine platinum (II) (DDP), and cisplatin), anthracyclines (e.g., daunorubicin and doxorubicin), antibiotics (e.g., dactinomycin, bleomycin, mithramycin, and anthramycin), and anti-mitotic agents (e.g., vincristine, vinblastine, taxol, and maytansinoids).

In some embodiments, the human OX40L, IL-23 and IL-36γ encoding mRNAs are administered to a subject having a solid tumor malignancy or lymphoma, wherein the subject has received or is receiving treatment with one or more anti-cancer agents. In some embodiments, the human OX40L, IL-23 and IL-36γ encoding mRNAs are administered in combination with one or more anti-cancer agents to a subject having a solid tumor malignancy or lymphoma. In some embodiments, the OX40L, IL-23 and IL-36γ encoding mRNAs and one or more anti-cancer agents are administered simultaneously or sequentially. In some embodiments, the OX40L, IL-23 and IL-36γ encoding mRNAs are administered after administration of one or more anti-cancer agents. In some embodiments, the OX40L, IL-23 and IL-36γ encoding mRNAs are administered before administration of one or more anti-cancer agents.

In some embodiments, the one or more anti-cancer agents are approved by the United States Food and Drug Administration. In other embodiments, the one or more anti-cancer agents are pre-approved by the United States Food and Drug Administration.

In some embodiments, the subject for the present methods has been treated with one or more standard of care therapies. In other embodiments, the subject for the present methods has not been responsive to one or more standard of care therapies or anti-cancer therapies.

In some embodiments, the subject has been previously treated with a PD-1 antagonist prior to an treatment with OX40L, IL-23 and IL-36γ encoding mRNAs. In some embodiments, the subject is treated with a monoclonal antibody that binds to PD-1 simultaneously with or subsequent to treatment with OX40L, IL-23 and IL-36γ encoding mRNAs. In some embodiments, the subject has been treated with an anti-PD-1 monoclonal antibody therapy prior to treatment with OX40L, IL-23 and IL-36γ encoding mRNAs. In some embodiments, the anti-PD-1 monoclonal antibody therapy comprises Nivolumab, Pembrolizumab, Pidilizumab, or any combination thereof.

In some embodiments, the anti-PD-1 antibody (or an antigen-binding portion thereof) useful for the disclosure is pembrolizumab. Pembrolizumab (also known as KEYTRUDA®, lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. No. 8,900,587. Pembrolizumab has been approved by the FDA for the treatment of relapsed or refractory melanoma and advanced NSCLC.

In some embodiments, the anti-PD-1 antibody useful for the disclosure is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 Cancer Immunol Res. 2(9):846-56). Nivolumab has shown activity in a variety of advanced solid tumors including renal cell carcinoma (renal adenocarcinoma, or hypernephroma), melanoma, and non-small cell lung cancer (NSCLC) (Topalian et al., 2012a; Topalian et al., 2014; Drake et al., 2013; WO 2013/173223).

In other embodiments, the anti-PD-1 antibody is MEDI0680 (formerly AMP-514), which is a monoclonal antibody against the PD-1 receptor. MEDI0680 is described, for example, in U.S. Pat. No. 8,609,089B2.

In some embodiments, the anti-PD-1 antibody is BGB-A317, which is a humanized monoclonal antibody. BGB-A317 is described in U.S. Publ. No. 2015/0079109.

In some embodiments, a PD-1 antagonist is AMP-224, which is a B7-DC Fc fusion protein. AMP-224 is discussed in U.S. Publ. No. 2013/0017199.

In some embodiments, the subject has been treated with a monoclonal antibody that binds to PD-L1 prior to treatment with OX40L, IL-23 and IL-36γ encoding mRNAs. In some embodiments, the subject has been treated with an anti-PD-L1 monoclonal antibody therapy simultaneously with or subsequent to treatment with OX40L, IL-23 and IL-36γ encoding mRNAs. In some embodiments, the anti-PD-L1 monoclonal antibody therapy comprises Durvalumab, Avelumab, MEDI473, BMS-936559, Atezolizumab, or any combination thereof.

Durvalumab is a human IgG1, kappa mAb that blocks the interaction of PD-L1 (but not PD-L2) with PD-1 on T-cells and CD80 proteins on immune cells. Durvalumab is developed for use in the treatment of cancer. The proposed mechanism of action for durvalumab is interference in the interaction of PD-L1 with PD-1 and CD80. Blockade of PD-L1/PD-1 and PD-L1/CD80 interactions releases the inhibition of immune responses, including those that may result in tumor elimination. Durvalumab is engineered to reduce antibody-dependent cellular cytotoxicity and complement-dependent cytotoxicity. Thus, durvalumab is expected to stimulate anti-tumor immune response by binding to PD-L1 and shifting the balance toward anti-tumor response.

In some embodiments, the anti-PD-L1 antibody useful for the disclosure is MSB0010718C (also called Avelumab; See US 2014/0341917) or BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446) (see, e.g., Herbst et al. (2013) *J Clin Oncol* 31(suppl):3000. Abstract; U.S. Pat. No. 8,217,149), MEDI4736 (also called Durvalumab; Khleif (2013) In: Proceedings from the European Cancer Congress 2013; Sep. 27-Oct. 1, 2013; Amsterdam, The Netherlands).

In some embodiments, the subject has been treated with a CTLA-4 antagonist prior to treatment with OX40L, IL-23 and IL-36γ encoding mRNAs. In some embodiments, the subject has been previously treated with a monoclonal antibody that binds to CTLA-4 prior to treatment with OX40L, IL-23 and IL-36γ encoding mRNAs. In some embodiments, the subject has been treated with an anti-CTLA-4 monoclonal antibody simultaneously with or subsequent to treatment with OX40L, IL-23 and IL-36γ encoding mRNAs. In other aspects, the anti-CTLA-4 antibody therapy comprises Ipilimumab or Tremelimumab.

An exemplary clinical anti-CTLA-4 antibody is the human mAb 10D1 (now known as ipilimumab and marketed as YERVOY®) as disclosed in U.S. Pat. No. 6,984,720. Another anti-CTLA-4 antibody useful for the present methods is tremelimumab (also known as CP-675,206). Tremelimumab is human IgG2 monoclonal anti-CTLA-4 antibody. Tremelimumab is described in WO/2012/122444, U.S. Publ. No. 2012/263677, or WO Publ. No. 2007/113648 A2.

In a preferred embodiment, an mRNA therapeutic of the invention is administered to a subject having a solid tumor malignancy or lymphoma in combination with a checkpoint inhibitor.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer may be administered concurrently with a chemotherapeutic agent), or they may achieve different effects (e.g., control of any adverse effects).

Combinations Comprising mRNAs Encoding OX40L, IL-23 and IL-36γ

The present disclosure provides compositions, including LNP encapsulated mRNA therapeutic agents for the treatment of cancer. In one embodiment, the compositions comprise, in a single formulation, at least three mRNAs, each of the compositions selected from a first mRNA encoding OX40L, a second mRNA encoding IL-23 and/or a third mRNA encoding IL-36γ. Accordingly, the present disclosure provides, for example, (i) a first mRNA encoding a first protein comprising an OX40L polypeptide, (ii) a second mRNA encoding a second protein comprising an IL-23 polypeptide, and (iii) a third mRNA encoding a third protein comprising an IL-36γ polypeptide, wherein the first mRNA, the second mRNA, and the third mRNA are used in various combinations. In one aspect, the composition comprises the first mRNA, the second mRNA, and the third mRNA.

In some aspects of the methods disclosed herein, the first mRNA encoding a human OX40L polypeptide, the second mRNA encoding a human IL-23 polypeptide, and the third mRNA encoding a human IL-36γ polypeptide, are formulated, e.g., encapsulated in an LNP for in vivo delivery, e.g., intratumoral injection. In some embodiments, the first mRNA, the second mRNA, and the third mRNA are co-formulated (e.g., encapsulated in an LNP) at varying weight ratios, for example, with equivalent amounts (by weight) of each mRNA or with any one of the mRNAs present at 2, 3, 4, 5, 6, 7, 8, 9, 10, 11, 12, 13, 14, 15, 16, 17, 18, 19, 20, 25, 30, 35, 40, 45, or 50 times the amount (by weight) of the other mRNA. In one embodiment, the IL-23:IL-36γ:OX40L mRNAs are co-formulated at a weight (mass) ratio such that the IL-23 and OX40L mRNAs are at about equal amounts and the IL-36γ mRNA is present at a higher weight (mass) amount, such as 1.5, 2.0, 2.5, 3.0, 3.5, 4.0, 4.5 or 5.0 times greater weight (mass) amount. In one particular embodiment, the IL-23:IL-36γ:OX40L mRNAs are co-formulated at a weight (mass) ratio of 1:2:1. In used herein, the mass ratio can also be referred to by reference to a composition comprising mRNAs encoding OX40L:IL-23:IL-36γ formulated at a weight (mass) ratio of 1:1:2.

In other embodiments, the IL-23:IL-36γ:OX40L mRNAs are co-formulated at a weight (mass) ratio of 1:1:1, 2:1:1, 1:2:1, 1:1:2, 3:1:1, 1:3:1, 1:1:3, 4:1:1, 1:4:1, 1:1:4, 5:1:1, 1:5:1, 1:1:5, 6:1:1, 1:6:1, 1:1:6, 7:1:1, 1:7:1, 1:1:8, 9:1:1, 1:9:1, 1:1:9, 10:1:1, 1:10:1, 1:1:10, 11:1:1, 1:11:1, 1:1:11, 12:1:1, 1:12:1, 1:1:12, 13:1:1, 1:13:1, 1:1:13, 14:1:1, 1:14:1, 1:1:14, 15:1:1, 1:15:1, 1:1:15, 16:1:1, 1:16:1, 1:1:16, 17:1:1, 1:17:1, 1:1:17, 18:1:1, 1:18:1, 1:1:18, 19:1:1, 1:19:1, 1:1:19, 20:1:1, 1:20:1, 1:1:20, 25:1:1, 1:25:1, 1:1:25, 30:1:1, 1:30:1, 1:1:30, 35:1:1, 1:35:1, 1:1:35, 40:1:1, 1:40:1, 1:1:40, 45:1:1, 1:45:1, 1:1:45, 50:1:1, 1:50:1, or 1:1:50. In other embodiments, each of the three mRNAs can be present in the co-formulation at a different weight. By way of example only, the IL-23:IL-36γ:OX40L mRNAss can be co-formulated at a weight (mass) ratio of 1:2:3, 1:3:2, 2:1:3, 2:3:1, 3:1:2, or 3:2:1; or alternative at a weight (mass) ratio of 1:3:5, 1:5:3, 3:5:1, 3:1:5, 5:1:3, or 5:3:1; or alternative at a weight (mass) ratio of 1:5:10, 1:10:5, 5:1:10, 5:10:1, 10:1:5, or 10:5:1. In a particular embodiment, (i) a first mRNA encoding a first protein comprising an OX40L polypeptide (e.g., SEQ ID NO: 1), (ii) a second mRNA encoding a second protein comprising an IL-36-γ polypeptide (e.g., SEQ ID NO: 35), and (iii) a third polypeptide encoding a third protein comprising an IL-23 polypeptide (e.g., SEQ ID NO: 32), are formulated in a weight (mass) ratio of 1:2:1. While this is one exemplary formulation, the skilled artisan will readily appreciate that amounts of any one of the three constituents outside of this ratio may also provide formulations which are suitable for use in any of the methods disclosed herein.

The mRNA co-formulation can be administered as a single dose or as multiple doses. Co-formulations with varying weight (mass) ratios, e.g., co-formulation #1 in which the first mRNA, the second mRNA, and the third mRNA are present at 1:2:1 w/w and co-formulation #2 in which the first mRNA, the second mRNA, and the third mRNA are present at 1:1:2 w/w, can each be administered once or multiple times sequentially, concurrently, or simultaneously.

In one embodiment, the 1:2:1 co-formulation of (i) a first mRNA encoding a first protein comprising an OX40L polypeptide (e.g., SEQ ID NO: 1), (ii) a second mRNA encoding a second protein comprising an IL-36-γ polypeptide (e.g., SEQ ID NO:35), and (iii) a third polypeptide encoding a third protein comprising an IL-23 polypeptide (e.g., SEQ ID NO: 32), is administered as a single dose or as multiple doses.

In one embodiment, the disclosure provides an LNP encapsulated mRNA therapeutic agent comprising three mRNA drug substances, wherein the first, second, and third mRNAs are formulated in the lipid nanoparticle at a mass ratio of OX40L:IL-23:IL-36γ of 1:1:2, and wherein:
 (i) the first mRNA encoding a human OX40L polypeptide comprises an ORF comprising a nucleotide sequence at least 80% identical to the nucleotide sequence set forth in SEQ ID NO: 4 or comprising, the nucleotide sequence set forth in SEQ ID NO: 4;
 (ii) the second mRNA encoding a human IL-23 polypeptide comprises an ORF comprising a nucleotide sequence at least 80% identical to the nucleotide sequence set forth in SEQ ID NO: 33 or comprises the nucleotide sequence set forth in SEQ ID NO: 33; and
 (iii) the third mRNA encoding a human IL-36γ polypeptide comprises an ORF comprising a nucleotide sequence at least 80% identical to the nucleotide sequence set forth in SEQ ID NO: 36 or comprises the nucleotide sequence set forth in SEQ ID NO: 36.

In one embodiment, the disclosure provides an LNP encapsulated mRNA therapeutic agent comprising three mRNA drug substances, wherein the first, second, and third mRNAs are formulated in the lipid nanoparticle at a mass ratio of OX40L:IL-23:IL-36γ of 1:1:2, and wherein:
(i) the first mRNA encoding the human OX40L polypeptide comprises a nucleotide sequence at least 90% identical to the nucleotide sequence set forth in SEQ ID NO: 5 or comprises the nucleotide sequence set forth in SEQ ID NO: 5;
(ii) the second mRNA encoding a human IL-23 polypeptide comprises a nucleotide sequence at least 90% identical to the nucleotide sequence set forth in SEQ ID NO: 34 or comprises the nucleotide sequence set forth in SEQ ID NO: 34; and
(iii) the third mRNA encoding a human IL-36γ polypeptide comprises a nucleotide sequence at least 90% identical to the nucleotide sequence set forth in SEQ ID NO: 37 or comprises the nucleotide sequence set forth in SEQ ID NO: 37.

It is to be understood that the term "combinations of the disclosure" is not limited to the physical combination of a first mRNA, a second mRNA, and/or a third mRNA, but also encompasses the separate administration of these mRNAs concurrently or sequentially.

mRNAs Encoding OX40L

The mRNAs of the present disclosure encode an OX40L polypeptide. OX40L, the ligand for OX40 (CD134), is a homo-trimeric transmembrane protein normally expressed on antigen-presenting cells upon immune stimulation (Mallett et al., (1990) EMBO J 9(4):1063-1068).

Binding of OX40 and OX40L in the presence of a recognized antigen (e.g., a tumor antigen) promotes the expansion of CD4+ and CD8+ T cells and enhances memory responses while inhibiting regulatory T cells. Expression of OX40L by tumor cells, or other cells presenting tumor antigens is known to induce cell-mediated immune responses with systemic anti-tumor effects. OX40L has also been designated CD252 (cluster of differentiation 252), tumor necrosis factor (ligand) superfamily, member 4, tax-transcriptionally activated glycoprotein 1, TXGP1, or gp34. Human OX40L is 183 amino acids in length and contains three domains: a cytoplasmic domain of amino acids 1-23; a transmembrane domain of amino acids 24-50, and an extracellular domain of amino acids 51-183.

Human OX40L was first identified on the surface of human lymphocytes infected with human T-cell leukemia virus type-I (HTLV-I) by Tanaka et al. (Tanaka et al., International Journal of Cancer (1985), 36(5):549-55). Human OX40L is a 34 kDa glycosylated type II transmembrane protein that exists on the surface of cells as a trimer. OX40L comprises a cytoplasmic domain (amino acids 1-23), a transmembrane domain (amino acids 24-50) and an extracellular domain (amino acids 51-183). OX40L is also referred to as Tumor Necrosis Factor Superfamily (ligand) Member 4 (TNFSF4), CD252, CD134L, Tax-Transcriptionally Activated Glycoprotein 1 (TXGP1), Glycoprotein 34 (GP34), and ACT-4-L.

In some embodiments, a composition suitable for use in the methods of the disclosure comprises an mRNA encoding a mammalian OX40L polypeptide. In some embodiments, the mammalian OX40L polypeptide is a human OX40L polypeptide. In some embodiments, the OX40L polypeptide comprises an amino acid sequence set forth in SEQ ID NOs: 1-3.

In some embodiments, the mRNA encoding a human OX40L polypeptide encodes a human OX40L polypeptide comprising an amino acid sequence at least 50%, at least 60%, at least 70%, at least 80%, at least 85%, at least 90%, at least 95%, at least 98%, at least 99%, or 100% identical to an amino acid sequence set forth in SEQ ID NOs: 1-3 or an amino acid sequence encoded by a nucleotide sequence set forth in SEQ ID NOs: 4-10, wherein the human OX40L polypeptide is capable of binding to an OX40 receptor. In some embodiments, the mRNA encoding a human OX40L polypeptide encodes a human OX40L polypeptide comprising an amino acid sequence at least 50%, at least 60%, at least 70%, at least 80%, at least 85%, at least 90%, at least 95%, at least 98%, at least 99%, or 100% identical to SEQ ID NO: 1 and is capable of binding to an OX40 receptor. In some embodiments, the mRNA encoding a human OX40L polypeptide encodes a human OX40L polypeptide that consists essentially of SEQ ID NO: 1 and is capable of binding to an OX40 receptor.

In certain embodiments, the mRNA encoding a human OX40L polypeptide encodes a human OX40L polypeptide comprising an amino acid sequence set forth in SEQ ID NOs: 1-3, optionally with one or more conservative substitutions, wherein the conservative substitutions do not significantly affect the binding activity of the OX40L polypeptide to its receptor, i.e., the OX40L polypeptide binds to the OX40 receptor after the substitutions. In some embodiments, the mRNA encoding a human OX40L polypeptide encodes a human OX40L polypeptide comprising an amino acid sequence having at least 80%, at least 85%, at least 90%, at least 95%, at least 99% or 100% identity to any one of the amino acid sequences set forth in SEQ ID NOs: 1-3.

In other embodiments, an mRNA encoding a human OX40L polypeptide comprises a nucleotide sequence at least 50%, at least 60%, at least 70%, at least 80%, at least 85%, at least 90%, at least 95%, at least 98%, at least 99%, or 100% identical to any one of the nucleic acid sequences set forth in SEQ ID NOs: 4-10. In some embodiments, the mRNA encoding a human OX40L polypeptide comprises an open reading frame comprising a nucleotide sequence selected from any one of SEQ ID NOs: 4 and 8-10. In some embodiments, the mRNA encoding a human OX40L polypeptide comprises an open reading frame comprising a nucleotide sequence having at least 80%, at least 85%, at least 90%, at least 95%, at least 99%, or 100% identity to a nucleotide sequence selected from any one of SEQ ID NOs: 4 and 8-10. In some embodiments, the mRNA encoding a human OX40L polypeptide comprises an open reading frame comprising the nucleotide sequence set forth in SEQ ID NO: 4. In some embodiments, the mRNA encoding a human OX40L polypeptide comprises an open reading frame comprising a nucleotide sequence having at least 80%, at least 85%, at least 90%, at least 95%, at least 99%, or 100% identity to the nucleotide sequence set forth in SEQ ID NO: 4. In some embodiments, the mRNA encoding a human OX40L polypeptide comprises an open reading frame comprising the nucleotide sequence set forth in SEQ ID NO: 8. In some embodiments, the mRNA encoding a human OX40L polypeptide comprises an open reading frame comprising a nucleotide sequence having at least 80%, at least 85%, at least 90%, at least 95%, at least 99%, or 100% identity to the nucleotide sequence set forth in SEQ ID NO: 8. In some embodiments, the mRNA encoding a human OX40L polypeptide comprises an open reading frame comprising the nucleotide sequence set forth in SEQ ID NO: 9. In some embodiments, the mRNA encoding a human OX40L polypeptide comprises an open reading frame comprising a nucleotide sequence having at least 80%, at least 85%, at least 90%, at least 95%, at least 99%, or 100% identity to the nucleotide sequence set forth in SEQ ID NO: 9. In some embodiments, the mRNA encoding a human OX40L polypeptide comprises an open reading frame comprising the nucleotide sequence set forth in SEQ ID NO: 10. In some embodiments, the mRNA encoding a human OX40L polypeptide comprises an open reading frame comprising a nucleotide sequence having at least 80%, at least 85%, at least 90%, at least 95%, at least 99%, or 100% identity to the nucleotide sequence set forth in SEQ ID NO: 10.

In some embodiments, the mRNA useful for the methods and compositions described herein comprises an open reading frame encoding an extracellular domain of OX40L. In other embodiments, the mRNA comprises an open reading frame encoding a cytoplasmic domain of OX40L. In some embodiments, the mRNA comprises an open reading frame encoding a transmembrane domain of OX40L. In certain embodiments, the mRNA comprises an open reading frame encoding an extracellular domain of OX40L and a transmembrane domain of OX40L. In other embodiments, the mRNA comprises an open reading frame encoding an extracellular domain of OX40L and a cytoplasmic domain of OX40L. In yet other embodiments, the mRNA comprises an open reading frame encoding an extracellular domain of OX40L, a transmembrane of OX40L, and a cytoplasmic domain of OX40L.

A person of skill in the art would understand that in addition to the native signal sequences and propeptide sequences implicitly disclosed in SEQ ID NOs: 1-10 (sequences present in the precursor form and absent in the mature corresponding form) and non-native signal peptides, other signal sequences can be used. Accordingly, references to OX40L polypeptide or mRNA according to SEQ ID NOs: 1-10 encompass variants in which an alternative signal peptide (or encoding sequence) known in the art has been attached to said OX40L polypeptide (or mRNA). It is also understood that references to the sequences disclosed in SEQ ID NOs: 1-10 through the application are equally applicable and encompass orthologs and functional variants (for example polymorphic variants) and isoforms of those sequences known in the art at the time the application was filed.

In some embodiments, the OX40L encoding mRNA comprises an open reading frame encoding OX40L, a 3'UTR, and a 5'UTR. In some embodiments, the OX40L encoding mRNA comprises an open reading frame encoding OX40L, a 3'UTR, a 5'UTR, and a poly-A tail. In some embodiments, the OX40L encoding mRNA comprises an open reading frame encoding OX40L, a 3'UTR, a 5'UTR, a poly-A tail and a 5'cap.

In some embodiments, the OX40L encoding mRNA comprises (i) a 5'UTR comprising the nucleotide sequence set forth in SEQ ID NO: 15; (ii) an open reading frame encoding OX40L comprising the nucleotide sequence set forth in SEQ ID NO: 4; and (iii) a 3'UTR comprising the nucleotide sequence set forth in SEQ ID NO: 17. In some embodiments, the OX40L encoding mRNA comprises (i) a 5'UTR comprising the nucleotide sequence set forth in SEQ ID NO: 16; (ii) an open reading frame encoding OX40L comprising the nucleotide sequence set forth in SEQ ID NO: 4; and (iii) a 3'UTR comprising the nucleotide sequence set forth in SEQ ID NO: 17.

In some embodiments, the OX40L encoding mRNA comprises the nucleotide sequence set forth in SEQ ID NO: 5. In some embodiments, the OX40L encoding mRNA comprises a nucleotide sequence having at least 80%, 85%, 90%, 95%, 96%, 97%, 98% or 99% identity to the nucleotide sequence set forth in SEQ ID NO: 5.

mRNA Encoding IL-23

The mRNAs of the present disclosure encode an IL-23 polypeptide. IL-23 is a pro-inflammatory cytokine that plays an important role in innate and adaptive immunity. Croxford et al. (2012) Eur. J. Immunol. 42:2263-2273. IL-23 functions primarily as a 60 kDa heterodimeric protein consisting of disulfide-linked p19 and p40 subunits. IL-23 is structurally and functionally similar to the pro-inflammatory cytokine IL-12. IL-23 contains the same p40 subunit as IL-12, but includes the p19 subunit rather than IL-12's p35. Oppman et al. (2000) Immunity 13:715-725. The precursor form of the p19 subunit (NCBI Reference Sequence: NP_057668; NM_016584; Uniprot: Q9NPF7; also referred to as IL-23A and IL-23 subunit alpha) is 189 amino acids in length, while its mature form is 170 amino acids long. The precursor form of the p40 subunit (NCBI Reference Sequence: NM_002187; Uniprot: P29460; also referred to as IL-12B, natural killer cell stimulatory factor 2, and cytotoxic lymphocyte maturation factor 2) is 328 amino acids in length, while its mature form is 306 amino acids long.

Many different immune cells, including dendritic cells and macrophages, produce IL-23 upon antigenic stimuli. One difference between IL-12 and IL-23 is that IL-12 is associated with the development and activity of Th1 T cell populations, while IL-23 is associated with the development and activity of Th17 T cell populations. See Vignali et al. (2014) Nat. Immunol. 13:722-728.

Although some early studies implicated IL-23 for anti-tumor therapy (Belladonna et al. (2002) J. Immunol. 168: 5448-5454), more recent studies indicate a potential pro-tumorigenic function for IL-23. See, e.g., Croxford et al. (2012) Eur. J. Immunol. 42:2263-2273; Langowski et al. (2007) Trends Immunol. 28:207-212; Langowski et al. (2006) Nature 442:461-465; Teng et al. (2010) Proc. Natl. Acad. Sci. USA 107:8328-8333; Teng et al. (2012) Cancer Res. 72:3987-3996. Langowski (2006) observed an increase of IL-23 in human tumors. See also Ngiow et al. (2013) Trends Immunol. 34:548-555; Wilke et al. (2011) Carcinogenesis 32:643-649; Xu et al. (2010) Clin. Dev. Immunol. 2010. For example, Wang et al. (2015) Clin. Exp. Rheumatol. 33 (Suppl. 92): S87-S90 teaches that elevated expression of IL-23 has a pathogenic function in cancer. IL-23 has a causal role in tumor development and progression and has been linked to adverse prognostic outcome and rapid progression to metastatic disease, suggesting that inhibition of IL-23 expression may be useful for therapy and prevention of cancer, particularly colorectal cancer. Teng et al. (2015) Nature Medicine 21: 719-29 teaches that IL-23 indirectly or directly promotes tumorigenesis, growth, and metastasis, and indicates that inhibition of IL-23 expression could be used for therapy and prevention of cancer.

As used in the present disclosure, the term "IL-23 polypeptide" refers to, e.g., a IL-12p40 subunit of IL-23, to an IL-23p19 subunit of IL-23, or to a fusion protein comprising an IL-12p40 subunit polypeptide and an IL-23p19 subunit polypeptide. In some aspects, the fusion protein comprises from N-terminus to C-terminus:

(a) an IL-12p40 subunit comprising the IL-12p40 signal peptide, a peptide linker, and a mature IL-23p19 subunit, or (b) an IL-23p19 subunit comprising the IL-23p19 signal peptide, a peptide linker, and a mature IL-12p40.

In one particular aspect, the IL-23 polypeptide comprises, consists of, or consists essentially of a human IL-23 polypeptide of SEQ ID NO: 32 (e.g., a precursor or mature IL-12p40 or IL-23p19) or a combination thereon. In one particular aspect, the mRNA encoding the IL-23 polypeptide comprises, consists of, or consists essentially of an IL-23- encoding mRNA of SEQ ID NO:33. In one particular aspect, the mRNA encoding the IL-23 polypeptide comprises, consists of, or consists essentially of an IL-23-encoding mRNA of SEQ ID NO:34.

In some embodiments, the IL-23 polypeptide comprises an amino acid sequence at least 50%, at least 60%, at least 70%, at least 80%, at least 85%, at least 90%, at least 95%, at least 98%, at least 99%, or 100% identical to an IL-23 amino acid sequence listed in SEQ ID NO: 32 or an amino acid sequence encoded by a nucleotide sequence of SEQ ID NO: 33, wherein the IL-23 polypeptide has at least 10% of the activity (e.g., binding to its receptor) of the corresponding wild type IL-23 polypeptide. In a particular embodiment, the IL-23 polypeptide comprises an amino acid sequence at least 50%, at least 60%, at least 70%, at least 80%, at least 85%, at least 90%, at least 95%, at least 98%, at least 99%, or 100% identical to SEQ ID NO: 32 and has at least 10% of the activity (e.g., binding to its receptor) of the corresponding wild type IL-23 polypeptide. In another particular embodiment, the IL-23 polypeptide consists essentially of SEQ ID NO: 32 and has at least 10% of the activity (e.g., binding to its receptor) of the corresponding wild type IL-23 polypeptide.

In other embodiments, the IL-23 polypeptide encoded by a mRNA of the disclosure comprises an amino acid sequence of SEQ ID NO: 32 with one or more conservative substitutions, wherein the conservative substitutions do not significantly affect the binding activity of the IL-23 polypeptide to its receptor, i.e., the IL-23 polypeptide binds to the IL-23 receptor after the substitutions.

In some embodiments, a nucleotide sequence (i.e., mRNA) encoding an IL-23 polypeptide comprises a sequence at least 50%, at least 60%, at least 70%, at least 80%, at least 85%, at least 90%, at least 95%, at least 98%, at least 99%, or 100% identical to an IL-23 polypeptide encoding nucleic acid sequence listed in Table 1. In a particular embodiment, the nucleotide sequence (i.e., mRNA) encoding an IL-23 polypeptide comprises a sequence at least 50%, at least 60%, at least 70%, at least 80%, at least 85%, at least 90%, at least 95%, at least 98%, at least 99%, or 100% identical to SEQ ID NO: 33 or SEQ ID NO: 34. In another particular embodiment, the nucleotide sequence (i.e., mRNA) encoding an IL-23 polypeptide consists essentially SEQ ID NO: 33 or SEQ ID NO: 34. It should be understood that the nucleotide sequence (i.e., mRNA, e.g., SEQ ID NO: 33) encoding an IL-23 polypeptide open reading frame (ORF) can be one element within a larger construct, e.g., further including a 5' terminal cap, 5'UTR, 3'UTR, and/or polyA tail.

In some embodiments, the IL-23 polypeptide comprises an IL-12p40 subunit comprising an amino acid sequence at least about 50%, at least about 55%, at least about 60%, at least about 65%, at least about 70%, at least about 75%, at least about 80%, at least about 85%, at least about 90%, at least about 95%, at least about 99%, or 100% to an IL-23 polypeptide sequence of SEQ ID NO: 32, wherein the amino acid sequence is capable of binding to an IL-23p19 subunit and forming IL-23, which has an IL-23 activity.

In some embodiments, the IL-12p40 subunit is encoded by a nucleic acid sequence at least about 70%, at least about 75%, at least about 80%, at least about 85%, at least about 90%, at least about 95%, at least about 99%, or 100% identical to an IL-23 polypeptide encoding SEQ ID NO: 32.

In some embodiments, the IL-23 polypeptide comprises an IL-23p19 subunit comprising an amino acid sequence at least about 50%, at least about 55%, at least about 60%, at least about 65%, at least about 70%, at least about 75%, at least about 80%, at least about 85%, at least about 90%, at least about 95%, at least about 99%, or 100% identical to an IL-23 polypeptide sequence listed of SEQ ID NO:32, wherein the amino acid sequence is capable of binding to an IL-12p40 subunit and forming IL-23, which has an IL-23 activity.

In some embodiments, the IL-23p19 subunit is encoded by a nucleic acid sequence at least about 70%, at least about 75%, at least about 80%, at least about 85%, at least about 90%, at least about 95%, at least about 99%, or 100% identical to a IL-23 polypeptide encoding SEQ ID NO: 33 or SEQ ID NO: 34.

In some embodiments, the IL-12p40 subunit and the IL-23p19 subunit of the IL-23 protein are on a single polypeptide chain or two different chains. In some embodiments, the IL-12p40 subunit and the IL-23p19 subunit are fused by a linker. In some embodiments, the IL-12p40 subunit comprises a signal peptide. In some embodiments, the IL-23p19 subunit comprises a signal peptide. In some embodiments, the IL-12p40 subunit is a mature IL-12p40 (i.e., it does not comprise a signal peptide). In some embodiments, the IL-23p19 subunit is a mature IL-23p19 (i.e., it does not comprise a signal peptide). In some embodiments, the IL-12p40 subunit comprises a non-native signal peptide. In some aspects, the IL-23p19 subunit comprises a non-native signal peptide.

In some embodiments, the IL-23 is a fusion polypeptide comprising an IL-12p40 subunit and an IL-23p19 subunit according to any of the following alternative formulas:

[signal peptide 1][IL-12p40]-[linker]-[IL-23p19]

[signal peptide 2]-[IL-23p19]-[linker]-[IL-12p40]

wherein [signal peptide 1] can be an IL-12p40 signal peptide or a non-native signal peptide, [signal peptide 2] can be an IL-23p19 signal peptide or a non-native signal peptide, [IL-12p40] is a mature IL-12p40, [IL-23p19] is a mature IL-23p29, and [linker] is a peptide linker.

mRNAS Encoding IL-36γ

The mRNAs of the present disclosure encode an IL-23 polypeptide. IL-36γ is a member of the Interleukin-1 family of cytokines Like other members of the interleukin-1 family of cytokines, IL-36γ requires N-terminal cleavage for full bioactivity. IL-36γ does not have a signal sequence and, therefore, is not secreted through the endoplasmic reticulum Golgi pathway. (See Gresnigt and van de Veerdonk (2013) Seminars in Immunology 25:458-465). It is unclear how IL-36γ is released from cells to act on, e.g., immune cells, other epithelial cells, and fibroblasts (Gabay et al. (2015) Journal of Leukocyte Biology 97:645-652). In exemplary aspects of the invention, a mRNA encoding IL-36, e.g., IL-36γ, includes a sequence encoding a heterologous signal peptide. Without being bound in theory, it is believed that mRNAs encoding such "engineered" signal peptide-interleukin chimeric proteins provide for the generation of active protein when expressed in vivo, in the absence of inflammasome activation.

In one particular aspect, the IL-36γ polypeptide comprises, consists of, or consists essentially of an IL-36γ polypeptide of Table 1. In one particular aspect, the mRNA encoding the IL-36γ-polypeptide comprises, consists of, or consists essentially of an IL-36γ-encoding mRNA of SEQ ID NO: 36. In one particular aspect, the mRNA encoding the IL-36γ-polypeptide comprises, consists of, or consists essentially of an IL-36γ-encoding mRNA of SEQ ID NO: 37.

In some embodiments, the IL-36γ polypeptide comprises an amino acid sequence at least 50%, at least 60%, at least 70%, at least 80%, at least 85%, at least 90%, at least 95%, at least 98%, at least 99%, or 100% identical to an IL-36γ amino acid sequence of SEQ ID NO: 35 or an amino acid sequence encoded by a nucleotide sequence listed SEQ ID NO: 36 or SEQ ID NO: 37, wherein the IL-36γ polypeptide has at least 10% of the activity (e.g., binding to its receptor) of the corresponding wild type IL-36γ polypeptide. In a particular embodiment, the IL-36γ polypeptide comprises an amino acid sequence at least 50%, at least 60%, at least 70%, at least 80%, at least 85%, at least 90%, at least 95%, at least 98%, at least 99%, or 100% identical to SEQ ID NO: 35 and has at least 10% of the activity (e.g., binding to its receptor) of the corresponding wild type IL-36γ polypeptide. In another particular embodiment, the IL-36γ polypeptide consists essentially of SEQ ID NO: 35 and has at least 10% of the activity (e.g., binding to its receptor) of the corresponding wild type IL-36γ polypeptide.

In other embodiments, the IL-36γ polypeptide encoded by a mRNA of the disclosure comprises an amino acid sequence of SEQ ID NO: 35 or shown in SEQ ID NO: 35 with one or more conservative substitutions, wherein the conservative substitutions do not significantly affect the binding activity of the IL-36γ polypeptide to its receptor, i.e., the IL-36γ polypeptide binds to the IL-36γ receptor after the substitutions.

In some embodiments, a nucleotide sequence (i.e., mRNA) encoding an IL-36γ polypeptide comprises a sequence at least 50%, at least 60%, at least 70%, at least 80%, at least 85%, at least 90%, at least 95%, at least 98%, at least 99%, or 100% identical to a IL-36γ polypeptide encoding nucleic acid sequence listed in Table 1. In a particular embodiment, the nucleotide sequence (i.e., mRNA) encoding an IL-36γ polypeptide comprises a sequence at least 50%, at least 60%, at least 70%, at least 80%, at least 85%, at least 90%, at least 95%, at least 98%, at least 99%, or 100% identical to NO: 36 or SEQ ID NO: 37. In another particular embodiment, the nucleotide sequence (i.e., mRNA) encoding an IL-36γ polypeptide consists essentially of SEQ ID NO: 36 OR SEQ ID NO: 37. It should be understood that the nucleotide sequence (i.e., mRNA, e.g., SEQ ID NO: 36) encoding an IL-23 polypeptide open reading frame (ORF) can be one element within a larger construct, e.g., further including a 5' terminal cap, 5'UTR, 3'UTR, and/or polyA tail.

The sequence summary presents, e.g., precursor and mature sequences for IL-23, IL-36γ, and OX40L as well as constructs comprising IL-23 or IL-36γ. In the context of the present disclosure IL-23 mRNA or IL-23 polypeptide encompass both "precursor" and "mature" forms. Furthermore, a construct comprising a mRNA encoding IL-23, IL-36γ, and OX40L and further comprising components such 3' UTR and 5' UTR would be considered an IL-23, IL-36γ, and OX40L encoding mRNA. A person of skill in the art would understand that in addition to the native signal sequences and propeptide sequences implicitly disclosed in the sequence summary (sequences present in the precursor for and absent in the mature corresponding form) and the non-native signal peptide disclosed in the sequence summary (IgKV4 signal peptide), other signal sequences can be used. Accordingly, references to an IL-23, IL-36-gamma, and OX40L polypeptide or mRNA according to the sequence summary encompass variants in which an alternative signal peptide (or encoding sequence) known in the art has been attached to said IL-23, IL-36γ, and OX40L polypeptide (or mRNA). It is also understood that references to the sequences disclosed in the sequence summary through the application are equally applicable and encompass orthologs and functional variants (for example polymorphic variants) and isoforms of those sequences known in the art at the time the application was filed mRNA Construct Components An mRNA may be a naturally or non-naturally occurring mRNA. An mRNA may include one or more modified nucleobases, nucleosides, or nucleotides, as described below, in which case it may be referred to as a "modified mRNA" or "mmRNA." As described herein "nucleoside" is defined as a compound containing a sugar molecule (e.g., a pentose or ribose) or derivative thereof in combination with an organic base (e.g., a purine or pyrimidine) or a derivative thereof (also referred to herein as "nucleobase"). As described herein, "nucleotide" is defined as a nucleoside including a phosphate group.

An mRNA may include a 5' untranslated region (5'-UTR), a 3' untranslated region (3'-UTR), and/or a coding region (e.g., an open reading frame). An exemplary 5' UTR for use in the constructs is shown in SEQ ID NO: 15. Another exemplary 5' UTR for use in the constructs is shown in SEQ ID NO: 16. Another exemplary 5' UTR for use in the constructs is shown in SEQ ID NO: 12. An exemplary 3' UTR for use in the constructs is shown in SEQ ID NO: 17. An exemplary 3' UTR comprising miR-122 and miR-142.3p binding sites for use in the constructs is shown in SEQ ID NO: 18. An mRNA may include any suitable number of base pairs, including tens (e.g., 10, 20, 30, 40, 50, 60, 70, 80, 90 or 100), hundreds (e.g., 200, 300, 400, 500, 600, 700, 800, or 900) or thousands (e.g., 1000, 2000, 3000, 4000, 5000, 6000, 7000, 8000, 9000, 10,000) of base pairs. Any number (e.g., all, some, or none) of nucleobases, nucleosides, or nucleotides may be an analog of a canonical species, substituted, modified, or otherwise non-naturally occurring. In certain embodiments, all of a particular nucleobase type may be modified.

In some embodiments, an mRNA as described herein may include a 5' cap structure, a chain terminating nucleotide, optionally a Kozak sequence (also known as a Kozak consensus sequence), a stem loop, a polyA sequence, and/or a polyadenylation signal.

A 5' cap structure or cap species is a compound including two nucleoside moieties joined by a linker and may be selected from a naturally occurring cap, a non-naturally occurring cap or cap analog, or an anti-reverse cap analog (ARCA). A cap species may include one or more modified nucleosides and/or linker moieties. For example, a natural mRNA cap may include a guanine nucleotide and a guanine (G) nucleotide methylated at the 7 position joined by a triphosphate linkage at their 5' positions, e.g., m$^7$G(5')ppp (5')G, commonly written as m$^7$GpppG. A cap species may also be an anti-reverse cap analog. A non-limiting list of possible cap species includes m$^7$GpppG, m$^7$Gpppm$^7$G, m$^7$3'dGpppG, m$_2$$^{7,O3'}$GpppG, m$_2$$^{7,O3'}$GppppG, m$_2$$^{7,O2'}$GppppG, m$^7$Gpppm$^7$G, m$^7$3'dGpppG, m$_2$$^{7,O3'}$GpppG, m$_2$$^{7,O3'}$GppppG, and m$_2$$^{7,O3'}$GppppG.

An mRNA may instead or additionally include a chain terminating nucleoside. For example, a chain terminating nucleoside may include those nucleosides deoxygenated at the 2' and/or 3' positions of their sugar group. Such species may include 3'-deoxyadenosine (cordycepin), 3'-deoxyuridine, 3'-deoxycytosine, 3'-deoxyguanosine, 3'-deoxythymine, and 2',3'-dideoxynucleosides, such as 2',3'-dideoxyadenosine, 2',3'-dideoxyuridine, 2',3'-dideoxycytosine, 2',3'-dideoxyguanosine, and 2',3'-dideoxythymine. In some embodiments, incorporation of a chain terminating nucleotide into an mRNA, for example at the 3'-terminus, may result in stabilization of the mRNA, as described, for example, in International Patent Publication No. WO 2013/103659.

An mRNA may instead or additionally include a stem loop, such as a histone stem loop. A stem loop may include 2, 3, 4, 5, 6, 7, 8, or more nucleotide base pairs. For example, a stem loop may include 4, 5, 6, 7, or 8 nucleotide base pairs. A stem loop may be located in any region of an mRNA. For example, a stem loop may be located in, before, or after an untranslated region (a 5' untranslated region or a 3' untranslated region), a coding region, or a polyA sequence or tail. In some embodiments, a stem loop may affect one or more function(s) of an mRNA, such as initiation of translation, translation efficiency, and/or transcriptional termination.

An mRNA may instead or additionally include a polyA sequence and/or polyadenylation signal. A polyA sequence may be comprised entirely or mostly of adenine nucleotides or analogs or derivatives thereof. A polyA sequence may be a tail located adjacent to a 3' untranslated region of an mRNA. In some embodiments, a polyA sequence may affect the nuclear export, translation, and/or stability of an mRNA.

An mRNA may instead or additionally include a microRNA binding site.

MicroRNA Binding Sites

In some embodiments, the OX40L, IL-23 and IL-36γ encoding mRNAs comprises one or more microRNA binding sites. microRNAs (or miRNA) are 19-25 nucleotides long noncoding RNAs that bind to the 3'UTR of nucleic acid molecules and down-regulate gene expression either by reducing nucleic acid molecule stability or by inhibiting translation.

By engineering microRNA target sequences into an mRNA, one can target the molecule for degradation or reduced translation, provided the microRNA in question is available. In some embodiments, the miRNA binding site (e.g., miR-122 binding site) binds to the corresponding mature miRNA that is part of an active RNA-induced silencing complex (RISC) containing Dicer. In some embodiments, binding of the miRNA binding site to the corresponding miRNA in RISC degrades the mRNA containing the miRNA binding site or prevents the mRNA from being translated.

Some microRNAs, e.g., miR-122, are abundant in normal tissue but are present in much lower levels in cancer or tumor tissue. Thus, engineering microRNA target sequences (i.e., microRNA binding site) into the OX40L, IL-23 and IL-36γ encoding mRNAs (e.g., in a 3'UTR like region or other region) can effectively target the molecule for degradation or reduced translation in normal tissue (where the microRNA is abundant) while providing high levels of translation in the cancer or tumor tissue (where the microRNA is present in much lower levels). This provides a tumor-targeting approach for the methods and compositions of the disclosure.

In some embodiments, the microRNA binding site (e.g., miR-122 binding site) is fully complementary to miRNA (e.g., miR-122), thereby degrading the mRNA fused to the miRNA binding site. In other embodiments, the miRNA binding site is not fully complementary to the corresponding miRNA. In certain embodiments, the miRNA binding site (e.g., miR-122 binding site) is the same length as the corresponding miRNA (e.g., miR-122). In other embodiments, the microRNA binding site (e.g., miR-122 binding site) is one nucleotide shorter than the corresponding microRNA (e.g., miR-122, which has 22 nts) at the 5' terminus, the 3' terminus, or both. In still other embodiments, the microRNA binding site (e.g., miR-122 binding site) is two nucleotides shorter than the corresponding microRNA (e.g., miR-122) at the 5' terminus, the 3' terminus, or both. In yet other embodiments, the microRNA binding site (e.g., miR-122 binding site) is three nucleotides shorter than the corresponding microRNA (e.g., miR-122) at the 5' terminus, the 3' terminus, or both. In some embodiments, the microRNA binding site (e.g., miR-122 binding site) is four nucleotides shorter than the corresponding microRNA (e.g., miR-122) at the 5' terminus, the 3' terminus, or both. In other embodiments, the microRNA binding site (e.g., miR-122 binding site) is five nucleotides shorter than the corresponding microRNA (e.g., miR-122) at the 5' terminus, the 3' terminus, or both. In some embodiments, the microRNA binding site (e.g., miR-122 binding site) is six nucleotides shorter than the corresponding microRNA (e.g., miR-122) at the 5' terminus, the 3' terminus, or both. In other embodiments, the microRNA binding site (e.g., miR-122 binding site) is seven nucleotides shorter than the corresponding microRNA (e.g., miR-122) at the 5' terminus or the 3' terminus. In other embodiments, the microRNA binding site (e.g., miR-122 binding site) is eight nucleotides shorter than the corresponding microRNA (e.g., miR-122) at the 5' terminus or the 3' terminus. In other embodiments, the microRNA binding site (e.g., miR-122 binding site) is nine nucleotides shorter than the corresponding microRNA (e.g., miR-122) at the 5' terminus or the 3' terminus. In other embodiments, the microRNA binding site (e.g., miR-122 binding site) is ten nucleotides shorter than the corresponding microRNA (e.g., miR-122) at the 5' terminus or the 3' terminus. In other embodiments, the microRNA binding site (e.g., miR-122 binding site) is eleven nucleotides shorter than the corresponding microRNA (e.g., miR-122) at the 5' terminus or the 3' terminus. In other embodiments, the microRNA binding site (e.g., miR-122 binding site) is twelve nucleotides shorter than the corresponding microRNA (e.g., miR-122) at the 5' terminus or the 3' terminus. The miRNA binding sites that are shorter than the corresponding miRNAs are still capable of degrading the mRNA incorporating one or more of the miRNA binding sites or preventing the mRNA from translation.

In some embodiments, the microRNA binding site (e.g., miR-122 binding site) has sufficient complementarity to miRNA (e.g., miR-122) so that a RISC complex comprising the miRNA (e.g., miR-122) cleaves the mRNA comprising the microRNA binding site. In other embodiments, the microRNA binding site (e.g., miR-122 binding site) has imperfect complementarity so that a RISC complex comprising the miRNA (e.g., miR-122) induces instability in the mRNA comprising the microRNA binding site. In another embodiment, the microRNA binding site (e.g., miR-122 binding site) has imperfect complementarity so that a RISC complex comprising the miRNA (e.g., miR-122) represses transcription of the mRNA comprising the microRNA binding site. In one embodiment, the miRNA binding site (e.g., miR-122 binding site) has one mismatch from the corresponding miRNA (e.g., miR-122). In another embodiment, the miRNA binding site has two mismatches from the corresponding miRNA. In other embodiments, the miRNA binding site has three mismatches from the corresponding miRNA. In other embodiments, the miRNA binding site has four mismatches from the corresponding miRNA. In some embodiments, the miRNA binding site has five mismatches from the corresponding miRNA. In other embodiments, the miRNA binding site has six mismatches from the corresponding miRNA. In certain embodiments, the miRNA binding site has seven mismatches from the corresponding miRNA. In other embodiments, the miRNA binding site has eight mismatches from the corresponding miRNA. In other embodiments, the miRNA binding site has nine mismatches from the corresponding miRNA. In other embodiments, the miRNA binding site has ten mismatches from the corresponding miRNA. In other embodiments, the miRNA binding site has eleven mismatches from the corresponding miRNA. In other embodiments, the miRNA binding site has twelve mismatches from the corresponding miRNA.

In certain embodiments, the miRNA binding site (e.g., miR-122 binding site) has at least about ten contiguous nucleotides complementary to at least about ten contiguous nucleotides of the corresponding miRNA (e.g., miR-122), at least about eleven contiguous nucleotides complementary to at least about eleven contiguous nucleotides of the corresponding miRNA, at least about twelve contiguous nucleotides complementary to at least about twelve contiguous nucleotides of the corresponding miRNA, at least about thirteen contiguous nucleotides complementary to at least about thirteen contiguous nucleotides of the corresponding miRNA, or at least about fourteen contiguous nucleotides complementary to at least about fourteen contiguous nucleotides of the corresponding miRNA. In some embodiments, the miRNA binding sites have at least about fifteen contiguous nucleotides complementary to at least about fifteen contiguous nucleotides of the corresponding miRNA, at least about sixteen contiguous nucleotides complementary to at least about sixteen contiguous nucleotides of the corresponding miRNA, at least about seventeen contiguous nucleotides complementary to at least about seventeen contiguous nucleotides of the corresponding miRNA, at least about eighteen contiguous nucleotides complementary to at least about eighteen contiguous nucleotides of the corresponding miRNA, at least about nineteen contiguous nucleotides complementary to at least about nineteen contiguous nucleotides of the corresponding miRNA, at least about twenty contiguous nucleotides complementary to at least about twenty contiguous nucleotides of the corresponding miRNA, or at least about twenty one contiguous nucleotides complementary to at least about twenty one contiguous nucleotides of the corresponding miRNA.

In some embodiments, the OX40L, IL-23 or IL-36γ encoding mRNAs comprise at least one miR-122 binding site, at least two miR-122 binding sites, at least three miR-122 binding sites, at least four miR-122 binding sites, or at least five miR-122 binding sites. In some embodiments, the miRNA binding site binds miR-122 or is complementary to miR-122. In some embodiments, the miRNA binding site binds to miR-122-3p or miR-122-5p. In some embodiments, the miRNA binding site comprises a nucleotide sequence at least 80%, at least 85%, at least 90%, at least 95%, or 100% identical to SEQ ID NO: 14, wherein the miRNA binding site binds to miR-122. In another particular aspect, the miRNA binding site comprises a nucleotide sequence at least 80%, at least 85%, at least 90%, at least 95%, or 100% identical to SEQ ID NO: 20, wherein the miRNA binding site binds to miR-122. These sequences are shown below in Table 2.

TABLE 2 miR-122 and miR-122 binding sites

| SEQ ID NO. | Description | Sequence |
|---|---|---|
| SEQ ID NO: 12 | miR-122 | CCUUAGCAGAGCUGUGGAGUGU GACAAUGGUGUUUGUGUCUAAA CUAUCAAACGCCAUUAUCACAC UAAAUAGCUACUGCUAGGC |

TABLE 2-continued miR-122 and miR-122 binding sites

| SEQ ID NO. | Description | Sequence |
|---|---|---|
| SEQ ID NO: 13 | miR-122-3p | AACGCCAUUAUCACACUAAAUA |
| SEQ ID NO: 14 | miR-122-3p binding site | UAUUUAGUGUGAUAAUGGCGUU |
| SEQ ID NO: 19 | miR-122-5p | UGGAGUGUGACAAUGGUGUUUG |
| SEQ ID NO: 20 | miR-122-5p binding site | CAAACACCAUUGUCACACUCCA |

In some embodiments, a miRNA binding site (e.g., miR-122 binding site) is inserted in the mRNA in any position (e.g., 3' UTR); the insertion site in the mRNA can be anywhere in the mRNA as long as the insertion of the miRNA binding site in the mRNA does not interfere with the translation of the functional OX40L, IL-23 and IL-36γ polypeptides in the absence of the corresponding miRNA (e.g., miR122); and in the presence of the miRNA (e.g., miR122), the insertion of the miRNA binding site in the mRNA and the binding of the miRNA binding site to the corresponding miRNA are capable of degrading the mRNA or preventing the translation of the mRNA. In one embodiment, a miRNA binding site is inserted in a 3'UTR of the mRNA.

In certain embodiments, a miRNA binding site is inserted in at least about 30 nucleotides downstream from the stop codons of the OX40L, IL-23 and/or IL-36γ encoding mRNA. In other embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codons of the OX40L, IL-23 and/or IL-36γ encoding mRNA. In other embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codons of the OX40L, IL-23 and/or IL-36γ encoding mRNAs.

Modified mRNAs

In some embodiments, an mRNA of the disclosure comprises one or more modified nucleobases, nucleosides, or nucleotides (termed "modified mRNAs" or "mmRNAs"). In some embodiments, modified mRNAs may have useful properties, including enhanced stability, intracellular retention, enhanced translation, and/or the lack of a substantial induction of the innate immune response of a cell into which the mRNA is introduced, as compared to a reference unmodified mRNA. Therefore, use of modified mRNAs may enhance the efficiency of protein production, intracellular retention of nucleic acids, as well as possess reduced immunogenicity.

In some embodiments, an mRNA includes one or more (e.g., 1, 2, 3 or 4) different modified nucleobases, nucleosides, or nucleotides. In some embodiments, an mRNA includes one or more (e.g., 1, 2, 3, 4, 5, 6, 7, 8, 9, 10, 20, 30, 40, 50, 60, 70, 80, 90, 100, or more) different modified nucleobases, nucleosides, or nucleotides. In some embodiments, the modified mRNA may have reduced degradation in a cell into which the mRNA is introduced, relative to a corresponding unmodified mRNA.

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridine or 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($τm^5U$), 1-taurinomethyl-pseudouridine, 5-taurinomethyl-2-thio-uridine ($τm^5s^2U$), 1-taurinomethyl-4-thio-pseudouridine, 5-methyl-uridine ($m^5U$, i.e., having the nucleobase deoxythymine), 1-methyl-pseudouridine ($m^1ψ$), 5-methyl-2-thio-uridine ($m^5s^2U$), 1-methyl-4-thio-pseudouridine ($m^1ψ$), 4-thio-1-methyl-pseudouridine, 3-methyl-pseudouridine ($m^3ψ$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine ($acp^3U$), 1-methyl-3-(3-amino-3-carboxypropyl) pseudouridine ($acp^3 ψ$), 5-(isopentenylaminomethyl)uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine (ψm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)]uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine ($m^3C$), N4-acetyl-cytidine ($ac^4C$), 5-formyl-cytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine ($s^2C$), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k_2C$), α-thio-cytidine, 2'-O-methyl-cytidine (Cm), 5,2'-O-dimethyl-cytidine ($m^5Cm$), N4-acetyl-2'-O-methyl-cytidine ($ac^4Cm$), N4,2'-O-dimethyl-cytidine ($m^4Cm$), 5-formyl-2'-O-methyl-cytidine ($f^5Cm$), N4,N4,2'-O-trimethyl-cytidine ($m^4_2Cm$), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include α-thio-adenosine, 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2, 6-diaminopurine, 7-deaza-8-aza-2,6-diaminopurine, 1-methyl-adenosine ($m^1A$), 2-methyl-adenine ($m^2A$), N6-methyl-adenosine ($m^6A$), 2-methylthio-N6-methyl-adenosine ($ms^2m^6A$), N6-isopentenyl-adenosine ($i^6A$), 2-methylthio-N6-isopentenyl-adenosine ($ms^2i^6A$), N6-(cis-hydroxyisopentenyl)adenosine ($io^6A$), 2-methylthio-N6-(cis-hydroxyisopentenyl)adenosine ($ms^2io^6A$), N6-glycinyl-carbamoyl-adenosine ($g^6A$), N6-threonylcarbamoyl-adenosine ($t^6A$), N6-methyl-N6-threonylcarbamoyl-adenosine ($m^6t^6A$), 2-methylthio-N6-threonylcarbamoyl-adenosine ($ms^2g^6A$), N6,N6-dimethyl-adenosine ($m^6_2A$), N6-hydroxynorvalylcarbamoyl-adenosine ($hn^6A$), 2-methylthio-N6-hydroxynorvalylcarbamoyl-adenosine ($ms^2hn^6A$), N6-acetyl-adenosine ($ac^6A$), 7-methyl-adenine, 2-methylthio-adenine, 2-methoxy-adenine, α-thio-adenosine, 2'-O-methyl-adenosine (Am), N6,2'-O-dimethyl-adenosine ($m^6Am$), N6,N6,2'-O-trimethyl-adenosine ($m^6_2Am$), 1,2'-O-dimethyl-adenosine ($m^1Am$), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-aminopentaoxanonadecyl)-adenosine.

In some embodiments, the modified nucleobase is a modified guanine. Exemplary nucleobases and nucleosides having a modified guanine include α-thio-guanosine, inosine (I), 1-methyl-inosine ($m^1I$), wyosine (imG), methyl-wyosine (mimG), 4-demethyl-wyosine (imG-14), isowyosine (imG2), wybutosine (yW), peroxywybutosine ($o_2yW$), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine (preQo), 7-aminomethyl-7-deaza-guanosine (preQi), archaeosine (G+), 7-deaza-8-aza-guanosine, 6-thio-guanosine, 6-thio-7-deaza-guanosine, 6-thio-7-deaza-8-aza-guanosine, 7-methyl-guanosine ($m^7G$), 6-thio-7-methyl-guanosine, 7-methyl-inosine, 6-methoxy-guanosine, 1-methyl-guanosine ($m^1G$), N2-methyl-guanosine ($m^2G$), N2,N2-dimethyl-guanosine ($m^2_2G$), N2,7-dimethyl-guanosine ($m^{2,7}G$), N2, N2,7-dimethyl-guanosine ($m^{2,2,7}G$), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine ($m^2Gm$), N2,N2-dimethyl-2'-O-methyl-guanosine ($m^2_2$ Gm), 1-methyl-2'-O-methyl-guanosine (m$^1$Gm), N2,7-dimethyl-2'-O-methyl-guanosine (m$^{2'7}$Gm), 2'-O-methyl-inosine (Im), 1,2'-O-dimethyl-inosine (m$^1$Im), 2'-O-ribosylguanosine (phosphate) (Gr(p)), 1-thio-guanosine, 06-methyl-guanosine, 2'-F-ara-guanosine, and 2'-F-guanosine.

In some embodiments, an mRNA of the disclosure includes a combination of one or more of the aforementioned modified nucleobases (e.g., a combination of 2, 3 or 4 of the aforementioned modified nucleobases).

In some embodiments, the modified nucleobase is pseudouridine (ψ), N1-methylpseudouridine (m$^1$ψ), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine. In some embodiments, an mRNA of the disclosure includes a combination of one or more of the aforementioned modified nucleobases (e.g., a combination of 2, 3 or 4 of the aforementioned modified nucleobases).

In some embodiments, the modified nucleobase is a modified cytosine. Exemplary nucleobases and nucleosides having a modified cytosine include N4-acetyl-cytidine (ac$^4$C), 5-methyl-cytidine (m$^5$C), 5-halo-cytidine (e.g., 5-iodo-cytidine), 5-hydroxymethyl-cytidine (hm$^5$C), 1-methyl-pseudoisocytidine, 2-thio-cytidine (s$^2$C), 2-thio-5-methyl-cytidine. In some embodiments, an mRNA of the disclosure includes a combination of one or more of the aforementioned modified nucleobases (e.g., a combination of 2, 3 or 4 of the aforementioned modified nucleobases).

In some embodiments, the modified nucleobase is a modified adenine. Exemplary nucleobases and nucleosides having a modified adenine include 7-deaza-adenine, 1-methyl-adenosine (m$^1$A), 2-methyl-adenine (m$^2$A), N6-methyl-adenosine (m$^6$A). In some embodiments, an mRNA of the disclosure includes a combination of one or more of the aforementioned modified nucleobases (e.g., a combination of 2, 3 or 4 of the aforementioned modified nucleobases).

In some embodiments, the modified nucleobase is a modified guanine. Exemplary nucleobases and nucleosides having a modified guanine include inosine (I), 1-methyl-inosine (m$^1$I), wyosine (imG), methylwyosine (mimG), 7-deaza-guanosine, 7-cyano-7-deaza-guanosine (preQo), 7-aminomethyl-7-deaza-guanosine (preQi), 7-methyl-guanosine (m$^7$G), 1-methyl-guanosine (m$^1$G), 8-oxo-guanosine, 7-methyl-8-oxo-guanosine. In some embodiments, an mRNA of the disclosure includes a combination of one or more of the aforementioned modified nucleobases (e.g., a combination of 2, 3 or 4 of the aforementioned modified nucleobases).

In some embodiments, the modified nucleobase is 1-methyl-pseudouridine (m$^1$ψ), 5-methoxy-uridine (mo$^5$U), 5-methyl-cytidine (m$^5$C), pseudouridine (ψ), α-thio-guanosine, or α-thio-adenosine. In some embodiments, an mRNA of the disclosure includes a combination of one or more of the aforementioned modified nucleobases (e.g., a combination of 2, 3 or 4 of the aforementioned modified nucleobases).

In some embodiments, the mRNA comprises pseudouridine (ψ). In some embodiments, the mRNA comprises pseudouridine (ψ) and 5-methyl-cytidine (m$^5$C). In some embodiments, the mRNA comprises 1-methyl-pseudouridine (m$^1$ψ). In some embodiments, the mRNA comprises 1-methyl-pseudouridine (m$^1$ψ) and 5-methyl-cytidine (m$^5$C). In some embodiments, the mRNA comprises 2-thiouridine (s$^2$U). In some embodiments, the mRNA comprises 2-thiouridine and 5-methyl-cytidine (m$^5$C). In some embodiments, the mRNA comprises 5-methoxy-uridine (mo$^5$U). In some embodiments, the mRNA comprises 5-methoxy-uridine (mo$^5$U) and 5-methyl-cytidine (m$^5$C). In some embodiments, the mRNA comprises 2'-O-methyl uridine. In some embodiments, the mRNA comprises 2'-O-methyl uridine and 5-methyl-cytidine (m$^5$C). In some embodiments, the mRNA comprises N6-methyl-adenosine (m$^6$A). In some embodiments, the mRNA comprises N6-methyl-adenosine (m$^6$A) and 5-methyl-cytidine (m$^5$C).

In certain embodiments, an mRNA of the disclosure is uniformly modified (i.e., fully modified, modified throughout the entire sequence) for a particular modification. In some embodiments, an mRNA of the disclosure is modified wherein at least 95%, at least 96%, at least 97%, at least 98%, at least 99% or 100% of a specified nucleotide or nucleobase is modified. For example, an mRNA can be uniformly modified with 5-methyl-cytidine (m$^5$C), meaning that all cytosine residues in the mRNA sequence are replaced with 5-methyl-cytidine (m$^5$C). Similarly, mRNAs of the disclosure can be uniformly modified for any type of nucleoside residue present in the sequence by replacement with a modified residue such as those set forth above. In some embodiments, an mRNA of the disclosure is uniformly modified with 1-methyl pseudouridine (m$^1$ψ), meaning that all uridine residues in the mRNA sequence are replaced with 1-methyl pseudouridine (m$^1$ψ). In some embodiments, at least 95%, at least 96%, at least 97%, at least 98%, at least 99% or 100% of uridines are 1-methyl pseudouridine (m$^1$ψ).

In some embodiments, an mRNA of the disclosure may be modified in a coding region (e.g., an open reading frame encoding a polypeptide). In other embodiments, an mRNA may be modified in regions besides a coding region. For example, in some embodiments, a 5'-UTR and/or a 3'-UTR are provided, wherein either or both may independently contain one or more different nucleoside modifications. In such embodiments, nucleoside modifications may also be present in the coding region.

Examples of nucleoside modifications and combinations thereof that may be present in mmRNAs of the present disclosure include, but are not limited to, those described in PCT Patent Application Publications: WO2012045075, WO2014081507, WO2014093924, WO2014164253, and WO2014159813.

The mRNAs of the disclosure can include a combination of modifications to the sugar, the nucleobase, and/or the internucleoside linkage. These combinations can include any one or more modifications described herein.

Examples of modified nucleosides and modified nucleoside combinations are provided below in Table 3 and Table 4. These combinations of modified nucleotides can be used to form the mmRNAs of the disclosure. In certain embodiments, the modified nucleosides may be partially or completely substituted for the natural nucleotides of the mRNAs of the disclosure. As a non-limiting example, the natural nucleotide uridine may be substituted with a modified nucleoside described herein. In another non-limiting example, the natural nucleoside uridine may be partially substituted (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9% of the natural uridines) with at least one of the modified nucleoside disclosed herein.

TABLE 3

Combinations of Nucleoside Modifications

| Modified Nucleotide | Modified Nucleotide Combination |
|---|---|
| α-thio-cytidine | α-thio-cytidine/5-iodo-uridine |
| | α-thio-cytidine/N1-methyl-pseudouridine |
| | α-thio-cytidine/α-thio-uridine |
| | α-thio-cytidine/5-methyl-uridine |
| | α-thio-cytidine/pseudo-uridine |
| | about 50% of the cytosines are α-thio-cytidine |
| pseudoisocytidine | pseudoisocytidine/5-iodo-uridine |
| | pseudoisocytidine/N1-methyl-pseudouridine |
| | pseudoisocytidine/α-thio-uridine |
| | pseudoisocytidine/5-methyl-uridine |
| | pseudoisocytidine/pseudouridine |
| | about 25% of cytosines are pseudoisocytidine |
| | pseudoisocytidine/about 50% of uridines are N1-methyl-pseudouridine and about 50% of uridines are pseudouridine |
| | pseudoisocytidine/about 25% of uridines are N1-methyl-pseudouridine and about 25% of uridines are pseudouridine |
| pyrrolo-cytidine | pyrrolo-cytidine/5-iodo-uridine |
| | pyrrolo-cytidine/N1-methyl-pseudouridine |
| | pyrrolo-cytidine/α-thio-uridine |
| | pyrrolo-cytidine/5-methyl-uridine |
| | pyrrolo-cytidine/pseudouridine |
| | about 50% of the cytosines are pyrrolo-cytidine |
| 5-methyl-cytidine | 5-methyl-cytidine/5-iodo-uridine |
| | 5-methyl-cytidine/N1-methyl-pseudouridine |
| | 5-methyl-cytidine/α-thio-uridine |
| | 5-methyl-cytidine/5-methyl-uridine |
| | 5-methyl-cytidine/pseudouridine |
| | about 25% of cytosines are 5-methyl-cytidine |
| | about 50% of cytosines are 5-methyl-cytidine |
| | 5-methyl-cytidine/5-methoxy-uridine |
| | 5-methyl-cytidine/5-bromo-uridine |
| | 5-methyl-cytidine/2-thio-uridine |
| | 5-methyl-cytidine/about 50% of uridines are 2-thio-uridine |
| | about 50% of uridines are 5-methyl-cytidine/about 50% of uridines are 2-thio-uridine |
| N4-acetyl-cytidine | N4-acetyl-cytidine/5-iodo-uridine |
| | N4-acetyl-cytidine/N1-methyl-pseudouridine |
| | N4-acetyl-cytidine/α-thio-uridine |
| | N4-acetyl-cytidine/5-methyl-uridine |
| | N4-acetyl-cytidine/pseudouridine |
| | about 50% of cytosines are N4-acetyl-cytidine |
| | about 25% of cytosines are N4-acetyl-cytidine |
| | N4-acetyl-cytidine/5-methoxy-uridine |
| | N4-acetyl-cytidine/5-bromo-uridine |
| | N4-acetyl-cytidine/2-thio-uridine |
| | about 50% of cytosines are N4-acetyl-cytidine/about 50% of uridines are 2-thio-uridine |

TABLE 4

Modified Nucleosides and Combinations Thereof 1-(2,2,2-Trifluoroethyl)pseudo-UTP
1-Ethyl-pseudo-UTP
1-Methyl-pseudo-U-alpha-thio-TP
1-methyl-pseudouridine TP, ATP, GTP, CTP
1-methyl-pseudo-UTP/5-methyl-CTP/ATP/GTP
1-methyl-pseudo-UTP/CTP/ATP/GTP
1-Propyl-pseudo-UTP
25% 5-Aminoallyl-CTP + 75% CTP/25% 5-Methoxy-UTP + 75% UTP
25% 5-Aminoallyl-CTP + 75% CTP/75% 5-Methoxy-UTP + 25% UTP
25% 5-Bromo-CTP + 75% CTP/25% 5-Methoxy-UTP + 75% UTP
25% 5-Bromo-CTP + 75% CTP/75% 5-Methoxy-UTP + 25% UTP
25% 5-Bromo-CTP + 75% CTP/1-Methyl-pseudo-UTP
25% 5-Carboxy-CTP + 75% CTP/25% 5-Methoxy-UTP + 75% UTP
25% 5-Carboxy-CTP + 75% CTP/75% 5-Methoxy-UTP + 25% UTP
25% 5-Ethyl-CTP + 75% CTP/25% 5-Methoxy-UTP + 75% UTP
25% 5-Ethyl-CTP + 75% CTP/75% 5-Methoxy-UTP + 25% UTP
25% 5-Ethynyl-CTP + 75% CTP/25% 5-Methoxy-UTP + 75% UTP
25% 5-Ethynyl-CTP + 75% CTP/75% 5-Methoxy-UTP + 25% UTP
25% 5-Fluoro-CTP + 75% CTP/25% 5-Methoxy-UTP + 75% UTP
25% 5-Fluoro-CTP + 75% CTP/75% 5-Methoxy-UTP + 25% UTP
25% 5-Formyl-CTP + 75% CTP/25% 5-Methoxy-UTP + 75% UTP
25% 5-Formyl-CTP + 75% CTP/75% 5-Methoxy-UTP + 25% UTP
25% 5-Hydroxymethyl-CTP + 75% CTP/25% 5-Methoxy-UTP + 75% UTP
25% 5-Hydroxymethyl-CTP + 75% CTP/75% 5-Methoxy-UTP + 25% UTP
25% 5-Iodo-CTP + 75% CTP/25% 5-Methoxy-UTP + 75% UTP
25% 5-Iodo-CTP + 75% CTP/75% 5-Methoxy-UTP + 25% UTP
25% 5-Methoxy-CTP + 75% CTP/25% 5-Methoxy-UTP + 75% UTP
25% 5-Methoxy-CTP + 75% CTP/75% 5-Methoxy-UTP + 25% UTP
25% 5-Methyl-CTP + 75% CTP/25% 5-Methoxy-UTP + 75% 1-Methyl-pseudo-UTP
25% 5-Methyl-CTP + 75% CTP/25% 5-Methoxy-UTP + 75% UTP
25% 5-Methyl-CTP + 75% CTP/50% 5-Methoxy-UTP + 50% 1-Methyl-pseudo-UTP
25% 5-Methyl-CTP + 75% CTP/50% 5-Methoxy-UTP + 50% UTP
25% 5-Methyl-CTP + 75% CTP/5-Methoxy-UTP
25% 5-Methyl-CTP + 75% CTP/75% 5-Methoxy-UTP + 25% 1-Methyl-pseudo-UTP
25% 5-Methyl-CTP + 75% CTP/75% 5-Methoxy-UTP + 25% UTP
25% 5-Phenyl-CTP + 75% CTP/25% 5-Methoxy-UTP + 75% UTP
25% 5-Phenyl-CTP + 75% CTP/75% 5-Methoxy-UTP + 25% UTP
25% 5-Trifluoromethyl-CTP + 75% CTP/25% 5-Methoxy-UTP + 75% UTP
25% 5-Trifluoromethyl-CTP + 75% CTP/75% 5-Methoxy-UTP + 25% UTP
25% 5-Trifluoromethyl-CTP + 75% CTP/1-Methyl-pseudo-UTP
25% N4-Ac-CTP + 75% CTP/25% 5-Methoxy-UTP + 75% UTP
25% N4-Ac-CTP + 75% CTP/75% 5-Methoxy-UTP + 25% UTP
25% N4-Bz-CTP + 75% CTP/25% 5-Methoxy-UTP + 75% UTP
25% N4-Bz-CTP + 75% CTP/75% 5-Methoxy-UTP + 25% UTP
25% N4-Methyl-CTP + 75% CTP/25% 5-Methoxy-UTP + 75% UTP
25% N4-Methyl-CTP + 75% CTP/75% 5-Methoxy-UTP + 25% UTP
25% Pseudo-iso-CTP + 75% CTP/25% 5-Methoxy-UTP + 75% UTP
25% Pseudo-iso-CTP + 75% CTP/75% 5-Methoxy-UTP + 25% UTP
25% 5-Bromo-CTP/75% CTP/Pseudo-UTP
25% 5-methoxy-UTP/25% 5-methyl-CTP/ATP/GTP
25% 5-methoxy-UTP/5-methyl-CTP/ATP/GTP
25% 5-methoxy-UTP/75% 5-methyl-CTP/ATP/GTP
25% 5-methoxy-UTP/CTP/ATP/GTP
25% 5-metoxy-UTP/50% 5-methyl-CTP/ATP/GTP
2-Amino-ATP
2-Thio-CTP
2-thio-pseudouridine TP, ATP, GTP, CTP
2-Thio-pseudo-UTP
2-Thio-UTP
3-Methyl-CTP
3-Methyl-pseudo-UTP
4-Thio-UTP
50% 5-Bromo-CTP + 50% CTP/1-Methyl-pseudo-UTP
50% 5-Hydroxymethyl-CTP + 50% CTP/1-Methyl-pseudo-UTP
50% 5-methoxy-UTP/5-methyl-CTP/ATP/GTP
50% 5-Methyl-CTP + 50% CTP/25% 5-Methoxy-UTP + 75% 1-Methyl-pseudo-UTP
50% 5-Methyl-CTP + 50% CTP/25% 5-Methoxy-UTP + 75% UTP
50% 5-Methyl-CTP + 50% CTP/50% 5-Methoxy-UTP + 50% 1-Methyl-pseudo-UTP
50% 5-Methyl-CTP + 50% CTP/50% 5-Methoxy-UTP + 50% UTP
50% 5-Methyl-CTP + 50% CTP/5-Methoxy-UTP
50% 5-Methyl-CTP + 50% CTP/75% 5-Methoxy-UTP + 25% 1-Methyl-pseudo-UTP
50% 5-Methyl-CTP + 50% CTP/75% 5-Methoxy-UTP + 25% UTP
50% 5-Trifluoromethyl-CTP + 50% CTP/1-Methyl-pseudo-UTP
50% 5-Bromo-CTP/50% CTP/Pseudo-UTP
50% 5-methoxy-UTP/25% 5-methyl-CTP/ATP/GTP
50% 5-methoxy-UTP/50% 5-methyl-CTP/ATP/GTP
50% 5-methoxy-UTP/75% 5-methyl-CTP/ATP/GTP
50% 5-methoxy-UTP/CTP/ATP/GTP
5-Aminoallyl-CTP
5-Aminoallyl-CTP/5-Methoxy-UTP
5-Aminoallyl-UTP
5-Bromo-CTP
5-Bromo-CTP/5-Methoxy-UTP
5-Bromo-CTP/1-Methyl-pseudo-UTP
5-Bromo-CTP/Pseudo-UTP
5-bromocytidine TP, ATP, GTP, UTP

TABLE 4-continued

Modified Nucleosides and Combinations Thereof

5-Bromo-UTP
5-Carboxy-CTP/5-Methoxy-UTP
5-Ethyl-CTP/5-Methoxy-UTP
5-Ethynyl-CTP/5-Methoxy-UTP
5-Fluoro-CTP/5-Methoxy-UTP
5-Formyl-CTP/5-Methoxy-UTP
5-Hydroxy-methyl-CTP/5-Methoxy-UTP
5-Hydroxymethyl-CTP
5-Hydroxymethyl-CTP/1-Methyl-pseudo-UTP
5-Hydroxymethyl-CTP/5-Methoxy-UTP
5-hydroxymethyl-cytidine TP, ATP, GTP, UTP
5-Iodo-CTP/5-Methoxy-UTP
5-Me-CTP/5-Methoxy-UTP
5-Methoxy carbonyl methyl-UTP
5-Methoxy-CTP/5-Methoxy-UTP
5-methoxy-uridine TP, ATP, GTP, UTP
5-methoxy-UTP
5-Methoxy-UTP
5-Methoxy-UTP/N6-Isopentenyl-ATP
5-methoxy-UTP/25% 5-methyl-CTP/ATP/GTP
5-methoxy-UTP/5-methyl-CTP/ATP/GTP
5-methoxy-UTP/75% 5-methyl-CTP/ATP/GTP
5-methoxy-UTP/CTP/ATP/GTP
5-Methyl-2-thio-UTP
5-Methylaminomethyl-UTP
5-Methyl-CTP/5-Methoxy-UTP
5-Methyl-CTP/5-Methoxy-UTP(cap 0)
5-Methyl-CTP/5-Methoxy-UTP(No cap)
5-Methyl-CTP/25% 5-Methoxy-UTP + 75% 1-Methyl-pseudo-UTP
5-Methyl-CTP/25% 5-Methoxy-UTP + 75% UTP
5-Methyl-CTP/50% 5-Methoxy-UTP + 50% 1-Methyl-pseudo-UTP
5-Methyl-CTP/50% 5-Methoxy-UTP + 50% UTP
5-Methyl-CTP/5-Methoxy-UTP/N6-Me-ATP
5-Methyl-CTP/75% 5-Methoxy-UTP + 25% 1-Methyl-pseudo-UTP
5-Methyl-CTP/75% 5-Methoxy-UTP + 25% UTP
5-Phenyl-CTP/5-Methoxy-UTP
5-Trifluoro-methyl-CTP/5-Methoxy-UTP
5-Trifluoromethyl-CTP
5-Trifluoromethyl-CTP/5-Methoxy-UTP
5-Trifluoromethyl-CTP/1-Methyl-pseudo-UTP
5-Trifluoromethyl-CTP/Pseudo-UTP
5-Trifluoromethyl-UTP
5-trifluromethylcytidine TP, ATP, GTP, UTP
75% 5-Aminoallyl-CTP + 25% CTP/25% 5-Methoxy-UTP + 75% UTP
75% 5-Aminoallyl-CTP + 25% CTP/75% 5-Methoxy-UTP + 25% UTP
75% 5-Bromo-CTP + 25% CTP/25% 5-Methoxy-UTP + 75% UTP
75% 5-Bromo-CTP + 25% CTP/75% 5-Methoxy-UTP + 25% UTP
75% 5-Carboxy-CTP + 25% CTP/25% 5-Methoxy-UTP + 75% UTP
75% 5-Carboxy-CTP + 25% CTP/75% 5-Methoxy-UTP + 25% UTP
75% 5-Ethyl-CTP + 25% CTP/25% 5-Methoxy-UTP + 75% UTP
75% 5-Ethyl-CTP + 25% CTP/75% 5-Methoxy-UTP + 25% UTP
75% 5-Ethynyl-CTP + 25% CTP/25% 5-Methoxy-UTP + 75% UTP
75% 5-Ethynyl-CTP + 25% CTP/75% 5-Methoxy-UTP + 25% UTP
75% 5-Fluoro-CTP + 25% CTP/25% 5-Methoxy-UTP + 75% UTP
75% 5-Fluoro-CTP + 25% CTP/75% 5-Methoxy-UTP + 25% UTP
75% 5-Formyl-CTP + 25% CTP/25% 5-Methoxy-UTP + 75% UTP
75% 5-Formyl-CTP + 25% CTP/75% 5-Methoxy-UTP + 25% UTP
75% 5-Hydroxymethyl-CTP + 25% CTP/25% 5-Methoxy-UTP + 75% UTP
75% 5-Hydroxymethyl-CTP + 25% CTP/75% 5-Methoxy-UTP + 25% UTP
75% 5-Iodo-CTP + 25% CTP/25% 5-Methoxy-UTP + 75% UTP
75% 5-Iodo-CTP + 25% CTP/75% 5-Methoxy-UTP + 25% UTP
75% 5-Methoxy-CTP + 25% CTP/25% 5-Methoxy-UTP + 75% UTP
75% 5-Methoxy-CTP + 25% CTP/75% 5-Methoxy-UTP + 25% UTP
75% 5-methoxy-UTP/5-methyl-CTP/ATP/GTP
75% 5-Methyl-CTP + 25% CTP/25% 5-Methoxy-UTP + 75% 1-Methyl-pseudo-UTP
75% 5-Methyl-CTP + 25% CTP/25% 5-Methoxy-UTP + 75% UTP
75% 5-Methyl-CTP + 25% CTP/50% 5-Methoxy-UTP + 50% 1-Methyl-pseudo-UTP
75% 5-Methyl-CTP + 25% CTP/50% 5-Methoxy-UTP + 50% UTP
75% 5-Methyl-CTP + 25% CTP/5-Methoxy-UTP
75% 5-Methyl-CTP + 25% CTP/75% 5-Methoxy-UTP + 25% 1-Methyl-pseudo-UTP
75% 5-Methyl-CTP + 25% CTP/75% 5-Methoxy-UTP + 25% UTP
75% 5-Phenyl-CTP + 25% CTP/25% 5-Methoxy-UTP + 75% UTP
75% 5-Phenyl-CTP + 25% CTP/75% 5-Methoxy-UTP + 25% UTP

TABLE 4-continued

Modified Nucleosides and Combinations Thereof

75% 5-Trifluoromethyl-CTP + 25% CTP/25% 5-Methoxy-UTP + 75% UTP
75% 5-Trifluoromethyl-CTP + 25% CTP/75% 5-Methoxy-UTP + 25% UTP
75% 5-Trifluoromethyl-CTP + 25% CTP/l-Methyl-pseudo-UTP
75% N4-Ac-CTP + 25% CTP/25% 5-Methoxy-UTP + 75% UTP
75% N4-Ac-CTP + 25% CTP/75% 5-Methoxy-UTP + 25% UTP
75% N4-Bz-CTP + 25% CTP/25% 5-Methoxy-UTP + 75% UTP
75% N4-Bz-CTP + 25% CTP/75% 5-Methoxy-UTP + 25% UTP
75% N4-Methyl-CTP + 25% CTP/25% 5-Methoxy-UTP + 75% UTP
75% N4-Methyl-CTP + 25% CTP/75% 5-Methoxy-UTP + 25% UTP
75% Pseudo-iso-CTP + 25% CTP/25% 5-Methoxy-UTP + 75% UTP
75% Pseudo-iso-CTP + 25% CTP/75% 5-Methoxy-UTP + 25% UTP
75% 5-Bromo-CTP/25% CTP/1-Methyl-pseudo-UTP
75% 5-Bromo-CTP/25% CTP/Pseudo-UTP
75% 5-methoxy-UTP/25% 5-methyl-CTP/ATP/GTP
75% 5-methoxy-UTP/50% 5-methyl-CTP/ATP/GTP
75% 5-methoxy-UTP/75% 5-methyl-CTP/ATP/GTP
75% 5-methoxy-UTP/CTP/ATP/GTP
8-Aza-ATP
Alpha-thio-CTP
CTP/25% 5-Methoxy-UTP + 75% 1-Methyl-pseudo-UTP
CTP/25% 5-Methoxy-UTP + 75% UTP
CTP/50% 5-Methoxy-UTP + 50% 1-Methyl-pseudo-UTP
CTP/50% 5-Methoxy-UTP + 50% UTP
CTP/5-Methoxy-UTP
CTP/5-Methoxy-UTP (cap 0)
CTP/5-Methoxy-UTP(No cap)
CTP/75% 5-Methoxy-UTP + 25% 1-Methyl-pseudo-UTP
CTP/75% 5-Methoxy-UTP + 25% UTP
CTP/UTP(No cap)
N1-Me-GTP
N4-Ac-CTP
N4Ac-CTP/1-Methyl-pseudo-UTP
N4Ac-CTP/5-Methoxy-UTP
N4-acetyl-cytidine TP, ATP, GTP, UTP
N4-Bz-CTP/5-Methoxy-UTP
N4-methyl CTP
N4-Methyl-CTP/5-Methoxy-UTP
Pseudo-iso-CTP/5-Methoxy-UTP
PseudoU-alpha-thio-TP
pseudouridine TP, ATP, GTP, CTP
pseudo-UTP/5-methyl-CTP/ATP/GTP
UTP-5-oxyacetic acid Me ester
Xanthosine According to the disclosure, mRNAs of the disclosure may be synthesized to comprise the combinations or single modifications of Table 3 or Table 4.

Where a single modification is listed, the listed nucleoside or nucleotide represents 100 percent of that A, U, G or C nucleotide or nucleoside having been modified. Where percentages are listed, these represent the percentage of that particular A, U, G or C nucleobase triphosphate of the total amount of A, U, G, or C triphosphate present. For example, the combination: 25% 5-Aminoallyl-CTP+75% CTP/25% 5-Methoxy-UTP+75% UTP refers to a mRNA where 25% of the cytosine triphosphates are 5-Aminoallyl-CTP while 75% of the cytosines are CTP; whereas 25% of the uracils are 5-methoxy UTP while 75% of the uracils are UTP. Where no modified UTP is listed then the naturally occurring ATP, UTP, GTP and/or CTP is used at 100% of the sites of those nucleotides found in the mRNA. In this example all of the GTP and ATP nucleotides are left unmodified.

The mRNAs of the present disclosure, or regions thereof, may be codon optimized. Codon optimization methods are known in the art and may be useful for a variety of purposes: matching codon frequencies in host organisms to ensure proper folding, bias GC content to increase mRNA stability or reduce secondary structures, minimize tandem repeat codons or base runs that may impair gene construction or expression, customize transcriptional and translational control regions, insert or remove proteins trafficking sequences, remove/add post translation modification sites in encoded proteins (e.g., glycosylation sites), add, remove or shuffle protein domains, insert or delete restriction sites, modify ribosome binding sites and mRNA degradation sites, adjust translation rates to allow the various domains of the protein to fold properly, or to reduce or eliminate problem secondary structures within the mRNA. Codon optimization tools, algorithms and services are known in the art; non-limiting examples include services from GeneArt (Life Technologies), DNA2.0 (Menlo Park, CA) and/or proprietary methods. In one embodiment, the mRNA sequence is optimized using optimization algorithms, e.g., to optimize expression in mammalian cells or enhance mRNA stability.

In certain embodiments, the present disclosure includes mRNAs having at least 80%, at least 85%, at least 90%, at least 95%, at least 98%, or at least 99% sequence identity to any of the mRNA sequences described herein.

mRNAs of the present disclosure may be produced by means available in the art, including but not limited to in vitro transcription (IVT) and synthetic methods. Enzymatic (IVT), solid-phase, liquid-phase, combined synthetic methods, small region synthesis, and ligation methods may be utilized. In one embodiment, mRNAs are made using IVT enzymatic synthesis methods. Methods of making mRNAs by IVT are known in the art and are described in International Application PCT/US2013/30062, the contents of which are incorporated herein by reference in their entirety. Accordingly, the present disclosure also includes mRNAs, e.g., DNA, constructs and vectors that may be used to in vitro transcribe an mRNA described herein.

Non-natural modified nucleobases may be introduced into mRNAs, e.g., mRNA, during synthesis or post-synthesis. In certain embodiments, modifications may be on internucleoside linkages, purine or pyrimidine bases, or sugar. In particular embodiments, the modification may be introduced at the terminal of a mRNA chain or anywhere else in the mRNA chain; with chemical synthesis or with a polymerase enzyme. Examples of modified nucleic acids and their synthesis are disclosed in PCT application No. PCT/US2012/058519. Synthesis of modified mRNAs is also described in Verma and Eckstein, Annual Review of Biochemistry, vol. 76, 99-134 (1998).

Either enzymatic or chemical ligation methods may be used to conjugate mRNAs or their regions with different functional moieties, such as targeting or delivery agents, fluorescent labels, liquids, nanoparticles, etc. Conjugates of mRNAs and modified mRNAs are reviewed in Goodchild, Bioconjugate Chemistry, vol. 1(3), 165-187 (1990).

Functional RNA Elements

In some embodiments, the disclosure provides mRNAs comprising a modification (e.g., an RNA element), wherein the modification provides a desired translational regulatory activity. Such modifications are described in PCT Application No. PCT/US2018/033519, herein incorporated by reference in its entirety.

In some embodiments, the disclosure provides a mRNA comprising a 5' untranslated region (UTR), an initiation codon, a full open reading frame encoding a polypeptide, a 3' UTR, and at least one modification, wherein the at least one modification provides a desired translational regulatory activity, for example, a modification that promotes and/or enhances the translational fidelity of mRNA translation. In some embodiments, the desired translational regulatory activity is a cis-acting regulatory activity. In some embodiments, the desired translational regulatory activity is an increase in the residence time of the 43S pre-initiation complex (PIC) or ribosome at, or proximal to, the initiation codon. In some embodiments, the desired translational regulatory activity is an increase in the initiation of polypeptide synthesis at or from the initiation codon. In some embodiments, the desired translational regulatory activity is an increase in the amount of polypeptide translated from the full open reading frame. In some embodiments, the desired translational regulatory activity is an increase in the fidelity of initiation codon decoding by the PIC or ribosome. In some embodiments, the desired translational regulatory activity is inhibition or reduction of leaky scanning by the PIC or ribosome. In some embodiments, the desired translational regulatory activity is a decrease in the rate of decoding the initiation codon by the PIC or ribosome. In some embodiments, the desired translational regulatory activity is inhibition or reduction in the initiation of polypeptide synthesis at any codon within the mRNA other than the initiation codon. In some embodiments, the desired translational regulatory activity is inhibition or reduction of the amount of polypeptide translated from any open reading frame within the mRNA other than the full open reading frame. In some embodiments, the desired translational regulatory activity is inhibition or reduction in the production of aberrant translation products. In some embodiments, the desired translational regulatory activity is a combination of one or more of the foregoing translational regulatory activities.

Accordingly, the present disclosure provides a mRNA, e.g., an mRNA, comprising an RNA element that comprises a sequence and/or an RNA secondary structure(s) that provides a desired translational regulatory activity as described herein. In some aspects, the mRNA comprises an RNA element that comprises a sequence and/or an RNA secondary structure(s) that promotes and/or enhances the translational fidelity of mRNA translation. In some aspects, the mRNA comprises an RNA element that comprises a sequence and/or an RNA secondary structure(s) that provides a desired translational regulatory activity, such as inhibiting and/or reducing leaky scanning. In some aspects, the disclosure provides an mRNA that comprises an RNA element that comprises a sequence and/or an RNA secondary structure(s) that inhibits and/or reduces leaky scanning thereby promoting the translational fidelity of the mRNA.

In some embodiments, the RNA element comprises natural and/or modified nucleotides. In some embodiments, the RNA element comprises of a sequence of linked nucleotides, or derivatives or analogs thereof, that provides a desired translational regulatory activity as described herein. In some embodiments, the RNA element comprises a sequence of linked nucleotides, or derivatives or analogs thereof, that forms or folds into a stable RNA secondary structure, wherein the RNA secondary structure provides a desired translational regulatory activity as described herein. RNA elements can be identified and/or characterized based on the primary sequence of the element (e.g., GC-rich element), by RNA secondary structure formed by the element (e.g. stem-loop), by the location of the element within the RNA molecule (e.g., located within the 5' UTR of an mRNA), by the biological function and/or activity of the element (e.g., "translational enhancer element"), and any combination thereof.

In some embodiments, the disclosure provides an mRNA having one or more structural modifications that inhibits leaky scanning and/or promotes the translational fidelity of mRNA translation, wherein at least one of the structural modifications is a GC-rich RNA element. In some embodiments, the disclosure provides an mRNA comprising at least one modification, wherein at least one modification is a GC-rich RNA element comprising a sequence of linked nucleotides, or derivatives or analogs thereof, preceding a Kozak consensus sequence in a 5' UTR of the mRNA. In one embodiment, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA.

In some embodiments, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is 70-80% cytosine, 60-70% cytosine, 50%-60% cytosine, 40-50% cytosine, 30-40% cytosine bases. In some embodiments, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is about 80% cytosine, about 70% cytosine, about 60% cytosine, about 50% cytosine, about 40% cytosine, or about 30% cytosine.

In some embodiments, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is 70-80% cytosine, 60-70% cytosine, 50%-60% cytosine, 40-50% cytosine, or 30-40% cytosine. In some embodiments, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is about 80% cytosine, about 70% cytosine, about 60% cytosine, about 50% cytosine, about 40% cytosine, or about 30% cytosine.

In some embodiments, the disclosure provides an mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA, and wherein the GC-rich RNA element comprises a sequence of 3, 4, 5, 6, 7, 8, 9, 10, 11, 12, 13, 14, 15, 16, 17, 18, 19, or 20 nucleotides, or derivatives or analogs thereof, linked in any order, wherein the sequence composition is >50% cytosine. In some embodiments, the sequence composition is >55% cytosine, >60% cytosine, >65% cytosine, >70% cytosine, >75% cytosine, >80% cytosine, >85% cytosine, or >90% cytosine.

In some embodiments, the disclosure provides an mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA, and wherein the GC-rich RNA element comprises a sequence of about 3-30, 5-25, 10-20, 15-20 or about 20, about 15, about 12, about 10, about 6 or about 3 nucleotides, or derivatives or analogues thereof, wherein the sequence comprises a repeating GC-motif, wherein the repeating GC-motif is [CCG]n, wherein n=1 to 10, n=2 to 8, n=3 to 6, or n=4 to 5. In some embodiments, the sequence comprises a repeating GC-motif [CCG]n, wherein n=1, 2, 3, 4 or 5. In some embodiments, the sequence comprises a repeating GC-motif [CCG]n, wherein n=1, 2, or 3. In some embodiments, the sequence comprises a repeating GC-motif [CCG]n, wherein n=1. In some embodiments, the sequence comprises a repeating GC-motif [CCG]n, wherein n=2. In some embodiments, the sequence comprises a repeating GC-motif [CCG]n, wherein n=3. In some embodiments, the sequence comprises a repeating GC-motif [CCG]n, wherein n=4 (SEQ ID NO: 23). In some embodiments, the sequence comprises a repeating GC-motif [CCG]n, wherein n=5 (SEQ ID NO: 24).

In some embodiments, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located about 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA.

In some embodiments, the disclosure provides an mRNA comprising at least one modification, wherein at least one modification is a GC-rich RNA element comprising the sequence set forth in SEQ ID NO: 25, or derivatives or analogs thereof, preceding a Kozak consensus sequence in the 5' UTR of the mRNA. In some embodiments, the GC-rich element comprises the sequence as set forth in SEQ ID NO: 25 located immediately adjacent to and upstream of the Kozak consensus sequence in the 5' UTR of the mRNA. In some embodiments, the GC-rich element comprises the sequence as set forth in SEQ ID NO: 25 located 1, 2, 3, 4, 5, 6, 7, 8, 9 or 10 bases upstream of the Kozak consensus sequence in the 5' UTR of the mRNA. In other embodiments, the GC-rich element comprises the sequence as set forth in SEQ ID NO: 25 located 1-3, 3-5, 5-7, 7-9, 9-12, or 12-15 bases upstream of the Kozak consensus sequence in the 5' UTR of the mRNA.

In some embodiments, the disclosure provides an mRNA comprising at least one modification, wherein at least one modification is a GC-rich RNA element comprising the sequence as set forth SEQ ID NO: 26, or derivatives or analogs thereof, preceding a Kozak consensus sequence in the 5' UTR of the mRNA. In some embodiments, the GC-rich element comprises the sequence as set forth SEQ ID NO: 26 located immediately adjacent to and upstream of the Kozak consensus sequence in the 5' UTR of the mRNA. In some embodiments, the GC-rich element comprises the sequence as set forth SEQ ID NO: 26 located 1, 2, 3, 4, 5, 6, 7, 8, 9 or 10 bases upstream of the Kozak consensus sequence in the 5' UTR of the mRNA. In other embodiments, the GC-rich element comprises the sequence as set forth SEQ ID NO: 26 located 1-3, 3-5, 5-7, 7-9, 9-12, or 12-15 bases upstream of the Kozak consensus sequence in the 5' UTR of the mRNA.

In some embodiments, the disclosure provides an mRNA comprising at least one modification, wherein at least one modification is a GC-rich RNA element comprising the sequence as set forth in SEQ ID NO: 27, or derivatives or analogs thereof, preceding a Kozak consensus sequence in the 5' UTR of the mRNA. In some embodiments, the GC-rich element comprises the sequence as set forth in SEQ ID NO: 27 located immediately adjacent to and upstream of the Kozak consensus sequence in the 5' UTR of the mRNA. In some embodiments, the GC-rich element comprises the sequence as set forth in SEQ ID NO: 27 located 1, 2, 3, 4, 5, 6, 7, 8, 9 or 10 bases upstream of the Kozak consensus sequence in the 5' UTR of the mRNA. In other embodiments, the GC-rich element comprises the sequence as set forth in SEQ ID NO: 27 located 1-3, 3-5, 5-7, 7-9, 9-12, or 12-15 bases upstream of the Kozak consensus sequence in the 5' UTR of the mRNA.

In some embodiments, the disclosure provides an mRNA comprising at least one modification, wherein at least one modification is a GC-rich RNA element comprising the sequence set forth in SEQ ID NO: 25, or derivatives or analogs thereof, preceding a Kozak consensus sequence in the 5' UTR of the mRNA, wherein the 5' UTR comprises the sequence set forth in SEQ ID NO: 28.

In some embodiments, the GC-rich element comprises the sequence set forth in SEQ ID NO: 25 located immediately adjacent to and upstream of the Kozak consensus sequence in a 5' UTR sequence described herein. In some embodiments, the GC-rich element comprises the sequence set forth in SEQ ID NO: 25 located 1, 2, 3, 4, 5, 6, 7, 8, 9 or 10 bases upstream of the Kozak consensus sequence in the 5' UTR of the mRNA, wherein the 5' UTR comprises the sequence shown in SEQ ID NO: 28.

In other embodiments, the GC-rich element comprises the sequence set forth in SEQ ID NO: 25 located 1-3, 3-5, 5-7, 7-9, 9-12, or 12-15 bases upstream of the Kozak consensus sequence in the 5' UTR of the mRNA, wherein the 5' UTR comprises the sequence set forth in SEQ ID NO: 28.

In some embodiments, the 5' UTR comprises the sequence set forth in SEQ ID NO: 29.

In some embodiments, the 5' UTR comprises the sequence set forth in SEQ ID NO: 30.

In some embodiments, the disclosure provides an mRNA comprising at least one modification, wherein at least one modification is a GC-rich RNA element comprising a stable RNA secondary structure comprising a sequence of nucleotides, or derivatives or analogs thereof, linked in an order which forms a hairpin or a stem-loop. In one embodiment, the stable RNA secondary structure is upstream of the Kozak consensus sequence. In another embodiment, the stable RNA secondary structure is located about 30, about 25, about 20, about 15, about 10, or about 5 nucleotides upstream of the Kozak consensus sequence. In another embodiment, the stable RNA secondary structure is located about 20, about 15, about 10 or about 5 nucleotides upstream of the Kozak consensus sequence. In another embodiment, the stable RNA secondary structure is located about 5, about 4, about 3, about 2, about 1 nucleotides upstream of the Kozak consensus sequence. In another embodiment, the stable RNA secondary structure is located about 15-30, about 15-20, about 15-25, about 10-15, or about 5-10 nucleotides upstream of the Kozak consensus sequence. In another embodiment, the stable RNA secondary structure is located 12-15 nucleotides upstream of the Kozak consensus sequence. In another embodiment, the stable RNA secondary structure has a deltaG of about −30 kcal/mol, about −20 to −30 kcal/mol, about −20 kcal/mol, about −10 to −20 kcal/mol, about −10 kcal/mol, about −5 to −10 kcal/mol.

In another embodiment, the modification is operably linked to an open reading frame encoding a polypeptide and wherein the modification and the open reading frame are heterologous.

In another embodiment, the sequence of the GC-rich RNA element is comprised exclusively of guanine (G) and cytosine (C) nucleobases.

RNA elements that provide a desired translational regulatory activity as described herein can be identified and characterized using known techniques, such as ribosome profiling. Ribosome profiling is a technique that allows the determination of the positions of PICs and/or ribosomes bound to mRNAs (see e.g., Ingolia et al., (2009) Science 324(5924):218-23, incorporated herein by reference). The technique is based on protecting a region or segment of mRNA, by the PIC and/or ribosome, from nuclease digestion. Protection results in the generation of a 30-bp fragment of RNA termed a 'footprint'. The sequence and frequency of RNA footprints can be analyzed by methods known in the art (e.g., RNA-seq). The footprint is roughly centered on the A-site of the ribosome. If the PIC or ribosome dwells at a particular position or location along an mRNA, footprints generated at these position would be relatively common. Studies have shown that more footprints are generated at positions where the PIC and/or ribosome exhibits decreased processivity and fewer footprints where the PIC and/or ribosome exhibits increased processivity (Gardin et al., (2014) eLife 3:e03735). In some embodiments, residence time or the time of occupancy of a the PIC or ribosome at a discrete position or location along an mRNA comprising any one or more of the RNA elements described herein is determined by ribosome profiling.

Delivery Agents

Lipid Compound

The present disclosure provides pharmaceutical compositions with advantageous properties. The lipid compositions described herein may be advantageously used in lipid nanoparticle compositions for the delivery of therapeutic and/or prophylactic agents, e.g., mRNAs, to mammalian cells or organs. For example, the lipids described herein have little or no immunogenicity. For example, the lipid compounds disclosed herein have a lower immunogenicity as compared to a reference lipid (e.g., MC3, KC2, or DLinDMA). For example, a formulation comprising a lipid disclosed herein and a therapeutic or prophylactic agent, e.g., mRNA, has an increased therapeutic index as compared to a corresponding formulation which comprises a reference lipid (e.g., MC3, KC2, or DLinDMA) and the same therapeutic or prophylactic agent.

In certain embodiments, the present application provides pharmaceutical compositions comprising:
(a) mRNAs comprising a nucleotide sequence encoding OX40L, IL-23 and/or IL-36☐; and
(b) a delivery agent.

Lipid Nanoparticle Formulations

In some embodiments, nucleic acids of the invention (e.g. mRNA) are formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the invention can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/

52117; PCT/US2012/069610; PCT/US2017/027492; PCT/US2016/059575 and PCT/US2016/069491 all of which are incorporated by reference herein in their entirety.

Nucleic acids of the present disclosure (e.g. mRNA) are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises a molar ratio of 20-60% ionizable cationic lipid. For example, the lipid nanoparticle may comprise a molar ratio of 20-50%, 20-40%, 20-30%, 30-60%, 30-50%, 30-40%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol. For example, the lipid nanoparticle may comprise a molar ratio of 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% sterol. In some embodiments, the lipid nanoparticle comprises a molar ratio of 25%, 30%, 35%, 40%, 45%, 50%, or 55% sterol.

In some embodiments, the lipid nanoparticle comprises a molar ratio of 0.5-15% PEG-modified lipid. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid, 5-25% non-cationic lipid, 25-55% sterol, and 0.5-15% PEG-modified lipid.

Ionizable Lipids

In some aspects, the ionizable lipids of the present disclosure may be one or more of compounds of Formula (I):

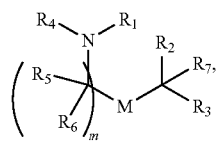

(I)

or their N-oxides, or salts or isomers thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of hydrogen, a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —N(R)S(O)$_2$R$_8$, —O(CH$_2$), OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —OC(O)-M"-C(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group, in which M" is a bond, $C_{1-13}$ alkyl or $C_{2-13}$ alkenyl;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-15}$ alkyl and $C_{3-15}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and wherein when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In certain embodiments, a subset of compounds of Formula (I) includes those of Formula (IA):

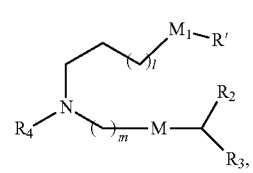

(IA)

or its N-oxide, or a salt or isomer thereof, wherein l is selected from 1, 2, 3, 4, and 5; m is selected from 5, 6, 7, 8, and 9; $M_1$ is a bond or M'; $R_4$ is hydrogen, unsubstituted $C_{1-3}$ alkyl, or —(CH$_2$)$_n$Q, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)
OR, heteroaryl or heterocycloalkyl; M and M' are
independently selected
from —C(O)O—, —OC(O)—, —OC(O)-M"-C(O)O—,
—C(O)N(R')—, —P(O)(OR')O—, —S—S—, an aryl
group, and a heteroaryl group; and R$_2$ and R$_3$ are
independently selected from the group consisting of H,
C$_{1-14}$ alkyl, and C$_{2-14}$ alkenyl. For example, m is 5, 7,
or 9. For example, Q is OH, —NHC(S)N(R)$_2$, or
—NHC(O)N(R)$_2$. For example, Q is —N(R)C(O)R, or
—N(R)S(O)$_2$R.

In certain embodiments, a subset of compounds of Formula (I) includes those of Formula (IB):

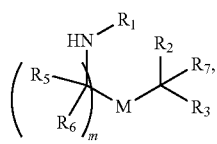

(IB)

or its N-oxide, or a salt or isomer thereof in which all
variables are as defined herein. For example, m is selected
from 5, 6, 7, 8, and 9; R$_4$ is hydrogen, unsubstituted C$_{1-3}$
alkyl, or —(CH$_2$)$_n$Q, in which Q is
OH, —NHC(S)N(R)$_2$, —NHC(O)N(R)$_2$, —N(R)C(O)R,
—N(R)S(O)$_2$R, —N(R)R$_8$, —NHC(=NR$_9$)N(R)$_2$,
—NHC(=CHR$_9$)N(R)$_2$, —OC(O)N(R)$_2$, —N(R)C(O)
OR, heteroaryl or heterocycloalkyl; M and M' are
independently selected
from —C(O)O—, —OC(O)—, —OC(O)-M"-C(O)O—,
—C(O)N(R')—, —P(O)(OR')O—, —S—S—, an aryl
group, and a heteroaryl group; and R$_2$ and R$_3$ are
independently selected from the group consisting of H,
C$_{1-14}$ alkyl, and C$_{2-14}$ alkenyl. For example, m is 5, 7,
or 9. For example, Q is OH, —NHC(S)N(R)$_2$, or
—NHC(O)N(R)$_2$. For example, Q is —N(R)C(O)R, or
—N(R)S(O)$_2$R.

In certain embodiments, a subset of compounds of Formula (I) includes those of Formula (II):

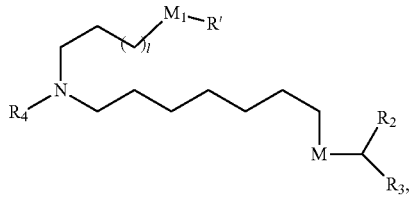

(II)

or its N-oxide, or a salt or isomer thereof, wherein l is
selected from 1, 2, 3, 4, and 5; M$_1$ is a bond or M'; R$_4$ is
hydrogen, unsubstituted C$_{1-3}$ alkyl, or —(CH$_2$)$_n$Q, in which
n is 2, 3, or 4, and Q is
OH, —NHC(S)N(R)$_2$, —NHC(O)N(R)$_2$, —N(R)C(O)R,
—N(R)S(O)$_2$R, —N(R)R$_8$, —NHC(=NR$_9$)N(R)$_2$,
—NHC(=CHR$_9$)N(R)$_2$, —OC(O)N(R)$_2$, —N(R)C(O)
OR, heteroaryl or heterocycloalkyl; M and M' are
independently selected
from —C(O)O—, —OC(O)—, —OC(O)-M"-C(O)O—,
—C(O)N(R')—, —P(O)(OR')O—, —S—S—, an aryl
group, and a heteroaryl group; and R$_2$ and R$_3$ are
independently selected from the group consisting of H,
C$_{1-14}$ alkyl, and C$_{2-14}$ alkenyl.

In one embodiment, the compounds of Formula (I) are of
Formula (IIa),

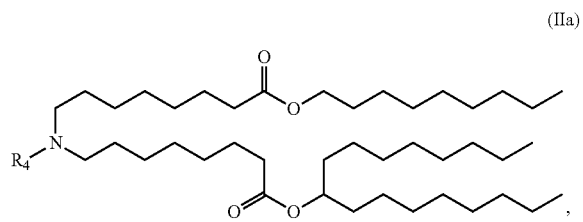

(IIa)

or their N-oxides, or salts or isomers thereof, wherein R$_4$
is as described herein.

In another embodiment, the compounds of Formula (I) are
of Formula (IIb),

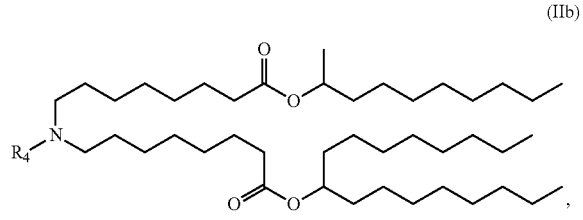

(IIb)

or their N-oxides, or salts or isomers thereof, wherein R$_4$
is as described herein.

In another embodiment, the compounds of Formula (I) are
of Formula (IIc) or (IIe):

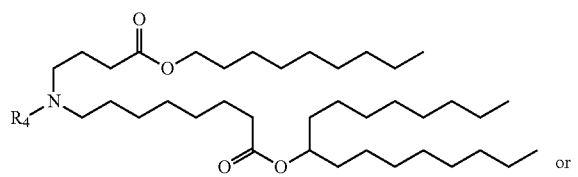

(IIc)

or

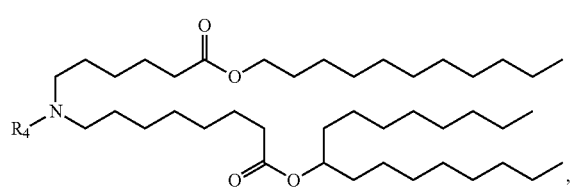

(IIe)

or their N-oxides, or salts or isomers thereof, wherein R$_4$
is as described herein.

In another embodiment, the compounds of Formula (I) are
of Formula (IIf):

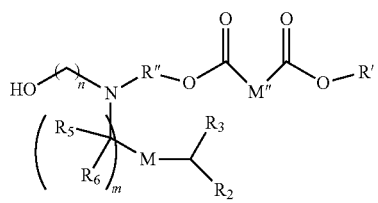

(IIf)

or their N-oxides, or salts or isomers thereof, wherein M is —C(O)O— or —OC(O)—, M" is $C_{1-6}$ alkyl or $C_{2-6}$ alkenyl, $R_2$ and $R_3$ are independently selected from the group consisting of $C_{5-14}$ alkyl and $C_{5-14}$ alkenyl, and n is selected from 2, 3, and 4.

In a further embodiment, the compounds of Formula (I) are of Formula (IId),

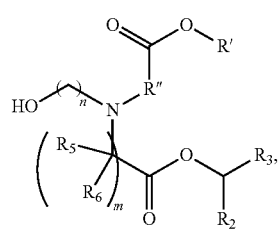

(IId)

or their N-oxides, or salts or isomers thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In a further embodiment, the compounds of Formula (I) are of Formula (IIg),

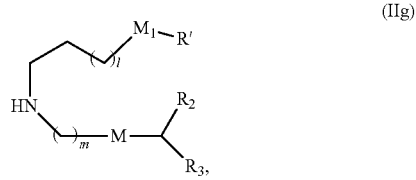

(IIg)

or their N-oxides, or salts or isomers thereof, wherein l is selected from 1, 2, 3, 4, and 5; m is selected from 5, 6, 7, 8, and 9; $M_1$ is a bond or M'; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, M" is $C_{1-6}$ alkyl (e.g., $C_{1-4}$ alkyl) or $C_{2-6}$ alkenyl (e.g. $C_{2-4}$ alkenyl). For example, $R_2$ and $R_3$ are independently selected from the group consisting of $C_{5-14}$ alkyl and $C_{5-14}$ alkenyl.

In some embodiments, the ionizable lipids are one or more of the compounds described in U.S. Application Nos. 62/220,091, 62/252,316, 62/253,433, 62/266,460, 62/333,557, 62/382,740, 62/393,940, 62/471,937, 62/471,949, 62/475,140, and 62/475,166, and PCT Application No. PCT/US2016/052352.

In some embodiments, the ionizable lipids are selected from Compounds 1-280 described in U.S. Application No. 62/475,166.

In some embodiments, the ionizable lipid is

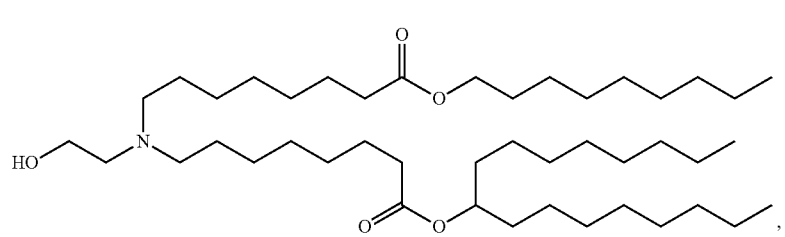

(Compound II)

or a salt thereof.

In some embodiments, the ionizable lipid is

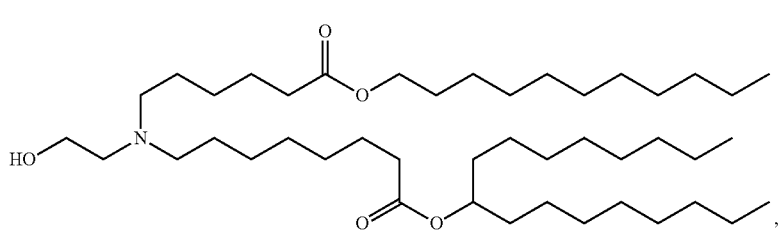

(Compound III)

or a salt thereof.

In some embodiments, the ionizable lipid is

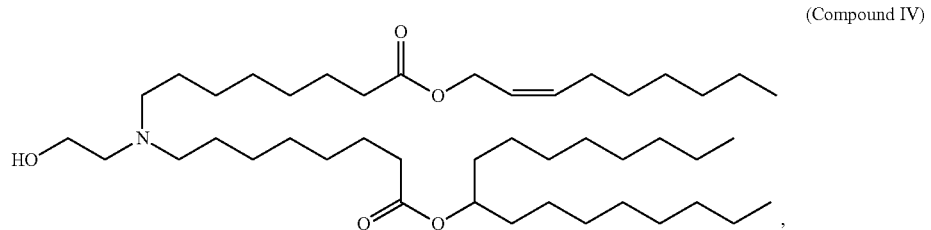 [SMILES: CCCCCC/C=C\COC(=O)CCCCCCCN(CCO)CCCCCCCC(=O)OC(CCCCCCCC)CCCCCCCC]

(Compound IV)

or a salt thereof.

In some embodiments, the ionizable lipid is

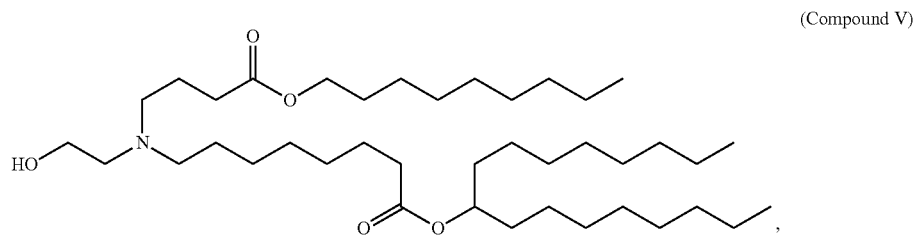 [SMILES: CCCCCCCCCOC(=O)CCCN(CCO)CCCCCCCC(=O)OC(CCCCCCCC)CCCCCCCC]

(Compound V)

or a salt thereof.

The central amine moiety of a lipid according to Formula (I), (IA), (IB), (II), (IIa), (IIb), (IIc), (IId), (IIe), (IIf), or (IIg) may be protonated at a physiological pH. Thus, a lipid may have a positive or partial positive charge at physiological pH. Such lipids may be referred to as cationic or ionizable (amino) lipids. Lipids may also be zwitterionic, i.e., neutral molecules having both a positive and a negative charge.

In some aspects, the ionizable lipids of the present disclosure may be one or more of compounds of formula (III),

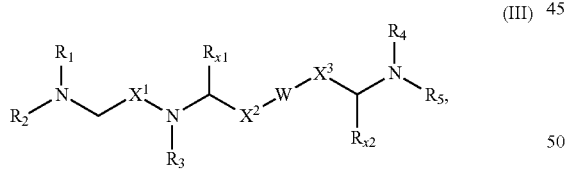

or salts or isomers thereof, wherein
W is

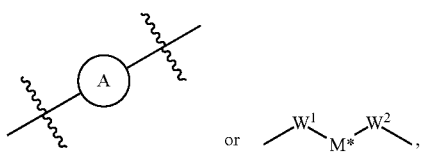

ring A is

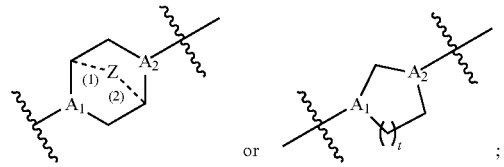

t is 1 or 2;
$A_1$ and $A_2$ are each independently selected from CH or N;
Z is $CH_2$ or absent wherein when Z is $CH_2$, the dashed lines (1) and (2) each represent a single bond; and when Z is absent, the dashed lines (1) and (2) are both absent;
$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";
$R_{X1}$ and $R_{X2}$ are each independently H or $C_{1-3}$ alkyl;
each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, —C(O)S—, —SC(O)—, an aryl group, and a heteroaryl group;
$M^*$ is $C_1$-$C_6$ alkyl,
$W^1$ and $W^2$ are each independently selected from the group consisting of —O— and —N($R_6$)—;
each $R_6$ is independently selected from the group consisting of H and $C_{1-5}$ alkyl;
$X^1$, $X^2$, and $X^3$ are independently selected from the group consisting of a bond, —CH$_2$—, —(CH$_2$)$_2$—, —CHR—, —CHY—, —C(O)—, —C(O)O—, —OC(O)—, —(CH$_2$)$_n$—C(O)—, —C(O)—(CH$_2$)$_n$—, —(CH$_2$)$_n$—C(O)O—, —OC(O)—(CH$_2$)$_n$—, —(CH$_2$)$_n$—OC(O)—, —C(O)O—(CH$_2$)$_n$—, —CH(OH)—, —C(S)—, and —CH(SH)—;
each Y is independently a $C_{3-6}$ carbocycle;
each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;
each R' is independently selected from the group consisting of $C_{1-12}$ alkyl, $C_{2-12}$ alkenyl, and H;
each R" is independently selected from the group consisting of $C_{3-12}$ alkyl, $C_{3-12}$ alkenyl and —R*MR';
and n is an integer from 1-6;
when ring A is

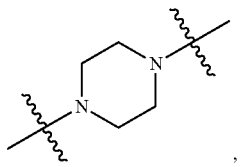 [SMILES: *N1CCN(*)CC1]

then
i) at least one of $X^1$, $X^2$, and $X^3$ is not —$CH_2$—; and/or
ii) at least one of $R_1$, $R_2$, $R_3$, $R_4$, and $R_5$ is —R"MR'.

In some embodiments, the compound is of any of formulae (IIIa1)-(IIIa8):

(IIIa1)

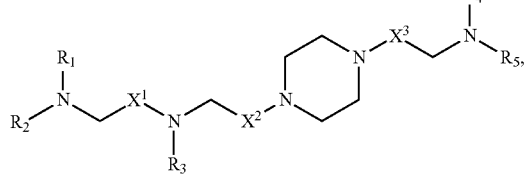

(IIIa2)

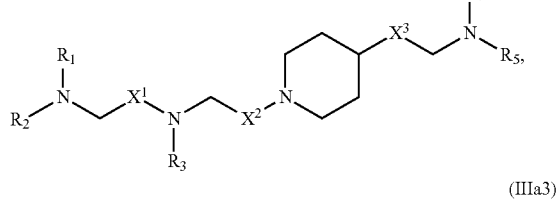

(IIIa3)

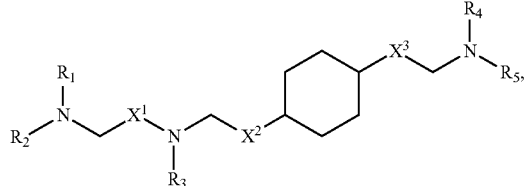

(IIIa4)

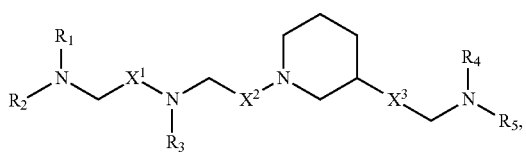

(IIIa5')

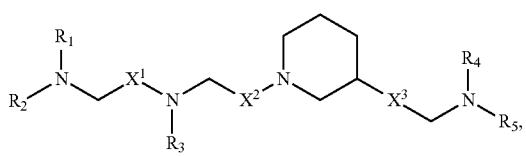

(IIIa6)

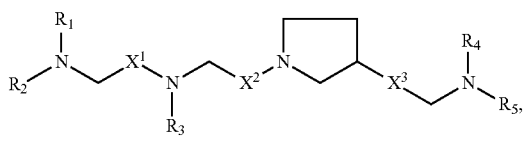

(IIIa7)

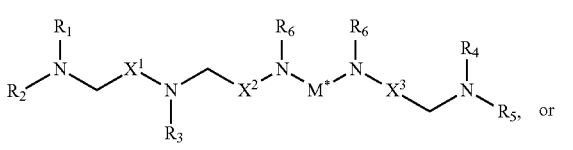

or (IIIa8)

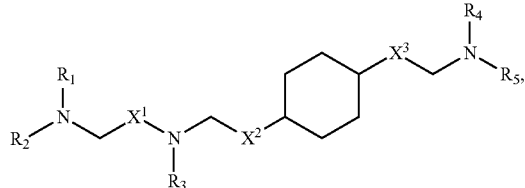

In some embodiments, the ionizable lipids are one or more of the compounds described in U.S. Application Nos. 62/271,146, 62/338,474, 62/413,345, and 62/519,826, and PCT Application No. PCT/US2016/068300.

In some embodiments, the ionizable lipids are selected from Compounds 1-156 described in U.S. Application No. 62/519,826.

In some embodiments, the ionizable lipids are selected from Compounds 1-16, 42-66, 68-76, and 78-156 described in U.S. Application No. 62/519,826.

In some embodiments, the ionizable livid is (Compound VI)

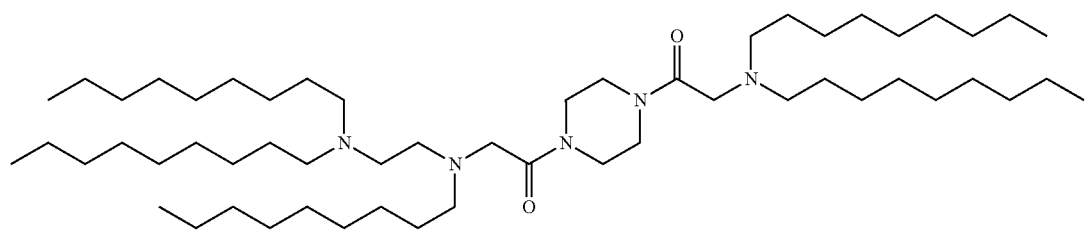

or a salt thereof.

In some embodiments, the ionizable lipid is (Compound VII), or a salt thereof.

The central amine moiety of a lipid according to Formula (III), (IIIa1), (IIIa2), (IIIa3), (IIIa4), (IIIa5), (IIIa6), (IIIa7), or (IIIa8) may be protonated at a physiological pH. Thus, a lipid may have a positive or partial positive charge at physiological pH. Such lipids may be referred to as cationic or ionizable (amino)lipids. Lipids may also be zwitterionic, i.e., neutral molecules having both a positive and a negative charge.

Phospholipids

The lipid composition of the lipid nanoparticle composition disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidyl glycerols, and phosphatidic acids. Phospholipids also include phosphosphingolipid, such as sphingomyelin.

In some embodiments, a phospholipid of the invention comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In certain embodiments, a phospholipid useful or potentially useful in the present invention is an analog or variant of DSPC. In certain embodiments, a phospholipid useful or potentially useful in the present invention is a compound of Formula (IV):

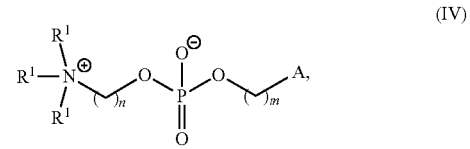

(IV)

or a salt thereof, wherein:

each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2, 3, 4, 5, 6, 7, 8, 9, or 10;

A is of the formula:

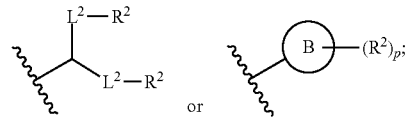

each instance of $L^2$ is independently a bond or optionally substituted $C_{1-6}$ alkylene, wherein one methylene unit of the optionally substituted $C_{1-6}$ alkylene is optionally replaced with O, N($R^N$), S, C(O), C(O)N($R^N$), $NR^NC$(O), C(O)O, OC(O), OC(O)O, OC(O)N($R^N$), $NR^NC$(O) O, or $NR^NC$(O)N($R^N$);

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclene, optionally substituted heterocyclene, optionally substituted arylene, optionally substituted heteroarylene, N($R^N$), O, S, C(O), C(O)N($R^N$), $NR^NC$(O), $NR^NC$(O)N($R^N$), C(O)O, OC(O), —OC(O)O, OC(O)N($R^N$), $NR^NC$(O)O, C(O)S, SC(O), C(=$NR^N$), C(=$NR^N$)N($R^N$), $NR^NC$(=$NR^N$), $NR^NC$(=$NR^N$)N ($R^N$), C(S), C(S)N($R^N$), $NR^NC$(S), $NR^NC$(S)N($R^N$), S(O), OS(O), S(O)O, —OS(O)O, OS(O)$_2$, S(O)$_2$O, OS(O)$_2$O, N(R$^N$)S(O), S(O)N(R$^N$), N(R$^N$)S(O)N(R$^N$), OS(O)N(R$^N$), N(R$^N$)S(O)O, S(O)$_2$, N(R$^N$)S(O)$_2$, S(O)$_2$N(R$^N$), N(R$^N$)S(O)$_2$N(R$^N$), OS(O)$_2$N(R$^N$), or —N(R$^N$)S(O)$_2$O;

each instance of R$^N$ is independently hydrogen, optionally substituted alkyl, or a nitrogen protecting group;

ring B is optionally substituted carbocyclyl, optionally substituted heterocyclyl, optionally substituted aryl, or optionally substituted heteroaryl; and p is 1 or 2;

provided that the compound is not of the formula:

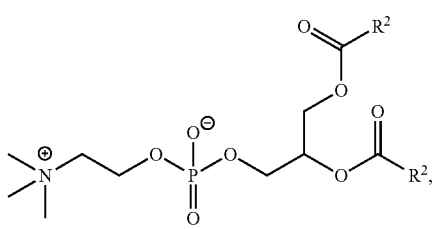

wherein each instance of R$^2$ is independently unsubstituted alkyl, unsubstituted alkenyl, or unsubstituted alkynyl.

In some embodiments, the phospholipids may be one or more of the phospholipids described in U.S. Application No. 62/520,530.

(i) Phospholipid Head Modifications

In certain embodiments, a phospholipid useful or potentially useful in the present invention comprises a modified phospholipid head (e.g., a modified choline group). In certain embodiments, a phospholipid with a modified head is DSPC, or analog thereof, with a modified quaternary amine. For example, in embodiments of Formula (IV), at least one of R$^1$ is not methyl. In certain embodiments, at least one of R$^1$ is not hydrogen or methyl. In certain embodiments, the compound of Formula (IV) is of one of the following formulae:

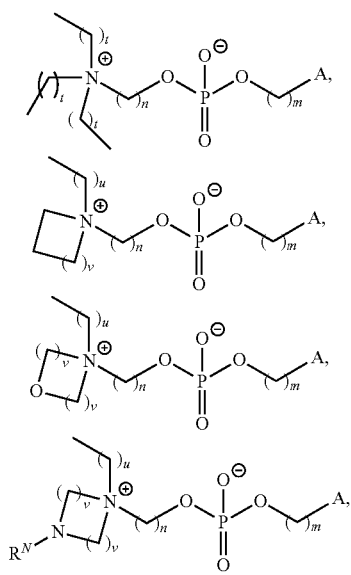

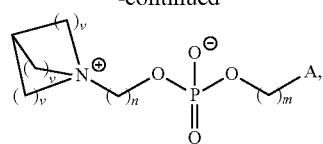

or a salt thereof, wherein:
each t is independently 1, 2, 3, 4, 5, 6, 7, 8, 9, or 10;
each u is independently 0, 1, 2, 3, 4, 5, 6, 7, 8, 9, or 10; and
each v is independently 1, 2, or 3.

In certain embodiments, a compound of Formula (IV) is of Formula (IV-a):

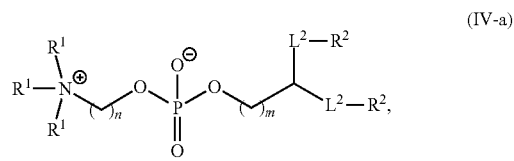

or a salt thereof.

In certain embodiments, a phospholipid useful or potentially useful in the present invention comprises a cyclic moiety in place of the glyceride moiety. In certain embodiments, a phospholipid useful in the present invention is DSPC, or analog thereof, with a cyclic moiety in place of the glyceride moiety. In certain embodiments, the compound of Formula (IV) is of Formula (IV-b):

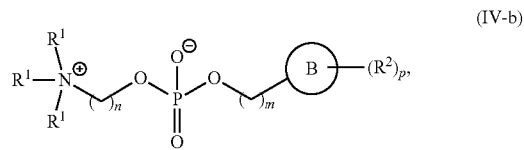

or a salt thereof.

(ii) Phospholipid Tail Modifications

In certain embodiments, a phospholipid useful or potentially useful in the present invention comprises a modified tail. In certain embodiments, a phospholipid useful or potentially useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (IV) is of Formula (IV-a), or a salt thereof, wherein at least one instance of R$^2$ is each instance of R$^2$ is optionally substituted C$_{1-30}$ alkyl, wherein one or more methylene units of R$^2$ are independently replaced with optionally substituted carbocyclylene, optionally substituted heterocyclylene, optionally substituted arylene, optionally substituted heteroarylene, N(R$^N$), O, S, C(O), C(O)N(R$^N$), —NR$^N$C(O), NR$^N$C(O)N(R$^N$), C(O)O, OC(O), OC(O)O, OC(O)N(R$^N$), NR$^N$C(O)O, C(O)S, SC(O), C(=NR$^N$), C(=NR$^N$)N(R$^N$), NR$^N$C(=NR$^N$), NR$^N$C(=NR$^N$)N(R$^N$), C(S), C(S)N(R$^N$), NR$^N$C(S), —NR$^N$C(S)N(R$^N$), S(O), OS(O), S(O)O, OS(O)O, OS(O)$_2$, S(O)$_2$O, OS(O)$_2$O, N(R$^N$)S(O), —S(O)N(R$^N$), N(R$^N$)S(O)

N(R$^N$), OS(O)N(R$^N$), N(R$^N$)S(O)O, S(O)$_2$, N(R$^N$)S(O)$_2$, S(O)$_2$N(R$^N$), —N(R$^N$)S(O)$_2$N(R$^N$), OS(O)$_2$N(R$^N$), or N(R$^N$)S(O)$_2$O.

In certain embodiments, the compound of Formula (IV) is of Formula (IV-c):

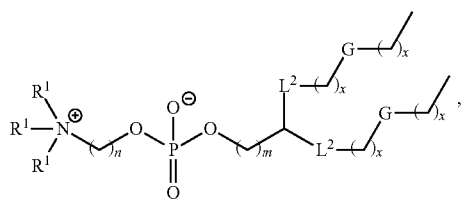

(IV-c)

or a salt thereof, wherein:

each x is independently an integer between 0-30, inclusive; and each instance is G is independently selected from the group consisting of optionally substituted carbocyclylene, optionally substituted heterocyclylene, optionally substituted arylene, optionally substituted heteroarylene, N(R$^N$), O, S, C(O), C(O)N(R$^N$), NR$^N$C(O), NR$^N$C(O)N(R$^N$), C(O)O, OC(O), OC(O)O, OC(O)N(R$^N$), NR$^N$C(O)O, C(O)S, SC(O), C(=NR$^N$), C(=NR$^N$)N(R$^N$), NR$^N$C(=NR$^N$), NR$^N$C(=NR$^N$)N(R$^N$), C(S), C(S)N(R$^N$), NR$^N$C(S), NR$^N$C(S)N(R$^N$), S(O), OS(O), S(O)O, OS(O)O, OS(O)$_2$, S(O)$_2$O, OS(O)$_2$O, N(R$^N$)S(O), S(O)N(R$^N$), N(R$^N$)S(O)N(R$^N$), —OS(O)N(R$^N$), N(R$^N$)S(O)O, S(O)$_2$, N(R$^N$)S(O)$_2$, S(O)$_2$N(R$^N$), N(R$^N$)S(O)$_2$N(R$^N$), OS(O)$_2$N(R$^N$), or N(R$^N$)S(O)$_2$O. Each possibility represents a separate embodiment of the present invention.

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful or potentially useful in the present invention is a compound of Formula (IV), wherein n is 1, 3, 4, 5, 6, 7, 8, 9, or 10. For example, in certain embodiments, a compound of Formula (IV) is of one of the following formulae:

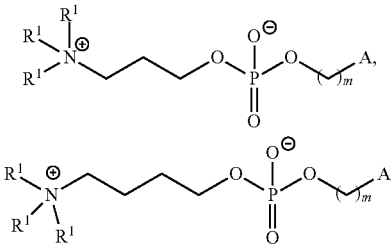

or a salt thereof.

Alternative Lipids

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful.

In certain embodiments, an alternative lipid is used in place of a phospholipid of the present disclosure.

In certain embodiments, an alternative lipid of the invention is oleic acid.

In certain embodiments, the alternative lipid is one of the following:

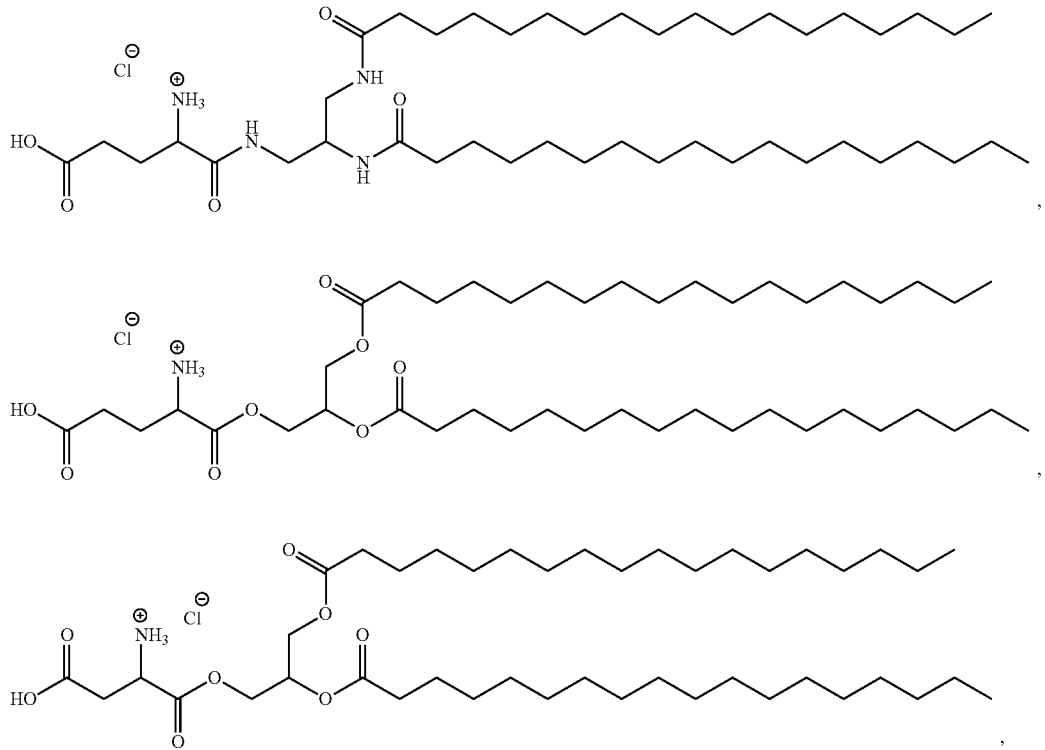

-continued

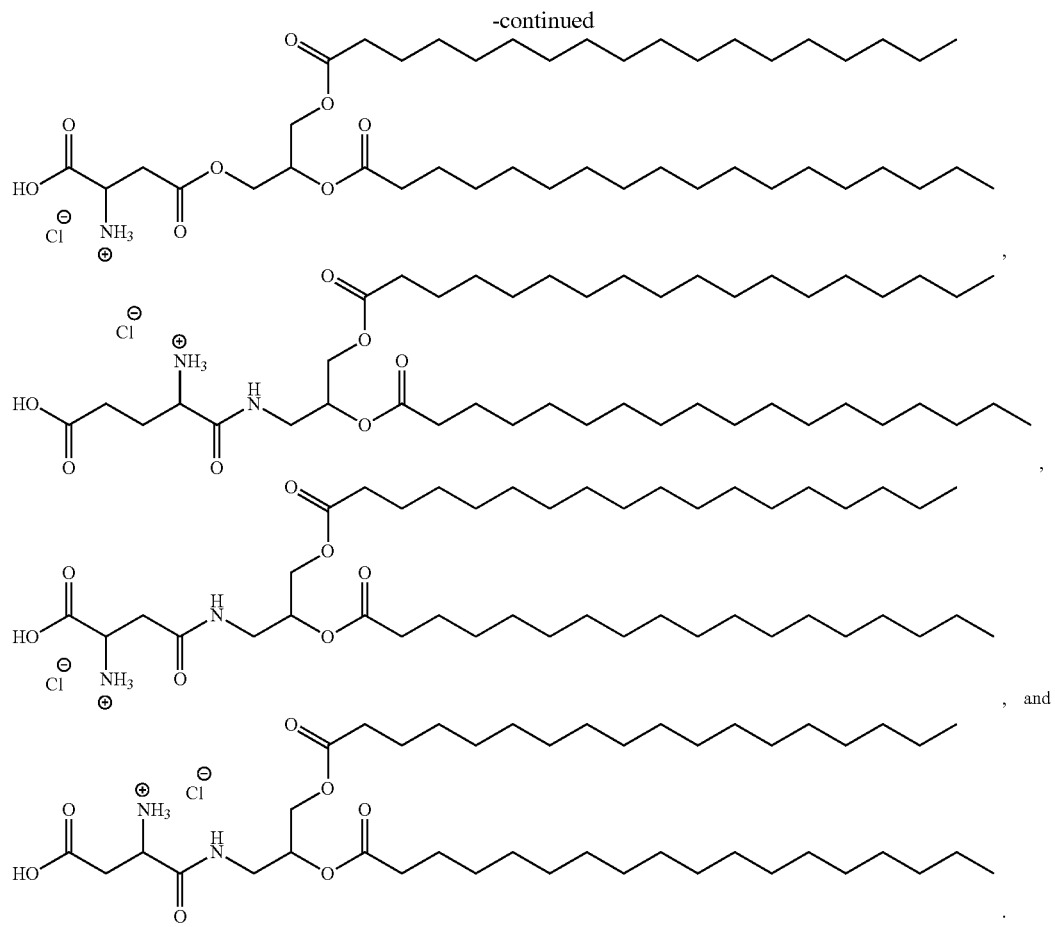

, and

.

Structural Lipids

The lipid composition of a pharmaceutical composition disclosed herein can comprise one or more structural lipids. As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol.

In some embodiments, the structural lipids may be one or more of the structural lipids described in U.S. Application No. 62/520,530.

Polyethylene Glycol (PEG)-Lipids

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidyletha- nolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidyletha- nolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example an mPEG-NH$_2$, has a size of about 1000, 2000, 5000, 10,000, 15,000 or 20,000 daltons. In one embodiment, the PEG-lipid is PEG$_{2k}$-DMG.

In one embodiment, the lipid nanoparticles described herein can comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

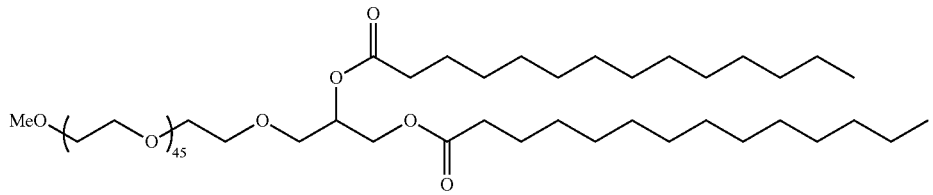

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In certain embodiments, a PEG lipid useful in the present invention is a compound of Formula (V). Provided herein are compounds of Formula (V):

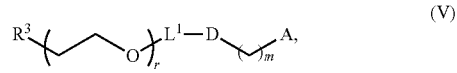

(V)

or salts thereof, wherein:
R$^3$ is —OR$^O$;
R$^O$ is hydrogen, optionally substituted alkyl, or an oxygen protecting group;
r is an integer between 1 and 100, inclusive;
L$^1$ is optionally substituted C$_{1-10}$ alkylene, wherein at least one methylene of the optionally substituted C$_{1-10}$ alkylene is independently replaced with optionally substituted carbocyclylene, optionally substituted heterocyclylene, optionally substituted arylene, optionally substituted heteroarylene, O, N(R$^N$), S, C(O), C(O)N(R$^N$), NR$^N$C(O), C(O)O, OC(O), OC(O)O, OC(O)N(R$^N$), NR$^N$C(O)O, or NR$^N$C(O)N(R$^N$);
D is a moiety obtained by click chemistry or a moiety cleavable under physiological conditions;
m is 0, 1, 2, 3, 4, 5, 6, 7, 8, 9, or 10;
A is of the formula:

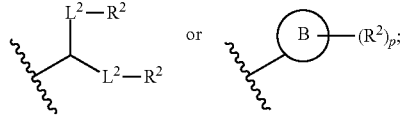

each instance of L$^2$ is independently a bond or optionally substituted C$_{1-6}$ alkylene, wherein one methylene unit of the optionally substituted C$_{1-6}$ alkylene is optionally replaced with O, N(R$^N$), S, C(O), C(O)N(R$^N$), NR$^N$C(O), C(O)O, OC(O), OC(O)O, OC(O)N(R$^N$), NR$^N$C(O)O, or NR$^N$C(O)N(R$^N$);

each instance of R$^2$ is independently optionally substituted C$_{1-30}$ alkyl, optionally substituted C$_{1-30}$ alkenyl, or optionally substituted C$_{1-30}$ alkynyl; optionally wherein one or more methylene units of R$^2$ are independently replaced with optionally substituted carbocyclylene, optionally substituted heterocyclylene, optionally substituted arylene, optionally substituted heteroarylene, N(R$^N$), O, S, C(O), C(O)N(R$^N$), NR$^N$C(O), NR$^N$C(O)N(R$^N$), C(O)O, OC(O), —OC(O)O, OC(O)N(R$^N$), NR$^N$C(O)O, C(O)S, SC(O), C(=NR$^N$), C(=NR$^N$)N(R$^N$), NR$^N$C(=NR$^N$), NR$^N$C(=NR$^N$)N(R$^N$), C(S), C(S)N(R$^N$), NR$^N$C(S), NR$^N$C(S)N(R$^N$), S(O), OS(O), S(O)O, —OS(O)O, S(O)$_2$, S(O)$_2$O, OS(O)$_2$O, N(R$^N$)S(O), S(O)N(R$^N$), N(R$^N$)S(O)N(R$^N$), OS(O)N(R$^N$), N(R$^N$)S(O)O, S(O)$_2$, N(R$^N$)S(O)$_2$, S(O)$_2$N(R$^N$), N(R$^N$)S(O)$_2$N(R$^N$), OS(O)$_2$N(R$^N$), or —N(R$^N$)S(O)$_2$O;
each instance of R$^N$ is independently hydrogen, optionally substituted alkyl, or a nitrogen protecting group;
ring B is optionally substituted carbocyclyl, optionally substituted heterocyclyl, optionally substituted aryl, or optionally substituted heteroaryl; and
p is 1 or 2.

In certain embodiments, the compound of Formula (V) is a PEG-OH lipid (i.e., R$^3$ is —OR$^O$, and R$^O$ is hydrogen). In certain embodiments, the compound of Formula (V) is of Formula (V-OH):

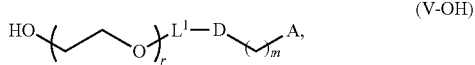

(V-OH)

or a salt thereof.

In certain embodiments, a PEG lipid useful in the present invention is a PEGylated fatty acid. In certain embodiments, a PEG lipid useful in the present invention is a compound of Formula (VI). Provided herein are compounds of Formula (VI):

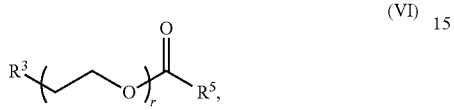

(VI)

or a salts thereof, wherein:
$R^3$ is $—OR^O$;
$R^O$ is hydrogen, optionally substituted alkyl or an oxygen protecting group;
r is an integer between 1 and 100, inclusive;
$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, $N(R^N)$, O, S, C(O), C(O)N(R^N), —NR^NC(O), NR^NC(O)N(R^N), C(O)O, OC(O), OC(O)O, OC(O)N(R^N), NR^NC(O)O, C(O)S, SC(O), C(=NR^N), C(=NR^N)N(R^N), NR^NC(=NR^N), NR^NC(=NR^N)N(R^N), C(S), C(S)N(R^N), NR^NC(S), —NR^NC(S)N(R^N), S(O), OS(O), S(O)O, OS(O)O, OS(O)_2, S(O)_2O, OS(O)_2O, N(R^N)S(O), —S(O)N(R^N), N(R^N)S(O)N(R^N), OS(O)N(R^N), N(R^N)S(O)O, S(O)_2, N(R^N)S(O)_2, S(O)_2N(R^N), —N(R^N)S(O)_2N(R^N), OS(O)_2N(R^N), or N(R^N)S(O)_2O; and
each instance of $R^N$ is independently hydrogen, optionally substituted alkyl, or a nitrogen protecting group.

In certain embodiments, the compound of Formula (VI) is of Formula (VI-OH):

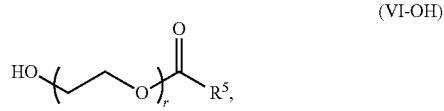

(VI-OH)

or a salt thereof. In some embodiments, r is 45.

In yet other embodiments the compound of Formula (VI) is:

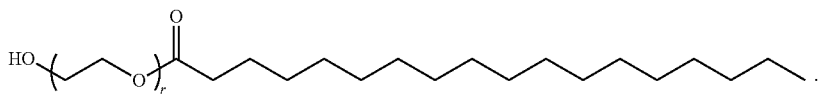

or a salt thereof.

In one embodiment, the compound of Formula (VI) is

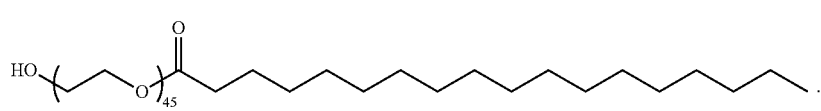

(Compound I)

In some aspects, the lipid composition of the pharmaceutical compositions disclosed herein does not comprise a PEG-lipid.

In some embodiments, the PEG-lipids may be one or more of the PEG lipids described in U.S. Application No. 62/520,530.

In some embodiments, a PEG lipid of the invention comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG, PEG-c-DOMG (also referred to as PEG-DOMG), PEG-DSG and/or PEG-DPG.

In some embodiments, a LNP of the invention comprises an ionizable cationic lipid of any of Formula I, II or III, a phospholipid comprising DSPC, a structural lipid, and a PEG lipid comprising PEG-DMG.

In some embodiments, a LNP of the invention comprises an ionizable cationic lipid of any of Formula I, II or III, a phospholipid comprising DSPC, a structural lipid, and a PEG lipid comprising a compound having Formula VI.

In some embodiments, a LNP of the invention comprises an ionizable cationic lipid of Formula I, II or III, a phospholipid comprising a compound having Formula IV, a structural lipid, and the PEG lipid comprising a compound having Formula V or VI.

In some embodiments, a LNP of the invention comprises an ionizable cationic lipid of Formula I, II or III, a phospholipid comprising a compound having Formula IV, a structural lipid, and the PEG lipid comprising a compound having Formula V or VI.

In some embodiments, a LNP of the invention comprises an ionizable cationic lipid of Formula I, II or III, a phospholipid having Formula IV, a structural lipid, and a PEG lipid comprising a compound having Formula VI.

In some embodiments, a LNP of the invention comprises an ionizable cationic lipid of

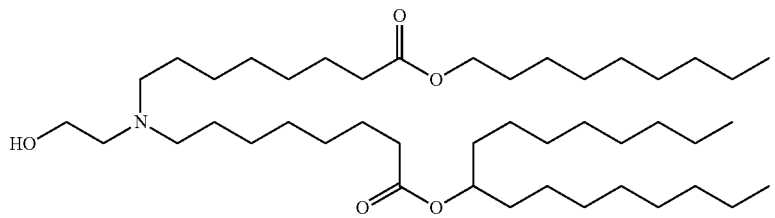

and a PEG lipid comprising Formula VI.

In some embodiments, a LNP of the invention comprises an ionizable cationic lipid of

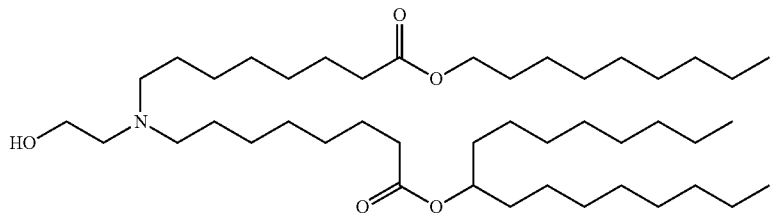

and an alternative lipid comprising oleic acid.

In some embodiments, a LNP of the invention comprises an ionizable cationic lipid of

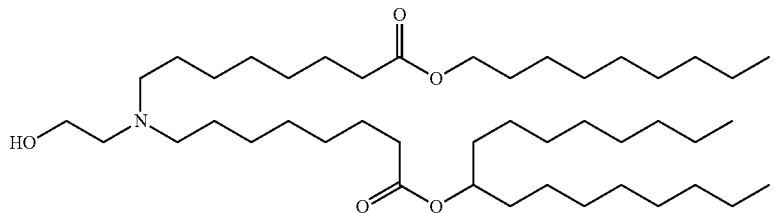

an alternative lipid comprising oleic acid, a structural lipid comprising cholesterol, and a PEG lipid comprising a compound having Formula VI.

In some embodiments, a LNP of the invention comprises an ionizable cationic lipid of

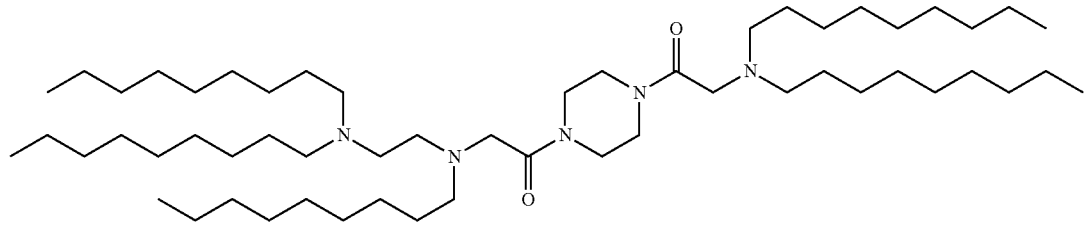 [SMILES: CCCCCCCCCN(CCCCCCCCC)CCN(CCCCCCCCC)CC(=O)N1CCN(C(=O)CN(CCCCCCCCC)CCCCCCCCC)CC1]

a phospholipid comprising DOPE, a structural lipid comprising cholesterol, and a PEG lipid comprising a compound having Formula VI.

In some embodiments, a LNP of the invention comprises an ionizable cationic lipid of a phospholipid comprising DOPE, a structural lipid comprising cholesterol, and a PEG lipid comprising a compound having Formula VII.

In some embodiments, a LNP of the invention comprises an N:P ratio of from about 2:1 to about 30:1.

In some embodiments, a LNP of the invention comprises an N:P ratio of about 6:1.

In some embodiments, a LNP of the invention comprises an N:P ratio of about 3:1.

In some embodiments, a LNP of the invention comprises a wt/wt ratio of the ionizable cationic lipid component to the RNA of from about 10:1 to about 100:1.

In some embodiments, a LNP of the invention comprises a wt/wt ratio of the ionizable cationic lipid component to the RNA of about 20:1.

In some embodiments, a LNP of the invention comprises a wt/wt ratio of the ionizable cationic lipid component to the RNA of about 10:1.

In some embodiments, a LNP of the invention has a mean diameter from about 50 nm to about 150 nm.

In some embodiments, a LNP of the invention has a mean diameter from about 70 nm to about 120 nm.

As used herein, the term "alkyl", "alkyl group", or "alkylene" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The notation "C1-14 alkyl" means an optionally substituted linear or branched, saturated hydrocarbon including 1 14 carbon atoms. Unless otherwise specified, an alkyl group described herein refers to both unsubstituted and substituted alkyl groups.

As used herein, the term "alkenyl", "alkenyl group", or "alkenylene" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "C2-14 alkenyl" means an optionally substituted linear or branched hydrocarbon including 2 14 carbon atoms and at least one carbon-carbon double bond. An alkenyl group may include one, two, three, four, or more carbon-carbon double bonds. For example, $C_{18}$ alkenyl may include one or more double bonds. A $C_{18}$ alkenyl group including two double bonds may be a linoleyl group. Unless otherwise specified, an alkenyl group described herein refers to both unsubstituted and substituted alkenyl groups.

As used herein, the term "alkynyl", "alkynyl group", or "alkynylene" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one carbon-carbon triple bond, which is optionally substituted. The notation "C2-14 alkynyl" means an optionally substituted linear or branched hydrocarbon including 2 14 carbon atoms and at least one carbon-carbon triple bond. An alkynyl group may include one, two, three, four, or more carbon-carbon triple bonds. For example, C18 alkynyl may include one or more carbon-carbon triple bonds. Unless otherwise specified, an alkynyl group described herein refers to both unsubstituted and substituted alkynyl groups.

As used herein, the term "carbocycle" or "carbocyclic group" means an optionally substituted mono- or multi-cyclic system including one or more rings of carbon atoms. Rings may be three, four, five, six, seven, eight, nine, ten, eleven, twelve, thirteen, fourteen, fifteen, sixteen, seventeen, eighteen, nineteen, or twenty membered rings. The notation "C3-6 carbocycle" means a carbocycle including a single ring having 3-6 carbon atoms. Carbocycles may include one or more carbon-carbon double or triple bonds and may be non-aromatic or aromatic (e.g., cycloalkyl or aryl groups). Examples of carbocycles include cyclopropyl, cyclopentyl, cyclohexyl, phenyl, naphthyl, and 1,2 dihydronaphthyl groups. The term "cycloalkyl" as used herein means a non-aromatic carbocycle and may or may not include any double or triple bond. Unless otherwise specified, carbocycles described herein refers to both unsubstituted and substituted carbocycle groups, i.e., optionally substituted carbocycles.

As used herein, the term "heterocycle" or "heterocyclic group" means an optionally substituted mono- or multi-cyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, twelve, thirteen, or fourteen membered rings. Heterocycles may include one or more double or triple bonds and may be non-aromatic or aromatic (e.g., heterocycloalkyl or heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. The term "heterocycloalkyl" as used herein means a non-aromatic heterocycle and may or may not include any double or triple bond. Unless otherwise specified, heterocycles described herein refers to both unsubstituted and substituted heterocycle groups, i.e., optionally substituted heterocycles.

As used herein, the term "heteroalkyl", "heteroalkenyl", or "heteroalkynyl", refers respectively to an alkyl, alkenyl, alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. Unless otherwise specified, heteroalkyls, heteroalkenyls, or heteroalkynyls described herein refers to both unsubstituted and substituted heteroalkyls, heteroalkenyls, or heteroalkynyls, i.e., optionally substituted heteroalkyls, heteroalkenyls, or heteroalkynyls.

As used herein, a "biodegradable group" is a group that may facilitate faster metabolism of a lipid in a mammalian entity. A biodegradable group may be selected from the group consisting of, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group. As used herein, an "aryl group" is an optionally substituted carbocyclic group including one or more aromatic rings. Examples of aryl groups include phenyl and naphthyl groups. As used herein, a "heteroaryl group" is an optionally substituted heterocyclic group including one or more aromatic rings. Examples of heteroaryl groups include pyrrolyl, furyl, thiophenyl, imidazolyl, oxazolyl, and thiazolyl. Both aryl and heteroaryl groups may be optionally substituted. For example, M and M' can be selected from the non-limiting group consisting of optionally substituted phenyl, oxazole, and thiazole. In the formulas herein, M and M' can be independently selected from the list of biodegradable groups above. Unless otherwise specified, aryl or heteroaryl groups described herein refers to both unsubstituted and substituted groups, i.e., optionally substituted aryl or heteroaryl groups.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., C(O)OH), an alcohol (e.g., a hydroxyl, OH), an ester (e.g., C(O)OR OC(O)R), an aldehyde (e.g., C(O)H), a carbonyl (e.g., C(O)R, alternatively represented by C=O), an acyl halide (e.g., C(O)X, in which X is a halide selected from bromide, fluoride, chloride, and iodide), a carbonate (e.g., OC(O)OR), an alkoxy (e.g., OR), an acetal (e.g., C(OR)2R"", in which each OR are alkoxy groups that can be the same or different and R"" is an alkyl or alkenyl group), a phosphate (e.g., $P(O)_{43}$—), a thiol (e.g., SH), a sulfoxide (e.g., S(O)R), a sulfinic acid (e.g., S(O)OH), a sulfonic acid (e.g., $S(O)_2OH$), a thial (e.g., C(S)H), a sulfate (e.g., S(O)42-), a sulfonyl (e.g., S(O)2), an amide (e.g., C(O)NR2, or N(R)C(O)R), an azido (e.g., N3), a nitro (e.g., $NO_2$), a cyano (e.g., CN), an isocyano (e.g., NC), an acyloxy (e.g., OC(O)R), an amino (e.g., NR2, NRH, or $NH_2$), a carbamoyl (e.g., OC(O)NR2, OC(O)NRH, or OC(O)NH2), a sulfonamide (e.g., S(O)2NR2, S(O)2NRH, S(O)2NH2, N(R)S(O)2R, N(H)S(O)2R, N(R)S(O)2H, or N(H)S(O)2H), an alkyl group, an alkenyl group, and a cyclyl (e.g., carbocyclyl or heterocyclyl) group. In any of the preceding, R is an alkyl or alkenyl group, as defined herein. In some embodiments, the substituent groups themselves may be further substituted with, for example, one, two, three, four, five, or six substituents as defined herein. For example, a C1 6 alkyl group may be further substituted with one, two, three, four, five, or six substituents as described herein.

Compounds of the disclosure that contain nitrogens can be converted to N-oxides by treatment with an oxidizing agent (e.g., 3-chloroperoxybenzoic acid (mCPBA) and/or hydrogen peroxides) to afford other compounds of the disclosure. Thus, all shown and claimed nitrogen-containing compounds are considered, when allowed by valency and structure, to include both the compound as shown and its N-oxide derivative (which can be designated as N☐O or N+—O—). Furthermore, in other instances, the nitrogens in the compounds of the disclosure can be converted to N-hydroxy or N-alkoxy compounds. For example, N-hydroxy compounds can be prepared by oxidation of the parent amine by an oxidizing agent such as m CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted C1-C 6 alkyl, C1-C6 alkenyl, C1-C6 alkynyl, 3-14-membered carbocycle or 3-14-membered heterocycle) derivatives.

Other Lipid Composition Components

The lipid composition of a pharmaceutical composition disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof).

A polymer can be included in and/or used to encapsulate or partially encapsulate a pharmaceutical composition disclosed herein (e.g., a pharmaceutical composition in lipid nanoparticle form). A polymer can be biodegradable and/or biocompatible. A polymer can be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The ratio between the lipid composition and the mRNA range can be from about 10:1 to about 60:1 (wt/wt).

In some embodiments, the ratio between the lipid composition and the mRNA can be about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the mRNA encoding a therapeutic agent is about 20:1 or about 15:1.

In some embodiments, the pharmaceutical composition disclosed herein can contain more than one polypeptides. For example, a pharmaceutical composition disclosed herein can contain two or more mRNAs.

In one embodiment, the lipid nanoparticles described herein can comprise mRNA in a lipid:mRNA weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein can comprise the mRNA in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

Nanoparticle Compositions

In some embodiments, the pharmaceutical compositions disclosed herein are formulated as lipid nanoparticles (LNP). Accordingly, the present disclosure also provides nanoparticle compositions comprising: (i) a lipid composition comprising a delivery agent such as compound as described herein, (ii) at least one mRNA encoding OX40L, (iii) at least one mRNA encoding IL-23, and (iv) at least one mRNA encoding IL-36γ. In such nanoparticle composition, the lipid composition disclosed herein can encapsulate the at least one mRNA encoding OX40L, IL-23 or IL-36γ.

Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

In one embodiment, a lipid nanoparticle comprises an ionizable lipid, a structural lipid, a phospholipid, and mRNA. In some embodiments, the LNP comprises an ionizable lipid, a PEG-modified lipid, a sterol and a structural lipid. In some embodiments, the LNP has a molar ratio of about 20-60% ionizable lipid:about 5-25% structural lipid: about 25-55% sterol; and about 0.5-15% PEG-modified lipid.

In some embodiments, the LNP has a polydispersity value of less than 0.4. In some embodiments, the LNP has a net neutral charge at a neutral pH. In some embodiments, the LNP has a mean diameter of 50-150 nm. In some embodiments, the LNP has a mean diameter of 80-100 nm.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid". In certain embodiments, an ionizable lipid molecule may comprise an amine group, and can be referred to as an ionizable amino lipid. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidazolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure.

In addition to these, an ionizable lipid may also be a lipid including a cyclic amine group.

In one embodiment, the ionizable lipid may be selected from, but not limited to, a ionizable lipid described in International Publication Nos. WO2013086354 and WO2013116126; the contents of each of which are herein incorporated by reference in their entirety.

In yet another embodiment, the ionizable lipid may be selected from, but not limited to, formula CLI-CLXXXXII of U.S. Pat. No. 7,404,969; each of which is herein incorporated by reference in their entirety.

In one embodiment, the lipid may be a cleavable lipid such as those described in International Publication No. WO2012170889, herein incorporated by reference in its entirety. In one embodiment, the lipid may be synthesized by methods known in the art and/or as described in International Publication Nos. WO2013086354; the contents of each of which are herein incorporated by reference in their entirety.

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

The size of the nanoparticles can help counter biological reactions such as, but not limited to, inflammation, or can increase the biological effect of the mRNA.

As used herein, "size" or "mean size" in the context of nanoparticle compositions refers to the mean diameter of a nanoparticle composition.

In one embodiment, the mRNA encoding a polypeptide is formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

The term "encapsulation efficiency" of a mRNA describes the amount of the mRNA that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the mRNA in a solution containing the nanoparticle composition before and after breaking up the nanoparticle composition with one or more organic solvents or detergents.

Fluorescence can be used to measure the amount of free mRNA in a solution. For the nanoparticle compositions described herein, the encapsulation efficiency of a mRNA can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

The amount of a mRNA present in a pharmaceutical composition disclosed herein can depend on multiple factors such as the size of the mRNA, desired target and/or application, or other properties of the nanoparticle composition as well as on the properties of the mRNA.

For example, the amount of an mRNA useful in a nanoparticle composition can depend on the size (expressed as length, or molecular mass), sequence, and other characteristics of the mRNA. The relative amounts of a mRNA in a nanoparticle composition can also vary.

The relative amounts of the lipid composition and the mRNA present in a lipid nanoparticle composition of the present disclosure can be optimized according to considerations of efficacy and tolerability. For compositions including an mRNA as a mRNA, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1. In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a mRNA. Such method comprises using any of the pharmaceutical compositions disclosed herein and producing lipid nanoparticles in accordance with methods of production of lipid nanoparticles known in the art. See, e.g., Wang et al. (2015) "Delivery of oligonucleotides with lipid nanoparticles" Adv. Drug Deliv. Rev. 87:68-80; Silva et al. (2015) "Delivery Systems for Biopharmaceuticals. Part I: Nanoparticles and Microparticles" Curr. Pharm. Technol. 16: 940-954; Naseri et al. (2015) "Solid Lipid Nanoparticles and Nanostructured Lipid Carriers: Structure, Preparation and Application" Adv. Pharm. Bull. 5:305-13; Silva et al. (2015) "Lipid nanoparticles for the delivery of biopharmaceuticals" Curr. Pharm. Biotechnol. 16:291-302, and references cited therein.

Other Delivery Agents a. Liposomes, Lipoplexes, and Lipid Nanoparticles

In some embodiments, the compositions or formulations of the present disclosure comprise a delivery agent, e.g., a liposome, a lioplexes, a lipid nanoparticle, or any combination thereof. The mRNAs described herein (e.g., a mRNA comprising a nucleotide sequence encoding a polypeptide) can be formulated using one or more liposomes, lipoplexes, or lipid nanoparticles. Liposomes, lipoplexes, or lipid nanoparticles can be used to improve the efficacy of the mRNAs directed protein production as these formulations can increase cell transfection by the mRNA; and/or increase the translation of encoded protein. The liposomes, lipoplexes, or lipid nanoparticles can also be used to increase the stability of the mRNAs.

Liposomes are artificially-prepared vesicles that can primarily be composed of a lipid bilayer and can be used as a delivery vehicle for the administration of pharmaceutical formulations. Liposomes can be of different sizes. A multi-lamellar vesicle (MLV) can be hundreds of nanometers in diameter, and can contain a series of concentric bilayers separated by narrow aqueous compartments. A small unicellular vesicle (SUV) can be smaller than 50 nm in diameter, and a large unilamellar vesicle (LUV) can be between 50 and 500 nm in diameter. Liposome design can include, but is not limited to, opsonins or ligands to improve the attachment of liposomes to unhealthy tissue or to activate events such as, but not limited to, endocytosis. Liposomes can contain a low or a high pH value in order to improve the delivery of the pharmaceutical formulations.

The formation of liposomes can depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

As a non-limiting example, liposomes such as synthetic membrane vesicles can be prepared by the methods, apparatus and devices described in U.S. Pub. Nos. US20130177638, US20130177637, US20130177636, US20130177635, US20130177634, US20130177633, US20130183375, US20130183373, and US20130183372. In some embodiments, the mRNAs described herein can be encapsulated by the liposome and/or it can be contained in an aqueous core that can then be encapsulated by the liposome as described in, e.g., Intl. Pub. Nos. WO2012031046, WO2012031043, WO2012030901, WO2012006378, and WO2013086526; and U.S. Pub. Nos. US20130189351, US20130195969 and US20130202684. Each of the references in herein incorporated by reference in its entirety.

In some embodiments, the mRNAs described herein can be formulated in a cationic oil-in-water emulsion where the emulsion particle comprises an oil core and a cationic lipid that can interact with the mRNA anchoring the molecule to the emulsion particle. In some embodiments, the mRNAs described herein can be formulated in a water-in-oil emulsion comprising a continuous hydrophobic phase in which the hydrophilic phase is dispersed. Exemplary emulsions can be made by the methods described in Intl. Pub. Nos. WO2012006380 and WO201087791, each of which is herein incorporated by reference in its entirety.

In some embodiments, the mRNAs described herein can be formulated in a lipid-polycation complex. The formation of the lipid-polycation complex can be accomplished by methods as described in, e.g., U.S. Pub. No. US20120178702. As a non-limiting example, the polycation can include a cationic peptide or a polypeptide such as, but not limited to, polylysine, polyornithine and/or polyarginine and the cationic peptides described in Intl. Pub. No. WO2012013326 or U.S. Pub. No. US20130142818. Each of the references is herein incorporated by reference in its entirety.

In some embodiments, the mRNAs described herein can be formulated in a lipid nanoparticle (LNP) such as those described in Intl. Pub. Nos. WO2013123523, WO2012170930, WO2011127255 and WO2008103276; and U.S. Pub. No. US20130171646, each of which is herein incorporated by reference in its entirety.

Lipid nanoparticle formulations typically comprise one or more lipids. In some embodiments, the lipid is an ionizable lipid (e.g., an ionizable amino lipid), sometimes referred to in the art as an "ionizable cationic lipid". In some embodiments, lipid nanoparticle formulations further comprise other components, including a phospholipid, a structural lipid, and a molecule capable of reducing particle aggregation, for example a PEG or PEG-modified lipid.

Exemplary ionizable lipids include, but not limited to, any one of Compounds 1-342 disclosed herein, DLin-MC3-DMA (MC3), DLin-DMA, DLenDMA, DLin-D-DMA, DLin-K-DMA, DLin-M-C2-DMA, DLin-K-DMA, DLin-KC2-DMA, DLin-KC3-DMA, DLin-KC4-DMA, DLin-C2K-DMA, DLin-MP-DMA, DODMA, 98N12-5, C12-200, DLin-C-DAP, DLin-DAC, DLinDAP, DLinAP, DLin-EG-DMA, DLin-2-DMAP, KL10, KL22, KL25, Octyl-CLinDMA, Octyl-CLinDMA (2R), Octyl-CLinDMA (2S), and any combination thereof. Other exemplary ionizable lipids include, (13Z,16Z)—N,N-dimethyl-3-nonyldocosa-13,16-dien-1-amine (L608), (20Z,23Z)—N,N-dimethyl-nonacosa-20,23-dien-10-amine, (17Z,20Z)—N,N-dimemyl-hexacosa-17,20-dien-9-amine, (16Z,19Z)—N5N- dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyleptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, N,N-dimethyl-1-[(1S,2R)-2-octylcyclopropyl]eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy) propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl] ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine, and (11E,20Z,23Z)—N,N-dimethylnonacosa-11,20,2-trien-10-amine, and any combination thereof.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin. In some embodiments, the phospholipids are DLPC, DMPC, DOPC, DPPC, DSPC, DUPC, 18:0 Diether PC, DLnPC, DAPC, DHAPC, DOPE, 4ME 16:0 PE, DSPE, DLPE, DLnPE, DAPE, DHAPE, DOPG, and any combination thereof. In some embodiments, the phospholipids are MPPC, MSPC, PMPC, PSPC, SMPC, SPPC, DHAPE, DOPG, and any combination thereof. In some embodiments, the amount of phospholipids (e.g., DSPC) in the lipid composition ranges from about 1 mol % to about 20 mol %.

The structural lipids include sterols and lipids containing sterol moieties. In some embodiments, the structural lipids include cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the amount of the structural lipids (e.g., cholesterol) in the lipid composition ranges from about 20 mol % to about 60 mol %.

The PEG-modified lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG DMPE, PEG-DPPC, or a PEG-DSPE lipid. In some embodiments, the PEG-lipid are 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In some embodiments, the PEG moiety has a size of about 1000, 2000, 5000, 10,000, 15,000 or 20,000 daltons. In some embodiments, the amount of PEG-lipid in the lipid composition ranges from about 0 mol % to about 5 mol %.

In some embodiments, the LNP formulations described herein can additionally comprise a permeability enhancer molecule. Non-limiting permeability enhancer molecules are described in U.S. Pub. No. US20050222064, herein incorporated by reference in its entirety.

The LNP formulations can further contain a phosphate conjugate. The phosphate conjugate can increase in vivo circulation times and/or increase the targeted delivery of the nanoparticle. Phosphate conjugates can be made by the methods described in, e.g., Intl. Pub. No. WO2013033438 or U.S. Pub. No. US20130196948. The LNP formulation can also contain a polymer conjugate (e.g., a water soluble conjugate) as described in, e.g., U.S. Pub. Nos. US20130059360, US20130196948, and US20130072709. Each of the references is herein incorporated by reference in its entirety.

The LNP formulations can comprise a conjugate to enhance the delivery of nanoparticles of the present invention in a subject. Further, the conjugate can inhibit phagocytic clearance of the nanoparticles in a subject. In some embodiments, the conjugate can be a "self" peptide designed from the human membrane protein CD47 (e.g., the "self" particles described by Rodriguez et al, Science 2013 339, 971-975, herein incorporated by reference in its entirety). As shown by Rodriguez et al. the self peptides delayed macrophage-mediated clearance of nanoparticles which enhanced delivery of the nanoparticles.

The LNP formulations can comprise a carbohydrate carrier. As a non-limiting example, the carbohydrate carrier can include, but is not limited to, an anhydride-modified phytoglycogen or glycogen-type material, phytoglycogen octenyl succinate, phytoglycogen beta-dextrin, anhydride-modified phytoglycogen beta-dextrin (e.g., Intl. Pub. No. WO2012109121, herein incorporated by reference in its entirety).

The LNP formulations can be coated with a surfactant or polymer to improve the delivery of the particle. In some embodiments, the LNP can be coated with a hydrophilic coating such as, but not limited to, PEG coatings and/or coatings that have a neutral surface charge as described in U.S. Pub. No. US20130183244, herein incorporated by reference in its entirety.

The LNP formulations can be engineered to alter the surface properties of particles so that the lipid nanoparticles can penetrate the mucosal barrier as described in U.S. Pat. No. 8,241,670 or Intl. Pub. No. WO2013110028, each of which is herein incorporated by reference in its entirety.

The LNP engineered to penetrate mucus can comprise a polymeric material (i.e., a polymeric core) and/or a polymer-vitamin conjugate and/or a tri-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates.

LNP engineered to penetrate mucus can also include surface altering agents such as, but not limited to, mRNAs, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin (34 dornase alfa, neltenexine, erdosteine) and various DNases including rhDNase.

In some embodiments, the mucus penetrating LNP can be a hypotonic formulation comprising a mucosal penetration enhancing coating. The formulation can be hypotonic for the epithelium to which it is being delivered. Non-limiting examples of hypotonic formulations can be found in, e.g., Intl. Pub. No. WO2013110028, herein incorporated by reference in its entirety.

In some embodiments, the mRNA described herein is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, MA), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In some embodiments, the mRNAs described herein are formulated as a solid lipid nanoparticle (SLN), which can be spherical with an average diameter between 10 to 1000 nm. SLN possess a solid lipid core matrix that can solubilize lipophilic molecules and can be stabilized with surfactants and/or emulsifiers. Exemplary SLN can be those as described in Intl. Pub. No. WO2013105101, herein incorporated by reference in its entirety.

In some embodiments, the mRNAs described herein can be formulated for controlled release and/or targeted delivery. As used herein, "controlled release" refers to a pharmaceutical composition or compound release profile that conforms to a particular pattern of release to effect a therapeutic outcome. In one embodiment, the mRNAs can be encapsulated into a delivery agent described herein and/or known in the art for controlled release and/or targeted delivery. As used herein, the term "encapsulate" means to enclose, surround or encase. As it relates to the formulation of the compounds of the invention, encapsulation can be substantial, complete or partial. The term "substantially encapsulated" means that at least greater than 50, 60, 70, 80, 85, 90, 95, 96, 97, 98, 99, or greater than 99% of the pharmaceutical composition or compound of the invention can be enclosed, surrounded or encased within the delivery agent. "Partially encapsulation" means that less than 10, 10, 20, 30, 40 50 or less of the pharmaceutical composition or compound of the invention can be enclosed, surrounded or encased within the delivery agent.

Advantageously, encapsulation can be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, or greater than 99% of the pharmaceutical composition or compound of the invention are encapsulated in the delivery agent.

In some embodiments, the mRNAs described herein can be encapsulated in a therapeutic nanoparticle, referred to herein as "therapeutic nanoparticle mRNAs." Therapeutic nanoparticles can be formulated by methods described in, e.g., Intl. Pub. Nos. WO2010005740, WO2010030763, WO2010005721, WO2010005723, and WO2012054923; and U.S. Pub. Nos. US20110262491, US20100104645, US20100087337, US20100068285, US20110274759, US20100068286, US20120288541, US20120140790, US20130123351 and US20130230567; and U.S. Pat. Nos. 8,206,747, 8,293,276, 8,318,208 and 8,318,211, each of which is herein incorporated by reference in its entirety.

In some embodiments, the therapeutic nanoparticle mRNA can be formulated for sustained release. As used herein, "sustained release" refers to a pharmaceutical composition or compound that conforms to a release rate over a specific period of time. The period of time can include, but is not limited to, hours, days, weeks, months and years. As a non-limiting example, the sustained release nanoparticle of the mRNAs described herein can be formulated as disclosed in Intl. Pub. No. WO2010075072 and U.S. Pub. Nos. US20100216804, US20110217377, US20120201859 and US20130150295, each of which is herein incorporated by reference in their entirety.

In some embodiments, the therapeutic nanoparticle mRNA can be formulated to be target specific, such as those described in Intl. Pub. Nos. WO2008121949, WO2010005726, WO2010005725, WO2011084521 and WO2011084518; and U.S. Pub. Nos. US20100069426, US20120004293 and US20100104655, each of which is herein incorporated by reference in its entirety.

The LNPs can be prepared using microfluidic mixers or micromixers. Exemplary microfluidic mixers can include, but are not limited to, a slit interdigital micromixer including, but not limited to those manufactured by Microinnova (Allerheiligen bei Wildon, Austria) and/or a staggered herringbone micromixer (SHM) (see Zhigaltsev et al., "Bottom-up design and synthesis of limit size lipid nanoparticle systems with aqueous and triglyceride cores using millisecond microfluidic mixing," Langmuir 28:3633-40 (2012); Belliveau et al., "Microfluidic synthesis of highly potent limit-size lipid nanoparticles for in vivo delivery of siRNA," Molecular Therapy-Nucleic Acids. 1:e37 (2012); Chen et al., "Rapid discovery of potent siRNA-containing lipid nanoparticles enabled by controlled microfluidic formulation," J. Am. Chem. Soc. 134(16):6948-51 (2012); each of which is herein incorporated by reference in its entirety). Exemplary micromixers include Slit Interdigital Microstructured Mixer (SIMM-V2) or a Standard Slit Interdigital Micro Mixer (SSIMM) or Caterpillar (CPMM) or Impinging-jet (IJMM,) from the Institut für Mikrotechnik Mainz GmbH, Mainz Germany. In some embodiments, methods of making LNP using SHM further comprise mixing at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Pub. Nos. US20040262223 and US20120276209, each of which is incorporated herein by reference in their entirety.

In some embodiments, the mRNAs described herein can be formulated in lipid nanoparticles using microfluidic technology (see Whitesides, George M., "The Origins and the Future of Microfluidics," Nature 442: 368-373 (2006); and Abraham et al., "Chaotic Mixer for Microchannels," Science 295: 647-651 (2002); each of which is herein incorporated by reference in its entirety). In some embodiments, the mRNAs can be formulated in lipid nanoparticles using a micromixer chip such as, but not limited to, those from Harvard Apparatus (Holliston, MA) or Dolomite Microfluidics (Royston, UK). A micromixer chip can be used for rapid mixing of two or more fluid streams with a split and recombine mechanism.

In some embodiments, the mRNAs described herein can be formulated in lipid nanoparticles having a diameter from about 1 nm to about 100 nm such as, but not limited to, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles can have a diameter from about 10 to 500 nm. In one embodiment, the lipid nanoparticle can have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the mRNAs can be delivered using smaller LNPs. Such particles can comprise a diameter from below 0.1 μm up to 100 nm such as, but not limited to, less than 0.1 μm, less than 1.0 μm, less than 5 μm, less than 10 μm, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, or less than 975 um.

The nanoparticles and microparticles described herein can be geometrically engineered to modulate macrophage and/or the immune response. The geometrically engineered particles can have varied shapes, sizes and/or surface charges to incorporate the mRNAs described herein for targeted delivery such as, but not limited to, pulmonary delivery (see, e.g., Intl. Pub. No. WO2013082111, herein incorporated by reference in its entirety). Other physical features the geometrically engineering particles can include, but are not limited to, fenestrations, angled arms, asymmetry and surface roughness, charge that can alter the interactions with cells and tissues.

In some embodiment, the nanoparticles described herein are stealth nanoparticles or target-specific stealth nanoparticles such as, but not limited to, those described in U.S. Pub. No. US20130172406, herein incorporated by reference in its entirety. The stealth or target-specific stealth nanoparticles can comprise a polymeric matrix, which can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates, or combinations thereof.

b. Lipidoids

In some embodiments, the compositions or formulations of the present disclosure comprise a delivery agent, e.g., a lipidoid. The mRNAs described herein (e.g., an mRNA comprising a nucleotide sequence encoding a polypeptide) can be formulated with lipidoids. Complexes, micelles, liposomes or particles can be prepared containing these lipidoids and therefore to achieve an effective delivery of the mRNA, as judged by the production of an encoded protein, following the injection of a lipidoid formulation via localized and/or systemic routes of administration. Lipidoid complexes of mRNAs can be administered by various means including, but not limited to, intravenous, intramuscular, or subcutaneous routes.

The synthesis of lipidoids is described in literature (see Mahon et al., Bioconjug. Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

Formulations with the different lipidoids, including, but not limited to penta[3-(1-laurylaminopropionyl)]-triethylenetetramine hydrochloride (TETA-5LAP; also known as 98N12-5, see Murugaiah et al., Analytical Biochemistry, 401:61 (2010)), C12-200 (including derivatives and variants), and MD1, can be tested for in vivo activity. The lipidoid "98N12-5" is disclosed by Akinc et al., Mol Ther. 2009 17:872-879. The lipidoid "C12-200" is disclosed by Love et al., Proc Natl Acad Sci USA. 2010 107:1864-1869 and Liu and Huang, Molecular Therapy. 2010 669-670. Each of the references is herein incorporated by reference in its entirety.

In one embodiment, the mRNAs described herein can be formulated in an aminoalcohol lipidoid. Aminoalcohol lipidoids can be prepared by the methods described in U.S. Pat. No. 8,450,298 (herein incorporated by reference in its entirety).

The lipidoid formulations can include particles comprising either 3 or 4 or more components in addition to mRNAs. Lipidoids and mRNA formulations comprising lipidoids are described in Intl. Pub. No. WO 2015051214 (herein incorporated by reference in its entirety).

Pharmaceutical Compositions

The present disclosure includes pharmaceutical compositions comprising OX40L, IL-23 and IL-36γ encoding mRNAs or a nanoparticle (e.g., a lipid nanoparticle) described herein, in combination with one or more pharmaceutically acceptable excipient, carrier or diluent. In particular embodiments, the mRNA is present in a nanoparticle, e.g., a lipid nanoparticle. In particular embodiments, the mRNA or nanoparticle is present in a pharmaceutical composition.

Pharmaceutical compositions may optionally include one or more additional active substances, for example, therapeutically and/or prophylactically active substances. Pharmaceutical compositions of the present disclosure may be sterile and/or pyrogen-free. General considerations in the formulation and/or manufacture of pharmaceutical agents may be found, for example, in *Remington: The Science and Practice of Pharmacy* 21$^{st}$ ed., Lippincott Williams & Wilkins, 2005 (incorporated herein by reference in its entirety). In particular embodiments, a pharmaceutical composition comprises an mRNA and a lipid nanoparticle, or complexes thereof.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may include between 0.1% and 100%, e.g., between 0.5% and 70%, between 1% and 30%, between 5% and 80%, or at least 80% (w/w) active ingredient.

The mRNAs of the disclosure can be formulated using one or more excipients to: (1) increase stability; (2) increase cell transfection; (3) permit the sustained or delayed release (e.g., from a depot formulation of the mRNA); (4) alter the biodistribution (e.g., target the mRNA to specific tissues or cell types); (5) increase the translation of a polypeptide encoded by the mRNA in vivo; and/or (6) alter the release profile of a polypeptide encoded by the mRNA in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present disclosure can include, without limitation, lipidoids, liposomes, lipid nanoparticles (e.g., liposomes and micelles), polymers, lipoplexes, core-shell nanoparticles, peptides, proteins, carbohydrates, cells transfected with mRNAs (e.g., for transplantation into a subject), hyaluronidase, nanoparticle mimics and combinations thereof. Accordingly, the formulations of the disclosure can include one or more excipients, each in an amount that together increases the stability of the mRNA, increases cell transfection by the mRNA, increases the expression of a polypeptide encoded by the mRNA, and/or alters the release profile of an mRNA-encoded polypeptide. Further, the mRNAs of the present disclosure may be formulated using self-assembled nucleic acid nanoparticles.

Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, MD, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition. Excipients may include, for example: antiadherents, antioxidants, binders, coatings, compression aids, disintegrants, dyes (colors), emollients, emulsifiers, fillers (diluents), film formers or coatings, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

In some embodiments, the formulations described herein may include at least one pharmaceutically acceptable salt. Examples of pharmaceutically acceptable salts that may be included in a formulation of the disclosure include, but are not limited to, acid addition salts, alkali or alkaline earth metal salts, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

In some embodiments, the formulations described herein may contain at least one type of mRNA. As a non-limiting example, the formulations may contain 1, 2, 3, 4, 5 or more than 5 mRNAs described herein. In some embodiments, the formulations described herein may contain at least one mRNA encoding a polypeptide and at least one nucleic acid sequence such as, but not limited to, an siRNA, an shRNA, a snoRNA, and an miRNA.

Liquid dosage forms for e.g., parenteral administration include, but are not limited to, pharmaceutically acceptable emulsions, microemulsions, nanoemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and/or suspending agents. In certain embodiments for parenteral administration, compositions are mixed with solubilizing agents such as CREMAPHOR®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables. Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In some embodiments, pharmaceutical compositions including at least one mRNA described herein are administered to mammals (e.g., humans). Although the descriptions of pharmaceutical compositions provided herein are principally directed to pharmaceutical compositions which are suitable for administration to humans, it will be understood by the skilled artisan that such compositions are generally suitable for administration to any other animal, e.g., to a non-human mammal. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys. In particular embodiments, a subject is provided with two or more mRNAs described herein. In particular embodiments, the first and second mRNAs are provided to the subject at the same time or at different times, e.g., sequentially. In particular embodiments, the first and second mRNAs are provided to the subject in the same pharmaceutical composition or formulation, e.g., to facilitate uptake of both mRNAs by the same cells.

The present disclosure also includes kits comprising a container comprising a mRNA encoding a polypeptide that enhances an immune response. In another embodiment, the kit comprises a container comprising a mRNA encoding a polypeptide that enhances an immune response, as well as one or more additional mRNAs encoding one or more antigens or interest. In other embodiments, the kit comprises a first container comprising the mRNA encoding a polypeptide that enhances an immune response and a second container comprising one or more mRNAs encoding one or more antigens of interest. In particular embodiments, the mRNAs for enhancing an immune response and the mRNA(s) encoding an antigen(s) are present in the same or different nanoparticles and/or pharmaceutical compositions. In particular embodiments, the mRNAs are lyophilized, dried, or freeze-dried.

Kits

In some embodiments, the disclosure provides a kit comprising OX40L, IL-23 and IL-36γ encoding mRNAs, or composition (e.g. lipid nanoparticle) comprising OX40L, IL-23 and IL-36γ encoding mRNAs, as described herein. In some embodiments, a kit comprises a container comprising a pharmaceutical composition comprising a lipid nanoparticle comprising mRNAs encoding human OX40L, IL-23 and IL-36γ polypeptides; and a pharmaceutically acceptable carrier, wherein the pharmaceutical composition comprises 2 mg/ml of the mRNA, and a package insert comprising instructions for administration of the mRNA by intratumoral injection to treat or delay progression of solid tumor malignancy or lymphoma in a human patient.

In some embodiments, a kit comprises a container comprising a pharmaceutical composition comprising a lipid nanoparticle comprising mRNAs encoding human OX40L, IL-23 and IL-36γ polypeptides; and a pharmaceutically acceptable carrier, wherein the pharmaceutical composition comprises 2 mg/ml of the mRNA, and a package insert comprising instructions for administration of the mRNA by intratumoral injection and instruction for use in combination with a second composition comprising a PD-1 antagonist, a PD-L1 antagonist or a CTLA-4 antagonist, for use in treating or delaying progression of solid tumor malignancy or lymphoma in a human patient.

In some embodiments, a kit comprises a container comprising a lipid nanoparticle encapsulating the mRNA described herein, and an optional pharmaceutically acceptable carrier, or a pharmaceutical composition, and a package insert comprising instructions for administration of the lipid nanoparticle or pharmaceutical composition. In some embodiments, a kit comprises a container comprising a lipid nanoparticle encapsulating the mRNA described herein, and an optional pharmaceutically acceptable carrier, or a pharmaceutical composition, and a package insert comprising instructions for administration of the lipid nanoparticle or pharmaceutical composition for treating or delaying progression of an solid tumor malignancy or lymphoma in an individual. In some aspects, the package insert further comprises instructions for administration of the lipid nanoparticle or pharmaceutical composition in combination with a composition comprising a checkpoint inhibitor polypeptide and an optional pharmaceutically acceptable carrier for treating or delaying progression of an solid tumor malignancy or lymphoma in an individual.

In some embodiments, a kit comprises a medicament comprising a lipid nanoparticle encapsulating the OX40L, IL-23 and IL-36γ encoding mRNAs described herein, and an optional pharmaceutically acceptable carrier, or a pharmaceutical composition, and a package insert comprising instructions for administration of the medicament alone or in combination with a composition comprising a checkpoint inhibitor polypeptide and an optional pharmaceutically acceptable carrier. In some embodiments, a kit comprises a medicament comprising a lipid nanoparticle encapsulating the OX40L, IL-23 and IL-36γ encoding mRNAs described herein, and an optional pharmaceutically acceptable carrier, or a pharmaceutical composition, and a package insert comprising instructions for administration of the medicament alone or in combination with a composition comprising a checkpoint inhibitor polypeptide and an optional pharmaceutically acceptable carrier for treating or delaying progression of solid tumor malignancy or lymphoma in an individual. In some aspects, the kit further comprises a package insert comprising instructions for administration of the first medicament prior to, current with, or subsequent to administration of the second medicament for treating or delaying progression of solid tumor malignancy or lymphoma in an individual.

Definitions

Abscopal effect: As used herein, "abscopal effect" refers to a phenomenon in the treatment of cancer, including metastatic cancer, where localized administration of a treatment (e.g., mRNAs encoding OX40L, IL-23 and IL-36γ) to a tumor causes not only a reduction in size of the treated tumor but also a reduction in size of tumors outside the treated area. In some embodiments, the abscopal effect is a local, regional abscopal effect, wherein a proximal or nearby tumor relative to the treated tumor is affected. In some embodiments, the abscopal effect occurs in a distal tumor relative to the treated tumor. In some embodiments, treatment (e.g., mRNAs encoding OX40L, IL-23 and IL-36γ) is administered via intratumoral injection, resulting in a reduction in tumor size of the injected tumor and a proximal or distal uninjected tumor.

Administering: As used herein, "administering" refers to a method of delivering a composition to a subject or patient. A method of administration may be selected to target delivery (e.g., to specifically deliver) to a specific region or system of a body. For example, an administration may be parenteral (e.g., subcutaneous, intracutaneous, intravenous, intraperitoneal, intramuscular, intraarticular, intraarterial, intrasynovial, intrasternal, intrathecal, intralesional, or intracranial injection, as well as any suitable infusion technique), oral, trans- or intra-dermal, interdermal, rectal, intravaginal, topical (e.g., by powders, ointments, creams, gels, lotions, and/or drops), mucosal, nasal, buccal, enteral, vitreal, intratumoral, sublingual, intranasal; by intratracheal instillation, bronchial instillation, and/or inhalation; as an oral spray and/or powder, nasal spray, and/or aerosol, and/or through a portal vein catheter.

Approximately, about: As used herein, the terms "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Cleavable Linker: As used herein, the term "cleavable linker" refers to a linker, typically a peptide linker (e.g., about 5-30 amino acids in length, typically about 10-20 amino acids in length) that can be incorporated into multicistronic mRNA constructs such that equimolar levels of multiple genes can be produced from the same mRNA. Non-limiting examples of cleavable linkers include the 2A family of peptides, including F2A, P2A, T2A and E2A, first discovered in picornaviruses, that when incorporated into an mRNA construct (e.g., between two polypeptide domains) function by making the ribosome skip the synthesis of a peptide bond at C-terminus of the 2A element, thereby leading to separation between the end of the 2A sequence and the next peptide downstream.

Conjugated: As used herein, the term "conjugated," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. In some embodiments, two or more moieties may be conjugated by direct covalent chemical bonding. In other embodiments, two or more moieties may be conjugated by ionic bonding or hydrogen bonding.

Contacting: As used herein, the term "contacting" means establishing a physical connection between two or more entities. For example, contacting a cell with an mRNA or a lipid nanoparticle composition means that the cell and mRNA or lipid nanoparticle are made to share a physical connection. Methods of contacting cells with external entities both in vivo, in vitro, and ex vivo are well known in the biological arts. In exemplary embodiments of the disclosure, the step of contacting a mammalian cell with a composition (e.g., an isolated mRNA, nanoparticle, or pharmaceutical composition of the disclosure) is performed in vivo. For example, contacting a lipid nanoparticle composition and a cell (for example, a mammalian cell) which may be disposed within an organism (e.g., a mammal) may be performed by any suitable administration route (e.g., parenteral administration to the organism, including intravenous, intramuscular, intradermal, and subcutaneous administration). For a cell present in vitro, a composition (e.g., a lipid nanoparticle or an isolated mRNA) and a cell may be contacted, for example, by adding the composition to the culture medium of the cell and may involve or result in transfection. Moreover, more than one cell may be contacted by a nanoparticle composition.

Dosing interval: As used herein, the term "dosing interval", "dosage interval" or "dosing regimen" refers to a discrete amount of time, expressed in units of time, (e.g., 14 days) that transpires between individual administrations (plural) of a dose of a therapeutic composition (e.g., a composition comprising an mRNA). For example, in some embodiments, a dosing interval starts on the day a first dose is administered (e.g., initial dose), and ends on the day a second dose (e.g., a subsequent dose) is administered. In some embodiments, there are multiple dosing intervals during treatment.

Encapsulate: As used herein, the term "encapsulate" means to enclose, surround, or encase. In some embodiments, a compound, an mRNA, or other composition may be fully encapsulated, partially encapsulated, or substantially encapsulated. For example, in some embodiments, an mRNA of the disclosure may be encapsulated in a lipid nanoparticle, e.g., a liposome.

Effective amount: As used herein, the term "effective amount" of an agent is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent. In some embodiments, a therapeutically effective amount is an amount of an agent to be delivered (e.g., nucleic acid, drug, therapeutic agent, diagnostic agent or prophylactic agent) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Fragment: A "fragment," as used herein, refers to a portion. For example, fragments of proteins may include polypeptides obtained by digesting full-length protein isolated from cultured cells or obtained through recombinant DNA techniques.

Heterologous: As used herein, "heterologous" indicates that a sequence (e.g., an amino acid sequence or the nucleic acid that encodes an amino acid sequence) is not normally present in a given polypeptide or nucleic acid. For example, an amino acid sequence that corresponds to a domain or motif of one protein may be heterologous to a second protein.

Hydrophobic amino acid: As used herein, a "hydrophobic amino acid" is an amino acid having an uncharged, nonpolar side chain. Examples of naturally occurring hydrophobic amino acids are alanine (Ala), valine (Val), leucine (Leu), isoleucine (Ile), proline (Pro), phenylalanine (Phe), methionine (Met), and tryptophan (Trp).

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two mRNA sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in *Computational Molecular Biology*, Lesk, A. M., ed., Oxford University Press, New York, 1988; *Biocomputing: Informatics and Genome Projects*, Smith, D. W., ed., Academic Press, New York, 1993; *Sequence Analysis in Molecular Biology*, von Heinje, G., Academic Press, 1987; *Computer Analysis of Sequence Data*, Part I, Griffin, A. M., and Griffin, H. G., eds., Humana Press, New Jersey, 1994; and *Sequence Analysis Primer*, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., *SIAM J Applied Math.*, 48:1073 (1988); incorporated herein by reference. Techniques for determining identity are codified in publicly available computer programs. Exemplary computer software to determine homology between two sequences include, but are not limited to, GCG program package, Devereux et al., *Nucleic Acids Research*, 12(1): 387, 1984, BLASTP, BLASTN, and FASTA, Altschul, S. F. et al., *J. Molec. Biol.*, 215, 403, 1990.

Immune checkpoint inhibitor: An "immune checkpoint inhibitor" or simply "checkpoint inhibitor" refers to a molecule that prevents immune cells from being turned off by cancer cells. As used herein, the term checkpoint inhibitor refers to polypeptides (e.g., antibodies) or mRNAs encoding such polypeptides that neutralize or inhibit inhibitory checkpoint molecules such as cytotoxic T-lymphocyte-associated protein 4 (CTLA-4), programmed death 1 receptor (PD-1), or PD-1 ligand 1 (PD-L1).

Immune response: The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues. In some cases, the administration of a nanoparticle comprising a lipid component and an encapsulated therapeutic agent can trigger an immune response, which can be caused by (i) the encapsulated therapeutic agent (e.g., an mRNA), (ii) the expression product of such encapsulated therapeutic agent (e.g., a polypeptide encoded by the mRNA), (iii) the lipid component of the nanoparticle, or (iv) a combination thereof.

Insertion: As used herein, an "insertion" or an "addition" refers to a change in an amino acid or nucleotide sequence resulting in the addition of one or more amino acid residues or nucleotides, respectively, to a molecule as compared to a reference sequence, for example, the sequence found in a naturally-occurring molecule. For example, an amino acid sequence of a heterologous polypeptide (e.g., a BH3 domain) may be inserted into a scaffold polypeptide (e.g. a SteA scaffold polypeptide) at a site that is amenable to insertion. In some embodiments, an insertion may be a replacement, for example, if an amino acid sequence that forms a loop of a scaffold polypeptide (e.g., loop 1 or loop 2 of SteA or a SteA derivative) is replaced by an amino acid sequence of a heterologous polypeptide.

Insertion Site: As used herein, an "insertion site" is a position or region of a scaffold polypeptide that is amenable to insertion of an amino acid sequence of a heterologous polypeptide. It is to be understood that an insertion site also may refer to the position or region of the mRNA that encodes the polypeptide (e.g., a codon of an mRNA that codes for a given amino acid in the scaffold polypeptide). In some embodiments, insertion of an amino acid sequence of a heterologous polypeptide into a scaffold polypeptide has little to no effect on the stability (e.g., conformational stability), expression level, or overall secondary structure of the scaffold polypeptide.

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Liposome: As used herein, by "liposome" is meant a structure including a lipid-containing membrane enclosing an aqueous interior. Liposomes may have one or more lipid membranes. Liposomes include single-layered liposomes (also known in the art as unilamellar liposomes) and multi-layered liposomes (also known in the art as multilamellar liposomes).

Linker: As used herein, a "linker" (including a subunit linker, and a heterologous polypeptide linker as referred to herein) refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker can be of sufficient length as to not interfere with incorporation into a nucleic acid sequence. The linker can be used for any useful purpose, such as to form polynucleotide multimers (e.g., through linkage of two or more chimeric polynucleotides molecules or IVT polynucleotides) or polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof. Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Metastasis: As used herein, the term "metastasis" means the process by which cancer spreads from the place at which it first arose as a primary tumor to distant locations in the body. A secondary tumor that arose as a result of this process may be referred to as "a metastasis."

mRNA: As used herein, an "mRNA" refers to a messenger ribonucleic acid. An mRNA may be naturally or non-naturally occurring. For example, an mRNA may include modified and/or non-naturally occurring components such as one or more nucleobases, nucleosides, nucleotides, or linkers. An mRNA may include a cap structure, a chain terminating nucleoside, a stem loop, a polyA sequence, and/or a polyadenylation signal. An mRNA may have a nucleotide sequence encoding a polypeptide. Translation of an mRNA, for example, in vivo translation of an mRNA inside a mammalian cell, may produce a polypeptide. Traditionally, the basic components of an mRNA molecule include at least a coding region, a 5'-untranslated region (5'-UTR), a 3'UTR, a 5' cap and a polyA sequence.

microRNA (miRNA): As used herein, a "microRNA (miRNA)" is a small non-coding RNA molecule which may function in post-transcriptional regulation of gene expression (e.g., by RNA silencing, such as by cleavage of the mRNA, destabilization of the mRNA by shortening its polyA tail, and/or by interfering with the efficiency of translation of the mRNA into a polypeptide by a ribosome). A mature miRNA is typically about 22 nucleotides long.

microRNA-122 (miR-122): As used herein, "microRNA-122 (miR-122)" refers to any native miR-122 from any vertebrate source, including, for example, humans, unless otherwise indicated. miR-122 is typically highly expressed in the liver, where it may regulate fatty-acid metabolism. miR-122 levels are reduced in liver cancer, for example, hepatocellular carcinoma. miR-122 is one of the most highly-expressed miRNAs in the liver, where it regulates targets including but not limited to CAT-1, CD320, AldoA, Hjv, Hfe, ADAM10, IGFR1, CCNG1, and ADAM17. Mature human miR-122 may have a sequence of AACGC-CAUUAUCACACUAAAUA (SEQ ID NO: 13, corresponding to hsa-miR-122-3p) or UGGAGU-GUGACAAUGGUGUUUG (SEQ ID NO: 19, corresponding to hsa-miR-122-5p).

microRNA (miRNA) binding site: As used herein, a "microRNA (miRNA) binding site" refers to a miRNA target site or a miRNA recognition site, or any nucleotide sequence to which a miRNA binds or associates. In some embodiments, a miRNA binding site represents a nucleotide location or region of an mRNA to which at least the "seed" region of a miRNA binds. It should be understood that "binding" may follow traditional Watson-Crick hybridization rules or may reflect any stable association of the miRNA with the target sequence at or adjacent to the microRNA site.

miRNA seed: As used herein, a "seed" region of a miRNA refers to a sequence in the region of positions 2-8 of a mature miRNA, which typically has perfect Watson-Crick complementarity to the miRNA binding site. A miRNA seed may include positions 2-8 or 2-7 of a mature miRNA. In some embodiments, a miRNA seed may comprise 7 nucleotides (e.g., nucleotides 2-8 of a mature miRNA), wherein the seed-complementary site in the corresponding miRNA binding site is flanked by an adenine (A) opposed to miRNA position 1. In some embodiments, a miRNA seed may comprise 6 nucleotides (e.g., nucleotides 2-7 of a mature miRNA), wherein the seed-complementary site in the corresponding miRNA binding site is flanked by an adenine (A) opposed to miRNA position 1. When referring to a miRNA binding site, an miRNA seed sequence is to be understood as having complementarity (e.g., partial, substantial, or complete complementarity) with the seed sequence of the miRNA that binds to the miRNA binding site.

Modified: As used herein "modified" refers to a changed state or structure of a molecule of the disclosure. Molecules may be modified in many ways including chemically, structurally, and functionally. In one embodiment, the mRNA molecules of the present disclosure are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Nanoparticle: As used herein, "nanoparticle" refers to a particle having any one structural feature on a scale of less than about 1000 nm that exhibits novel properties as compared to a bulk sample of the same material. Routinely, nanoparticles have any one structural feature on a scale of less than about 500 nm, less than about 200 nm, or about 100 nm. Also routinely, nanoparticles have any one structural feature on a scale of from about 50 nm to about 500 nm, from about 50 nm to about 200 nm or from about 70 to about 120 mn. In exemplary embodiments, a nanoparticle is a particle having one or more dimensions of the order of about 1-1000 nm. In other exemplary embodiments, a nanoparticle is a particle having one or more dimensions of the order of about 10-500 nm. In other exemplary embodiments, a nanoparticle a particle having one or more dimensions of the order of about 50-200 nm. A spherical nanoparticle would have a diameter, for example, of between about 50-100 or 70-120 nanometers. A nanoparticle most often behaves as a unit in terms of its transport and properties. It is noted that novel properties that differentiate nanoparticles from the corresponding bulk material typically develop at a size scale of under 1000 nm, or at a size of about 100 nm, but nanoparticles can be of a larger size, for example, for particles that are oblong, tubular, and the like. Although the size of most molecules would fit into the above outline, individual molecules are usually not referred to as nanoparticles.

Nucleic acid: As used herein, the term "nucleic acid" is used in its broadest sense and encompasses any compound and/or substance that includes a polymer of nucleotides. These polymers are often referred to as polynucleotides. Exemplary nucleic acids or polynucleotides of the disclosure include, but are not limited to, ribonucleic acids (RNAs), deoxyribonucleic acids (DNAs), DNA-RNA hybrids, RNAi-inducing agents, RNAi agents, siRNAs, shRNAs, miRNAs, antisense RNAs, ribozymes, catalytic DNA, RNAs that induce triple helix formation, threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

Operably linked: As used herein, the phrase "operably linked" refers to a functional connection between two or more molecules, constructs, transcripts, entities, moieties or the like.

Patient: As used herein, "patient" refers to a subject who may seek or be in need of treatment, requires treatment, is receiving treatment, will receive treatment, or a subject who is under care by a trained professional for a particular disease or condition. In particular embodiments, a patient is a human patient. In some embodiments, a patient is a patient suffering from cancer (e.g., liver cancer or colorectal cancer).

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipient: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, *Pharmaceutical Salts: Properties, Selection, and Use,* P. H. Stahl and C. G. Wermuth (eds.), Wiley-VCH, 2008, and Berge et al., *Journal of Pharmaceutical Science,* 66, 1-19 (1977), each of which is incorporated herein by reference in its entirety.

Polypeptide: As used herein, the term "polypeptide" or "polypeptide of interest" refers to a polymer of amino acid residues typically joined by peptide bonds that can be produced naturally (e.g., isolated or purified) or synthetically.

Subject: As used herein, the term "subject" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants. In some embodiments, a subject may be a human patient having a solid tumor malignancy or lymphoma.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of a disease, disorder, and/or condition.

Targeting moiety: As used herein, a "targeting moiety" is a compound or agent that may target a nanoparticle to a particular cell, tissue, and/or organ type.

Therapeutic Agent: The term "therapeutic agent" refers to any agent that, when administered to a subject, has a therapeutic, diagnostic, and/or prophylactic effect and/or elicits a desired biological and/or pharmacological effect.

Transfection: As used herein, the term "transfection" refers to methods to introduce a species (e.g., a polynucleotide, such as an mRNA) into a cell.

Treating: As used herein, the term "treating" refers to partially or completely alleviating, ameliorating, improving, relieving, delaying onset of, inhibiting progression of, reducing severity of, and/or reducing incidence of one or more symptoms or features of a solid tumor malignancy or lymphoma. For example, "treating" cancer may refer to inhibiting survival, growth, and/or spread of a tumor. Treatment may be measured by reduction in numbers of tumors or reduction in size of a particular tumor and/or reduction in metastasis. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Preventing: As used herein, the term "preventing" refers to partially or completely inhibiting the onset of one or more symptoms or features of a particular infection, disease, disorder, and/or condition.

Tumor: As used herein, a "tumor" is an abnormal growth of tissue, whether benign or malignant.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

EQUIVALENTS AND SCOPE

Those skilled in the art will recognize, or be able to ascertain using no more than routine experimentation, many equivalents to the specific embodiments in accordance with the disclosure described herein. The scope of the present disclosure is not intended to be limited to the Description below, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

Example 1: Synergistic Efficacy of Triple Combination of mRNAs Encoding OX40L, IL-23 and IL-36γ in the Immunosuppressive MC38-M Colon Cancer Model The efficacy of triple combination therapy comprising mRNA encoding OX40L, mRNA encoding IL-23, and mRNA encoding IL-36γ was assessed in the MC38 colon cancer model.

mRNA encoding a mouse OX40L polypeptide (amino acid sequence SEQ ID NO: 3), mRNA encoding a human IL-23 polypeptide comprising IL-12p40 subunit and IL-23p19 subunit linked by GS Linker (amino acid sequence SEQ ID NO: 32), and mRNA encoding a human IL-36γ polypeptide (amino acid sequence SEQ ID NO: 35) were prepared. Each mRNA comprised a miR-122 binding site in the 3'UTR.

MC-38 colon adenocarcinoma tumors were established subcutaneously in C57BL/6 mice. See Rosenberg et al., Science 233(4770):1318-21 (1986). Tumors were monitored for size and palpability. See Kim et al., Journal of Immunology 122(2):549-554 (1979); Donnou et al., Advances in Hematology 2012:701704 (2012). Once the MC-38 tumors reached a mean size of approximately 100 mm$^3$, animals were treated with single intratumoral doses of mRNAs formulated in Compound II-based lipid particles (SM68 LNP), at 5 µg total mRNA/dose, every 7 days for 4 cycles (Q7Dx4). FIGS. 1A-1E, dashed vertical lines. The number of complete responders (CRs) are indicated, n/group=15.

Control animals were treated with an equivalent dose of negative control mRNA formulated in the same LNP. Negative controls were non-translatable versions of an mRNA encoding a control protein, wherein the mRNA comprises multiple stop codons.

The results demonstrate that intratumoral (ITU) administration of LNP comprising triplet combination of mRNAs encoding OX40L/IL-23/IL-36γ polypeptides achieved 11/15 CRs (FIG. 1D). This response rate is superior to combinations with doublet mRNAs. There was 1/15 CR in the group administered LNP comprising doublet mRNAs encoding OX40L/IL-36γ polypeptides (FIG. 1A). The groups administered LNP comprising doublet mRNAs encoding IL-23/IL-36γ and IL-23/OX-40L polypeptides have responder rates of 4/15 and 7/15, respectively. FIGS. 1B, 1C.

Example 2: Marked Efficacy in Both Primary Treated and Untreated Distal Tumors with Triplet mRNA Therapy Experiments were conducted using the MC38-S dual flank mice tumor model and mRNA as described in Example 1. The MC38-S variant is less aggressive and allows multiple tumor modeling in single mice. MC38-S cells were implanted in each flank of each animal. See FIG. 2E. Only one tumor in each mice were treated, whereas a distal tumor was left untreated. A primary tumor on one flank was administered doublet combinations of mRNAs encoding IL-23/IL-36γ or OX40L/IL-23; a triplet combination of mRNAs encoding OX40L, IL-23, IL-36γ; or control mRNA (non-translating mRNA encoding for OX40L). FIGS. 2A-2D. The total dose of mRNA per treatment was 5 μg of mRNA. LNP encapsulated mRNAs were administered as single intratumoral doses. N/group=20.

The combined effect of ITu treatment on the first and second (untreated) tumor was measured as combined tumor volume. FIGS. 2A-2D.

FIG. 2D shows combined tumor volumes in mice treated with control mRNA. When doublet mRNA IL-23/IL-36γ or OX40L/IL-23 therapy were administered to the primary tumors, approximately 50% CRs were observed. (FIGS. 2A, 2B). When the triplet mRNA therapy was administered to the primary tumors (FIG. 2C), 20 complete responses (100%) were observed.

This data indicates that treatment of a tumor with an mRNA therapeutic composition can effectively treat tumors at other locations. As shown in FIG. 2C, a single, relatively low ITu dose of triplet mRNA was able to induce complete disease control in mice bearing two tumors at both treated and uninjected distal sites. The results demonstrate that local therapy is efficacious for treatment of multi-lesional and metastatic cancers. FIG. 2F shows the effect of doublet mRNA combinations and a triplet mRNA combination therapies on survival rate. Animals that were not treated or administered control mRNA did not survive past day 45 of the study. After day 70, 70% of the mice administered doublet mRNAs encoding OX40L/IL-23 or IL-23/IL-36γ survived implantation with MC38 tumors. All mice treated with triplet mRNA encoding OX40L/IL-23/IL-36γ achieved complete response and survived implantation with MC8 tumors. Thus local therapy with triplet mRNA was able to achieve complete disease control, and is superior to doublet mRNA combinations.

Example 3: Efficacy of a Combination Treatment Comprising Triplet mRNA Therapy and Anti-PD-L1 Antibodies in MC38 Model The administration of doublet and triplet therapy increased levels of PD-L1. Slight increases in PD-L1 levels were observed in cancer cells, e.g., CD45-, FSC-hi and MHCII-, after the administration of triplet therapy. The administration of the doublet IL-23/IL-36γ also resulted in an increased percentage of CD11b+ cells positive for PD-L1. This observation correlated with an increase in PD-L1 expression in CD11b+ cells. Administration of the triplet combination also resulted in an increased percentage of CD11b+ cells positive for PD-L1 and an increase in PD-L1 expression in CD11b+ cells. Data not shown.

Figures 3A, 3B, 3C, 3D:
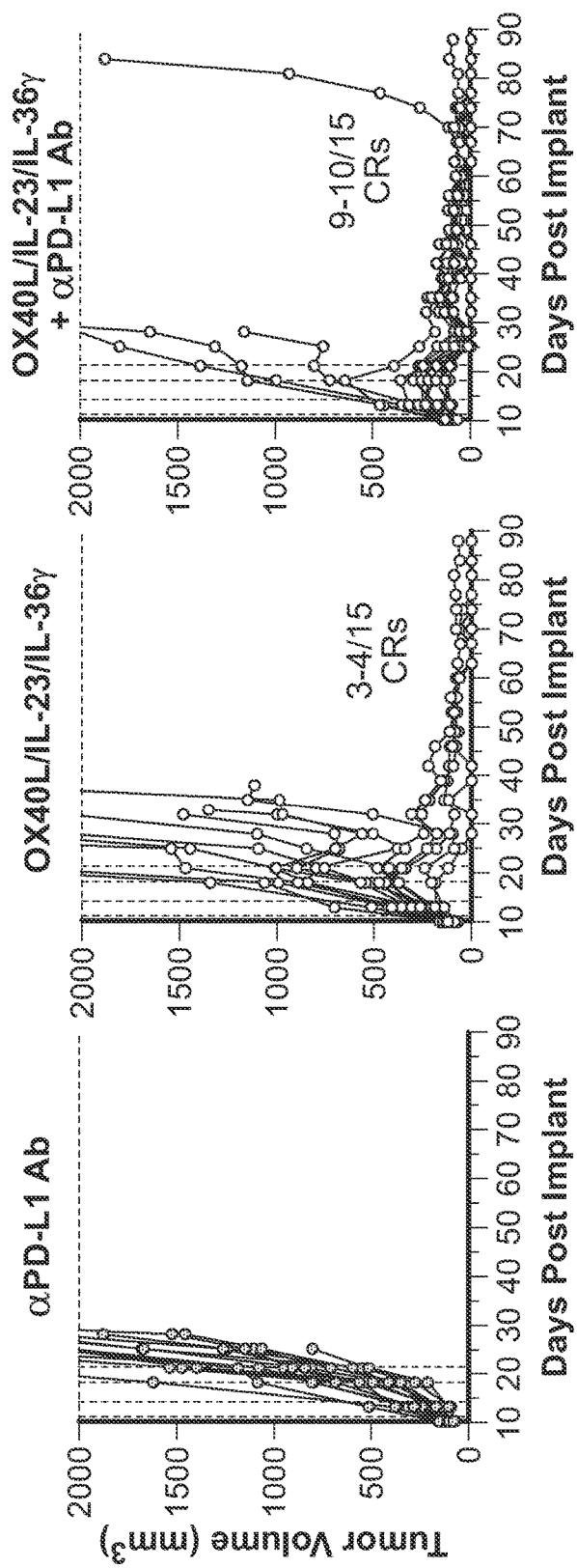
FIGS. 3A-3D show in vivo anti-tumor efficacy of triplet mRNA therapy combined with an antiPD-L1 antibody (10F.9G2) in immunosuppressive MC38 tumors.

The increase in expression of PD-L1 in the MC38 model in response to treatment with triplet mRNA therapy provided a rationale to combine the triplet therapy with anti-PD-L1 antibodies. Total mRNA dosing was 5 μg of total mRNA, administered intratumorally as a single dose of LNP encapsulated mRNAs as described in Example 1. FIGS. 3B, 3C, 3D blue/purple vertical lines. The antibody (anti-PD-L1 antibody 10F.9G2 or control) was dosed intraperitoneally twice per week at 10 mg/kg. FIGS. 3A, 3B, 3C, purple/red vertical lines. N/group=15.

No responses were observed when the negative control mRNA (FIG. 3D) or the anti-PD-L1 antibody (FIG. 3A) were administered alone. When the triplet mRNA therapy (mRNAs encoding OX40L/IL-23/IL-36γ) was administered, 3-4 out of 15 mice showed CRs. FIG. 3B. On the other hand, when the triplet mRNA therapy was administered in combination with the anti-PD-L1 antibody, 9-10 out of 15 mice experienced complete responses. FIG. 3C. In a follow-up study with anti-PD-L1 antibody in combination with triplet mRNA, 12/15 CRs were observed. Data not shown. Synergy (12/15 CRs) was also observed with anti-PD-1 antibody combination with triplet mRNA. Data not shown. These data indicate that tumors refractory to treatment with a systemic conventional therapy, e.g., an anti-PD-L1 antibody, can be effectively treated by combining such therapy with a triple therapy comprising mRNAs encoding OX40L/IL-23/IL-36γ.

Example 4: Efficacy of a Combination Treatment Comprising Triplet mRNA Therapy and Anti-CTLA4 Antibodies in MC38 Model The efficacy of a combination of the triplet therapy with anti-CTLA4 antibodies was assessed in the MC38 model. Total mRNA dosing was 5 μg of total mRNA, administered intratumorally as a single dose of LNP encapsulated mRNAs as described in Example 1. FIGS. 4B, 4C, 4D, blue/purple vertical lines. The antibody (anti-CTLA4 antibody 9D9 or control) was dosed intraperitoneally twice per week at 10 mg/kg. FIGS. 4A, 4B, 4C, purple/redlines. N/group=15.

No responses were observed when the negative control mRNA (FIG. 4D) or the anti-CTLA-4 antibody (FIG. 4A) were administered alone. When the triplet mRNA therapy (mRNAs encoding OX40L/IL-23/IL-36γ) was administered, 6 out of 15 mice showed CRs. FIG. 4B. On the other hand, when the triplet mRNA therapy was administered in combination with the anti-CTLA-4 antibody, 12 out of 15 mice experienced complete responses. FIG. 4C. These data indicate that tumors refractory to treatment with a systemic conventional therapy, e.g., an anti-CTLA-4 antibody, can be effectively treated by combining such therapy with a triple therapy comprising mRNAs encoding OX40L/IL-23/IL-36γ. Further, the synergistic efficacy of triplet mRNA therapy is shown with checkpoint inhibitors that target biologically distinct (anti-PD-L1 and anti-CTLA4) pathways. FIGS. 3C, 4C.

Figure 5:
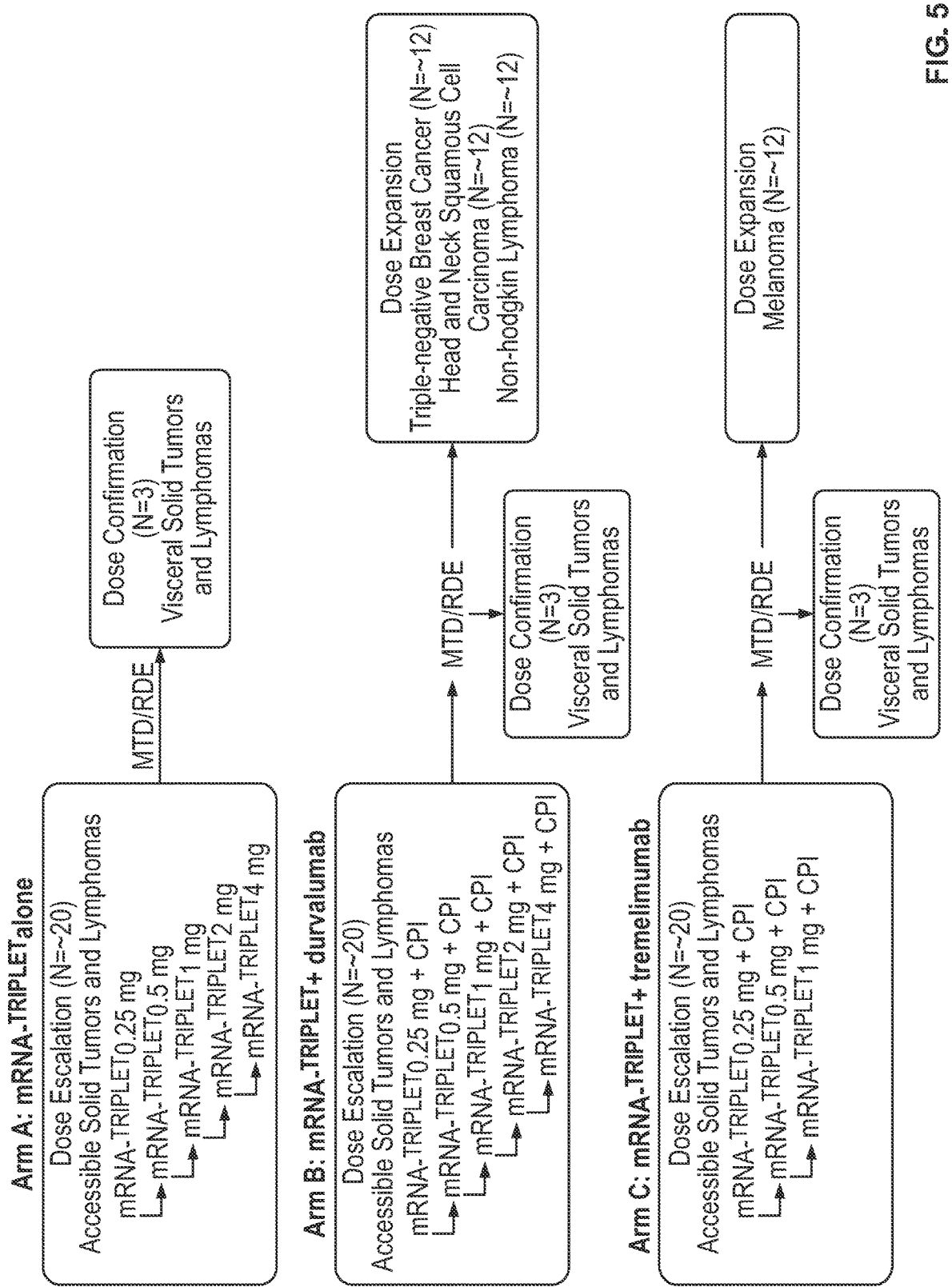
FIG. 5 provides a schematic depicting the clinical study design to evaluate mRNA-TRIPLET (mRNAs encoding OX40L/IL-23/IL-36γ) administered alone and in combination with checkpoint inhibitors: durvalumab (anti-PD-L1), or tremelimumab (anti-CTLA-4). The study comprises a dose escalation phase with three arms: mRNA-TRIPLET alone (Arm A), mRNA-TRIPLET with durvalumab (Arm B), and mRNA-TRIPLET with tremelimumab (Arm C). Once maximum tolerated dose (MTD) and/or recommended dose for expansion (RDE) is defined for mRNA-TRIPLET alone and in combination with checkpoint inhibitors, a dose expansion phase will be conducted to assess anti-tumor activity of mRNA-TRIPLET and durvalumab in Triple-negative breast cancer (TNBC), head and neck squamous cell carcinoma (HNSCC), and non-Hodgkin lymphoma (NHL); or the anti-tumor activity of mRNA-TRIPLET and tremelimumab in melanoma.

Example 5: Clinical Study Design to Evaluate Anti-Tumor Efficacy of mRNAs Encoding OX40L, IL-23 and IL-36γ Alone or in Combination with Immune Checkpoint Blockade FIG. 5 is the study design of a Phase 1, dose escalation study of ITu injections of mRNA-TRIPLET comprising mRNAs encoding polypeptides of OX40L, IL-23 and IL-36γ alone and in combination with intravenously administered immune checkpoint blockade therapy in patients with histologically confirmed advanced or metastatic solid tumor malignancies or lymphomas. The study includes the following three treatment arms:

Arm A: mRNA-TRIPLET alone, administered every two weeks (Q2W) for 3 doses.

Arm B: mRNA-TRIPLET in combination with durvalumab (PD-L1 inhibitor) every four weeks (Q4W) for three cycles. Following completion of 3 cycles of mRNA-TRIPLET, patients may continue with durvalumab as a single-agent until disease progression, unacceptable toxicity, or total of twenty-four months of treatment, whichever is sooner.

Arm C: mRNA-TRIPLET in combination with tremelimumab (CTLA-4 inhibitor) Q4W for three cycles. Following completion of 3 cycles of mRNA-TRIPLET, patients may continue with tremelimumab as a single-agent for one additional cycle (4 cycles total) until disease progression or unacceptable toxicity, whichever is sooner.

The study comprises 3 dose escalation and dose confirmation parts (Arms A, B, and C) followed by a dose expansion part in select indications for combination Arms B and C. The dose expansion will comprise four treatment groups across the treatment arms summarized as follows:

Arm B: mRNA-TRIPLET in combination with durvalumab
  Group 1: Triple-negative breast cancer (TNBC)
  Group 2: Head and neck squamous cell carcinoma (HNSCC)
  Group 3: Non-Hodgkin lymphoma (NHL)
Arm C: mRNA-TRIPLET in combination with tremelimumab
  Group 4: Melanoma Dose escalation will be conducted in patients with solid tumors or lymphoma with cutaneous or subcutaneous accessible lesions, and will start with mRNA-TRIPLET alone (Arm A). Once the first 2 dose levels of mRNA-TRIPLET alone (Arm A) are cleared for safety, dose escalation for mRNA-TRIPLET in combination with fixed dose of durvalumab (Arm B) will start. Once the first dose level of Arm B is cleared for safety, dose escalation for mRNA-TRIPLET in combination with a fixed dose of tremelimumab (Arm C) will start.

The dose levels for mRNA-TRIPLET for all treatment arms is as in the following table:

| Dose Level | mRNA-TRIPLET Dose |
| --- | --- |
| −1* | 0.10 mg |
| 1 (starting dose) | 0.25 mg |
| 2 | 0.50 mg |
| 3 | 1 mg |
| 4 | 2 mg |
| 5 | 4 mg |
| 6 | 8 mg |

*Represents a treatment dose if de-escalation from the starting dose is required.

The dose and treatment schedule for the different study treatments are summarized in the following table:

| Study Drugs | Pharmaceutical Form and Route of Administration | Dose | Frequency |
| --- | --- | --- | --- |
| mRNA-TRIPLET | Solution for intratumoral injection | 0.25 mg (starting dose) | Q2W (Treatment Arm A) Q4W (Treatment Arms B and C) |
| Durvalumab | 500-mg vial solution for infusion after dilution, 50 mg/mL | 1500 mg | Q4W |
| Tremelimumab | 400-mg vial solution for infusion after dilution, 20 mg/mL | 225 mg | Q4W for 4 cycles |

Once the maximum tolerated dose (MTD) and/or recommended dose for expansion (RDE) have been determined in the dose escalation parts, dose confirmation of MTD and/or RDE for each treatment arm will be conducted with solid tumors or lymphoma with visceral lesions injectable with ultrasound or CT guidance.

Once the MTD and/or RDE have been determined in the dose escalation/dose confirmation parts, patients will be enrolled in the respective dose-expansion parts in order to assess the preliminary anti-tumor activity of mRNA-TRIPLET in combination with either durvalumab or tremelimumab in select indications. FIG. 5

---

SEQUENCE TABLE 1

SEQ ID NO: DESCRIPTION

1 MERVQPLEENVGNAARPRFERNKLLLVASViQGLGLLLCFTYiCLHFSALQVSHRYPRIQSIKVQFTE
YKKEKGFILTSQKEDEIMKVQNNSVIINCDGFYLISLKGYFSQEVNISLHYQKDEEPLFQLKKVRSVN
SLMVASLTYKDKVYLNVTTDNTSLDDFHVNGGELILIHQNPGEFCVL
OX40L (TNSFR4) - Tumor necrosis factor ligand superfamily member 4 isoform 1 [Homo sapiens] NP_003317 (bold is intracellular domain, italics is transmembrane domain, and underline is extracellular domain)

2 MVSHRYPRIQSIKVQFTEYKKEKGFILTSQKEDEIMKVQNNSVIINCDGFYLISLKGYFSQEVNISLH
YQKDEEPLFQLKKVRSVNSLMVASLTYKDKVYLNVTTDNTSLDDFHVNGGELILIHQNPGEFCVL
OX40L (TNSFR4) - TNFSF4 isoform 2 [Homo sapiens] NP_001284491

3 MEGEGVQPLDENLENGSRPRFKWKKTLRLVVSGIKGAGMLLCFIYVCLQLSSSPAKDPPIQRLRGAVT
RCEDGQLFISSYKNEYQTMEVQNNSVVIKCDGLYIIYLKGSFFQEVKIDLHFREDHNPISIPMLNDGR
RIVFTVVASLAFKDKVYLTVNAPDTLCEHLQINDGELIVVQLTPGYCAPEGSYHSTVNQVPL
OX40L (TNSFR4) - TNFSF4 [Mus musculus] NP_033478

SEQUENCE TABLE 1

SEQ ID NO: DESCRIPTION

4 AUGGAAAGGGUCCAACCCCUGGAAGAGAAUGUGGGAAAUGCAGCCAGGCCAAGAUUCGAGAGGAACAA
AGCUAUUGCUGGUGGCCUCUGUAAUUCAGGGACUGGGGCUGCUCCUGUGCUUCACCUACAUCUGCCUGC
ACUUCUCUGCUCUUCAGGUAUCACAUCGGUAUCCUCGAAUUCAAAGUAUCAAAGUACAAUUUACCGAA
UAUAAGAAGGAGAAAGGUUUCAUCCUCACUUCCCAAAAGGAGGAUGAAAUCAUGAAGGUGCAGAACAA
CUCAGUCAUCAUCAACUGUGAUGGGUUUUAUCUCAUCUCCCUGAAGGGCUACUUCUCCCAGGAAGUCA
ACAUUAGCCUUCAUUACCAGAAGGAUGAGGAGCCCCUCUUCCAACUGAAGAAGGUCAGGUCUGUCAAC
UCCUUGAUGGUGGCCUCUCUGACUUACAAAGACAAAGUCUACUUGAAUGUGACCACUGACAAUACCUC
CCUGGAUGACUUCCAUGUGAAUGGCGGAGAACUGAUUCUUAUCCAUCAAAAUCCUGGUGAAUUCUGUG
UCCUU
Human OX40L mRNA (ORF)

5 5'$^{7me}$G$_{ppp}$G$_{2'\cdot OMe}$GGAAAUAAGAGAGAAAAGAAGAGUAAGAAGAAAUAUAAGAGCCACCAUGGAAA
GGGUCCAACCCCUGGAAGAGAAUGUGGGAAAUGCAGCCAGGCCAAGAUUCGAGAGGAACAAGCUAUUG
CUGGUGGCCUCUGUAAUUCAGGGACUGGGGCUGCUCCUGUGCUUCACCUACAUCUGCCUGCACUUCUC
UGCUCUUCAGGUAUCACAUCGGUAUCCUCGAAUUCAAAGUAUCAAAGUACAAUUUACCGAAUAUAAGA
AGGAGAAAGGUUUCAUCCUCACUUCCCAAAAGGAGGAUGAAAUCAUGAAGGUGCAGAACAACUCAGUC
AUCAUCAACUGUGAUGGGUUUUAUCUCAUCUCCCUGAAGGGCUACUUCUCCCAGGAAGUCAACAUUAG
CCUUCAUUACCAGAAGGAUGAGGAGCCCCUCUUCCAACUGAAGAAGGUCAGGUCUGUCAACUCCUUGA
UGGUGGCCUCUCUGACUUACAAAGACAAAGUCUACUUGAAUGUGACCACUGACAAUACCUCCCUGGAU
GACUUCCAUGUGAAUGGCGGAGAACUGAUUCUUAUCCAUCAAAAUCCUGGUGAAUUCUGUGUCCUUUG
AUAAUAGGCUGGAGCCUCGGUGGCCAUGCUUCUUGCCCCUUGGGCUCCCCCCAGCCCUCCUCCCCCU
UCCUGCACCCGUACCCCCCAAACACCAUUGUCACACUCCAGUGGUCUUUGAAUAAAGUCUGAGUGGGC
GGCAAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAUCUAG$_{OH}$3'
Where: A,C G & U = AMP, CMP, GMP & N1-ΨUMP, respectively;
Me = methyl; p = inorganic phosphate
Full-length mRNA Nucleotide sequence (5' UTR, ORF, 3' UTR, polyA
tail) of human OX40L 6 GGCCCUGGGACCUUUGCCUAUUUUCUGAUUGAUAGGCUUUGUUUUGUCUUUACCUCCUUCUUUCUGGG
GAAAACUUCAGUUUUAUCGCACGUUCCCCUUUUCCAUAUCUUCAUCUUCCUCUACCCAGAUUGUGAA
GAUGGAAAGGGUCCAACCCCUGGAAGAGAAUGUGGGAAAUGCAGCCAGGCCAAGAUUCGAGAGGAACA
AGCUAUUGCUGGUGGCCUCUGUAAUUCAGGGACUGGGGCUGCUCCUGUGCUUCACCUACAUCUGCCUG
CACUUCUCUGCUCUUCAGGUAUCACAUCGGUAUCCUCGAAUUCAAAGUAUCAAAGUACAAUUUACCGA
AUAUAAGAAGGAGAAAGGUUUCAUCCUCACUUCCCAAAAGGAGGAUGAAAUCAUGAAGGUGCAGAACA
ACUCAGUCAUCAUCAACUGUGAUGGGUUUUAUCUCAUCUCCCUGAAGGGCUACUUCUCCCAGGAAGUC
AACAUUAGCCUUCAUUACCAGAAGGAUGAGGAGCCCCUCUUCCAACUGAAGAAGGUCAGGUCUGUCAA
CUCCUUGAUGGUGGCCUCUCUGACUUACAAAGACAAAGUCUACUUGAAUGUGACCACUGACAAUACCU
CCCUGGAUGACUUCCAUGUGAAUGGCGGAGAACUGAUUCUUAUCCAUCAAAAUCCUGGUGAAUUCUGU
GUCCUUUGAGGGGCUGAUGGCAAUAUCUAAAACCAGGCACCAGCAGAACACCAAGCUGGGGGUGGAC
AGGGCAUGGAUUCUUCAUUGCAAGUGAAGGAGCCUCCCAGCUCAGCCACGUGGGGAUGUGACAAGAAGC
AGAUCCUGGCCCUCCCGCCCCCACCCCUCAGGGAUAUUUAAAACUUAUUUUAUAUACCAGUUAAUCUU
AUUUAUCCUUAUAUUUUCUAAAUUGCCUAGCCGUCACACCCCAAGAUUGCCUUGAGCCUACUAGGCAC
CUUUGUGAGAAAGAAAAAAAUAGAGCCUCUUCUUCAAGAUGCAUUUUCUAUUGGUCAUUGGUCAAUUGU
CAUAAUAAACUUUAUGUCAUUGAAAACGGUACCUGACUACCAUUUGCUGGAAAUUUGACAUGUGUGUGG
CAUUAUCAAAUGAAGAGGAGCAAGGAGUGAAGGAGUGGGGUUAUGAAUCUGCAAAGGUGGUAUGAA
CCAACCCCUGGAAGCCAAAGCGGCCUCUCCAAGGUUAAAUUGAUUGCAGUUUGCAUAUUGCCUAAAUU
UAAACUUUCUCAUUUGGUGGGGGUUCAAAAGAAGAAUCUUGUGAAAAAUCAGGACUUGAAGAAGA
CCGUCUAAGAAAUACCACGUGCUUUUUUUCUUUACCAUUUUGCUUUCCCAGCCUCCAAACAUAGUUAA
UAGAAAUUUCCCUUCAAAGAACUGUCUGGGGAUGUGAUGCUUUGAAAAAUCUAAUCAGUGACUUAAGA
GAGAUUUUCUUGUAUACAGGGAGAGUGAGAUAACUUAUUGUGAAGGGUUAGCUUUACUGUACAGGAUA
GCAGGGAACUGGACAUCUCAGGGUAAAAGUCAGUACGGAUUUUAAUAGCCUGGGGAGGAAAACACAUU
CUUUGCCACAGACAGGCAAAGCAACACAUGCUCAUCCUCCUGCCUAUGCUGAGAUACGCACUCAGCUC
CAUGUCUUGUACACACAGAAACAUUGCUGGUUUCAAGAAAUGAGGUGAUCCUAUUAUCAAAUUCAAUC
UGAUGUCAAAUAGCACUAAGAAGUUAUUGUGCCUUAUGAAAAAUAAUGAUCUCUGUCUAGAAAUACCA
UAGACCAUAUAUAGUCUCACAUUGAUAAUUGAAACUAGAAGGGUCUAUAAUCAGCCUAUGCCAGGGCU
UCAAUGGAAUAGUAUCCCCUUAUGUUUAGUUGAAAUGUCCCCUUAACUUGAUAUAAUGUGUUUAUGCUU
AUGGCGCUGUGGACAAUCUGAUUUUUCAUGUCAACUUUCCAGAUGAUUUGUAACUUCUCUGUGCCAAA
CCUUUUAUAAACAUAAAAUUUUUGAGAUAUGUAUUUUAAAAUUGUAGCACAUGUUUCCCUGACAUUUC
AAUAGAGGAUCAACAUCACAGAAUCUUUCUGGAUGAUUCUGUGUUAUCAAGGAAUUGUACUGUGCUA
CAAUUAUCUCUAGAAUCUCCAGAAGGUGGAGGGCUGUUCGCCCUUCAACUGAAAAUGGUCAGUUGGA
UUUUUUUUUCCUGUUUUCUAUUUCCUCUUUAAGUACACCUUCAACUAUAUUCCCAUCCCUCUAUUUUAA
UCUGUUAUGAAGGAAGGUAAAUAAAAAUGCUAAAUGAAGAAAUUGUAGGUAAGGUAAGAGGAAUCAA
GUUCUGAGUGGCUGCCAAGGCACUCACAGAAUCAUAAUCAUGGCUAAAUAUUUAUGGAGGGCCUACUG
UGGACCAGGCACUGGGCUAAAUACUUACAUUUACAAGAAUCAUUCUGAGACAGAUAUUCAAUGAUAUC
UGGCUUCACUACUCAGAAGAUUGUGUGUGUGUUUGUGUGUUGUGUGUCUUUGAUGUCAUGGUCCC
UAUUGACCAUGUUCUGCAAAAUUGCAGUUACUCAGUGAGUGAUAUCCGAAAAAGUAAACGUUUAUGAC
UAUAGGUAAUAUUUAAGAAAAUGCAUGGUUCAUUUUAAGUUUGGAAUUUUAUCUAUAUUUCUCACA
GAUGUGCAGUGCACAUGCAGGCCUAAGUAUAUGUUGUGUGUUGUUUGUCUUUGAUGUCAUGGUCCC
CUCUCUUAGGUGCUCACUGCUUUGGGUGCACCUGGCCUGCUCUUCCCAUGUUGGCCUCUGCAACCAC
ACAGGGAUAUUUCUGCUAUGCACCAGCCUCACUCCACCUUCCUUCCAUCAAAAAUAUGUGUGUGUGUC
UCAGUCCCUGUAAGUCAUGUCCUUCACAGGGAGAAUUAACCCUUCGAUAUACAUGGCAGAGUUUUGUG

SEQUENCE TABLE 1

| SEQ ID NO: | DESCRIPTION |
|---|---|
| | GGAAAAGAAUUGAAUGAAAAGUCAGGAGAUCAGAAUUUUAAAUUUGACUUAGCCACUAACUAGCCAUG<br>UAACCUUGGGAAAGUCAUUUCCCAUUUCUGGGUCUUGCUUUUCUUUCUGUUAAAUGAGAGGAAUGUUA<br>AAUAUCUAACAGUUUAGAAUCUUAUGCUUACAGUGUUAUCUGUGAAUGCACAUAUUAAAUGUCUAUGU<br>UCUUGUUGCUAUGAGUCAAGGAGUGUAACCUUCUCCUUUACUAUGUUGAAUGUAUUUUUUUCUGGACA<br>AGCUUACAUCUUCCUCAGCCAUCUUUGUGAGUCCUUCAAGAGCAGUUAUCAAUUGUUAGUUAGAUAUU<br>UUCUAUUUAGAGAAUGCUUAAGGGAUUCCAAUCCCGAUCCAAAUCAUAAUUUGUUCUUAAGUAUACUG<br>GGCAGGUCCCCUAUUUUAAGUCAUAAUUUUGUAUUUAGUGCUUUCCUGGCUCUCAGAGAGUAUUAAUA<br>UUGAUAUUAAUAAUAUAGUUAAUAGUAAUAUUGCUAUUUACAUGGAAACAAAUAAAAGAUCUCAGAAU<br>UCACUAAAAAAAAAAA<br>OX40L - TNFSF4, transcript variant 1, mRNA NM 003326 |
| 7 | GGGAAAUAAGAGAGAAAAGAAGAGUAAGAAGAAAUAUAAGAGCCACCAUGGAAAGGGUCCAACCCCUG<br>GAAGAGAAUGUGGGAAAUGCAGCCAGGCCAAGAUUCGAGAGGAACAAGCUAUUGCUGGUGGCCUCUGU<br>AAUUCAGGGACUGGGGCUGCUCCUGUGCUUCACCUACAUCUGCCUGCACUUCUCUGCUCUUCAGGUAU<br>CACAUCGGUAUCCUCGAAUUCAAAGUAUCAAAGUACAAUUUACCGAAUAUAAGAAGGAGAAAGGUUUC<br>AUCCUCACUUCCCAAAAGGAGGAUGAAAUCAUGAAGGUGCAGAACUCCAGUCAUCAUCAACUGUGA<br>UGGGUUUUAUCUCAUCUCCCUGAAGGGCUACUUCUCCCAGGAAGUCAACAUUAGCCUUCAUUACCAGA<br>AGGAUGAGGAGCCCCUCUUCCAACUGAAGAAGGUCAGGUCUGUCAACUCCUUGAUGGUGGCCUCUCUG<br>ACUUACAAAGACAAAGUCUACUUGAAUGUGACCACUGACAAUACCUCCCUGGAUGACUUCCAUGUGAA<br>UGGCGGAGAACUGAUUCUUAUCCAUCAAAAUCCUGGUGAAUUCUGUGUCCUUUGAUAAUAGGCUGGAG<br>CCUCGUGGCCAUGCUUCUUGCCCCUUGGGCCUCCCCCCAGCCCCUCCUCCCCUUCCUGCACCCGUAC<br>CCCCCAAACACCAUUGUCACACUCCAGUGGUCUUUGAAUAAAGUCUGAGUGGGCGGC<br>mRNA sequence: Human OX40L with 5'-UTR, 3'-UTR, and miR-122 binding site |
| 8 | AUGGAGCGGGUGCAGCCCCUGGAGGAGAACGUGGGCAACGCCGCUCGGCCACGGUUCGAGCGGAACAA<br>GCUGCUGCUGGUGGCUAGCGUGAUCCAGGGCCUGGGCCUGCUGCUGUGCUUCACCUACAUCUGCCUGC<br>ACUUCAGCGCCCUGCAGGUGAGCCACCGGUAUCCCGGAUCCAGAGCAUCAAGGUGCAGUUCACCGAG<br>UACAAGAAGGAGAAGGGCUUCAUCCUGACCAGCCAGAAGGAGGACGAGAUCAUGAAGGUGCAGAACAA<br>CAGCGUGAUCAUCAACUGCGACGGCUUCUACCUGAUCAGCCUGAAGGGCUACUUCAGCCAGGAGGUGA<br>ACAUCAGCCUGCACUACCAGAAGGACGAGGAGCCCCUGUUCCAGCUGAAGAAGGUGCGGAGCGUGAAC<br>AGCCUGAUGGUGGCCAGCCUGACCUACAAGGACAAGGUGUACCUGAACGUGACCACCGACAACACCAG<br>CCUGGACGACUUCCACGUGAACGGCGGCGAGCUGAUCCUGAUCCACCAGAACCCCGGCGAGUUCUGCG<br>UGCUG<br>mRNA open reading frame sequence 1 for Human OX40L |
| 9 | AUGGAAAGGGUCCAACCCCUCGAAGAGAACGUGGGAAACGCAGCCAGGCCAAGAUUCGAGAGGAACAA<br>GCUAUUGCUCGUGGCCUCAGUAAUUCAGGGACUCGGGUUACUCCUUUGCUUCACCUACAUCUGCUUGC<br>ACUUCAGUGCUCUGCAGGUAUCACAUCGGUAUCCUCGAAUUCAAAGUAUCAAAGUACAAUUUACCGAA<br>UAUAAGAAGGAGAAAGGUUUCAUCCUCACUUCCCAGAAGGAGGAUGAAAUCAUGAAGGUGCAGAACAA<br>CUCAGUCAUCAUCAACUGUGAUGGGUUUUAUCUCAUCUCCCUGAAGGGCUACUUCUCCCAGGAAGUCA<br>ACAUUAGCCUUCAUUACCAGAAGGAUGAGGAGCCCCUCUUCCAACUGAAGAAGGUCAGGUCUGUCAAC<br>UCCUUGAUGGUAGCCUCUCUGACUUACAAAGACAAAGUCUACUUGAAUGUGACCACUGACAAUACCUC<br>CCUGGAUGACUUCCAUGUGAAUGGCGGAGAACUGAUUCUUAUCCAUCAGAAUCCUGGUGAAUUCUGUG<br>UCCUU<br>mRNA open reading frame sequence 2 for Human OX40L |
| 10 | AUGGAGCGGGUGCAGCCCCUGGAGGAGAACGUGGGCAACGCCGCUCGGCCACGGUUCGAGCGGAACAA<br>GCUGCUGCUGGUGGCUAGCGUGAUCCAGGGCCUGGGCCUGCUGCUGUGCUUCACCUACAUCUGCCUGC<br>ACUUCAGCGCCCUGCAGGUGAGCCACCGGUAUCCCGGAUCCAGAGCAUCAAGGUGCAGUUCACCGAG<br>UACAAGAAGGAGAAGGGCUUCAUCCUGACCAGCCAGAAGGAGGACGAGAUCAUGAAGGUGCAGAACAA<br>CAGCGUGAUCAUCAACUGCGACGGCUUCUACCUGAUCAGCCUGAAGGGCUACUUCAGCCAGGAGGUGA<br>ACAUCAGCCUGCACUACCAGAAGGACGAGGAGCCCCUGUUCCAGCUGAAGAAGGUGCGGAGCGUGAAC<br>AGCCUGAUGGUGGCCAGCCUGACCUACAAGGACAAGGUGUACCUGAACGUGACCACCGACAACACCAG<br>CCUGGACGACUUCCACGUGAACGGCGGCGAGCUGAUCCUGAUCCACCAGAACCCCGGCGAGUUCUGCG<br>UGCUG<br>mRNA open reading frame sequence 3 for Human OX40L |
| 11 | AGGAAAUAAGAGAGAAAAGAAGAGUAAGAAGAAAUAUAAGACCCCGGCGCCGCCACC<br>5' UTR |
| 12 | CCUUAGCAGAGCUGUGGAGUGUGACAAUGGUGUUUGUGUCUAAACUAUCAAACGCCAUUAUCACACUA<br>AAUAGCUACUGCUAGGC<br>(miR-122) |
| 13 | AACGCCAUUAUCACACUAAAUA<br>(miR-122-3p) |
| 14 | UAUUUAGUGUGAUAAUGGCGUU (miR-122-3p binding site) |
| 15 | UCAAGCUUUUGGACCCUCGUACAGAAGCUAAUACGACUCACUAUAGGGAAAUAAGAGAGAAAAGAAGA<br>GUAAGAAGAAAUAUAAGAGCCACC<br>(5' UTR) |

SEQUENCE TABLE 1

SEQ
ID
NO: DESCRIPTION

16 GGGAAAUAAGAGAGAAAAGAAGAGUAAGAAGAAAUAUAAGAGCCACC
   (5' UTR)

17 UGAUAAUAGGCUGGAGCCUCGGUGGCCAUGCUUCUUGCCCCUUGGGCCUCCCCCCAGCCCCUCCUCCC
   CUUCCUGCACCCGUACCCCCCAAACACCAUUGUCACACUCCAGUGGUCUUUGAAUAAAGUCUGAGUGG
   GCGGC (3' UTR)

18 UGAUAAUAGGCUGGAGCCUCGGUGGCCAUGCUUCUUGCCCCUUGGGCCCAAACACCAUUGUCACACUC
   CAUCCCCCAGCCCCUCCUCCCCUUCCUCCAUAAAGUAGGAAACACUACAUGCACCCGUACCCCCGUG
   GUCUUUGAAUAAAGUCUGAGUGGGCGGC
   (3' UTR with mi-122 and mi-142.3p sites)

19 UGGAGUGUGACAAUGGUGUUUG
   (miR-122-5p)

20 CAAACACCAUUGUCACACUCCA (miR-122-5p binding site)

21 GCCA/GCC
   Kozak Consensus

22 UGAUAAUAGGCUGGAGCCUCGGUGGCCUAGCUUCUUGCCCCUUGGGCCUCCCCCCAGCCCCUCCUCCC
   CUUCCUGCACCCGUACCCCCCAAACACCAUUGUCACACUCCAGUGGUCUUUGAAUAAAGUCUGAGUGG
   GCGGC
   3'UTR with miR-122

23 CCGCCGCCGCCG
   [CCG]₄

24 CCGCCGCCGCCGCCG
   [CCG]₅

25 CCCCGGCGCC
   V1 GC-rich RNA element

26 CCCCGGC
   V2 GC-rich RNA element

27 GCCGCC
   EK GC-rich RNA element

28 GGGAAATAAGAGAGAAAAGAAGAGTAAGAAGAAATATAAGA
   5'UTR

29 GGGAAATAAGAGAGAAAAGAAGAGTAAGAAGAAATATAAGACCCCGGCGCCGCCACC
   V1-5'UTR

30 GGGAAATAAGAGAGAAAAGAAGAGTAAGAAGAAATATAAGACCCCGGCGCCACC
   V2-5'UTR

31 GGGAAATAAGAGAGAAAAGAAGAGTAAGAAGAAATATAAGAGCCACC
   Standard UTR

32 MCHQQLVISWFSLVFLASPLVAIWELKKDVYVVELDWYPDAPGEMVVLTCDTPEEDGITWTLDQSSEV
   LGSGKTLTIQVKEFGDAGQYTCHKGGEVLSHSLLLLHKKEDGIWSTDILKDQKEPKNKTFLRCEAKNY
   SGRFTCWWLTTISTDLTFSVKSSRGSSDPQGVTCGAATLSAERVRGDNKEYEYSVECQEDSACPAAEE
   SLPIEVMVDAVHKLKYENYTSSFFIRDIIKPDPPKNLQLKPLKNSRQVEVSWEYPDTWSTPHSYFSLT
   FCVQVQGKSKREKKDRVFTDKTSATVICRKNASISVRAQDRYYSSSWSEWASVPCSGGGGGGSRAVPG
   GSSPAWTQCQQLSQKLCTLAWSAHPLVGHMDLREEGDEETTNDVPHIQCGDGCDPQGLRDNSQFCLQR
   IHQGLIFYEKLLGSDIFTGEPSLLPDSPVGQLHASLLGLSQLLQPEGHHWETQQIPSLSPSQPWQRLL
   LRFKILRSLQAFVAVAARVFAHGAATLSP
   Amino Acid sequence of human IL-23 (IL-12p40 subunit and IL-23p19
   subunit linked by GS Linker)

33 AUGUGUCACCAGCAGUUGGUCAUCUCUUGGUUUUCCUUGGUAUUUCUGGCAUCUCCCCUCGUGGCCAU
   AUGGGAACUGAAGAAAGAUGUUUAUGUCUAGAAUUGGAUUGGUAUCCGGAUGCCCCUGGAGAAAUGG
   UGGUCCUCACCUGUGACACCCCUGAAGAAGAUGGUAUCACCUGGACCCUUGGACCAGAGCAGUGAGGUC
   UUAGGCUCUGGCAAGACCCUGACCAUCCAAGUCAAAGAGUUUGGAGAUGCUGGCCAGUACACCUGUCA
   CAAAGGAGGCGAGGUUCUAAGCCAUUCGCUCCUGCUGCUUCACAAGAAGGAAGAUGGAAUUUGGUCCA
   CUGAUAUUUUAAAGGACCAGAAAGAACCCAAGAAUAAGACCUUUCUAAGAUGCGAGGCCAAGAAUUAU
   UCUGGACGUUUCACCUGCUGGUGGCUGACGACAAUCAGUACUGAUUUGACAUUCAGUGUCAAGAGCAG
   CAGAGGCUCUUCUGACCCCCAAGGGGUGACGUGCGGAGCUGCUACACUCUCUGCAGAGAGUCAGAG
   GGGACAACAAGGAGUAUGAGUACUCAGUGGAGUGCCAGGAGGACAGUGCCUGCCCAGCUGCUGAGGAG

SEQUENCE TABLE 1

| SEQ ID NO: | DESCRIPTION |
|---|---|
| | AGUCUGCCCAUUGAGGUCAUGGUGGAUGCCGUUCACAAGCUCAAGUAUGAGAACUACACCAGCAGCUU<br>CUUCAUCAGGGACAUCAUCAAACCUGACCCACCCAAGAACUUGCAGCUGAAGCCAUUAAAGAAUUCUC<br>GGCAGGUGGAGGUCAGCUGGGAGUACCCUGACACCUGGAGUACUCCACAUUCCUACUUCUCCCUGACA<br>UUCUGCGUUCAGGUCCAGGGCAAGAGCAAGAGAGAAGAAAGAUAGAGUCUUCACGGACAAGACCUC<br>AGCCACGGUCAUCUGCCGCAAGAAUGCCAGCAUUAGCGUGCGGGCCCAGGACCGCUACUAUAGCUCAU<br>CUUGGAGCGAAUGGGCAUCUGUGCCCUGCAGUGGCGGAGGGGCGGAGGGAGCAGAGCUGUGCCUGGG<br>GGCAGCAGCCCUGCCUGGACUCAGUGCCAGCAGCUUUCACAGAAGCUCUGCACACUGGCCUGGAGUGC<br>ACAUCCACUAGUGGGACACAUGGAUCUAAGAGAAGAGGGAGAUGAAGAGACUACAAAUGAUGUUCCCC<br>AUAUCCAGUGUGGAGAUGGCUGUGACCCCCAAGGACUCAGGGACAACAGUCAGUUCUGCUUGCAAAGG<br>AUCCACCAGGGUCUGAUCUUUUAUGAGAAGCUGCUAGGAUCGGAUAUUUUCACAGGGGAGCCUUCUCU<br>GCUCCCUGAUAGCCCUGUGGGCCAGCUUCAUGCCUCCCUACUGGGCCUCAGCCAACUCCUGCAGCCUG<br>AGGGUCACCACUGGGAGACUCAGCAGAUUCCAAGCCUCAGUCCCAGCCAGCCAUGGCAGCGUCUCCUU<br>CUCCGCUUCAAGAUCCUUCGCAGCCUCCAGGCCUUUGUGGCUGUAGCCGCCCGGGUCUUUGCCCAUGG<br>AGCAGCAACCCUGAGUCCC<br>Nucleotide sequence (ORF) of human IL-23 (IL-12p40 subunit and IL-23p19 subunit linked by GS Linker) |
| 34 | 5'$^{7me}$G$_{ppp}$G$_{2'OMe}$GGAAAUAAGAGAGAAAAGAAGAGUAAGAAGAAAUAUAAGAGCCACCAUGUGUC<br>ACCAGCAGUUGGUCAUCUCUUGGUUUUCCCUGGUAUUUCUGGCAUCUCCCCUCGUGGCCAUAUGGGAA<br>CUGAAGAAAGAUGUUUAUGUCGUAGAAUUGGAUUGGUAUCCUGAUGCCCUGGAGAAAUGGUGGUCCU<br>CACCUGUGACACCCCUGAAGAAGAUGGUAUCACCUGGACCUUGGACCAGAGCAGUGAGGUCUUAGGCU<br>CUGGCAAGACCCUGACCAUCCAAGUCAAAGAGUUUGGAGAUGCUGGCCAGUACACCUGUCACAAAGGA<br>GGCGAGGUUCUAAGCCAUUCGCUCCUGCUGCUUCACAAGAAGGAAGAUGGAAUUUGGUCCACUGAUAU<br>UUUAAAGGACCAGAAAGAACCCAAGAAUAAGACCUUUCUAAGAUGCGAGGCCAAGAAUAUUCUGGAC<br>GUUUCACCUGCUGGUGGCUGACGACAAUCAGUACUGAUUUGACAUUCAGUGUCAAGAGCAGCAGAGGC<br>UCUUCUGACCCCCAAGGGUGACGUGCGAGCUGCUACACUCUCUGCAGAGAGAGUCAGAGGGGACAA<br>CAAGGAGUAUGAGUACUCAGUGGAGUGCCAGGAGGACAGUGCCUGCCCAGCUGCUGAGGAGAGUCUGC<br>CCAUUGAGGUCAUGGUGGAUGCCGUUCACAAGCUCAAGUAUGAGAACUACACCAGCAGCUUCUUCAUC<br>AGGGACAUCAUCAAACCUGACCCACCCAAGAACUUGCAGCUGAAGCCAUUAAAGAAUUCUCGGCAGGU<br>GGAGGUCAGCUGGGAGUACCCUGACACCUGGAGUACUCCACAUUCCUACUUCUCCCUGACAUUCUGCG<br>UUCAGGUCCAGGGCAAGAGCAAGAGAGAAGAAAGAUAGAGUCUUCACGGACAAGACCUCAGCCACG<br>GUCAUCUGCCGCAAGAAUGCCAGCAUUAGCGUGCGGGCCCAGGACCGCUACUAUAGCUCAUCUUGGAG<br>CGAAUGGGCAUCUGUGCCCUGCAGUGGCGGAGGGGCGGAGGGAGCAGAGCUGUGCCUGGGGGCAGCA<br>GCCCUGCCUGGACUCAGUGCCAGCAGCUUUCACAGAAGCUCUGCACACUGGCCUGGAGUGCACAUCCA<br>CUAGUGGGACACAUGGAUCUAAGAGAAGAGGGAGAUGAAGAGACUACAAAUGAUGUUCCCCAUAUCCA<br>GUGUGGAGAUGGCUGUGACCCCCAAGGACUCAGGGACAACAGUCAGUUCUGCUUGCAAAGGAUCCACC<br>AGGGUCUGAUCUUUUAUGAGAAGCUGCUAGGAUCGGAUAUUUUCACAGGGGAGCCUUCUCUGCUCCCU<br>GAUAGCCCUGUGGGCCAGCUUCAUGCCUCCCUACUGGGCCUCAGCCAACUCCUGCAGCCUGAGGGUCA<br>CCACUGGGAGACUCAGCAGAUUCCAAGCCUCAGUCCCAGCCAGCCAUGGCAGCGUCUCCUUCUCCGCU<br>UCAAGAUCCUUCGCAGCCUCCAGGCCUUUGUGGCUGUAGCCGCCCGGGUCUUUGCCCAUGGAGCAGCA<br>ACCCUGAGUCCCUGAUAAUAGCCUGGAGCCUCGGUGGCCAUGCUUCUGCCCUUGGGCCUCCCCCCA<br>GCCCCUCCUCCCCUUCCUGCACCCGUACCCCCCAAACACCAUUGUCACACUCCAGUGGUCUUUGAAUA<br>AAGUCUGAGUGGGCGGCAAAAAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAAAAAAUCUAG$_{OH}$3'<br>Where: A,C G & U = AMP, CMP, GMP & N1-ΨUMP, respectively; Me = methyl; p = inorganic phosphate<br>Full-length mRNA Nucleotide sequence (5' UTR, ORF, 3' UTR, mir-122-5p (underlined) polyA tail) of human IL-23 (IL-12p40 subunit and IL-23p19 subunit linked by GS Linker) |
| 35 | MVLQTQVFISLLLWISGAYGSMCKPITGTINDLNQQVWTLQGQNLVAVPRSDSVTPVTVAVITCKYPE<br>ALEQGRGDPIYLGIQNPEMCLYCEKVGEQPTLQLKEQKIMDLYGQPEPVKPFLFYRAKTGRTSTLESV<br>AFPDWFIASSKRDQPIILTSELGKSYNTAFELNIND<br>hIGKV4-hIL-36γ construct (protein) |
| 36 | AUGGUGUUGCAGACCCAGGUCUUCAUUUCUCUGUUGCUCUGGAUCUCUGGUGCCUACGGGUCAAUGUG<br>UAAACCUAUUACUGGGACUAUUAAUGAUUUGAAUCAGCAAGUGUGGACCCUUCAGGGUCAGAACCUUG<br>UGGCAGUUCCACGAAGUGACAGUGUGACCCCAGUCACUGUUGCUGUUAUCACAUGCAAGUAUCCAGAG<br>GCUCUUGAGCAAGGCAGAGGGGAUCCCAUUUAUUUGGGAAUCCAGAAUCCAGAAAUGUGUUUGUAUUG<br>UGAGAAGGUUGGAGAACAGCCCACAUUGCAGCUAAAAGAGCAGAAGAUCAUGGAUCUGUAUGGCCAAC<br>CCGAGCCCGUGAAACCCUUCCUUUUCUACCGUGCCAAGACUGGUAGGACCUCCACCCUUGAGUCUGUG<br>GCCUUCCCGGACUGGUUCAUUGCCUCCUCCAAGAGAGACCAGCCCAUCAUUCUGACUUCAGAACUUGG<br>GAAGUCAUACAACACUGCCUUUGAAUUAAAUAUAAAUGAC<br>Human IL-36γ mRNA (ORF) |
| 37 | 5'$_{7Me}$G$_{ppp}$G$_{2'OMe}$GGAAAUAAGAGAGAAAAGAAGAGUAAGAAGAAAUAUAAGAGCCACCAUGGUGU<br>UGCAGACCCAGGUCUUCAUUUCUCUGUUGCUCUGGAUCUCUGGUGCCUACGGGUCAAUGUGUAAACCU<br>AUUACUGGGACUAUUAAUGAUUUGAAUCAGCAAGUGUGGACCCUUCAGGGUCAGAACCUUGUGGCAGU<br>UCCACGAAGUGACAGUGUGACCCCAGUCACUGUUGCUGUUAUCACAUGCAAGUAUCCAGAGGCUCUUG<br>AGCAAGGCAGAGGGGAUCCCAUUUAUUUGGGAAUCCAGAAUCCAGAAAUGUGUUUGUAUUGUGAGAAG<br>GUUGGAGAACAGCCCACAUUGCAGCUAAAAGAGCAGAAGAUCAUGGAUCUGUAUGGCCAACCCGAGCC<br>CGUGAAACCCUUCCUUUUCUACCGUGCCAAGACUGGUAGGACCUCCACCCUUGAGUCUGUGGCCUUCC<br>CGGACUGGUUCAUUGCCUCCUCCAAGAGAGACCAGCCCAUCAUUCUGACUUCAGAACUUGGGAAGUCA |

SEQUENCE TABLE 1

SEQ ID NO: DESCRIPTION

```
UACAACACUGCCUUUGAAUUAAAUAUAAAUGACUGAUAAUAGGCUGGAGCCUCGGUGGCCAUGCUUCU
UGCCCCUUGGGCCUCCCCCCAGCCCCUCCUCCCCUUCCUGCACCCGUACCCCCCAAACACCAUUGUCA
CACUCCAGUGGUCUUUGAAUAAAGUCUGAGUGGGCGGCAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAA
AAUCUAG$_{OH}$3'
```
Where: A,C G & U = AMP, CMP, GMP & N1-ΨUMP, respectively; Me = methyl; p = inorganic phosphate
Full-length mRNA Nucleotide sequence (5' UTR, ORF, 3' UTR, mir-122-5p (underlined) polyA tail) of human IL-36-gamma

What is claimed:

1. A method for treating triple negative breast cancer, head and neck squamous cell carcinoma, melanoma, or Non-Hodgkin lymphoma in a human patient, comprising administering to the patient by intratumoral injection an LNP encapsulated mRNA composition comprising:
   (i) a first mRNA comprising an open reading frame (ORF) encoding a human OX40L polypeptide comprising the amino acid sequence of SEQ ID NO: 1;
   (ii) a second mRNA comprising an ORF encoding a human IL-23 polypeptide comprising the amino acid sequence of SEQ ID NO: 32; and
   (iii) a third mRNA comprising an ORF encoding a human IL-36γ polypeptide comprising the amino acid sequence of SEQ ID NO: 35,
   wherein the patient is administered a dose of 0.25 mg to 8 mg of the LNP encapsulated mRNA composition, and
   wherein the first, second, and third mRNAs comprise modified uridines,
   thereby treating the triple negative breast cancer, head and neck squamous cell carcinoma, melanoma, or Non-Hodgkin lymphoma in the patient.

2. The method of claim 1, wherein the patient is administered the LNP encapsulated mRNA composition in a dosing regimen from 7 to 28 days.

3. The method of claim 1, wherein the patient is administered a dose of the LNP encapsulated mRNA composition selected from 0.25-4.0 mg; 0.25-2.0 mg; 0.25-1.0 mg;

0.5-8.0 mg; 0.5-4.0 mg; 0.5-2.0 mg; 0.5-1.0 mg; 1.0-8.0 mg; 1.0-4.0 mg; 1.0-2.0 mg; 2.0-8.0 mg; 2.0-4.0 mg; and 4.0-8.0 mg.

4. The method of claim 1, wherein the patient is administered a dose of the LNP encapsulated mRNA composition of 0.25 mg.

5. The method of claim 1, wherein the patient is administered a dose of the LNP encapsulated mRNA composition of 0.5 mg.

6. The method of claim 1, wherein the patient is administered a dose of the LNP encapsulated mRNA composition of 1 mg.

7. The method of claim 1, wherein the patient is administered a dose of the LNP encapsulated mRNA composition of 2 mg.

8. The method of claim 1, wherein the patient is administered a dose of the LNP encapsulated mRNA composition of 4 mg.

9. The method of claim 1, wherein the patient is administered a dose of the LNP encapsulated mRNA composition of 8 mg.

10. The method of claim 1, wherein the patient is administered a dose of the LNP encapsulated mRNA composition in combination with a checkpoint inhibitor polypeptide.

11. The method of claim 10, wherein the checkpoint inhibitor polypeptide is a PD-1 antagonist.

12. The method of claim 10, wherein the checkpoint inhibitor polypeptide is a PD-L1 antagonist.

13. The method of claim 12, wherein the PD-L1 antagonist is an antibody or antigen-binding fragment thereof that specifically binds to PD-L1.

14. The method of claim 12, wherein the PD-L1 antagonist is durvalumab.

15. The method of claim 10, wherein the checkpoint inhibitor polypeptide is a CTLA-4 antagonist.

16. The method of claim 15, wherein the CTLA-4 antagonist is an antibody or antigen-binding fragment thereof that specifically binds to CTLA-4.

17. The method of claim 1, wherein each of the first mRNA, second mRNA, and third mRNA comprise a 3' untranslated region (UTR) comprising at least one microRNA-122 (miR-122) binding site, wherein the miR-122 binding site is a miR-122-3p binding site or a miR-122-5p binding site.

18. The method of claim 1, wherein the modified uridine is selected from N1-methylpseudouridines (m1ψ) and pseudouridine (ψ).

19. The method of claim 1, wherein treatment results in a reduction in size or inhibition of growth of an injected tumor and/or an uninjected tumor.

20. The method of claim 1, wherein the patient is administered the LNP encapsulated mRNA composition at a dose of 0.1 mg, 0.25 mg, 0.5 mg, 1 mg, 2 mg, 4 mg, or 8 mg once every two weeks (Q2W).

21. The method of claim 14, wherein the patient is administered the LNP encapsulated mRNA composition at a dose of 0.1 mg, 0.25 mg, 0.5 mg, 1 mg, 2 mg, 4 mg, or 8 mg once every four weeks (Q4W).

22. The method of claim 21, wherein the patient is administered durvalumab at a dose of 1500 mg once every four weeks (Q4W).

23. The method of claim 16, wherein the antibody or antigen-binding fragment thereof that specifically binds to CTLA-4 is tremelimumab.

24. The method of claim 23, wherein the patient is administered the LNP encapsulated mRNA composition at a dose of 0.1 mg, 0.25 mg, 0.5 mg, 1 mg, 2 mg, 4 mg, or 8 mg once every four weeks (Q4W).

25. The method of claim 24, wherein the patient is administered tremelimumab at a dose of 225 mg once every four weeks (Q4W).

* * * * *